(12) United States Patent
Carson et al.

(10) Patent No.: US 10,959,757 B2
(45) Date of Patent: *Mar. 30, 2021

(54) RECOVERY AND PROCESSING OF HUMAN EMBRYOS FORMED IN VIVO

(71) Applicant: Previvo Genetics, Inc., San Carlos, CA (US)

(72) Inventors: Sandra Ann Carson, Providence, RI (US); John E. Buster, Providence, RI (US); Moses Cesario, Piedmont, CA (US); Steven Paul Woodard, Cupertino, CA (US)

(73) Assignee: Previvo Genetics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,245

(22) Filed: Mar. 1, 2018

(65) Prior Publication Data

US 2018/0289395 A1 Oct. 11, 2018

Related U.S. Application Data

(63) Continuation of application No. 14/814,252, filed on Jul. 30, 2015, now Pat. No. 10,226,280, and a
(Continued)

(51) Int. Cl.
*A61B 17/435* (2006.01)
*A61B 17/42* (2006.01)
(Continued)

(52) U.S. Cl.
CPC ............ *A61B 17/435* (2013.01); *A61B 17/42* (2013.01); *A61B 17/425* (2013.01);
(Continued)

(58) Field of Classification Search
CPC ...... A61B 17/42; A61B 17/425; A61B 17/435; A61D 19/00; A61D 19/04
See application file for complete search history.

(56) References Cited

U.S. PATENT DOCUMENTS 3,587,588 A 6/1971 Murr
4,100,923 A 7/1978 Southern
(Continued)

FOREIGN PATENT DOCUMENTS

EP 131166 A1 1/1985
EP 131166 B1 9/1988
(Continued)

OTHER PUBLICATIONS

International Search Report and Written Opinion for International Application No. PCT/US12/66828, dated Apr. 17, 2013, 41 pages.
(Continued)

*Primary Examiner* — Carrie R Dorna
(74) *Attorney, Agent, or Firm* — Sterne, Kessler, Goldstein & Fox P.L.L.C.

(57) ABSTRACT

A kit having instructions for use for performing uterine lavage in a female patient includes a uterine lavage catheter configured for insertion into a woman's uterus to remove viable blastocysts from the uterus, and one or more first containers having a sufficient dosage amount of a GnRH antagonist to cause desynchronization of the endometrium of the patient prior to, during and/or following recovery of viable blastocysts from the uterus.

21 Claims, 104 Drawing Sheets

Related U.S. Application Data continuation of application No. 14/814,184, filed on Jul. 30, 2015, now Pat. No. 10,213,230, said application No. 14/814,252 is a continuation of application No. 14/642,437, filed on Mar. 9, 2015, now abandoned, and a continuation-in-part of application No. 13/924,520, filed on Jun. 21, 2013, now Pat. No. 9,216,037, and a continuation-in-part of application No. 13/335,170, filed on Dec. 22, 2011, now Pat. No. 9,282,995.

(51) Int. Cl.

| | | |
|---|---|---|
| *A61K 38/09* | (2006.01) | |
| *A61K 38/08* | (2019.01) | |
| *A61K 31/57* | (2006.01) | |
| *A61K 31/215* | (2006.01) | |
| *A61K 31/575* | (2006.01) | |
| *A61K 31/573* | (2006.01) | |
| *A61K 31/58* | (2006.01) | |
| *C12Q 1/6883* | (2018.01) | |
| *A61K 38/24* | (2006.01) | |
| *A61K 45/06* | (2006.01) | |
| *A61K 9/00* | (2006.01) | |
| *A61B 17/425* | (2006.01) | |
| *A61P 15/08* | (2006.01) | |
| *A61K 47/26* | (2006.01) | |
| *A61B 50/31* | (2016.01) | |
| *A61B 50/30* | (2016.01) | |
| *A61B 50/20* | (2016.01) | |

(52) U.S. Cl.
CPC .......... *A61K 9/0034* (2013.01); *A61K 31/215* (2013.01); *A61K 31/57* (2013.01); *A61K 31/573* (2013.01); *A61K 31/575* (2013.01); *A61K 31/58* (2013.01); *A61K 38/08* (2013.01); *A61K 38/09* (2013.01); *A61K 38/24* (2013.01); *A61K 45/06* (2013.01); *A61K 47/26* (2013.01); *A61P 15/08* (2018.01); *C12Q 1/6883* (2013.01); *A61B 50/20* (2016.02); *A61B 2017/4216* (2013.01); *A61B 2050/3008* (2016.02); *A61B 2050/3011* (2016.02); *A61B 2050/311* (2016.02); *A61B 2217/005* (2013.01); *A61B 2217/007* (2013.01); *C12Q 2600/156* (2013.01)

(56) References Cited

U.S. PATENT DOCUMENTS

| | | |
|---|---|---|
| 4,178,936 A | 12/1979 | Newcomb |
| 4,468,216 A | 8/1984 | Muto |
| 4,533,345 A | 8/1985 | Louw |
| 4,601,698 A | 7/1986 | Moulding, Jr. |
| 5,005,583 A | 4/1991 | Bustillo |
| 5,030,202 A | 7/1991 | Harris |
| 5,217,466 A | 6/1993 | Hasson |
| 5,409,457 A | 4/1995 | del Cerro et al. |
| 5,421,346 A | 6/1995 | Sanyal |
| 5,445,168 A | 8/1995 | Krebs |
| 5,451,208 A | 9/1995 | Goldrath |
| 5,514,119 A | 5/1996 | Curtis |
| 5,938,098 A | 8/1999 | Fife |
| 6,106,506 A | 8/2000 | Abell |
| 6,234,958 B1 | 5/2001 | Snoke et al. |
| 6,281,013 B1 | 8/2001 | Grondahl et al. |
| 6,287,863 B1 | 9/2001 | Hodgson |
| 6,436,072 B1 | 8/2002 | Kullas et al. |
| 6,485,452 B1 | 11/2002 | French et al. |
| 6,585,982 B1 | 7/2003 | Grøndahl et al. |
| 6,827,703 B1 | 12/2004 | Ackerman |
| 6,939,336 B2 | 9/2005 | Silfver |
| 7,378,388 B2 | 5/2008 | Seifer et al. |
| 7,419,500 B2 | 9/2008 | Marko et al. |
| 7,963,946 B2 | 6/2011 | Moubayed et al. |
| 8,052,669 B2 | 11/2011 | Lee-Sepsick et al. |
| 8,221,403 B2 | 7/2012 | Sharkey et al. |
| 8,257,244 B2 | 9/2012 | Mock |
| 8,316,853 B2 | 11/2012 | Lee-Sepsick et al. |
| 8,316,854 B2 | 11/2012 | Lee-Sepsick et al. |
| 8,336,552 B2 | 12/2012 | Lee-Sepsick et al. |
| 8,585,616 B2 | 11/2013 | Swann |
| 2002/0115054 A1 | 8/2002 | Forest et al. |
| 2003/0108586 A1 | 6/2003 | Ramey |
| 2004/0022739 A1 | 2/2004 | Daniels et al. |
| 2004/0083498 A1 | 4/2004 | DeSousa et al. |
| 2004/0219028 A1 | 11/2004 | Demarais et al. |
| 2004/0267198 A1 | 12/2004 | Torstensen et al. |
| 2005/0049199 A1 | 3/2005 | Hillier et al. |
| 2005/0235374 A1 | 10/2005 | Bunschoten et al. |
| 2005/0256464 A1 | 11/2005 | Pallas |
| 2006/0002966 A1 | 1/2006 | Pauletti et al. |
| 2006/0015421 A1 | 1/2006 | Grimberg et al. |
| 2006/0069031 A1 | 5/2006 | Loumaye |
| 2006/0135405 A1 | 6/2006 | Rischer et al. |
| 2006/0135421 A1 | 6/2006 | Filicori |
| 2006/0217315 A1 | 9/2006 | Bennink et al. |
| 2006/0241125 A1 | 10/2006 | Bradley et al. |
| 2006/0247177 A1 | 11/2006 | Millar |
| 2007/0213671 A1 | 9/2007 | Hiatt et al. |
| 2008/0045924 A1* | 2/2008 | Cox ............... A61B 10/0045 604/515 |
| 2008/0071210 A1 | 3/2008 | Moubayed et al. |
| 2008/0091119 A1 | 4/2008 | Moffitt |
| 2008/0103446 A1 | 5/2008 | Torrance et al. |
| 2008/0172013 A1 | 7/2008 | Kucklick |
| 2008/0245371 A1 | 10/2008 | Gruber |
| 2009/0024108 A1 | 1/2009 | Lee-Sepsick et al. |
| 2009/0054871 A1 | 2/2009 | Sharkey et al. |
| 2010/0086492 A1 | 4/2010 | Lee-Sepsick et al. |
| 2010/0106108 A1 | 4/2010 | Hirsch et al. |
| 2010/0160717 A1 | 6/2010 | Scott et al. |
| 2010/0303688 A1 | 12/2010 | Andersen et al. |
| 2011/0002273 A1 | 1/2011 | Youn et al. |
| 2011/0022073 A1 | 1/2011 | Gross et al. |
| 2011/0092762 A1 | 4/2011 | Wong et al. |
| 2011/0098524 A1 | 4/2011 | Barcelo Rojas |
| 2011/0105834 A1 | 5/2011 | Wong et al. |
| 2012/0055492 A1 | 3/2012 | Nikolchev et al. |
| 2012/0197245 A1 | 8/2012 | Burnett et al. |
| 2013/0150418 A1 | 6/2013 | Goedeke et al. |
| 2013/0165744 A1 | 6/2013 | Carson et al. |
| 2014/0048074 A1 | 2/2014 | Tal et al. |
| 2014/0188042 A1 | 7/2014 | Browning et al. |
| 2014/0309486 A1 | 10/2014 | Carson et al. |
| 2014/0378750 A1 | 12/2014 | Buster et al. |
| 2014/0378751 A1 | 12/2014 | Buster et al. |
| 2014/0378752 A1 | 12/2014 | Buster et al. |
| 2014/0378753 A1 | 12/2014 | Buster et al. |
| 2014/0378754 A1 | 12/2014 | Buster et al. |
| 2014/0378756 A1 | 12/2014 | Buster et al. |
| 2015/0173826 A1 | 6/2015 | Churchill et al. |
| 2015/0272622 A1 | 10/2015 | Carson et al. |
| 2015/0335354 A1 | 11/2015 | Carson et al. |
| 2015/0335701 A1 | 11/2015 | Carson et al. |

FOREIGN PATENT DOCUMENTS

| | | |
|---|---|---|
| EP | 630658 A1 | 12/1994 |
| EP | 1870451 A1 | 12/2007 |
| EP | 1987814 A1 | 11/2008 |
| EP | 1987820 A1 | 11/2008 |
| JP | 2007045790 A | 2/2007 |
| JP | 2007045790 A1 | 2/2007 |
| WO | WO1982000754 A1 | 3/1982 |
| WO | WO1988007056 A1 | 9/1988 |
| WO | WO1998007056 A1 | 2/1998 |
| WO | WO1999043365 A1 | 9/1999 |
| WO | WO2010118325 | 10/2010 |
| WO | WO2010118325 A1 | 10/2010 |

(56) References Cited

FOREIGN PATENT DOCUMENTS

| WO | WO2011032984 A1 | 3/2011 |
|---|---|---|
| WO | WO2014140217 A1 | 9/2014 |
| WO | WO2014140217 | 12/2014 |

OTHER PUBLICATIONS

Office Action for U.S. Appl. No. 13/335,170, dated Jul. 18, 2014, 33 pages.
Office Action dated Feb. 25, 2016, in U.S. Appl. No. 14/814,252, Carson et al., filed Jul. 30, 2015, 16 pages.
Office Action dated Apr. 7, 2016, in U.S. Appl. No. 14/814,252, Carson et al., filed Jul. 30, 2015, 12 pages.
Office Action dated Apr. 3, 2017, in U.S. Appl. No. 14/814,252, Carson et al., filed Jul. 30, 2015, 11 pages.
Office Action dated Sep. 20, 2017, in U.S. Appl. No. 14/814,252, Carson et al., filed Jul. 30, 2015, 20 pages.
Office Action dated May 14, 2018, in U.S. Appl. No. 14/814,252, Carson et al., filed Jul. 30, 2015, 7 pages.
Office Action dated Jul. 13, 2017, in U.S. Appl. No. 14/642,437, Carson et al., filed Mar. 9, 2015, 10 pages.
Office Action dated Sep. 29, 2017, in U.S. Appl. No. 14/642,437, Carson et al., filed Mar. 9, 2015, 13 pages.
Bustillo, M. et al., "Delivery of a Healthy Infant Following Non-surgical Ovum Transfer," *JAMA* 251:889, American Medical Association (1984).
Humaidan, P. et al., "GnHR agonist (buserelin) or hCG for ovulation induction in GnRH antagonist IVF/ICSI cycles: a prospective randomized study," *Hum. Reprod.* 20:1213-1220, Oxford University Press (2005).
Struthers, R.S. et al., "Suppression of Gonadotropins and Estradiol in Premenopausal Women by Oral Admistration of Nonpeptide Gonadotropin-Releasing Hormone Antagonists Elagolix," *J. Clin. Endocrinol. Metab.* 94:554-551, The Endocrine Society (2009).
Buster, J., et al, "First Birth: Letters," Jama, The Journal of the American Medical Association, Feb. 17, 1984 (1 page).
Buster, J.E. et al. "Non-surgical transfer of an in-vivo fertilised donated ovum to an infertility patient," First Transfer and Failure, The Lancet, Apr. 9, 1983, 1 page.
Buster, J.E., et al. "Non-surgical transfer of in vivo fertilised donated ova to five infertile women: report of two pregnancies", announcing the First Two Ongoing Pregnancies, reprinted from The Lancet, Jul. 23, 1983, p. 223-224.
Buster, J.E., et al. Clinical Articles: Third Birth, "Biologic and morphologic development of donated human ova recovered by nonsurgical uterine lavage," Torrance, California, reprinted from American Journal of Obstetrics and Gynecology, St. Louis, vol. 153, No. 2, pp. 211-217, Sep. 15, 1985.
Buster, John E. and Sandra A. Carson, "Genetic Diacnosis of the Preimplantation Embryo", American Journal of Medical Genetics 34:211-216 (1989) (8 pages).
Buster, John E., "Embryo Donation by Uterine Flushing and Embryo Transfer", Clinics in Obstetrics and Gynaecology, vol. 12, No. 4, Dec. 1985, pp. 815-824 (10 pages).
Buster, John E., "The First Live", SRM vol. 6 No. 4, Nov. 2008, pp. 22-28 (7 pages).
Bustillo, M., et al, "Nonsurgical Ovum transfer as a treatment for intractable infertility: What effectiveness can we realistically expect?" Jun. 15, 1984, American Journal of Obstetrics and Gynecology, pp. 371-375.
Bustillo, Maria, MD, et al., "Nonsurgical Ovum Transfer as a Treatment in Infertile Women: Preliminary Experience", Jama: The Journal of the American Medical Association, Mar. 2, 1984, vol. 251, No. 9, pp. 1171-1173 (3 pages).
Carson, Sandra, A., "Superovulation Fails to increase Human Blastocyst Yield After Uterine Lavage", Prenatal Diagnosis, vol. 11, 513-522 (1991) (10 pages).
Croxatto, HB, et al., "Studies on the duration of egg transport by the human ovlduct. II. Ovum location at various intervals following luteinizing hormone peak", American Journal of Obstetrics and Gynecology, Nov. 15, 1978:132(6);629-34, retrieved from http://www.ncbi.nlm.gov/pubmed/71746 on Nov. 20, 2011 (1 page).
Croxotto, HB, et al., "Attemps to Modify Ovum Transport in Women", J. Reprod Fertil. Jan. 1979:55 (1):231-237.
Diaz, S., et al., "Studies on the duration of ovum transport by the human oviduct. III. Time interval between the luteinizing hormone peak and recovery of ova by transcervical flushing of the uterus in normal women," American Journal of Obstetrics and Gynecology, May 1, 1980; 13791):116-21., retrieved from http://www.ncbi.nim.nih.gov/pubmed/7389274 on Nov. 20, 2011 (1 page).
Formigli, L., et al., "Non-Surgical Flushing of the Uterus for Pre-Embryo Recovery: Possible Clinical Applications", Centre for Reproductive Medicine and CECOS—Milan, Viale Umbria, 44, 20135 Milano, Italy, Human Reproduction vol. 5, No. 3, pp. 329-335, 1990 (7 pages).
Sauer, Mark V., et al., "An Instrument for the Recovery of Preimplantation Uterine Ova", Obstetrics & Gynecology, 0029-7844/88, vol. 71, No. 5, May 1988, pp. 804-806 (3 pages).
Sauer, Mark V., et al., "Pregnancy following nonsurgical donor transfer to a functionally agonadal woman", Fertility and Sterility, The American Fertility Society, vol. 48, No. 2, Aug. 1987 (2 pages).
Sauer, MV, et al., "In-vivo blastocyst production and ovum yield among fertile women", Human Reproduction, Nov. 1987: 2(8):701-3, PubMed, Department of Obstetrics and Gynecology, Harbor—UCLA Medical Center, Torrance, PMID: 3437049, http://www.ncbi.nlm.nih.gov/pubmed?term=sauer . . . Retrieved from internet on Oct. 21, 2011 (1 page).
Seidel, George E. Jr., "Superovulation and Embryo Transfer in Cattle", downloaded from www.sciencemag.org on Nov. 18, 2011, Science, vol. 211, Jan. 23, 1981, pp. 351-358 (8 pages).
The New York Times, "Screening Embryos for Future Disease," copyright 2003, retrieved from the Internet from website: http://www.nytimes.com/imagespages/2006/09/02/health/20060903_GENE_GRAPHIC.html, 1 page.
Wade, Nicholas, "Treatment for Blood Disease is Gene Therapy Landmark," The New York Times, Hemophilia B Gene Therapy Breakthrough—NYTimes.com, Dec. 10, 2011, 3 pages.
Offce Action for U.S. Appl. No. 14/132,235, dated Mar. 31, 2014, 20 pages.
Office Action for U.S. Appl. No. 14/132,235, dated Nov. 24, 2014.
Office Action for U.S. Appl. No. 13/924,470, dated Jan. 14, 2015.
Office Action for U.S. Appl. No. 13/924,520, dated Feb. 17, 2015.
Office Action for U.S. Appl. No. 14/250,240, dated Feb. 11, 2015.
Lainas, T.G., et al., "Management of Severe Early Ovarian Hyperstimulation Syndrome by Re-Initiation of GnRH Antagonist," RBM Online, vol. 15, No. 4, 2007, 408-412, Reproductive BioMedicine Online; www.rbmobline.com/Article/2880 on web Aug. 20, 2007.
Lainas, T.G., et al., "Management of Severe OHSS and GnRH Antagonist and Blastocyst Cryopreservation in PCOS Patients Treated with Long Protocol," RBM Online, vol. 18, No. 1, 2009, 16-20, Reproductive BioMedicine Online; www.rbmonline.com/Article/3470 on web Nov. 5, 2008.
Lainas, T.G., et al., "Live Births after Management of Severe OHSS using GnRH Antagonist Administration in the Luteal Phase," RBM Online, vol. 19, No. 6, 2009, 789-795, Reproductive BioMedicine Online; www.rbmonline.com/Article/4166 on web Oct. 3, 2009.
Lainas, T.G., et al., "Outpatient Management of Severe Early OHSS by Administration of GnRH Antagonist in the Luteal Phase: An Observational Cohort Study," Reproductive Biology and Endocrinology, 2012, 10:69; http://www.rbej.com/10/1/69.
Office Action for U.S. Appl. No. 13/335,170, dated Mar. 10, 2015.
International Search Report and Written Opinion for International Application No. PCT/US14/43664, dated Mar. 10, 2015.
Office Action for U.S. Appl. No. 13/924,510, dated Apr. 27, 2015.
Office Action for U.S. Appl. No. 13/924,494, dated Apr. 28, 2015.
Office Action for U.S. Appl. No. 14/642,437, dated Apr. 24, 2017.
Communication Pursuant to Article 94(3) EPC issued in European Application No. 15 191 684.8 dated Sep. 20, 2017.
Notification of the Third Office Action for Chinese Application No. 201280068943.7 dated Apr. 19, 2017.
Extended European Search Report for European Application No. 15191684.8, dated Apr. 29, 2016.

(56) References Cited

OTHER PUBLICATIONS

"Cetrotide™ (Cetrorelix Acetate for Injection) 0.25 MG and 3 MG for Subcutaneous Use Only," European Journal of Obstetrics & Gynecology and Reproductive Biology, Elsevier Ireland Ltd., Nov. 8, 2000.
Ilan Tur-Kaspa et al., "GnRH Antagonist, Cetrorelix, for Pituitary Suppression in Modern, Patient-Friendly Assisted Reproduductive Technology," Expert Opinion on Drug Metabolism & Toxicology, vol. 5, No. 10, Sep. 17, 2009, pp. 1323-1336.
Kulier, R., et al., "Medical Methods for First Trimester Abortion," Cochrane Database Syst Rev., No. 11, Nov. 2011, p. CD002855.
Office Action for U.S. Appl. No. 14/814,151, dated Mar. 21, 2016.
International Search Report and Written Opinion for International Application PCT/US16/62171, dated Mar. 16, 2017.
Office Action for U.S. Appl. No. 13/924,520, dated Jul. 1, 2015.
Office Action for U.S. Appl. No. 14/132,235, dated Jun. 26, 2015.
Partial European Search Report for European Application No. 12860540.9, dated Jul. 15, 2015.
International Search Report and Written Opinion in International Application No. PCT/US2015/019465, dated Jun. 4, 2015, 14 pages.
Office Action for U.S. Appl. No. 14/814,151, dated Sep. 30, 2015.
Office Action for U.S. Appl. No. 14/814,252, dated Sep. 22, 2015.
Office Action for U.S. Appl. No. 14/132,235, dated Nov. 6, 2015.
Office Action for U.S. Appl. No. 14/814,151, dated Dec. 10, 2015.
Notification of Third Office Action in Chinese Application No. 2012800689437 dated Apr. 19, 2017.
International Search Report and Written Opinion for International Application No. PCT/US16/62171, dated Mar. 16, 2017.
Ilan Tur-Kaspa et al., "GnRH Antagonist, Cetrorelix, for Pituitary Suppression in Modern, Patient-Friendly Assisted Reproductive Technology," Expert Opinion on Drug Metabolism & Toxicology, vol. 5, No. 10, Sep. 17, 2009, pp. 1323-1336.
Office Action for U.S. Appl. No. 14/814,184, dated Nov. 23, 2015.
Lainas, T.G., et al., "Management of Severe OHSS using GnRH Antagonist and Blastocyst Cryopreservation in PCOS Patients Treated with Long Protocol," RBM Online, vol. 18, No. 1, 2009, 15-20, Reproductive BioMedicine Online; www.rbmonline.com/Article/3470 on web Nov. 5, 2008.
Lainas, T.G., et al., "Management of Severe Early Ovarian Hyperstimulation Syndrome by Re-Initiation of GnRH Antagonist," RBM Online, vol. 15, No. 4, 2007, 408-412, Reproductive BioMedicine Online; www.rbmonline.com/Article/2880 on web Aug. 20, 2007.
Office Action for U.S. Appl. No. 14/132,235, dated Mar. 31, 2014, 20 pages.
The New York Times, "Screening Embryos for Future Disease," copyright 2006, retrieved from the Internet from website: http://www.nytimes.com/imagespages/2006/09/02/health/20060903_GENE_GRAPHIC.html, 1 page.
Diaz, S., et al., "Studies on the duration of ovum transport by the human oviduct. III. Time interval between the uteinizing hormone peak and recovery of ova by transcervical flushing of the uterus in normal women." American Journal of Obstetrics and Gynecology, May 1, 1980; 13791):116-21., retrieved from http://www.ncbi.nim.nih.gov/pubmed/7369274 on Nov. 20, 2011 (1 page).
Croxotto, HB, et al., "Attempts to Modify Ovum Transport in Women", J. Reprod Fertil. Jan. 1979:55 (1):231-237.
Croxatto, HB, et al., "Studies on the duration of egg transport by the human oviduct. II. Ovum location at various intervals following luteinizing hormone peak", American Journal of Obstetrics and Gynecology, Nov. 1978, 15:132(6);629-34, retrieved from http://www.ncbi.nlm.gov/pubmed/71746 on Nov. 20, 2011 (1 page).
Buster, John E. and Sandra A. Carson, "Genetic Diagnosis of the Preimplantation Embryo", American Journal of Medical Genetics 34:211-216 (1989) (6 pages).

* cited by examiner

RECOVERY AND PROCESSING OF HUMAN EMBRYOS FORMED IN VIVO

CROSS-REFERENCE TO RELATED APPLICATION

The present application is a continuation of U.S. patent application Ser. No. 14/814,252, filed Jul. 30, 2015, now allowed, and a continuation of U.S. patent application Ser. No. 14/814,184, filed Jul. 30, 2015, now allowed, both which are continuations of U.S. patent application Ser. No. 14/642,437, filed Mar. 9, 2015. U.S. patent application Ser. Nos. 14/814,252 and 14/814,184 are also continuations-in-part of U.S. patent application Ser. No. 13/924,520, filed Jun. 21, 2013, now U.S. Pat. No. 9,216,037 and continuations-in-part of U.S. patent application Ser. No. 13/335,170, filed Dec. 22, 2011, now U.S. Pat. No. 9,282,995. The contents of the prior applications are incorporated herein by reference in their entirety.

BACKGROUND

Uterine lavage for recovery of human embryos was developed and reported in human subjects by the applicant three decades ago. A University of California Los Angeles team, directed by the applicant, recovered and transferred in vivo fertilized embryos from fertile to infertile recipient women. This technique produced donor-to-recipient transplanted human pregnancies, reported in 1983 and delivered in 1984.

SUMMARY

In general, in an aspect, at a time when a woman's uterus contains in vivo fertilized preimplantation embryos, a seal is provided, between the uterus and the external environment, against flow of fluid from the uterus to the external environment. While the seal is provided, fluid is delivered past the seal and into the uterus. The delivered fluid is withdrawn, with the embryos, past the seal and from the uterus to the external environment.

Implementations may include one or more of the following features. The recovered in vivo pre-implantation embryos are recovered for genetic diagnosis or genetic therapy or sex determination or any combination of two or more of them. One or more of the embryos are returned to the uterus of the woman. The one or more embryos are returned to the uterus of the woman without having frozen the embryos. The embryos resulted from artificial insemination. The embryos resulted from causing superovulation in the woman. The superovulation is caused in the woman.

The artificial insemination is caused in the woman. At least one of the pre-implantation embryos is treated. The treating includes gene therapy. The in vivo fertilized preimplantation embryos are withdrawn from the uterus with an efficiency of greater than 50%. The in vivo fertilized pre-implantation embryos are withdrawn from the uterus with an efficiency of greater than 80%. The in vivo fertilized pre-implantation embryos are withdrawn from the uterus with an efficiency of greater than 90%. The in vivo fertilized pre-implantation embryos are withdrawn from the uterus with an efficiency of greater than 95%. The embryos are frozen. The delivering or withdrawing or both of the fluid is pulsatile. The fluid is withdrawn while the seal is being provided. The seal enables essentially all of the fluid to be withdrawn. The withdrawing of fluid includes aspirating the fluid from the uterus. Both the delivering and the withdrawing are pulsatile and the pulses of the delivering of the fluid and of the withdrawing of the fluid are coordinated.

In one embodiment, a kit having instructions for use for performing uterine lavage in a female patient is disclosed which comprises a uterine lavage catheter configured for insertion into a woman's uterus to remove blastocysts from the uterus; and at least a first container comprising a GnRH antagonist. The GnRH antagonist may be provided in a sufficient dosage amount to prevent premature ovulation while stimulating the ovaries with FSH and/or LH, and/or an additional, separate container of GnRH antagonist may be provided comprising a sufficient dosage amount of a GnRH antagonist to cause corpus luteum apoptosis leading to desynchronization of the endometrium following superovulation and prior to, during and/or following recovery of viable blastocysts from the uterus.

Another embodiment of a kit for uterine lavage comprises a uterine lavage catheter configured for insertion into a woman's uterus to remove blastocysts from the uterus; one or more first containers comprising a sufficient dosage amount of FSH and/or LH appropriate for induction of superovulation in a woman; and one or more second containers comprising a sufficient dosage amount of a GnRH antagonist to cause corpus luteum apoptosis leading to desynchronization of the endometrium following superovulation. The kit may include instructions for use for administering the FSH and/or LH by self-injection, in which the dosage amount of FSH and/or LH is appropriate for induction of superovulation, in vivo fertilization, and embryonic maturation. For example, the kit may include instructions for use for self-injecting the FSH and/or LH using 5 to 20 daily injections at ranges of 12.5 to 1200 mIU per day. The FSH and/or LH may comprise at least one of at least one of injectable menotropins containing both FSH and LH; uro-follitropins containing purified FSH; recombinant pure FSH; or single doses of recombinant long acting pure FSH.

The kit may also comprise one or more additional containers comprising a sufficient dosage amount of GnRH antagonists to prevent premature ovulation while stimulating the ovaries with FSH and/or LH. The GnRH antagonists may comprise receptor blocker peptides, such as at least one of CETROTIDE 0.25 to 3 mg, GANIRELIX, ABARELIX, CETRORELIX, DEGARELIX, or ELAGOLIX. The kit may further comprise one ore more additional containers comprising a sufficient dosage amount of GnRH agonist to prevent premature ovulation while stimulating the ovaries with FSH and/or LH, and/or including instructions for use for administering a single or multiple doses of GnRH agonist subcutaneously or nasally to trigger superovulation. The GnRH agonist for superovulation may comprise, for example, at least one of Leuprorelin, Leuprolide acetate, nafarelin, or naferilin acetate snuff, or Buserelin. The kit may further include instructions for use for administering a single or multiple doses of urinary or recombinant hCG or LH surrogate nasally, orally, subcutaneously, intramuscularly, transdermally, vaginally, rectally, or buccally to trigger ovulation. The kit may further include one or more additional containers with a sufficient dosage amount of hCG or LH surrogate to cause superovulation. The hCG or LH surrogate for superovulation may be, for example, at least one of PREGNYL, NOVAREL or OVIDREL In another embodiment of a kit for uterine lavage, a kit is disclosed which comprises a uterine lavage catheter configured for insertion into a woman's uterus to remove blastocysts from the uterus; one or more first containers comprising a sufficient dosage amount of FSH and/or LH appropriate for induction of superovulation; one or more second containers comprising a sufficient dosage amount of a GnRH antagonist to prevent premature ovulation while stimulating the ovaries with FSH and/or LH; and one or more third containers comprising a GnRH antagonist to be administered after superovulation.

In another embodiment of the invention, a kit is disclosed which comprises a uterine lavage catheter configured for insertion into a woman's uterus to remove blastocysts from the uterus; one or more first containers for storing one or more of a biopsied trophectoderm cells or inner cell mass recovered from the one or more blastocysts following a biopsy procedure to remove the one or more biopsied cells from the recovered blastocysts; and one or more second containers for storing and cryopreserving the one or more of the recovered blastocysts following the biopsy procedure, wherein the one or more first and second containers each comprise one or more labels for identifying the one or more biopsied cells and the blastocyst from which the one or more biopsied cells was removed. The kit may further comprise one or more third containers comprising a sufficient dosage amount of a GnRH antagonist to cause corpus luteum apoptosis leading to desynchronization of the endometrium of the patient prior to, during and/or following recovery of blastocysts from the uterus. Both of the one or more second and third containers preferably comprises an electronic or other coding label including the biopsied cell and blastocyst identification information. The one or more second containers may comprise, for example, one or more vials for storing and cryopreserving one or more of the recovered blastocysts following the biopsy procedure.

The kit may further comprise instructions for use for performing at least one molecular diagnostic assay test on one or more of the recovered blastocysts following recovery of same from the uterus. The kit may comprise at least one instrument or agent for performing a biopsy procedure to remove biopsied cells, e.g., trophectoderm cells or targeted inner cell mass, from the one or more recovered blastocysts. For example, the instrument may comprise a holding tool to stabilize one or more of the recovered blastocysts during the biopsy procedure. The instrument may also comprise a control kit to ensure there is no contamination in the biopsied cells. The kit may further comprise a micropipette for performing the biopsy and removing the cells from the blastocysts. The kit can include instructions for use for processing and handling (e.g., cryopreserving) the biopsied cells.

With respect to the molecular genetic testing, the kit may comprise one or more reagents comprising nucleotide sequences capable of hybridizing with known chromosonal abnormalities, e.g., that may be found in the biopsied cells. The kit may further comprise a microarray and/or a gene chip which is configured to hybridize with such chromosomal abnormalities, single gene mutations, corresponding normal sequences and/or sequences neighboring the chromosomal abnormalities. The instructions for performing at least one molecular diagnostic assay test may comprise instructions for molecular testing for a variety of known genetic disorders such as Down syndrome, and the kit may comprise instructions for use for therapeutic embryonic intervention using selective replacement or gene therapy with specific corrective genetic constructs, specific non-genetic constructs, or stem cell/embryonic cell transplants following the at least one molecular diagnostic assay test. The kit may also include instructions for use for inserting the therapeutically treated embryo into the woman's uterus following embryonic intervention.

The kits noted above and herein may additionally comprise additional compound containers including, for example, progesterone and estradiol, respectively. The progesterone may be at least one of vaginal progesterone or oral progesterone. The estradiol may be at least one of oral or transdermal estradiol, e.g., the estradiol may be transdermal estradiol patches 400 ug per day or oral estradiol 4.0 mg per day.

Other possible components of the kit include a controller for controlling the pressure and vacuum applied to the uterine lavage catheter, catheter introducers, a pump and/or vacuum system and/or tubes, a cell culture vial for containing the blastocysts following recovery and which maintains optimal CO2/O2 concentration for blastocyst culture without the requirement of an incubator, or other cell-culture devices. The kit may be in packaged combination, such as in a pouch, bag or the like. The kit may further include instructions for the use of components of the kit in a uterine lavage procedure, such as instructions for use of the compounds to induce superovulation, prevent premature ovulation while stimulating the ovaries with FSH and/or LH, and/or cause corpus luteum apoptosis leading to desynchronization of the endometrium of a patient undergoing a uterine lavage procedure.

In another aspect of the invention, a composition suitable for administration to a human female patient during superovulation is disclosed. The composition may include a GnRH antagonist in an amount sufficient to prevent premature ovulation while stimulating the ovaries with FSH and/or LH. The composition may be, for example a GnRH antagonist in a pharmaceutically acceptable solution at a dosage amount of about 0.10 to 400 mg, e.g., about 0.5 to 400 mg, e.g., about 0.25 to 10.0 mg. e.g., at a dosage amount of between about 0.5 to 10.0 mg, e.g., about 0.5 to 5.0 mg, e.g., in certain cases at a dosage amount of between 0.25 and 3.0 mg. The GnRH antagonist may include at least one of CETROTIDE, GANIRELIX, ABARELIX, CETRORELIX, DEGARELIX, or ELAGOLIX.

In another aspect of the invention, a composition suitable for administration to a human female patient following superovulation and prior to, during and/or following removal of blastocysts from the uterus is disclosed. The composition may comprise a GnRH antagonist in an amount sufficient to cause corpus lutuem apoptosis leading to desynchronization of the endometrium to reduce the chance that any embryos remain in the uterus will form a viable pregnancy following superovulation. The GnRH antagonist is in, for example, a pharmaceutically acceptable carrier at a dosage amount of about 0.10 to 400 mg, e.g., about 0.5 to 400 mg, e.g., about 0.25 to 10.0 mg, e.g., about 0.5 to 10.0 mg, and in certain cases between about 0.25 to 3.0 mg. Desynchronization may include administering GnRH antagonist before the day or on the day on which the blastocysts are recovered, and daily for up to ten days or until the onset of menses following blastocyst recovery to induce corpus luteum apoptosis, suppress luteal phase progesterone, and further decrease risk of a retained (on account of blastocysts missed by the intrauterine lavage) pregnancy. The GnRH antagonist may include at least one of CETROTIDE, GANIRELIX, ABARELIX, CETRORELIX, DEGARELIX, or ELAGOLIX, e.g., at a dosage of between about 0.5 to 10.0 mg, e.g., at a dosage amount of between about 0.5 to 5.0 mg, e.g., at a dosage amount of between 0.5 and 3.0 mg. In one embodiment, CETROTIDE at 3.0 mg is administered to cause said corpus luteum apoptosis leading to said desynchronization. The method may further comprise administering a progesterone receptor antagonist to the patient. The progesterone receptor antagonist may comprise, for example, Mifepristone at a dosage of about 600 mg. The progesterone receptor antagonist may comprise, for example, Onapristone at a dosage of between about 100 to 200 mg. The progesterone receptor antagonist may comprises Ulipristal, Org 31710 (e.g., 10 to 75 mg) or other suitable GnRH receptor blocker antagonists.

Methods are provided for administering an effective amount of the compositions (e.g., orally, nasally, intramuscularly, subcutaneously, etc.) to a patient to cause corpus luteum apoptosis leading to desynchronization. Use of this method will reduce or eliminate the possibility that unrecovered blastocysts will implant and result in unintended pregnancy. Previous uterine lavage studies were done on non-stimulated cycles, as such the risk of retained pregnancy was significantly lower.

In another embodiment, a sterile dosage form of GnRH antagonist is provided, which may be provided in a form suitable for use in a surgical procedure. The dosage form of GnRH antagonist may be in a pharmaceutically acceptable form for parenteral administration, for example to the uterus. The GnRH antagonist may be provided in a variety of pharmaceutically acceptable carriers. In one embodiment, a sterile dosage form of GnRH antagonist is provided comprising about 0.25 to 10.0 mg, e.g., about 0.5 to 5.0 mg, e.g., 0.25 to 3.0 mg of antagonist in a pharmaceutically acceptable carrier. Carriers may include aqueous solutions including saline, aqueous solutions including dextrose, water and buffered aqueous solutions, as well as oral formulations of the antagonist.

In another aspect of the invention, a uterine lavage system comprises a fluid delivery and collection device; and a controller programmed to deliver lavage liquid to the uterus to assist with the recovery of blastocysts from the uterus at a flow of fluid supply that substantially limits or prevents the flow of fluid into the fallopian tubes where blastocysts may be lost, e.g., that does not exceed a maximum pressure of the device of between about 2 ounces per square inch and 50 pounds of pressure per square inch, e.g., between about 2 ounces and 20 pounds of pressure per square inch. The controller may be programmed to control the delivery of the fluid through the fluid delivery and collection device into the uterus in a series of pulses at a pre-determined pulse rate. For example, the pulse rate may have a preset frequency in the range of one pulse per 0.5 to 4 seconds, e.g., one pulse per 1 to 3 seconds, e.g. one pulse per 2 to 3 seconds, e.g. one pulse per 3 seconds.

In another aspect, a uterine lavage system is disclosed which comprises a fluid delivery and collection device; and a controller programmed to deliver lavage liquid to the uterus from the device to assist with the recovery of blastocysts from the uterus and to apply vacuum pressure to the fluid to maintain the integrity of the blastocysts during fluid delivery and removal, e.g., between about 2 to 30 Hg of vacuum, e.g., between about 10 to 30 Hg of vacuum, e.g., between about 10 to 14 Hg of vacuum pressure. The uterine cavity is preferably not expanded or pressurized. The lavage device does not include any members that act to expand the uterine cavity; as such an expansion can introduce air into the uterine cavity, which can kill blastocysts. The lavage process is designed to prevent the introduction of air into the uterine cavity to ensure the health and integrity of the recovered blastocysts.

In another aspect, lavage fluid may be collected directly into a cell-culture system capable of maintaining blastocyst viability during shipment to the central embryological laboratory. Such a system would maintain blastocyst-safe O2/CO2 levels without the requirement of an incubator and eliminate the need to dilute lavage fluid with physiologic transport media thus streamlining the recovery and shipment of pre-implantation embryos captured through uterine lavage.

A method of uterine lavage is disclosed which comprises delivering lavage fluid to the uterus of a female patient and applying a vacuum pressure to the fluid to recover blastocysts from the uterus, wherein the flow of fluid is controlled so as not to exceed a maximum pressure of between about 2 ounces per square inch and 50 pounds of pressure per square inch, e.g., between about 2 ounces and 20 pounds of pressure per square inch to limit or prevent leakage of fluid into the fallopian tubes.

In another aspect of the invention, a uterine lavage system is disclosed which comprises a fluid delivery and collection device; and a controller programmed to both deliver lavage liquid to the uterus and apply vacuum to the fluid delivery and collection device, wherein the controller includes control logic which controls the fluid delivery and collection device so as to cause injecting a first small amount of fluid into the uterus to form a first puddle of fluid encompassing one or more blastocysts and to cause said first puddle of fluid to be suctioned into the device along with the one or more entrained blastocysts, and to inject at least one second amount of fluid into the uterus to form a second puddle which is larger than the first puddle and to suction the second puddle into the device along with one or more entrained blastocysts. The lavage cycle is started when the controller is prompted to begin the preset lavage cycle consisting pulsed fluid delivery and collection cycles. The first stage of the lavage cycle is begun by injecting a small amount of fluid into the uterine cavity to form a puddle of fluid encompassing the pre-implantation embryos. All of the fluid present in the uterine cavity is then suctioned into the system with one or more entrained pre-implantation embryos. The second stage of the lavage cycle is begun by injecting a larger amount of fluid into the uterus to form a larger puddle. All of the fluid present in the uterine cavity is then suctioned into the catheter.

The controller may be programmed to control the delivery of the fluid through the fluid delivery and collection device into the uterus in a series of pulses at a pre-determined pulse rate. For example, the pulse rate may have a preset frequency in the range of one pulse per 0.5 to 4 seconds. The controller may also be programmed to control the withdrawal of the fluid through the fluid delivery and collection device from the uterus in a series of vacuum pulses at a pre-determined pulse rate, e.g., at a vacuum pressure between about 2 to 30 Hg of vacuum, e.g., between about 10 to 30 Hg of vacuum, e.g., between about 10 to 14 Hg of vacuum pressure.

These and other aspects, features, and implementations, and others, and combinations of them, can be expressed as methods, apparatus, systems, components, program products, business methods, means or steps for performing functions, and in other ways.

These and other aspects, features, and implementations will become apparent from the following description and from the claims.

DESCRIPTION

FIGS. 1, 2, 3, 4, 7b, 9, 10, 11, 35a through 35f, 52, through 58, 63a through 63q, and 64a through 64e are sectional views of female reproductive tracts.

FIGS. 13a, 14, 36, and 37 are side views of lavage instruments.

Figure 13A:
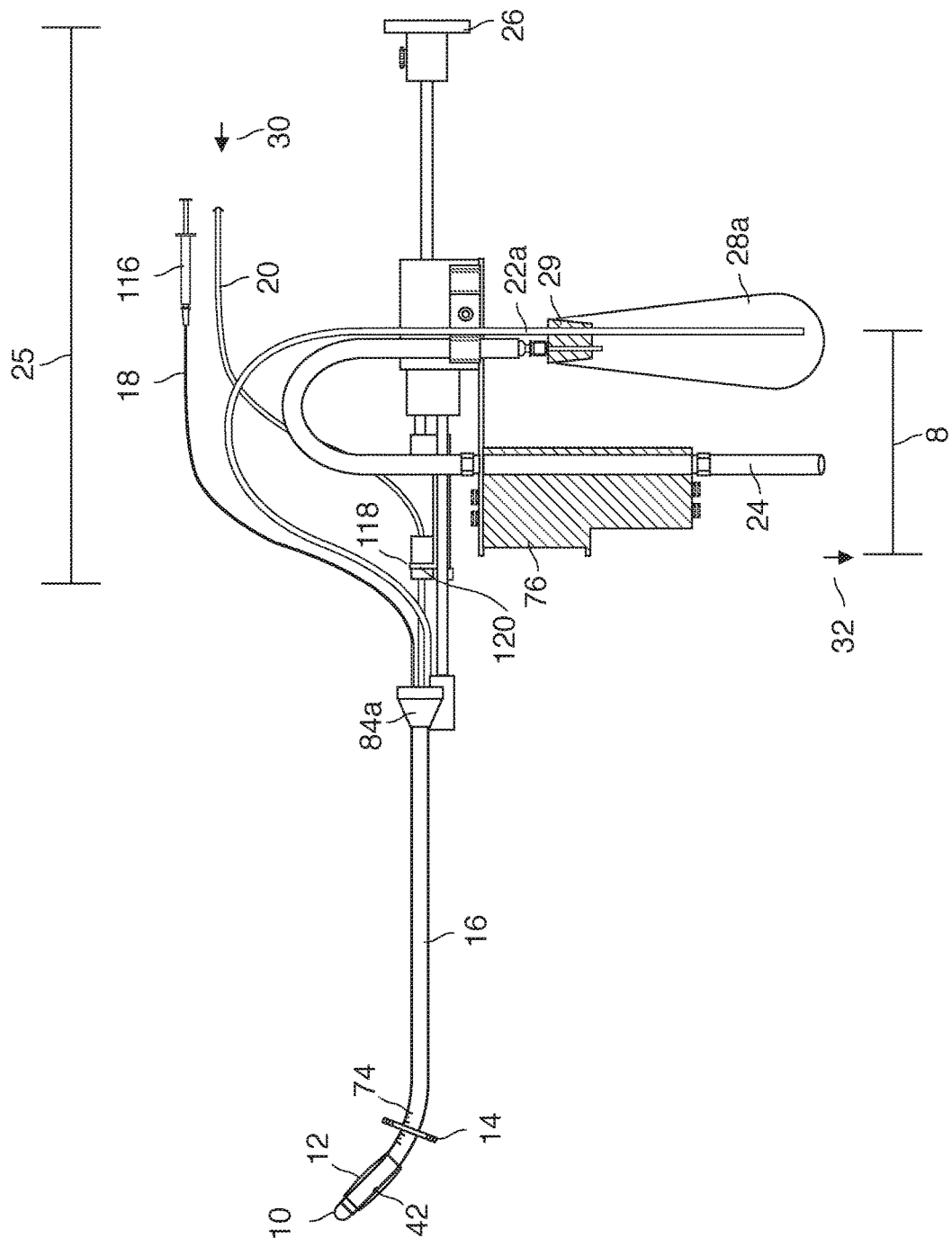
Figure 13B:
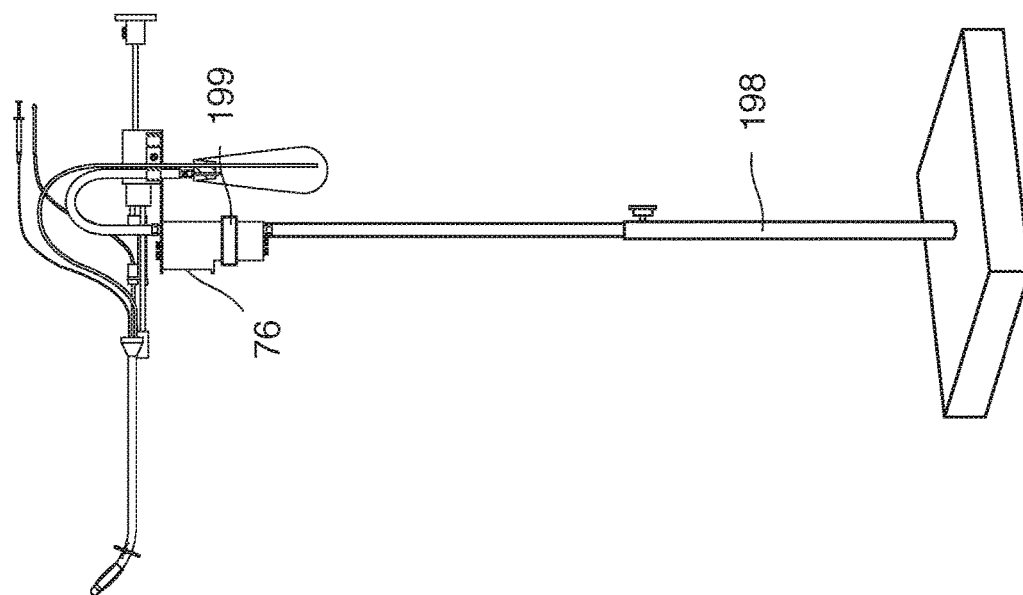

FIG. 13b is a perspective view of a lavage instrument on a stand.

FIGS. 15, 16, 38, and 39 are top views of lavage instruments.

Figure 17:
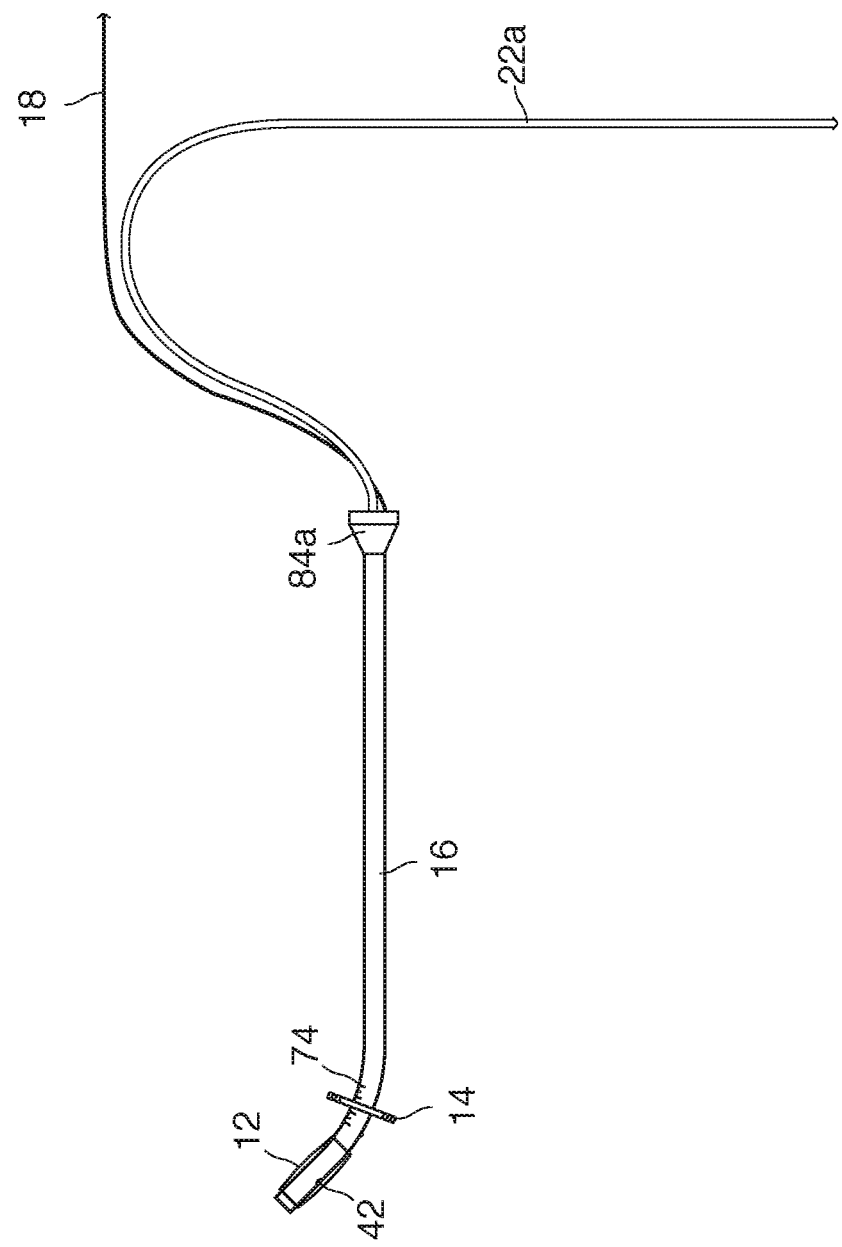

FIG. 17 is a side view of a catheter.

FIGS. 18, 19, 21, 24, 41, 42, 45, and 48 are perspective views of portions of lavage instruments.

Figure 20:
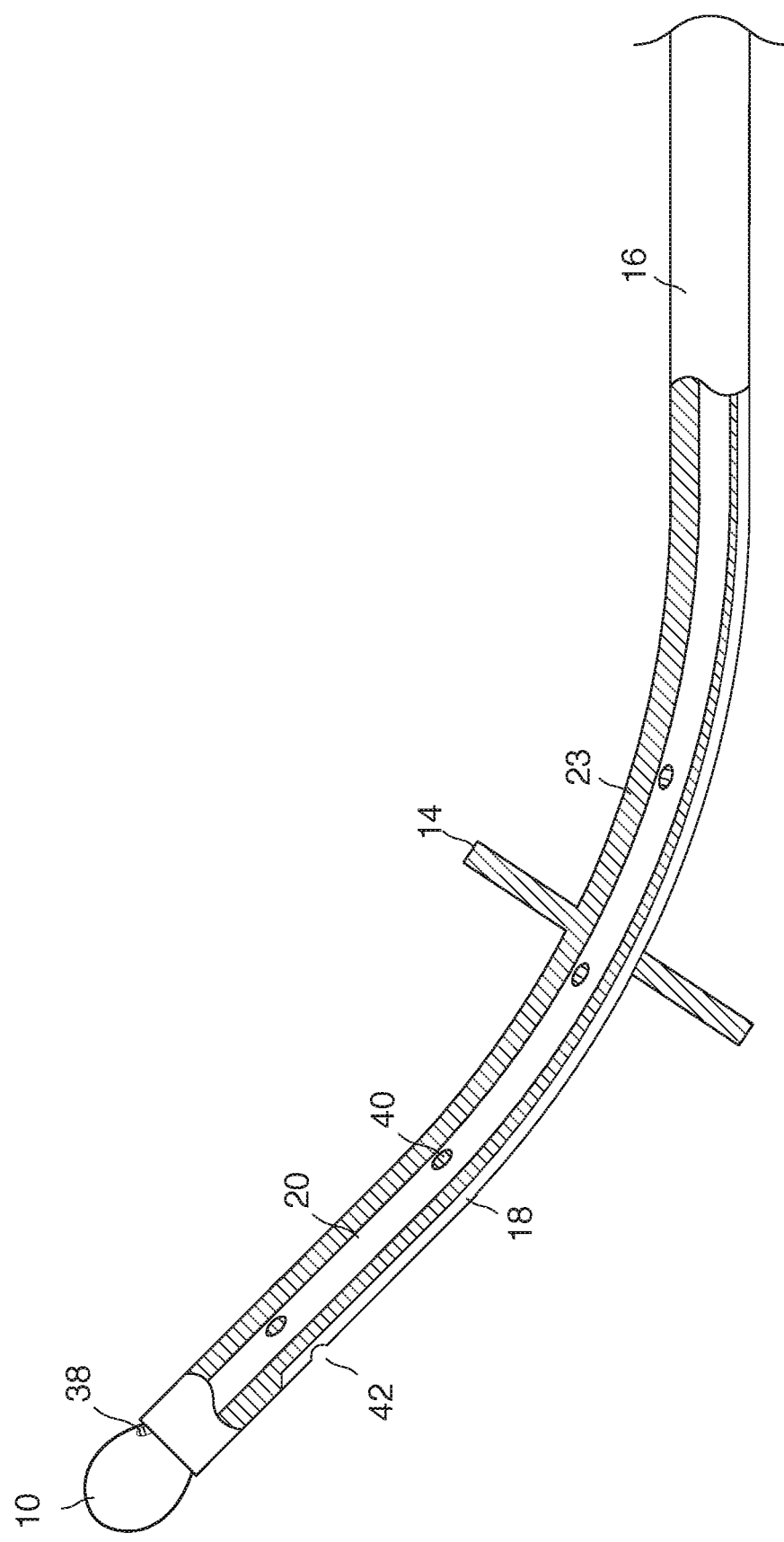

FIG. 20 is an enlarged side sectional view, partially cut away, of a catheter.

FIGS. 22, 25, 46, and 49 are cross-sectional views of catheters.

Figure 23:
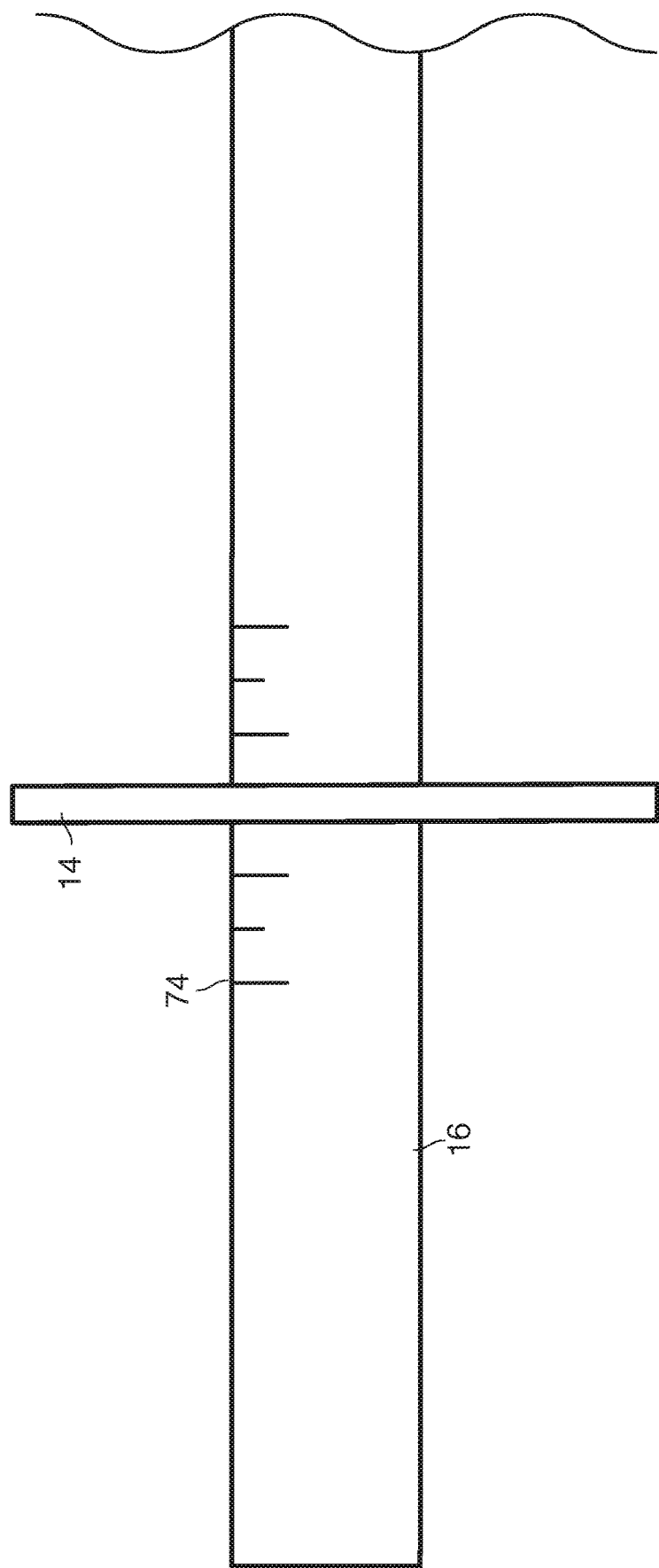
Figure 47:
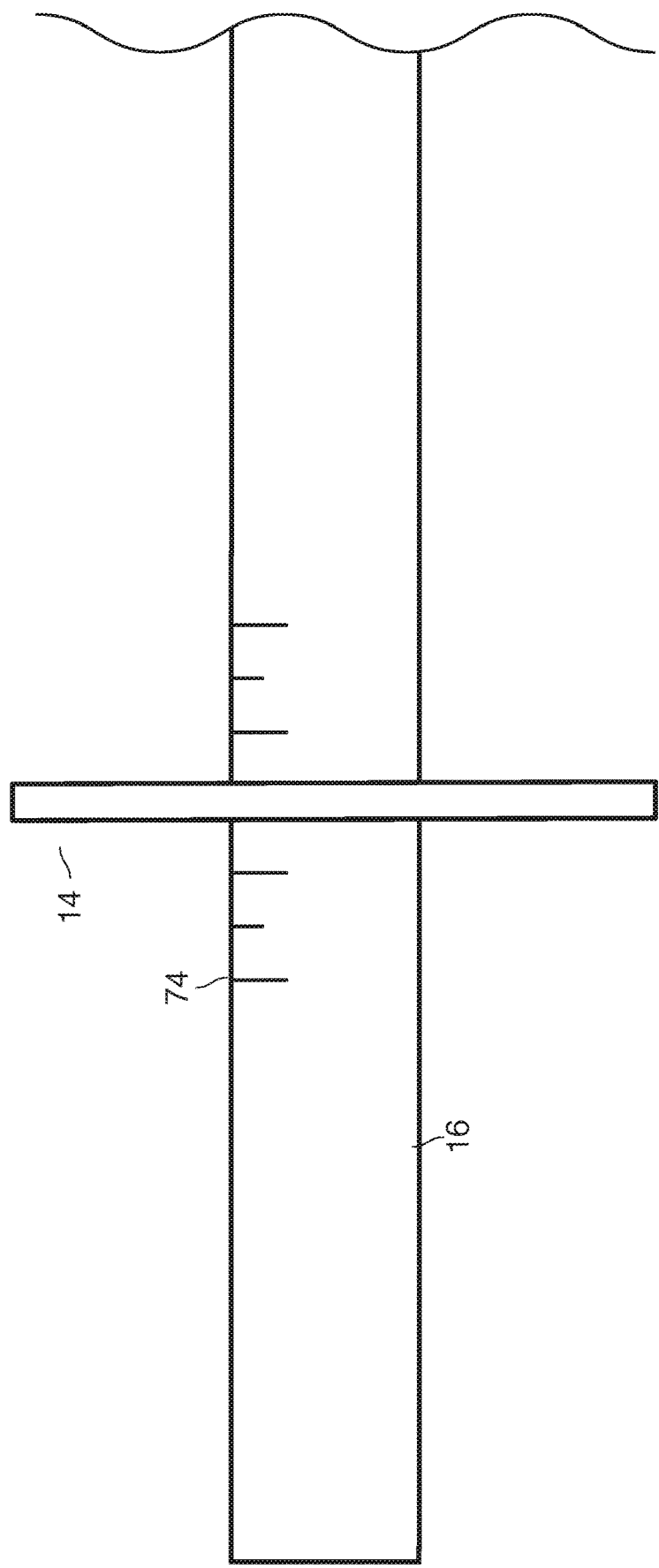

FIGS. 23 and 47 are side views of portions of lavage instruments.

FIGS. 26, 27, 28, 29, 30, 40, 50, and 51 are side views of catheters.

Figure 31:
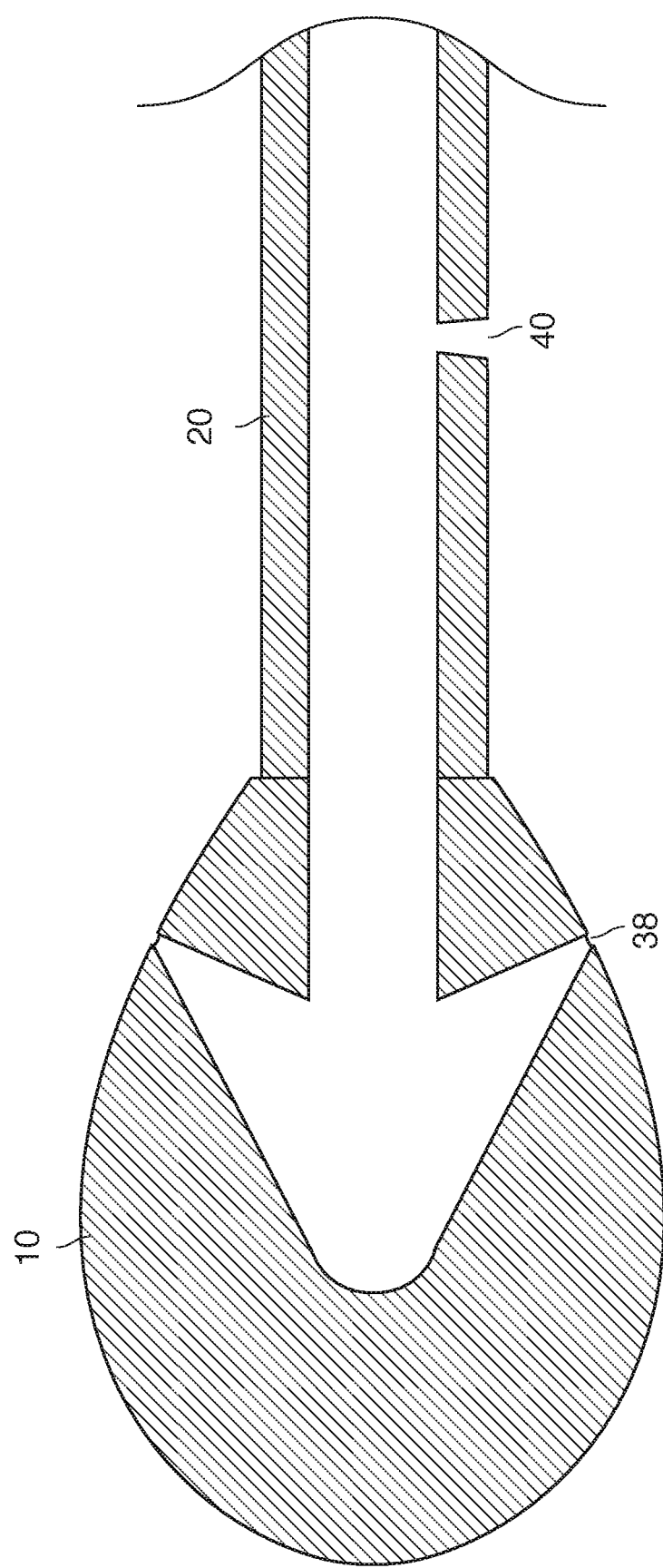

FIG. 31 is an enlarged sectional view of a tip of a catheter.

FIGS. 32, 33, 34a, 34b, 61a, 61b, 62a, and 62b are perspective views of cannula tips with balloons.

Figure 43:
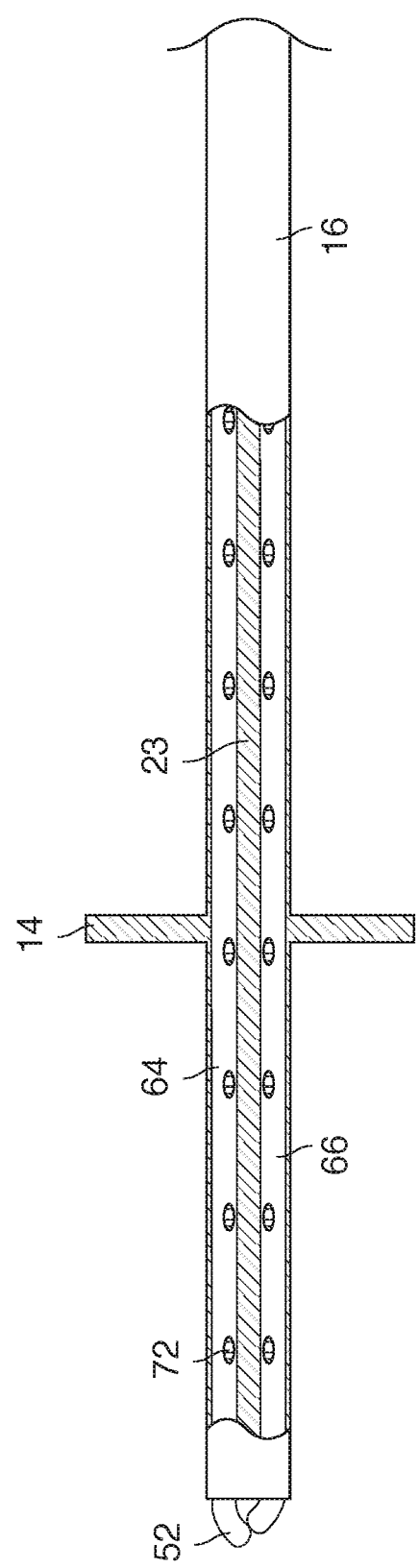
Figure 44:
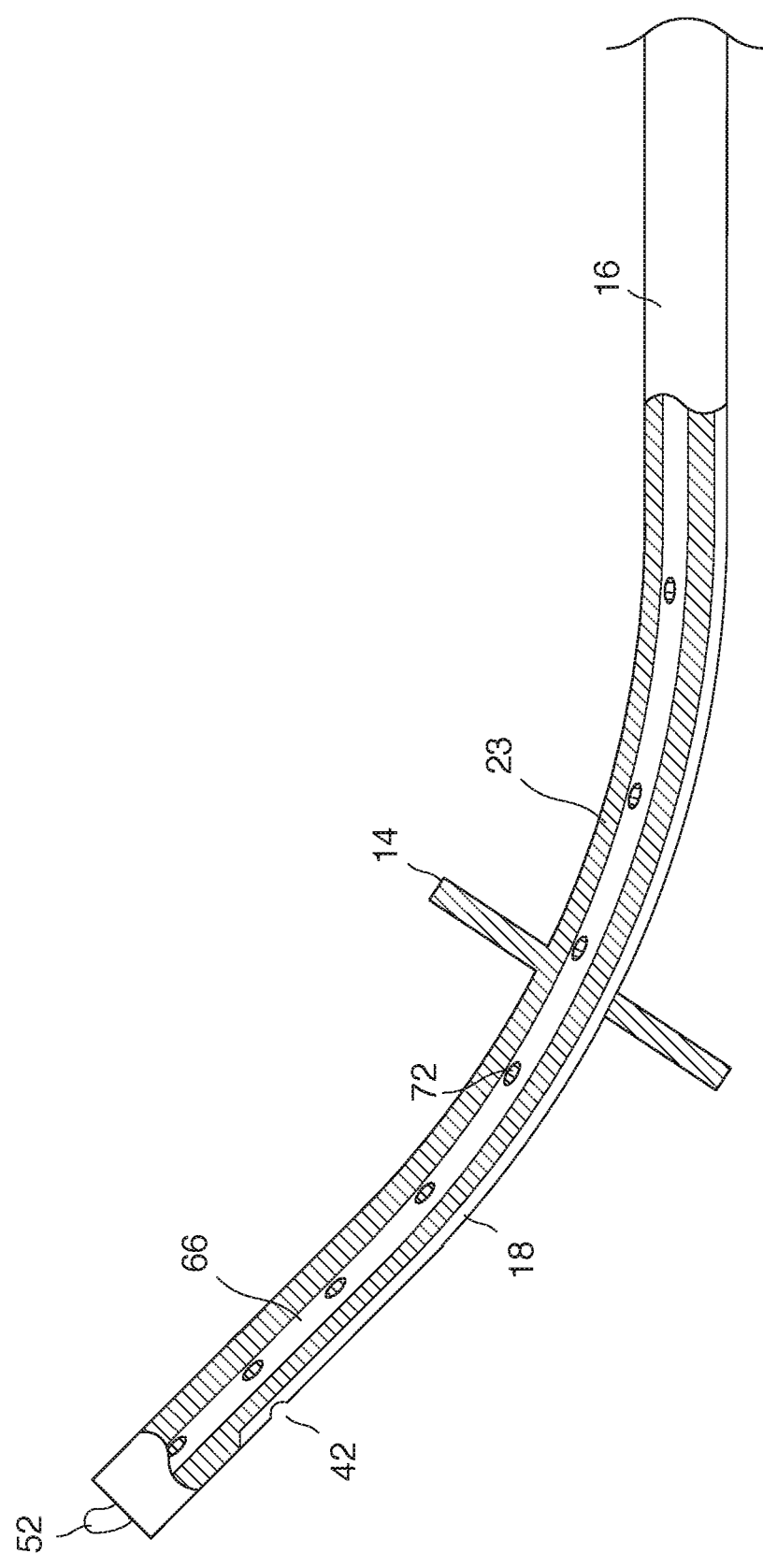

FIGS. 43 and 44 are side views of catheters partly in section.

Figure 59A:
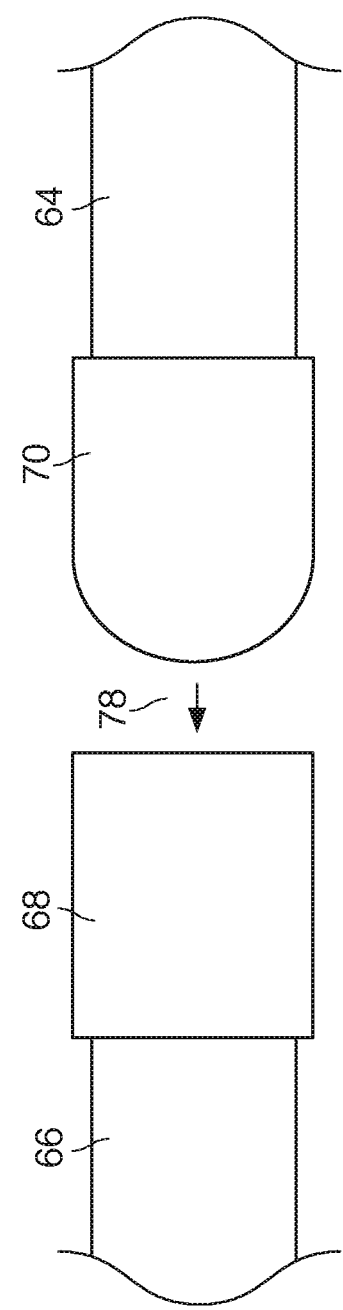
Figure 59B:
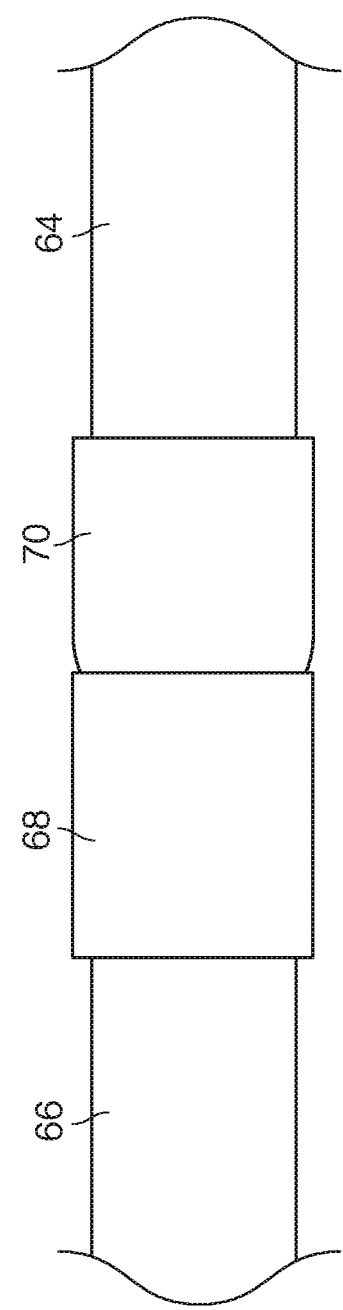

FIGS. 59a and 59b are side views of tips of catheters.

Figure 60A:
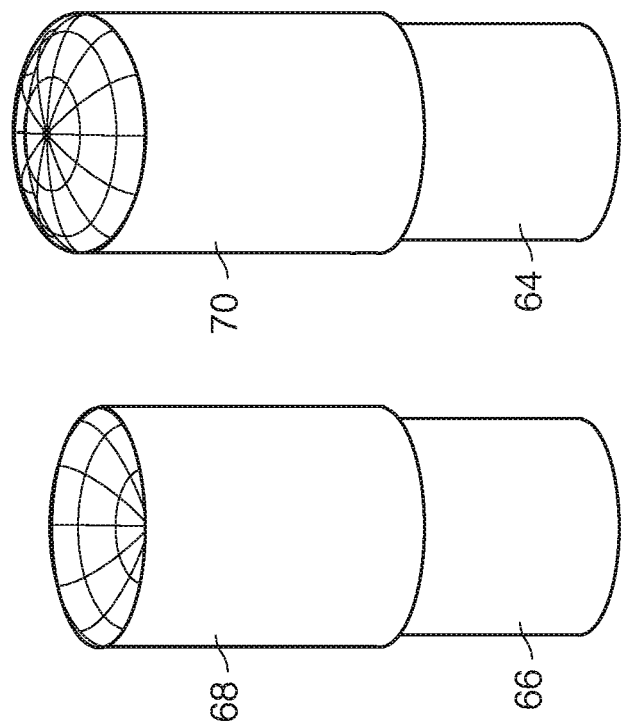

FIG. 60a is a perspective view of tips of catheters.

Figure 60B:
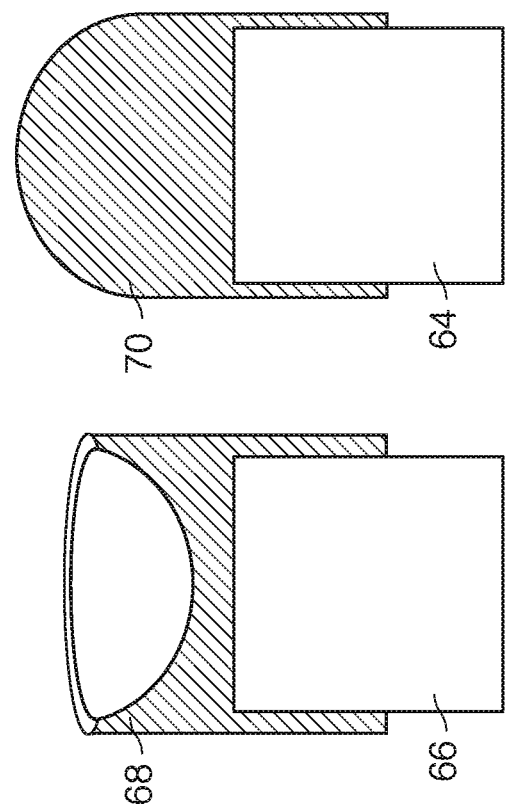

FIG. 60b is a side sectional view of tips of catheters.

Here we describe a way to achieve early (e.g., very early) diagnosis and treatment of genetic disorders in human preimplantation embryos (blastocysts) conceived in vivo and recovered from the reproductive tracts of fertile women. Important beneficiaries of what we describe here are women who, in specific unions with their male partners, are faced with parenting yet-to-be-born children at (significant) risk for childhood or adult onset genetic diseases.

Figure 1:
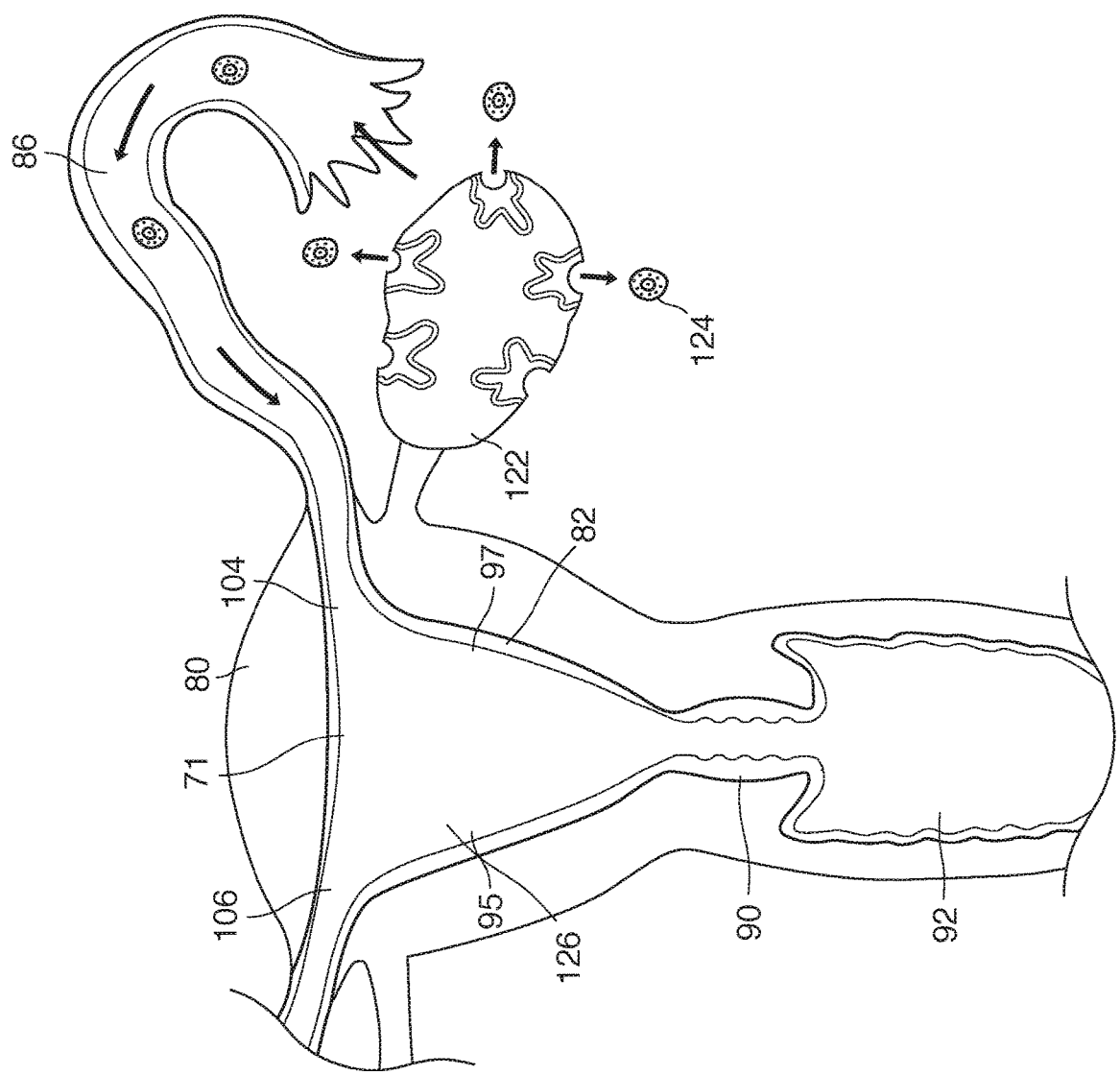
Figure 2:
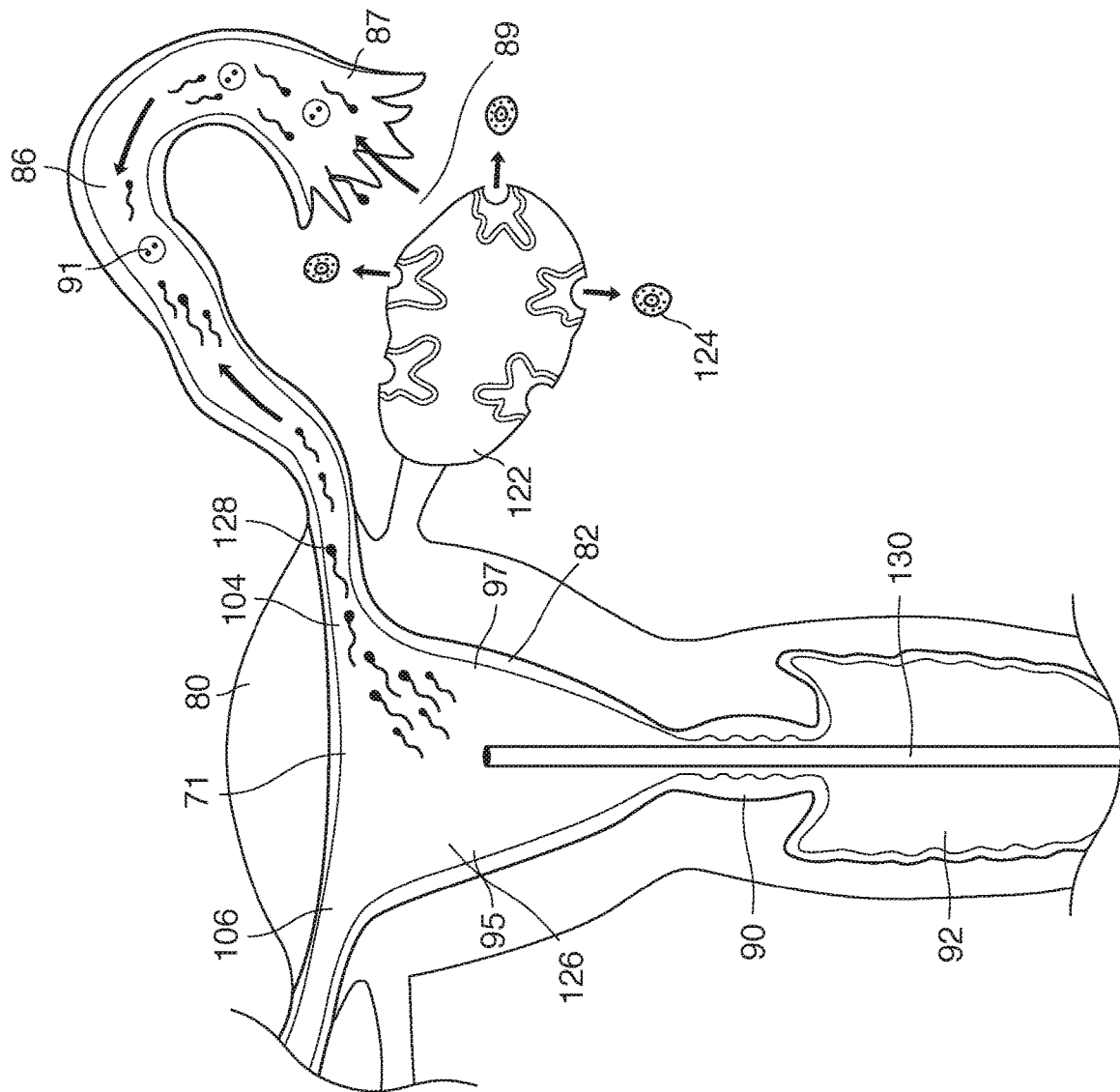
Figure 3:
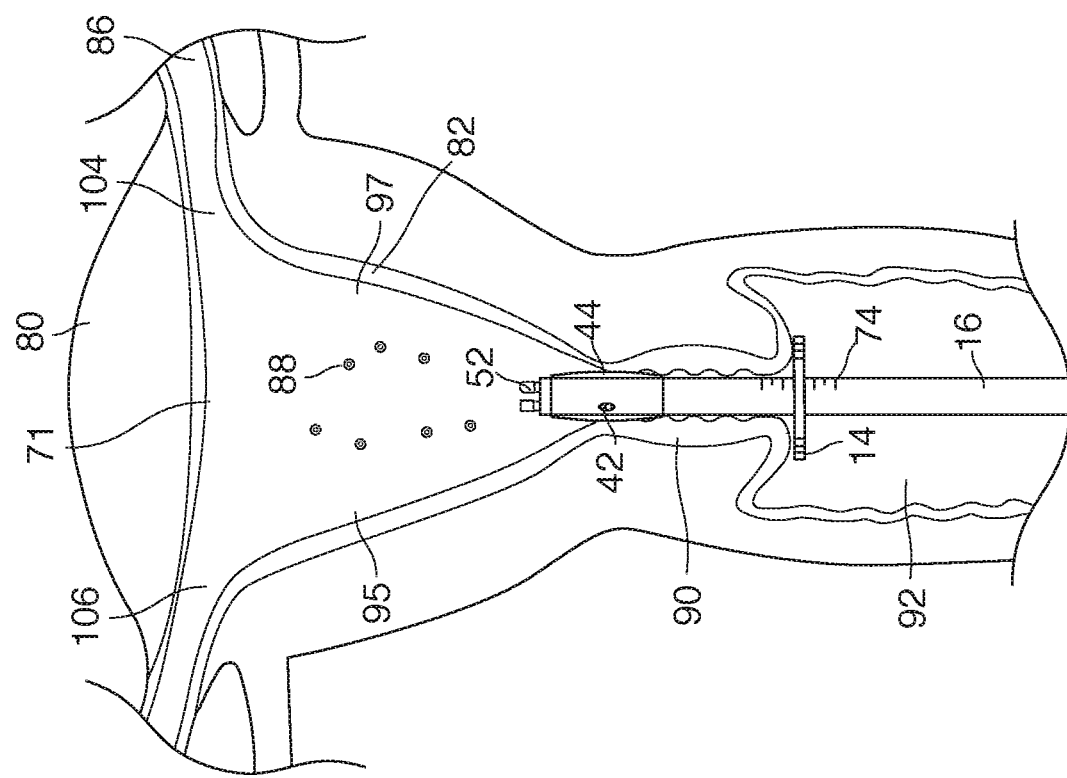
Figure 4:
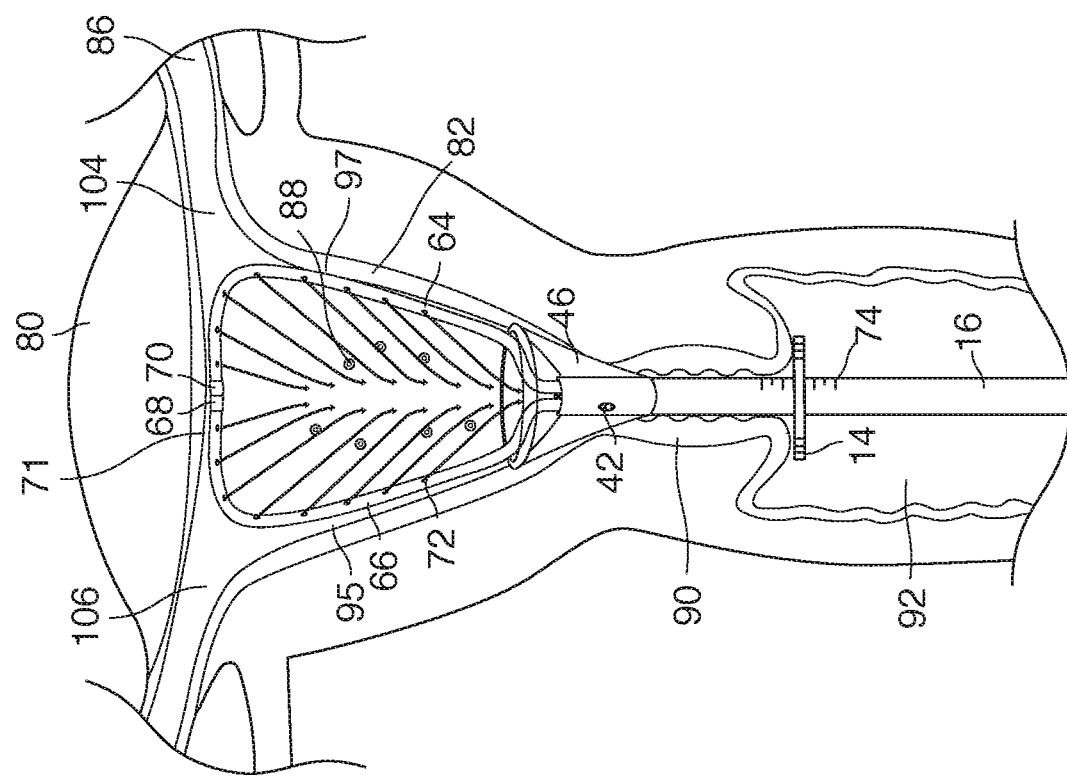
Figure 5:
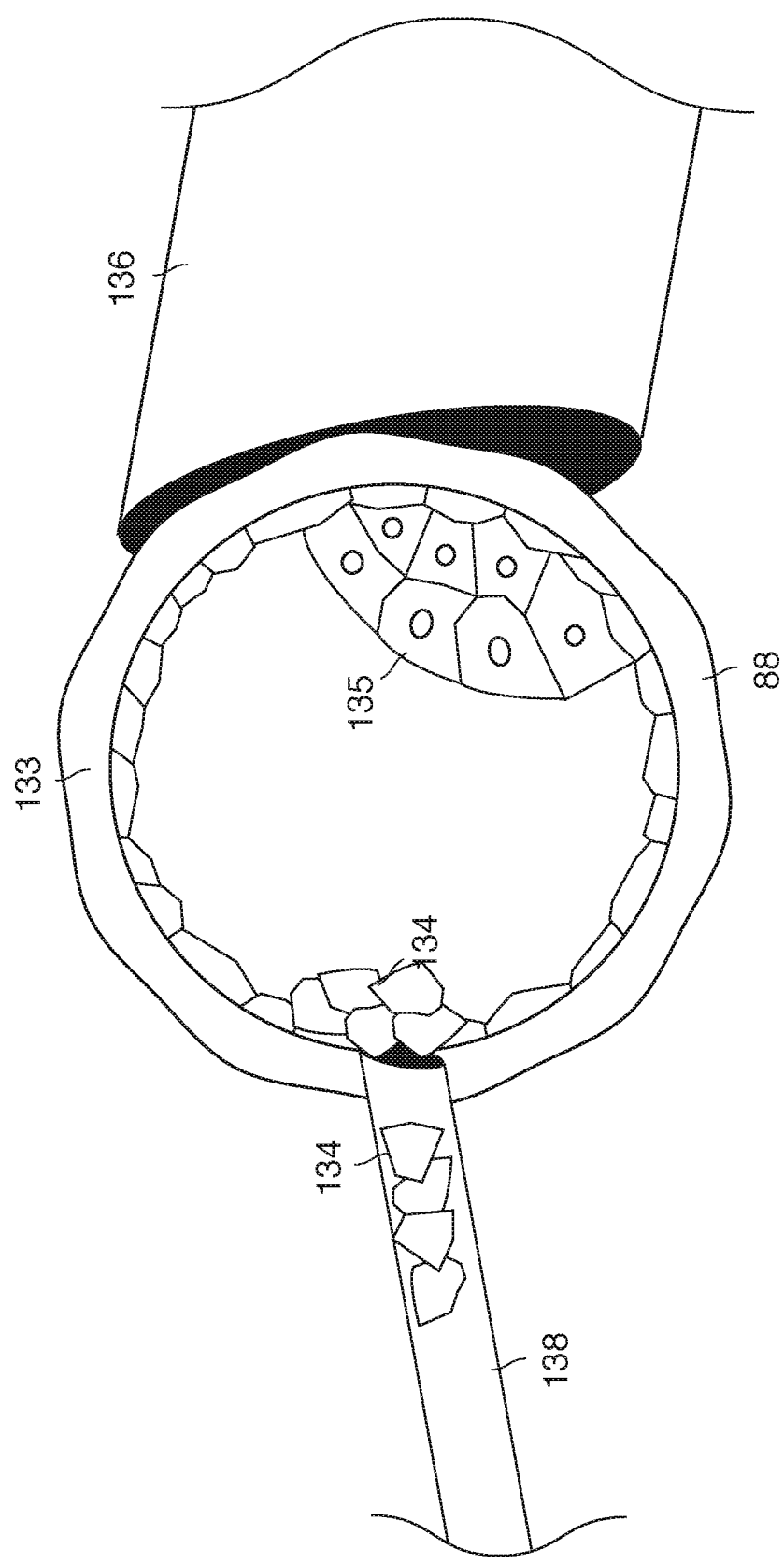
FIG. 5 is a schematic perspective view of a procedure on a blastocyst.

As shown in FIG. 1, in examples of the technique that we describe here, such an at-risk woman is induced to super-ovulate multiple oocytes 124 using fertility drugs. Super-ovulation is followed by artificial intrauterine insemination (FIG. 2) by her partner's sperm 128 and in vivo fertilization in her reproductive tract to produce preimplantation embryos (blastocysts) (FIG. 3). The blastocysts 88 (blastocysts of 5-8 days gestational age) are recovered by uterine lavage (FIGS. 3, 4). Embryonic micromanipulation with biopsy then is used to remove trophectoderm 134 (early placenta) or targeted inner cell mass (early fetal cells) from one or more of the recovered blastocysts (FIG. 5). The biopsied trophectoderm cells 134 are used, for example, for molecular diagnosis of specific genetic disorders, for example (FIG. 6) Down syndrome where there is an extra #21 chromosome, three instead of two. The diagnosis is followed by therapeutic embryonic intervention using selective replacement or gene therapy with specific corrective genetic constructs or stem cell/embryonic cell transplants. The diagnosed or treated embryos 132 are then replaced into the woman's uterine cavity 126 leading to a viable unaffected birth nine months later (FIG. 7)

An important feature of this process is uterine lavage, typically a nonsurgical office technique that allows recovery of human preimplantation embryos naturally conceived in vivo, in a woman's body.

In some examples of the approach that we describe here, uterine lavage, and ancillary devices, steps, and services related to it and built around it, provide a simple, safe, and inexpensive way to diagnose and treat human embryos before implantation (preimplantation genetic diagnosis, PGD) or to make a sex determination or both.

One known platform for performing PGD is in vitro fertilization (IVF), a treatment for infertility in clinical use for over 30 years. Exploitation of PGD by IVF has been limited since the introduction of PGD 20 years ago. PGD by uterine lavage is expected to be less expensive, less technically difficult, and more cost efficient than PGD using IVF.

PGD by uterine lavage is technically simpler than IVF because it exploits natural in vivo fertilization in the body of the patient to avoid the laboratory complexities of IVF. The efficiency of lavage (that is, the cost per recovered viable blastocysts) is not fully known; however, there are reasons to believe the efficiency of in vivo fertilization and recovery by uterine lavage will be higher than IVF in part because it can be repeated until successful. It also should cost considerably less than with IVF, because the laboratory complexities of fertilization in vitro are bypassed and uterine lavage is technically a simpler office procedure. The procedural cost to recover embryos for diagnosis is expected to be in the range of $2,500 to $5,000 per attempt. It is expected that the number of lavage attempts needed to generate a viable pregnancy, depending on the woman's age, will range between 1 and 4 lavages.

Certain of the specific steps that we describe here (FIG. 8a) have individually been the subject of previous fragmentary reports: superovulation 152, artificial insemination 154, in vivo fertilization 156, embryo recovery by uterine lavage 158, embryo biopsy 160, preimplantation diagnosis 162, preimplantation therapy when feasible 164, embryo freezing 165, embryo replacement 166, and development to birth 168.

For convenience, we briefly discuss certain terms that we use in our description.

When we use the term superovulation, as shown, for example, as element 152 in FIG. 1, we intend to refer broadly to any production and release of many (for example, three or more) mature eggs 124 in one menstrual cycle, triggered, for example, by a medication that stimulates the ovaries.

Figure 8A:
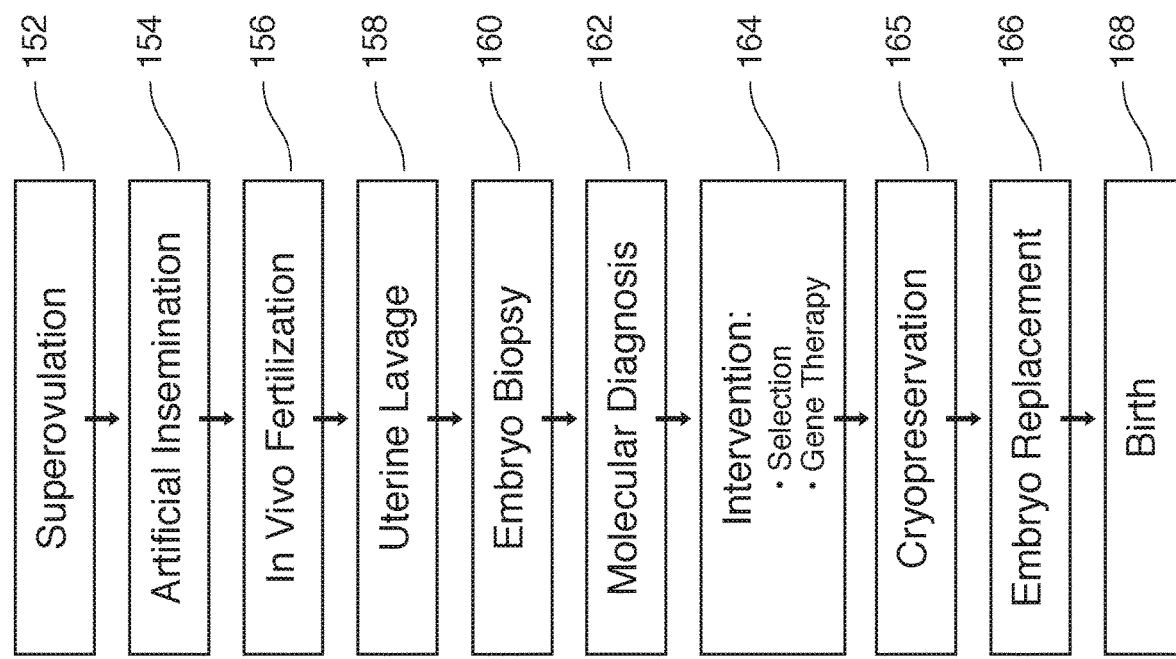
FIG. 8a is a flow chart.

When we use the term artificial insemination (AI), as shown, for example, as element 154 in FIG. 8a, we include broadly any process by which sperm 128 is placed into the reproductive tract of a woman, for the purpose of impregnating her, by other than sexual intercourse. In some examples, the artificial insemination 154 involves placing sperm, which has been processed by washing her partner's semen, into the uterine cavity 126, and is sometimes called artificial intrauterine insemination 126, 154 (IUI), for example, as shown in FIG. 2. When IUI is combined with a sequence of injectable fertility drugs, there is an expected marked increase in pregnancy rates compared to insemination by sexual intercourse and spontaneous ovulation.

We use the term in vivo fertilization broadly to include any fertilization within a woman's body, for example, the natural combination of an oocyte (egg) 124 and sperm 128 in the female reproductive tract that occurs as a result of sexual intercourse or after artificial insemination.

We use the term in vitro fertilization (IVF) to refer broadly to any fertilization that occurs outside of the woman's body, for example, when the oocyte and the sperm are combined in a laboratory dish. In some examples, the fertilized oocyte is incubated for 3 to 5 days in a chamber (incubator) that provides warmth and nutrients. After IVF, the embryo 88 may be implanted into the uterus of a woman to carry the baby to term. IVF tends to be complex, inefficient, and expensive. Typically, the oocyte is recovered in an operating room under general anesthesia and is fertilized by injecting sperm (for example, ICSI: intracytoplasmic sperm injection) in a sophisticated laboratory facility. Live birth rates for PGD done by IVF normally run between 20 to 30% per treatment cycle; these rates are improving only modestly in recent years and are not expected to improve dramatically in the foreseeable future.

We use the term blastocyst to refer broadly to, for example, any human preimplantation embryo when it is in a developmental stage, for example, a stage that is typically reached at 4-5 days after fertilization and is observable in the uterus for up to 8 days after fertilization and just prior to implantation. A human blastocyst normally consists of 100 to 300 cells and is a thin-walled embryonic structure that contains a partially differentiated cluster of cells called the inner cell mass from which the embryo arises. An outer layer of cells gives rise to the placenta and other supporting tissues needed for fetal development within the uterus, while the inner cell mass cells give rise to the tissues of the body. Located at the center of the blastocyst is a fluid-filled or gel-filled, hollow center or core called the blastocoel. The blastocoel core and the gel or fluid that comprises it comes into direct physical contact with the trophectoderm or inner cell mass cells that make up the blastocyst walls that surround that core. Human blastocysts, if removed from the woman, produce high singleton pregnancy rates when transferred back into the uterus and are considered to be at a good stage for preimplantation diagnosis, because there are many cells and a high likelihood of survival. In our discussion, the terms blastocyst and embryo are commonly used interchangeably.

When we refer to a catheter, we mean to refer broadly to, for example, any hollow tube that has any shape, form, weight, material, configuration, size, rigidity, durability, or other characteristics to be inserted into the uterus to permit fluid to pass to or from the uterus.

Figure 9:
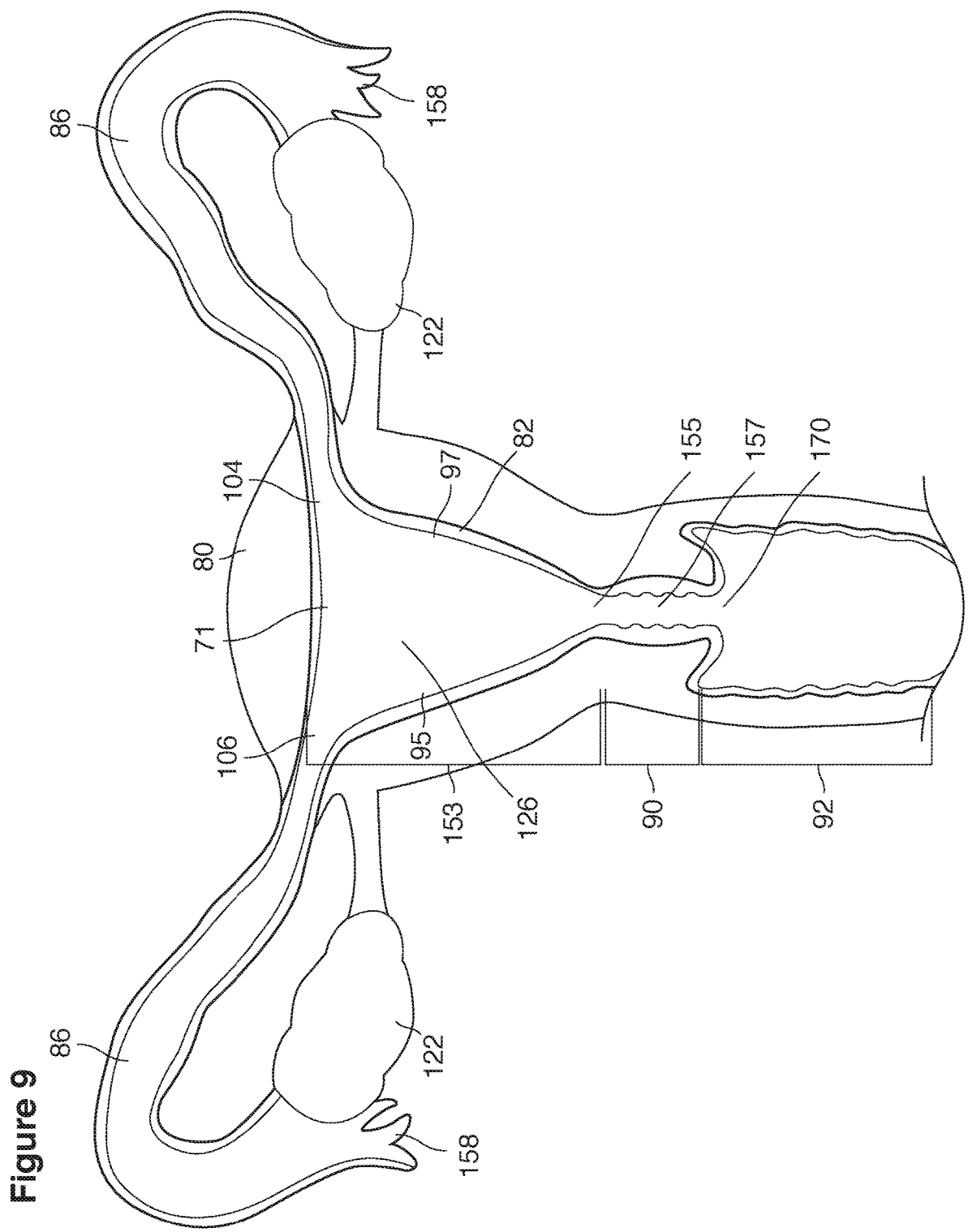

The term uterus as shown, for example, in FIG. 9 refers to a hollow, muscular, pear-shaped organ, located in a pelvis of a woman between the bladder and the rectum where pregnancy implants, grows and is carried to viability.

We use the term cervix as shown, for example, as element 90 in FIG. 9 to refer broadly to the lower, narrow segment of the uterus that embraces at its center an endocervical canal 157 connecting the uterine cavity with the vagina. The cervix typically is dilated (that is, the canal must be expanded or enlarged) to pass the instruments required for uterine lavage or for transfer of embryos back into the uterus.

We use the term fundus as shown, for example, as element 153 in FIG. 9 to refer broadly to all parts of the uterus and its cavity that are distal to the cervix and extend to and include the internal openings to the fallopian tubes.

Figure 10:
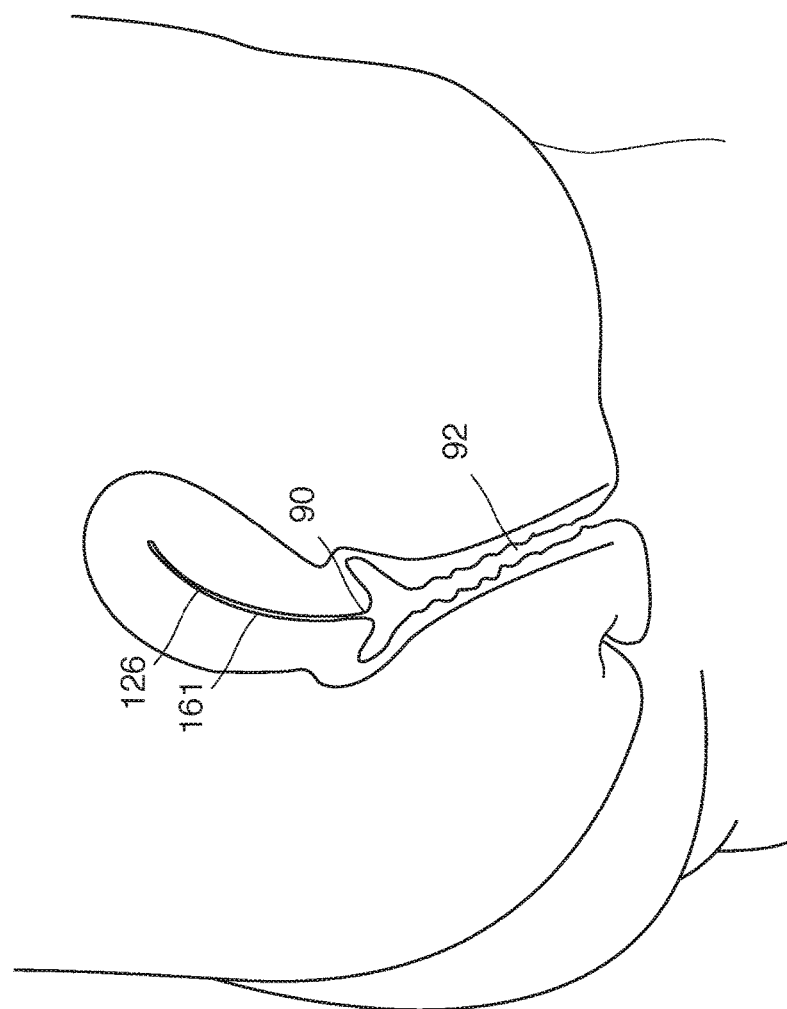
Figure 11:
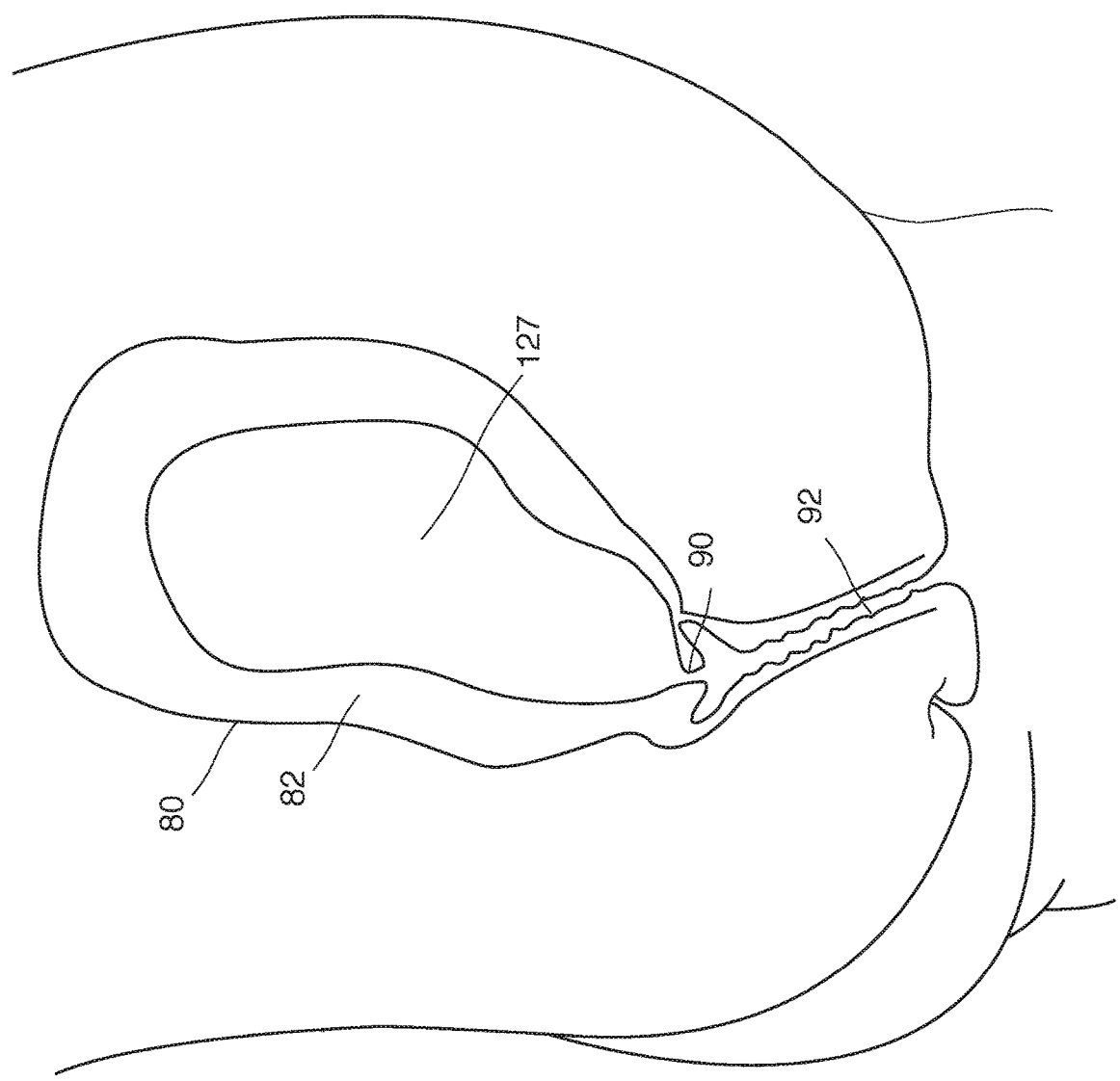
Figure 12A:
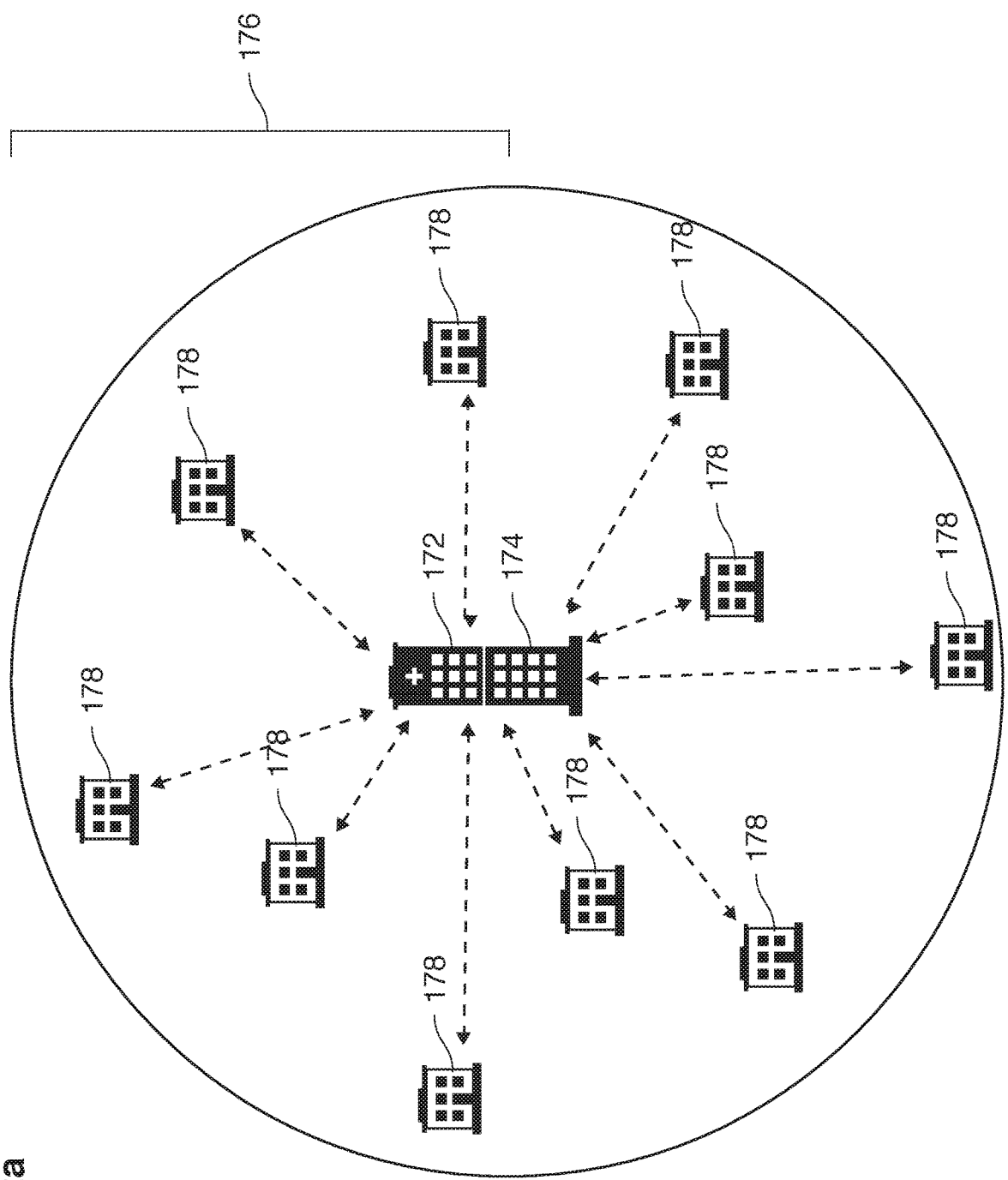
FIGS. 12a through 12d illustrate aspects of business models.
Figure 12B:
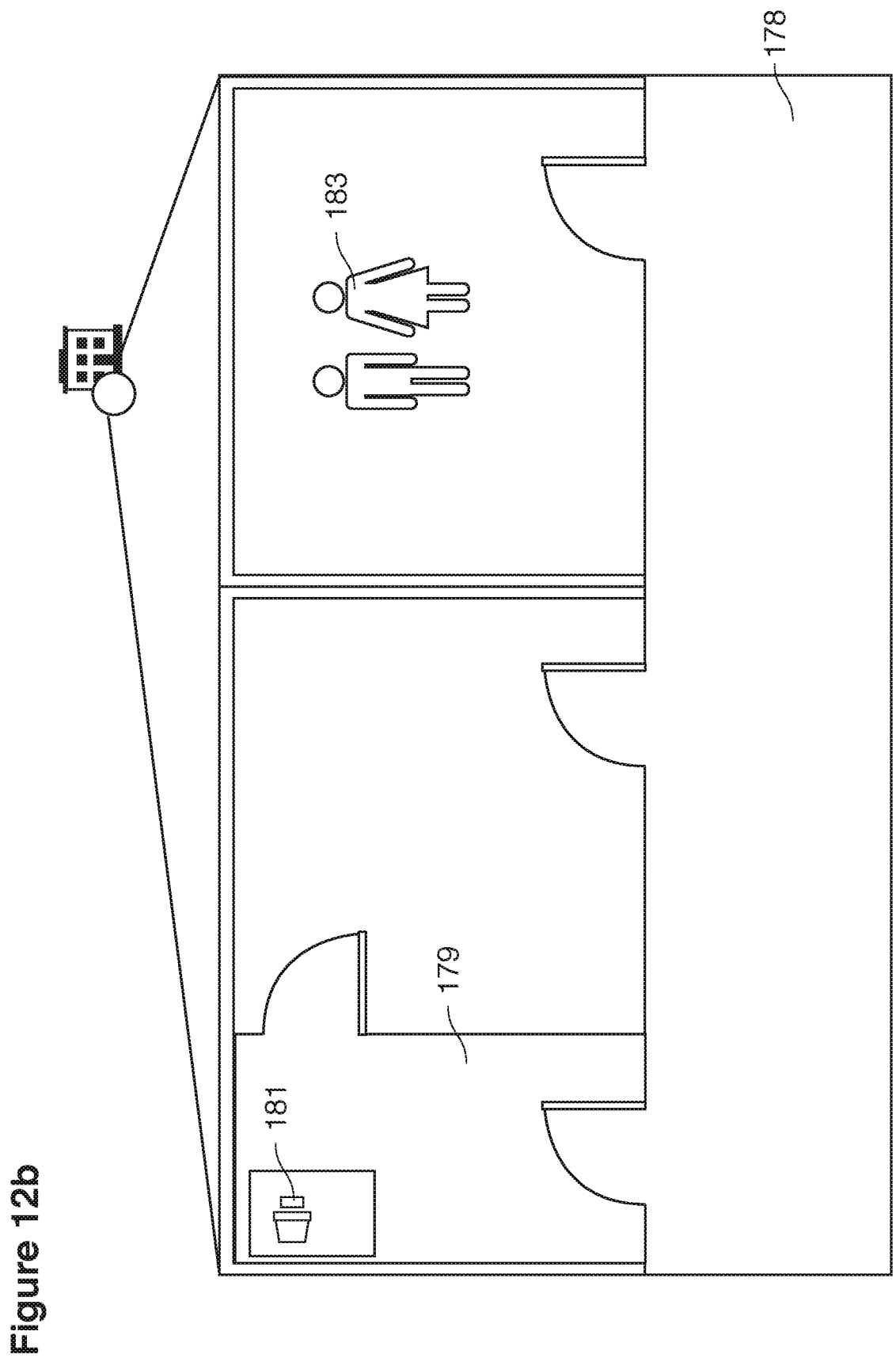
Figure 12C:
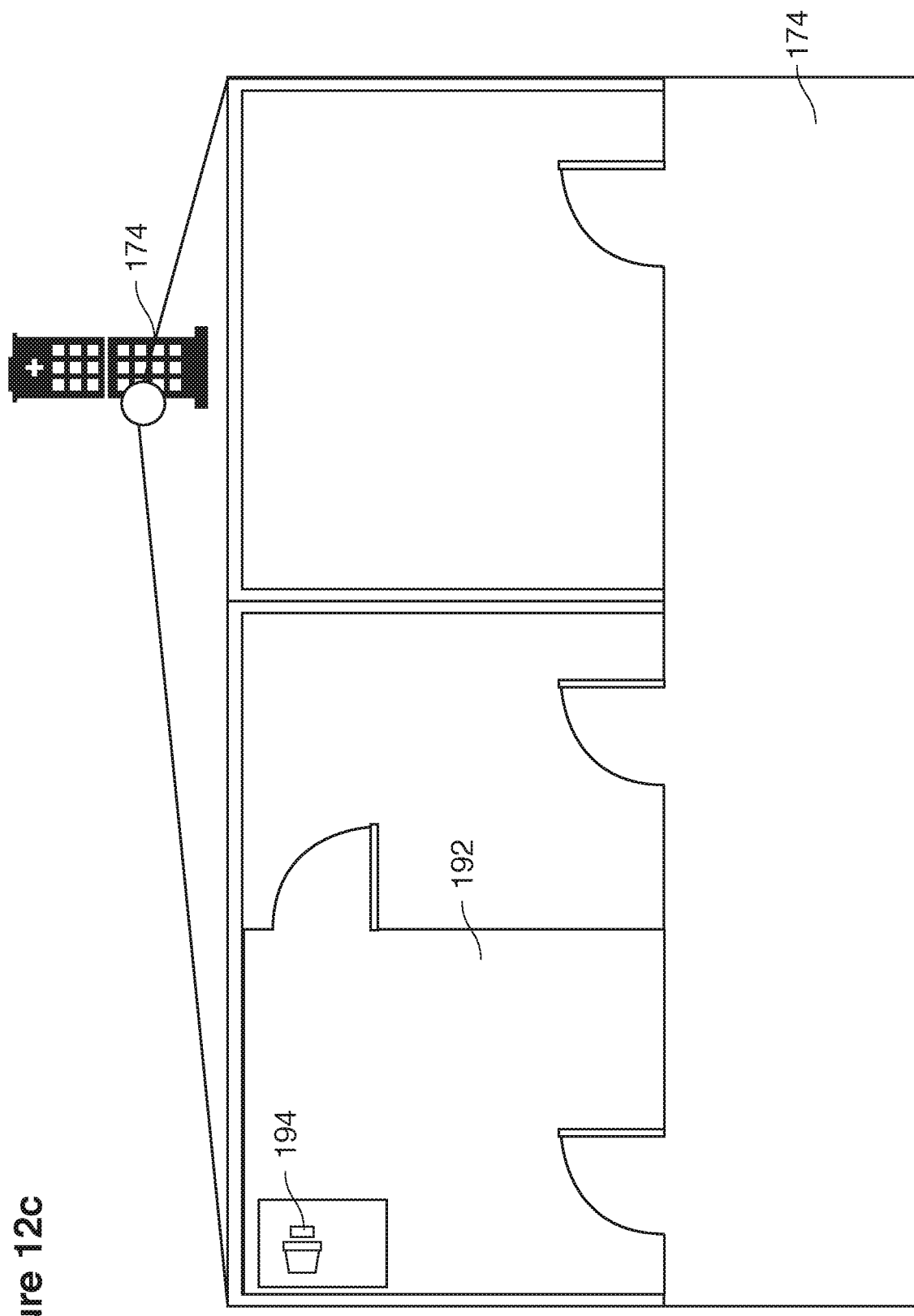
Figure 12D:
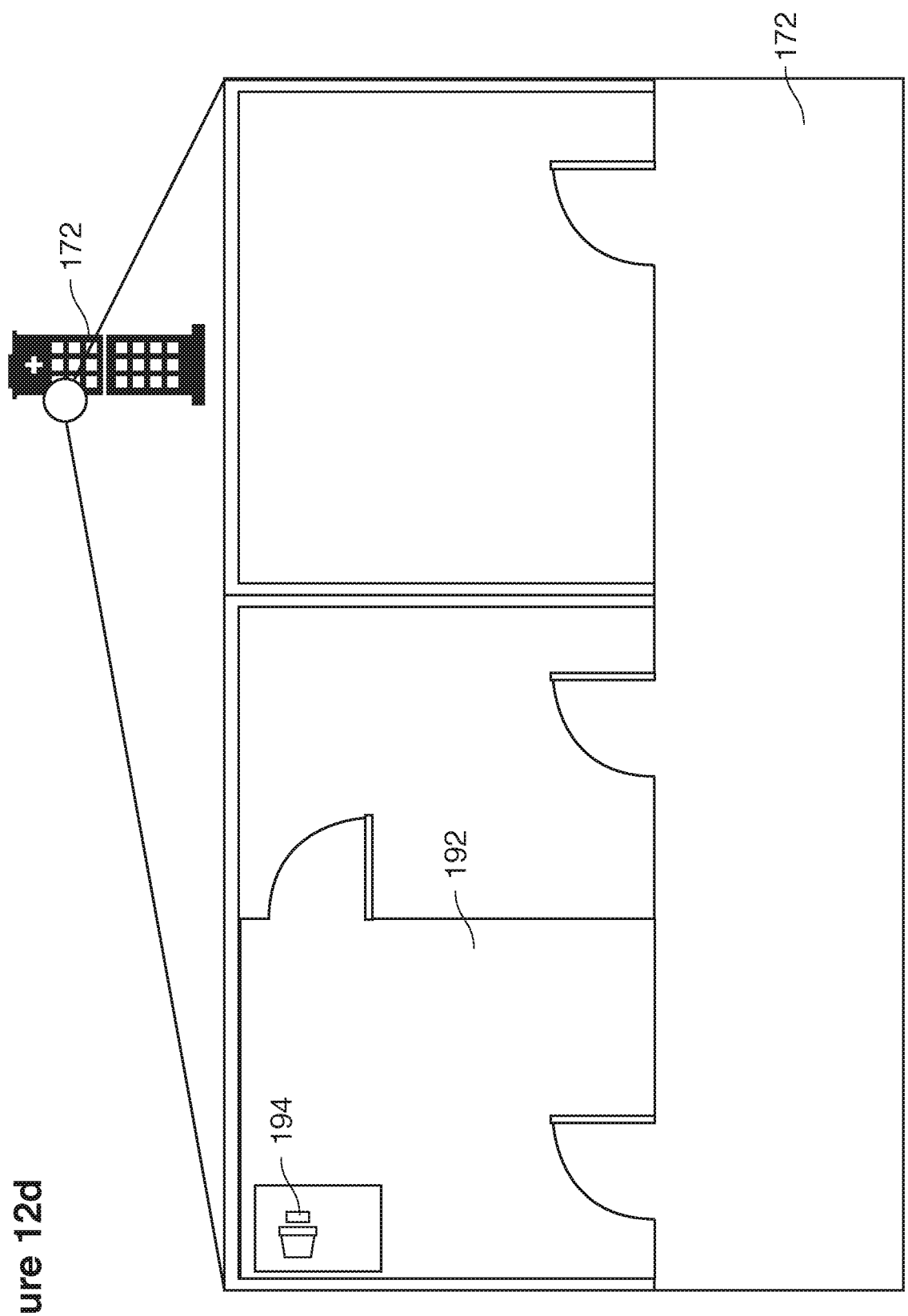

We use the term uterine cavity broadly to describe the heart-shaped space shown, for example, as element 126 in an anterior-posterior view in FIG. 9. Viewed as a lateral exposure as in FIG. 10, the uterine cavity 126 between the cervical canal and the Fallopian tubes appears as a narrow slit. The uterine cavity space represents a potential space in the non-pregnant state, when the muscular front and rear (anterior and posterior) uterine walls are in direct contact with each other and separated only by a thin film of uterine fluid. The direct apposition of (contact between) the anterior and posterior walls of the uterine cavity 126 is apparent in the lateral view in FIG. 10. Blastocysts and other preimplantation embryos are freely suspended in this film of intrauterine fluid before they implant into the wall of the uterus. The potential space becomes a real space when greatly expanded when, for example, the walls are separated 127 mechanically by surgical instruments (such as catheters) or in the pregnant state when the pregnancy and its surrounding membranes separate the walls widely apart as in FIG. 11.

We use the term Fallopian tube as shown, for example, as element 86 in FIG. 9 broadly to describe oviduct structures that enable, for example, transport of sperm cells from the uterus to the ovaries where fertilization takes place and for return transport of embryos back to the uterus for implantation.

Internal ostia refers broadly to openings in the uppermost uterine cavity that link and complete the passageway of the Fallopian tubes from the ovaries to the uterus as shown, for example, as elements 104, 106, in FIG. 9.

The term internal os refers to the opening of the cervix into the uterine cavity as shown, for example, as element 155 in FIG. 9.

The term external os refers to the opening of the cervix into the vagina as shown, for example, as element 170 in FIG. 9.

As we use the term, cryopreservation refers broadly to a process in which, for example, one or more cells, whole tissues, or preimplantation embryos are preserved by cooling to a temperature at which, for example, biological activity including biochemical reactions that would lead to cell death, are slowed significantly or stopped. The temperature could be a sub-zero ° C. temperature, for example, 77° K or −196° C. (the boiling point of liquid nitrogen). Human embryos can be cryopreserved and thawed with a high probability of viability after storage even of many years.

Figure 8B:
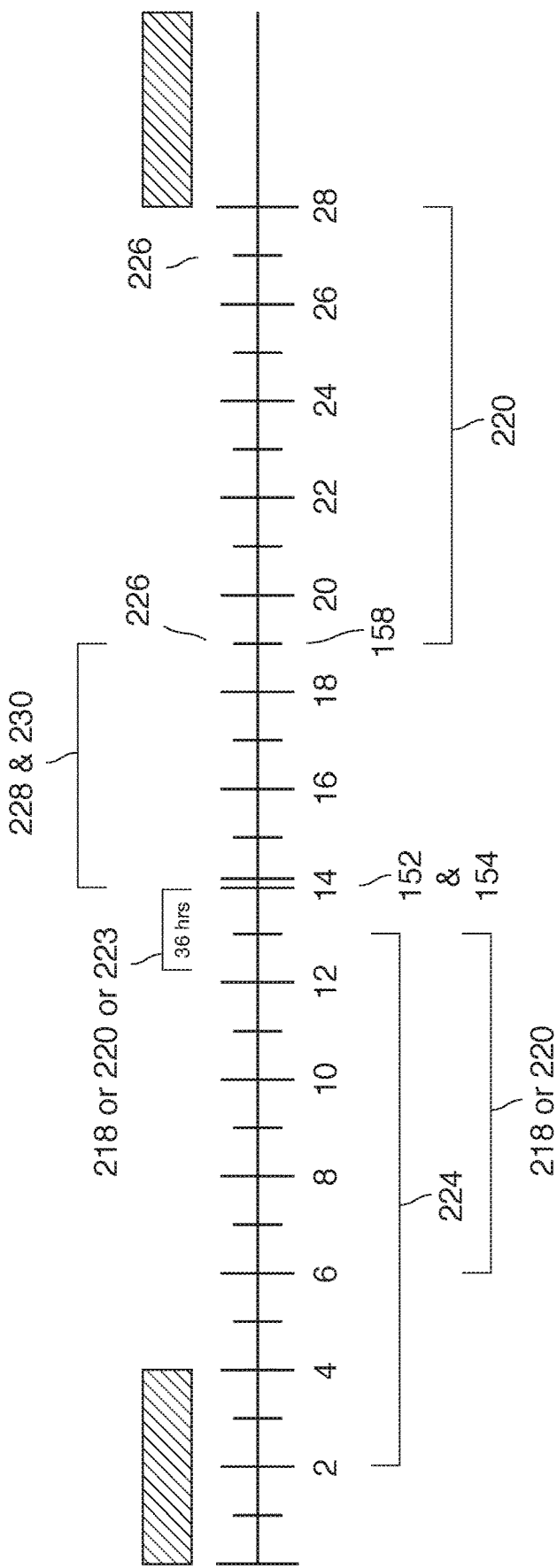
FIG. 8b is a time diagram.

When we refer to intervention by embryo (gene) therapy, for example, as shown as element 164 in FIG. 8, we intend to include broadly any strategy for altering a human physical condition, including, for example, treating a disease by placing (e.g., injecting) cells into an embryo, blastocyst or its blastocoele core, or placing (e.g., injecting) DNA (such as modified or reconstructed DNA) into individual embryonic cells or inner cell mass or trophectoderm cells or surrounding media so as to modify the genome of the embryo or blastocyst to correct, for example, a defective gene or genome.

In a general strategy, gene therapy at the embryonic blastocyst stage may involve replacing a defective gene of any genetic disease with an intact and normally functioning version of that gene. Replacement is performed by placing the replacement gene in the surrounding media or injecting the replacement gene by nanosurgical methods directly into the blastocoele of a blastocyst or selectively into its trophectoderm cells or inner cell mass.

In one strategy, the replacement gene or DNA sequence can be loaded onto a virus (for example retrovirus or adenovirus vector) which delivers the sequence into the trophectoderm cells or cells of the inner cell mass. Other intracellular delivery methods include use of other viruses and non-viral methods including naked DNA, chemical complexes of DNA or physical methods such as electroporation, sonoporation, or magnetofection.

The blastocyst is an excellent (perhaps ideal) site to implement gene therapy because the genetic constructs and viral vectors are likely not destroyed by the immunological response of an adult organism that may impair the success of gene therapy when applied to adults. Thus it is expected that incorporation of replacement genes and their viral vectors will be highly efficient at the blastocyst stage.

One example would be prevention or deletion or inactivation of the Hemophilia B gene in a human blastocyst Hemophilia B male carrier by injection of the replacement gene with an adenovirus vector into the surrounding media or blastocoel core allowing vector to contact and transfect virtually all trophectoderm and inner mass cells and be incorporated ultimately into all fetal and adult cells of the resulting newborn. Hemophilia B has been successfully treated in adult human subjects by gene therapy.

We use the term fertile couple to refer broadly to a man and a woman who have no known fertility disorders (for example, a biological inability of one of them to contribute to conception). Conversely, we use the term infertile couple to refer broadly to a man and a woman known to have a fertility disorder, for example a disorder in which unprotected sexual intercourse for over one year fails to achieve a viable pregnancy if the woman is 35 years old or less or six months of unprotected intercourse if 36 years old or older.

We use the term lavage fluid to refer broadly to any physiologic fluid that can be used in the process of recovering blastocysts from the uterus, for example, a wide variety of aqueous tissue-culture life-sustaining buffered salt solutions (media) (for example—Heapes based HTF with 20% protein) commonly used in embryology laboratories to sustain embryonic viability for long or short periods of time.

We use the term lavage fluid filtering broadly to refer to any kind of processing of uterine lavage fluid (for example, after it has been recovered from the uterus) to, for example, isolate human blastocysts from the fluid. Such filtering can include, for example, separating maternal intrauterine cells, mucous, and debris from the blastocysts.

We use the term preimplantation embryo to refer in a broad sense to, for example, an embryo that is free floating in a woman's reproductive tract after fertilization. A preimplantation embryo can have, for example, one cell with a male and female pronuclear (day 0) graduating to two cells (day 1) to 2-4 cells (on day 2) to 6-10 cells (day 3), to blastocysts (day 5 to 8) with 100 to 300 cells. Typically, a pregnancy is established when a preimplantation embryo implants into the uterine wall on day 7 or 8 and begins to interact with the maternal blood supply.

We use the phrase preimplantation genetic diagnosis (PGD) broadly to refer, for example (element 162 in FIG. 8), to any kind of genetic diagnosis of embryos prior to implantation. PGD can, for example, reduce the need for selective pregnancy termination based on pre natal diagnosis as the method makes it highly likely that the baby will be free of the disease under consideration. In the current practice, PGD uses in vitro fertilization to obtain oocytes or embryos for evaluation. More broadly, although sex determination does not necessarily imply disease, we include in genetic diagnosis the possibility of sex determination of the embryo.

We use the phrase pre-implantation genetic screening (PGS) broadly to denote, for example, procedures that do not look for a specific disease but use PGD techniques to identify embryos at risk. An early-stage embryo has no symptoms of disease. To "screen" means, for example, to test for anatomical, physiological, or genetic conditions in the absence of symptoms of disease. So both PGD and PGS may be referred to as types of embryo screening.

When we use the term uterine lavage (examples shown in FIGS. 3, 4, 8), we intend to refer broadly to any possible lavage technique for recovery of one or more human embryos (e.g., blastocysts) from a living healthy woman after formation of the embryos, for example, before the embryos have established a pregnancy by attachment to the uterus. In some examples, the lavage includes flushing fluid, for example, cell culture fluid, into the uterus and capturing the flushed fluid from the uterus to recover the blastocysts.

When we use the term recovery in reference to blastocysts, we intend to include broadly any process of any kind, form, duration, location, frequency, complexity, simplicity, or other characteristic that is used to retrieve one or more blastocysts from a woman.

The term recovery efficiency refers broadly to, for example, the number of blastocysts recovered (e.g., by uterine lavage) from a woman expressed as a percentage of a total number of blastocysts expected to be recovered based on the number of blastocysts that actually result from a superovulation cycle. It is possible to estimate the number of blastocysts that will result from a superovulation cycle relatively accurately by using ultrasound to image the ovaries and counting the number of mature follicles that are expected to release eggs. The number of blastocysts and unfertilized eggs recovered during lavage can also be counted directly in the recovered fluid. The ratio of the number of recovered blastocysts to the number expected to be released yields the recovery efficiency.

Younger women (under age 35 years) with normal reproductive efficiency are expected to produce from 1 to 5 healthy blastocysts per superovulated cycle, and the expected recovery efficiency for those blastocysts is at least 95%-100%, or in some cases at least 95% or in some cases at least 90% or in some cases at least 80% or in some cases at least 50%. Recovery efficiency is expected to decrease with advancing maternal age, and applying the techniques described here for more than one ovulation cycle is expected to be required for older women or women with borderline fertility.

It may be desirable to adjust the parameters and approach to the procedures that we have described here to achieve the greatest possible recovery efficiency. Achieving a high recovery efficiency is both advantageous to the woman because it implies that fewer blastocysts will remain in the uterus that could potentially implant. High recovery efficiency is also desirable because it will improve the statistical likelihood that, among the blastocysts recovered, one or more will be suitable for treatment (or will not need treatment) and can be read implanted in the woman, without requiring repetitions of the procedure. In this sense, higher recovery efficiency will also mean lower cost.

As we have described here, appropriate treatments delivered to the woman at the appropriate times can reduce or eliminate the chance of any unintended implantation of a blastocyst that has not been recovered during the lavage.

In some cases we expect to achieve 100% recovery efficiency, but any recovery efficiency of 50% or more is expected to be desirable and useful. Commercial viability of the procedure is expected to be good if the recovery efficiency can be at least 80% or at least 90%. Recovery efficiency of at least 95% should provide excellent commercial feasibility possibilities.

The terms GnRH (gonadotropins releasing hormone) antagonist or agonist are used broadly to refer, for example, to a class of modified central nervous system neurohormones that are used as injectable drugs to stimulate or shut down release of pituitary hormones (e.g., FSH) that regulate human ovulation and release of ovarian hormones.

The term FSH (follicle stimulating hormone) refers to a pituitary hormone that naturally regulates the maturation and release of ovarian follicles and oocytes. Injected as a therapeutic agent, FSH can stimulate the maturation of multiple oocytes.

The term LH refers (luteinizing hormone) refers to a pituitary hormone that naturally induces the release of oocytes at ovulation. Injected as therapeutic agent, LH (or various surrogates) can induce release of oocytes at ovulation at a time determined by the time of injection.

We now describe in overview the process of uterine lavage from superovulation to embryo recovery, embryo management, and uterine replacement of selected or treated in vivo embryos. In some examples, the process is implemented in nine steps described below and shown in FIGS. 1-8.

Superovulation 152 (FIG. 8b) is induced using injectable FSH 224 to stimulate maturation of multiple oocytes. Injectable GnRH agonist, LH or hCG, or an LH surrogate (which stimulates the pituitary to secrete natural LH) is then used to trigger the superovulation (the release of multiple unfertilized oocytes 124 from both of the ovaries 122). FSH is combined with GnRH agonists 218 or antagonists 220 to quiet the ovaries 122 into a pseudo-menopause state. In some implementations, one or more of these steps used for in vivo fertilization are similar to, but not exactly the same as, those used to induce superovulation by fertility clinics for IVF cycles. For in vivo fertilization, standard IVF superovulation methods, for example, are highly modified to reduce risks of ovarian hyperstimulation and retained pregnancies resulting from blastocysts not recovered in the uterine lavage.

In some implementations (FIG. 8b), the modifications include that the superovulation cycles use GnRH antagonists 220 (GnRH receptor blocker peptides such as CETROTIDE 0.25 to 3 mg, GANIRELIX, ABARELIX, CETRORELIX, or DEGARELIX) to quiet the ovaries during stimulation with FSH. The FSH 224 stimulates maturation of multiple oocytes. In some instances, FSH is self-injected using daily (5 to 15 daily injections given at ranges of 37.5 to 600 mIU per day) doses of FSH (preparations including injectable menotropins containing both FSH and LH, purified FSH given as urofollitropins, or recombinant pure FSH) or single doses of long acting pure FSH (recombinant depo FSH).

In some implementations, a single subcutaneous dose (e.g. 0.5 mg) of GnRH agonist 218 (GnRH analog Leuprorelin or Leuprolide acetate or Nafarelin or Nafarelin Acetate snuff or Buserelin) is injected or snuffed (which releases endogenous LH) to trigger the superovulation 152 (released of multiple oocytes). Compared to traditional methods of triggering superovulation, the GnRH agonist 218 trigger minimizes risk of hyperstimulation because the release of the patient's own pituitary LH is short lived and the released natural LH has a short half-life (dissipates quickly). The GnRH agonist trigger will only minimally aggravate continued hyperstimulation of a superovulated ovary.

In some implementations, traditional LH 222 (injectable recombinant luteinizing hormone or LH) or hCG 223, may be used without GnRH agonist or in combination with agonist in some cases if release of endogenous pituitary LH is not adequate.

In some implementations, because there is risk of corpus luteum apoptosis (collapse) with antagonist suppressed cycles, progesterone 228 (given as vaginal progesterone, Crinone® (progesterone gel) 1 application per day or Prometrium® (progesterone, USP) 200 mg 3 applications per day) or oral progesterone 228 (or Prometrium® (progesterone, USP) 200 mg 3 oral capsules per day) and oral or transdermal estradiol 230 (transdermal estradiol patches 400 ug per day or oral estradiol 4.0 mg per day) are administered until the day of lavage.

In some implementations, after lavage, both progesterone and estradiol are discontinued. Uterine lavage is performed between days 5 and 8 and the embryos are recovered. At the end of the lavage, before or shortly after removal of the catheters, a single dose of progesterone receptor antagonist 226 (Mifepristone 600 mg) is injected into the uterine cavity with a second dose (Mifepristone 600 mg) mg given by mouth one day prior to expected menses.

In some implementations, after lavage, GnRH antagonist 220 is administered (e.g. CETROTIDE 3 mg) on the day of lavage recovery to induce corpus luteum apoptosis and suppress luteal phase progesterone and decrease further risk of a retained (on account of blastocysts missed by the intrauterine lavage) pregnancy. GnRH antagonist administration starts before or on the day of lavage recovery and may continue daily utilizing dosages of about 0.25 to 10 mg for up to 10 days following lavage. This novel use of a GnRH antagonist for corpus luteum suppression following blastocyst recovery after superovulation reduces or eliminates the possibility that unrecovered blastocysts will implant and result in unintended pregnancy. Uterine lavage done on non-stimulated cycles has a significantly lower risk of retained and/or ectopic pregnancy.

As explained, because the superovulation and artificial insemination produce viable multiple blastocysts within the uterus, and because the lavage may possibly not recover all of the blastocysts from the uterus, it is important to take steps, such as though mentioned above, to reduce or eliminate the possibility that unrecovered blastocysts will implant and result in unintended pregnancy.

Although examples of protocols for achieving superovulation and steps that follow it are described above, a variety of other protocols may be safe and effective. Other protocols may be able to achieve the functions and results mentioned. For example, other regimes may be possible to quiet the ovaries into a pseudo-menopausal state, to trigger maturation of multiple oocytes, to stimulate superovulation, to minimize the risk of overstimulation, to reduce the risk of collapse, and in general to reduce the risk of an unintended retained pregnancy.

The released oocytes 124 are captured in the open end of the Fallopian tube 86 and move towards the uterine cavity 126 naturally after ovulation (FIGS. 1-2).

The oocytes 124 are fertilized in the woman's Fallopian tubes 86 or in the area 89 peritubal-ovarian interface adjacent to the ovary where the tubes open in contact with or in close approximation to the ovary (FIG. 1,2).

Approximately 90% of reproductive age couples should be able successfully to undergo superovulation with uterine lavage for embryo recovery. Approximately 10% of couples will be infertile and should undergo preimplantation diagnosis by in vitro fertilization.

As shown in FIG. 2, artificial intrauterine insemination (IUI) is performed using an ordinary commercially available intrauterine insemination catheter 130 to inject washed semen 128 through the vagina 92 and cervix 90 directly into the uterine cavity 126 one time per superovulatory cycle. IUI is performed after superovulation, 36 hours after triggering this event with the GnRH agonist and/or hCG or LH surrogate. This IUI procedure delivers sperm 128 cells into the uterus that then become available in very large numbers for in vivo fertilization.

In vivo fertilization (FIG. 2) occurs by natural means after artificial insemination with washed semen 128. The sperm cells 128 migrate to and through the internal ostia 104, 106 into the oviducts 86 migrating to the distal oviduct 87 into the peritubal-ovarian interface 89 in contact with and adjacent to the ovary 122 where sperm cells contact and interact with the released oocytes 124 to fertilize these oocytes 124 in vivo.

In vivo fertilization (FIGS. 2, 3) in the woman's reproductive tract occurs naturally after artificial intrauterine insemination (IUI). Typically the sperm 128 travel up the Fallopian tube toward and fertilize the oocytes, which then become embryos 124. The embryos 88 (FIGS. 3, 9, 10) then continue to move toward and into the uterine cavity 126 where by the fifth to sixth day they mature to blastocysts 88 and are free floating in a thin film of uterine fluid between the anterior and posterior surfaces of the middle uterine cavity. (126, 161).

The section broadly reviews the clinical strategy of uterine lavage and its role in embryo recovery. Technical details of some implementations of devices, catheters, maneuvers for deploying them, and support apparatus for performance of uterine lavage and embryo recovery are described in text associated with FIGS. 13-64*e*

Here we provide a brief summary of uterine lavage.

The lavage begins.

With a suction cannula 16 and collapsed funnel balloon 44 in place under ultrasound guidance (FIG. 3), the operator (for example, a specially trained technician or nurse) inserts and steers one or two fluid supply catheters 64, 66 into the uterine cavity (FIGS. 3, 4). The lavage controller connected to the system is prompted to begin the lavage with preset delivery frequencies of lavage fluid and collection of embryos into a suction (or aspiration) trap 28.

The lavage cycle is started when the controller is prompted to begin the preset lavage cycle of pulsed fluid delivery and collection cycles. The first stage of the lavage cycle is begun by injecting a small amount of fluid into the uterine cavity to form a puddle of fluid encompassing the pre-implantation embryos. All of the fluid present in the uterine cavity is then suctioned into the system with one or more entrained pre-implantation embryos. The second stage of the lavage cycle is begun by injecting a larger amount of fluid into the uterus to form a larger puddle. All of the fluid present in the uterine cavity is then suctioned into the catheter along with one or more entrained embryos.

The uterine lavage procedure is performed under low flow and vacuum conditions, as managed by the controller, not to exceed the maximum pressure allowed by the device of between 2 ounces per square inch and 20 pounds of pressure per square inch and 2-30 in Hg of vacuum pressure to maintain the integrity of the blastocysts during fluid removal and removal. The uterine cavity is not expanded or pressurized. The lavage device does not include any members that act to expand the uterine cavity; as such an expansion can introduce air into the uterine cavity, which can kill blastocysts. The lavage process was designed to prevent the introduction of air into the uterine cavity to ensure the health and integrity of the recovered blastocysts.

Figure 64A:
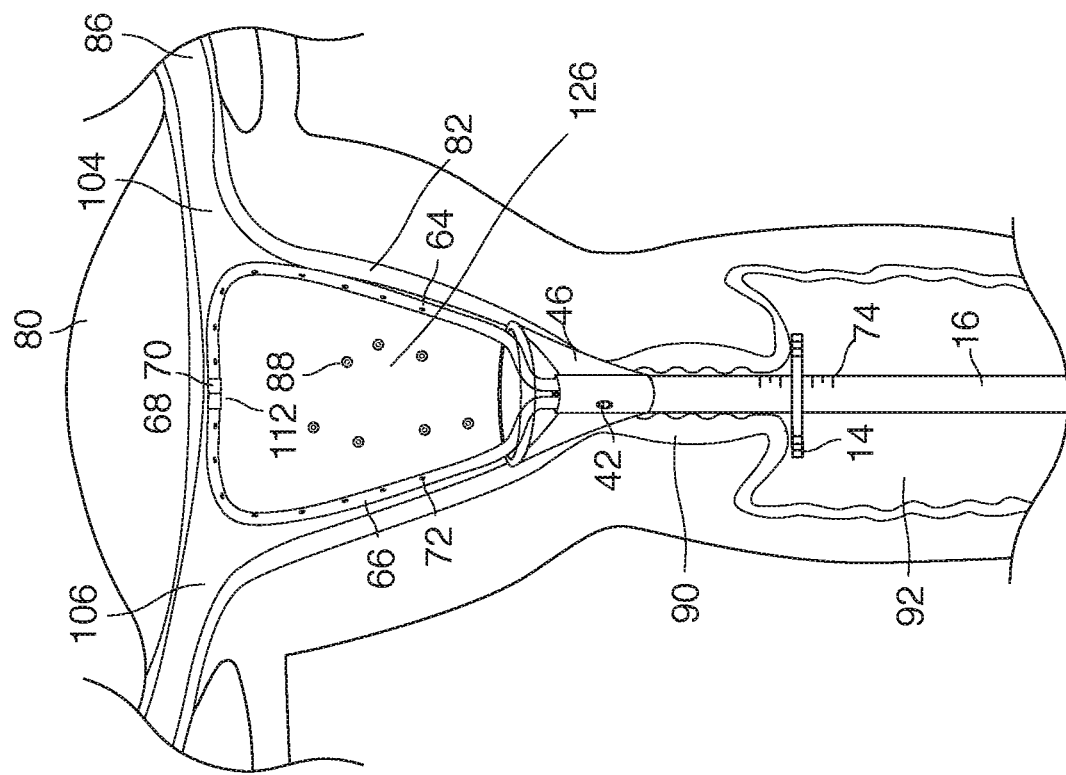
Figure 64B:
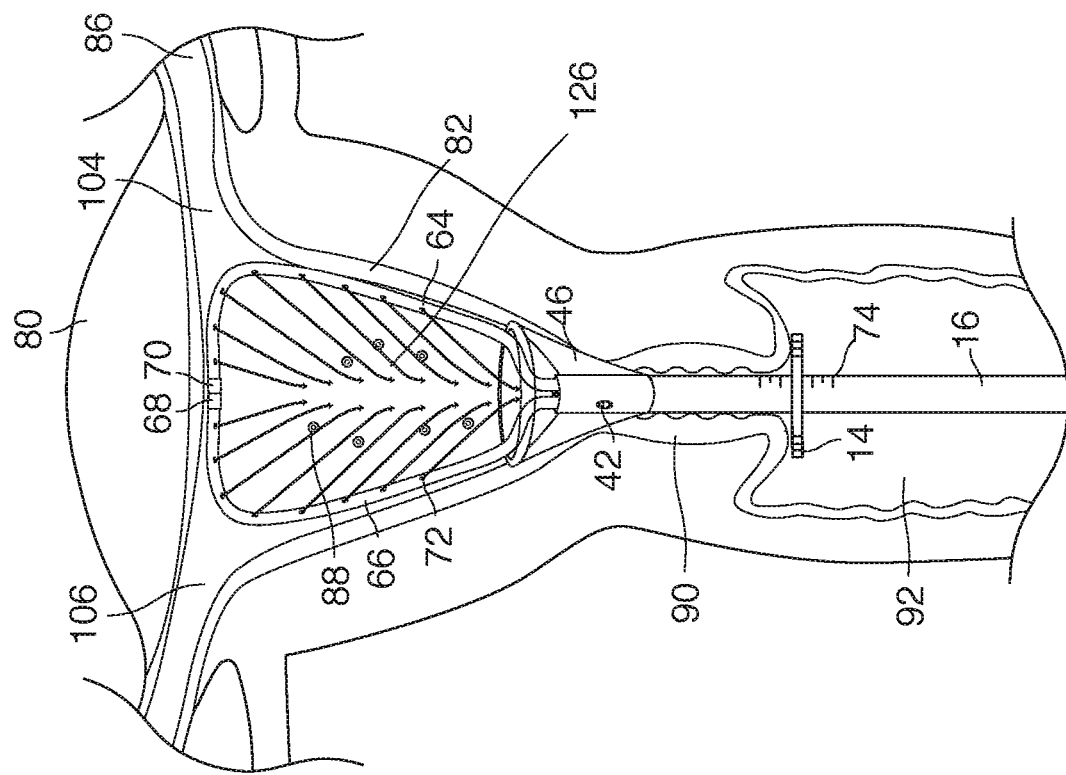
Figure 64C:
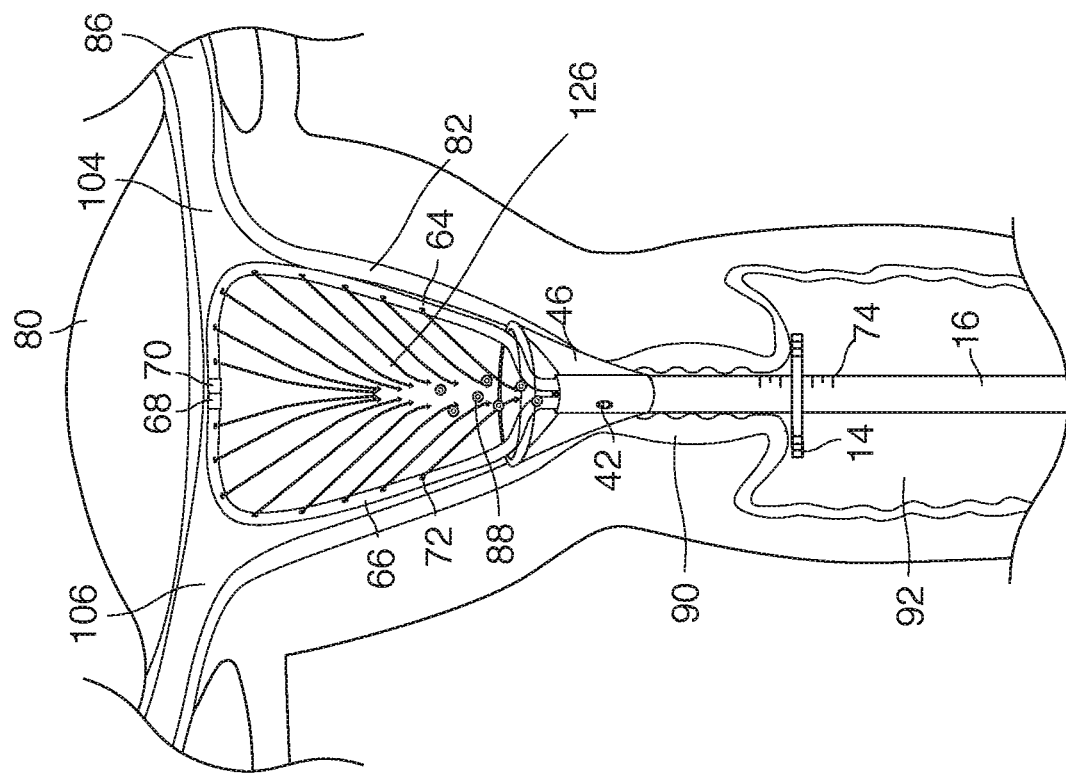
Figure 64D:
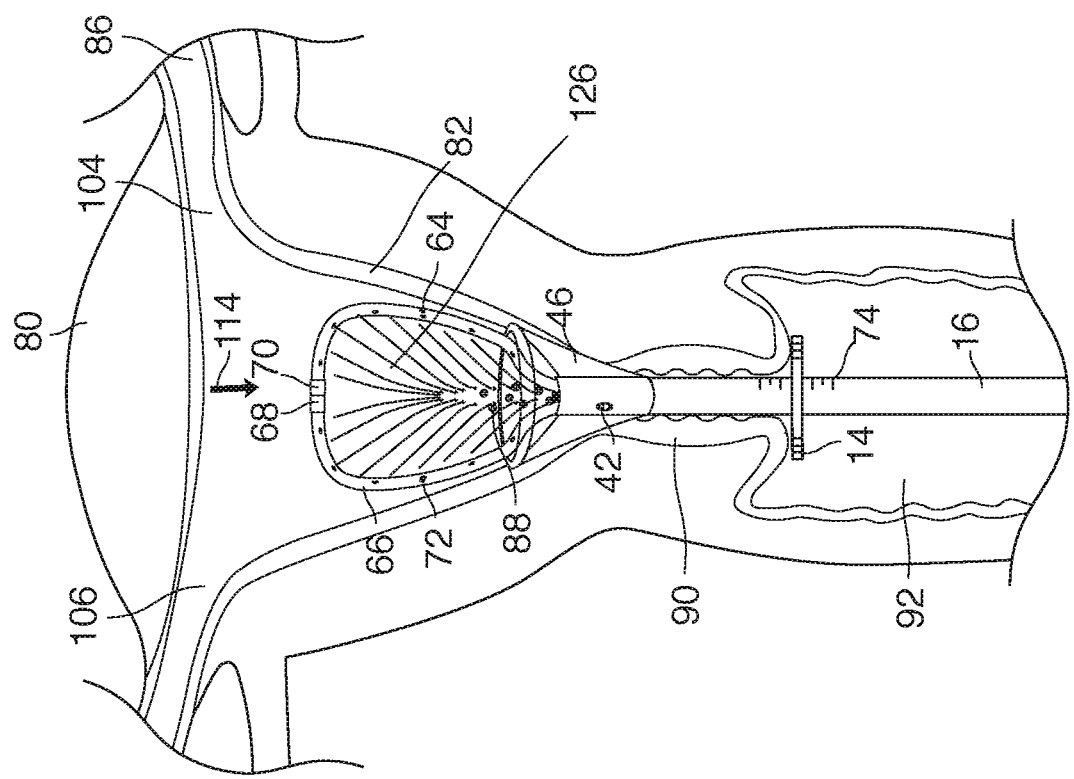
Figure 64E:
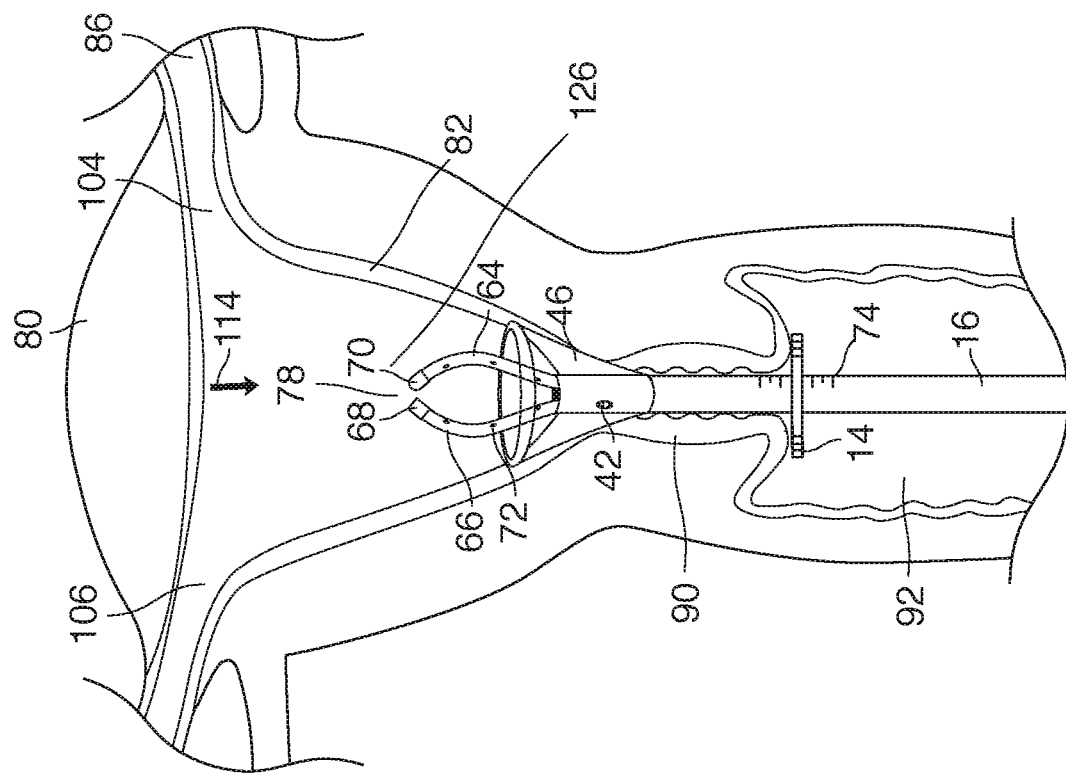

We now outline briefly two examples of uterine lavage techniques and apparatus described in substantial detail in sections dealing with FIGS. 13-64*e*.

In one example approach, a single fluid supply line (catheter) 20 (which we sometimes refer to as version #1) is steered with ultrasound guidance to the top of the uterine cavity 126. A more complete description of the one uterine supply line catheter (version #1) system is given in text dealing with FIGS. 13-64*e*.

In a second example approach, dual fluid supply catheters 64, 66 (FIG. 4) (which we sometimes call version #2) are steered with ultrasound guidance individually both superiorly and laterally 94 inside the uterine cavity along the right and left uterine sidewalls 94, 98 to the top of the uterine cavity 127. In one example (version #2b) the two catheters snap together magnetically at the top of the uterine cavity to form a mechanical hydraulic perimeter around the embryos (FIG. 4). A more complete description of the double supply line catheters (version #2b) system showing steerage and placement is given in text dealing with FIGS. 36-64*e*

Lavage fluid is collected in a non-embryotoxic glass recovery trap 28 at volumes expected to be in a range of 5 and 100 cc's. The lavage fluid is then diluted in additional physiologic transport media (for example—Heapes based HTF with 20% protein), and the resulting mixture containing embryos is sealed in the collection transport trap 28*b* with a tightly fitting glass 33 non perforated stopper. The collection trap 28*a*, after sealing, thus becomes the transport vial 28*b* for transport to the core embryology laboratory. The transport vial 28*b* (FIG. 13*e*) will maintain viability in excess of 24 hours. The transport vial 28*b* containing embryos, secured within an anti-shock insulated transport block 31, is then transported in a secure carrying case 190 to the central embryological laboratory by hand or overnight air transport.

In another iteration, lavage fluid may be collected directly into a cell-culture system capable of maintaining blastocyst viability during shipment to the central embryological laboratory. Such a system would maintain blastocyst-safe O2/CO2 levels without the requirement of an incubator and eliminate the need to dilute lavage fluid with physiologic transport media thus streamlining the recovery and shipment of pre-implantation embryo captured through uterine lavage.

Embryos are recovered in the central embryological laboratory 174.

On arrival in the embryology laboratory, the transported lavage fluid is passed from the transport vial 28*b* through a filter 37, 39 to remove cells and debris and into a large flat petri dish 28*c* where it is scanned by an embryologist using a standard binocular microscope. Scanning devices to automate this step are under development. The blastocysts are recovered by the embryologist using embryological glass pipettes and transferred individually into smaller individual embryological culture (Petri dishes) 28*d* containing standard embryo tissue culture fluid buffered for stability, e.g. Gardner's G-2.2 media)

Utilizing a micromanipulation apparatus, individual blastocysts 88 are positioned in side their individual Petri dishes under blastocyst culture fluid onto the tip of a fire-polished pipette 136 and stabilized by application of gentle suction on the lumen of the pipette. The zone pellucida (FIG. 5) is opened mechanically with another pipette 138 or with a laser beam to expose either the trophectoderm (future placenta—134) or inner cell mass (future fetus—135) of the blastocysts. It is likely that with existing or future nano surgical technology it will be possible to remove from one to many targeted cells 134, 135 for molecular genetic diagnosis or sex determination.

Trophectoderm cells 134 (early placenta) or early fetal cells 135 (inner cell mass) obtained from targeted embryonic regions are placed in blastocyst media in petri dishes or small tubes 28*c* and then undergo molecular genetic diagnosis or sex determination or both. Molecular methods are selected for the condition being evaluated. Established techniques include one or more of (or combinations of any two or more of: in situ hybridization 148 (FIG. 6) to evaluate chromosomal structures, polymerase chain reaction directed to detect specific mutations or other defects gene organization, whole genome hybridization, microarray gene chips, exome sequencing, or analysis of the entire human genome. A geneticist evaluates the molecular analysis in combination with information about specific clinical factors of the case. A decision is then made that leads to (a) replacing the embryo in the mother, as unaffected by the disease in question, (b) recommending an intervention such as gene therapy or transplantation of donated stem cells, or (c) recommending that the embryo not be replaced and that another embryo which is unaffected be replaced at a later time.

Figure 6:
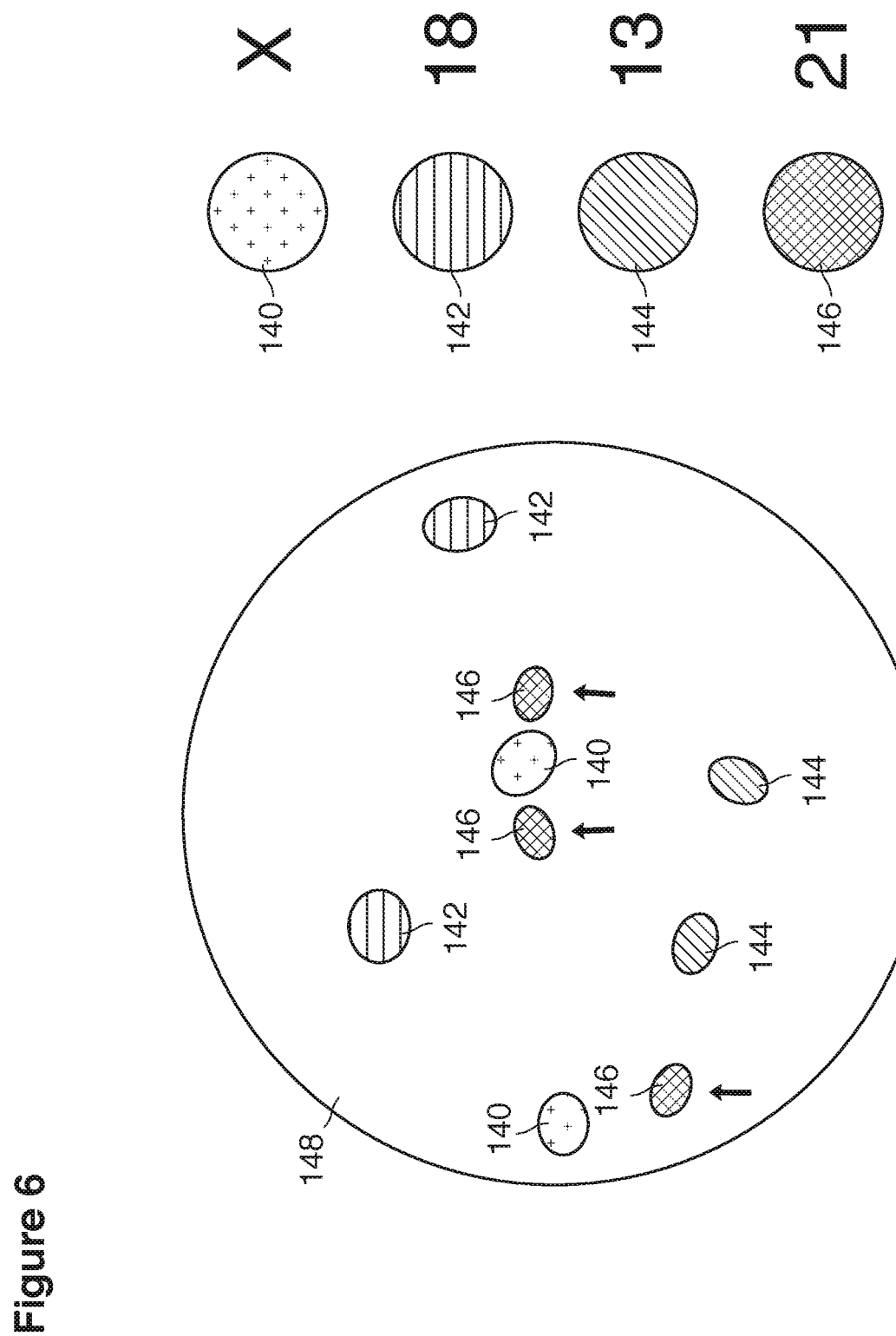
FIG. 6 illustrates a genetic diagnosis

A common example of a molecular diagnosis (Down syndrome) 146 currently possible from human blastocysts using either single trophectoderm 134 or very early fetal cells is illustrated in FIG. 6. This figure depicts an example in which specific areas of chromosomes are targeted at a molecular level fluorescent in situ hybridization (FISH) 148 with fluorochromes, which produce a microscopically visible signal when linked. In this example (FIG. 6), a diagnosis of Down syndrome is demonstrated by the presence of three #21 chromosome signals 146. Also seen are two X-signals 140 indicating female gender, two (#18)-signals 142, two (#13) signals 144 and two (#18) 142 signals as would be encountered normally.

Other molecular methods, besides FISH, available for detection of specific single mutations or groups of mutations, include polymerase chain reaction, whole genome hybridization, microarray gene chips, exome sequencing, and analysis of the entire genome. Any one or two or more of these in combination could be applied. When the result is available, a geneticist evaluates the molecular analysis, including combining the information with specific clinical factors unique to the family that led to the indication for preimplantation diagnosis in that embryo. A decision is then made to replace the embryo 132 in the woman (FIG. 7) if it is unaffected by a disease in question, to recommend an intervention such as gene therapy or transplantation donated stem cells, or to recommend that the embryo not be replaced and that another embryo, which is unaffected, be replaced from another procedure.

With current technology, the identification of many hundreds of childhood and adult diseases at the molecular genetic level in single or a few trophectoderm 134 cells is possible. In the future, the varieties of single cell diagnoses will expand into the thousands as increasing knowledge of the molecular bases of common multigenic disorders expands. This list likely will include disorders such as schizophrenia, autism, diabetes, coronary artery disease, malignancies, and many others. As public awareness of the molecular bases of common diseases becomes commonplace, the occurrence of these problems in yet to be born children and will be of major concern. There is likely to be substantial demand for this information in yet to be born children.

A variety of therapeutic scenarios will become available with advances in molecular genetic technology, including the three following examples.

1. PGD allows for identification of embryos that are carriers of genetic disorders or of desired genetic traits. PGD facilitates selection of the unaffected or carrier embryos for transfer to (replacement in) the uterus. Embryos afflicted with the genetic disease in question are not replaced in the uterus and are discarded. PGD allows identification of embryonic sex. Embryonic sex selection may be used for prevention of sex-linked genetic diseases. Sex selection may also be used for culture, social indications, or family balancing by gender/sex or any combination of them.

2. Embryonic gene and stem cell therapy has been achieved in experimental and domestic animals, in human adults and children, but not yet at the human embryonic stage. Gene and stem cell therapy targeted at the preimplantation embryo is especially promising because it repairs cells with abnormal genetics before differentiation of the cells, by adding to, replacing, or manipulating (or a combination of them) a dysfunctional sequence of DNA. Also, human gene therapy may readily be delivered by blastocoel injection because blastocoel gel comes into direct contact with virtually all cells. Human gene therapy at the blastocyst stage though not yet achieved, is foreseeable in the future, particularly with recent adult human successes with treatment of genetic diseases by gene therapy, e.g. Hemophilia B.

One technique potentially useful at the blastocyst stage is to remove a few stem cells from the inner cell mass, transfect the cells directly using a retroviral vector or by actual micro insertion of the construct into the isolated stem cell. Once the correction is incorporated into the genome of the stem cell, it can be reintroduced back to the inner cell mass where it would be incorporated into the growing embryo. Since the transected stem cells are totipotential, the corrected genetics can be incorporated into any organ including germ cells then transmitted to future generations.

3. Embryos suitable for replacement in the uterus, either because they are genetically unaffected or have been successfully treated, are cryopreserved 165 for transfer either in the following spontaneous menstrual cycles or at a more remote future date.

Following cryopreservation, embryos suitable for replacement are thawed and transferred back into the uterine cavity 126 (FIG. 7). To do this, the embryo is suspended in tissue culture fluid. The fluid is loaded into an embryo transfer 150 catheter. This catheter can be any one of many commercially available device widely used for embryo transfer in fertility clinics for this purpose. The embryo transfer catheter is passed through the cervix by the same technique commonly used in fertility clinics for in vitro fertilization. The embryo 132 is placed into the geometric center of the uterine cavity, as determined by ultrasound and external markings of the catheter tubing. By natural processes, the embryo free-floats 132 in a film of uterine fluid within the uterine cavity 126, 161 for approximately another 24 hours and then attaches to the uterine wall at the center of the uterine cavity 88, 126, 161. The embryo ultimately implants in the uterine lining 82 (endometrium), accesses the maternal blood supply, and then develops for a normal gestation period resulting in the birth of a newborn free of the genetic disorder under treatment.

We have described examples of the procedure in a series of steps performed on a single patient. In making this procedure available to a very large number of patients all over the world (including in large and small communities, and in rural and urban areas), techniques can applied to reduce the cost, improve the safety, and enhance the efficiency and performance of the procedure, among other things. One or more appropriate business models can be used to provide these advantages to patients while offering revenue and profit opportunities for manufacturers and distributers of the devices used in the procedure, providers of the services that are part of or associated with the procedure (including PGD, genetic disease prevention, embryonic gene therapy, and stem cell transplantation), medical professionals, and other parties. The business model can include a variety of transactional features including sale, rental, and licensing of devices and equipment, fees for services, licensing of services, and others.

Shown in FIG. 12 are some examples of how the procedures would be delivered and managed. A corporate managed regional coordination center 172 (also sometimes called the host of the network) would own and manage or franchise the operation of a number of core laboratories 174 (only one shown) located in high-density population centers across the United States. Location of each of these laboratories is based upon a service area 176 that is within a defined surface travel time or distance of the laboratory. For example, a service area could be one served by ground transportation of a distance of approximately 150 miles radius or less than 4 hours transportation time from the laboratory, or with reliable delivery by air to the laboratory within a flight time of less than 4 hours. Examples of suitable cities (Table 1) could include New York (2 centers), San Francisco, Los Angeles, Boston, Chicago, Philadelphia, Washington D.C., Seattle, Minneapolis, Miami, Atlanta, Denver, Dallas, Phoenix, and Memphis.

TABLE 1

Core Network laboratory locations 174 within surface transportation of 4 hour or less or 4-hour direct airfreight services from network subscriber clinics.

| Center | Population/Square Mile |
| --- | --- |
| 1. New York (2 centers) | 26,821 |
| 2. San Francisco | 17,179 |
| 3. Boston | 12,792 |
| 4. Chicago | 11,841 |
| 5. Philadelphia | 11,379 |
| 6. Washington DC | 9,856 |
| 7. Seattle | 7,250 |
| 8. Minneapolis | 7,019 |
| 9. Miami | 5,878 |
| 10. Atlanta | 4,019 |
| 11. Denver | 3,698 |
| 12. Dallas | 3,517 |
| 13. Phoenix | 2,797 |
| 14. Memphis | 2,053 (FedEx 4 hour night service all USA) |

In some implementations, each of the core laboratories 174 (FIG. 12) will be imbedded in an existing embryological molecular genetic service laboratory already existing in a major, high profile medical center. Each of the core laboratories would be supported and electronically linked to its own regional network of subscriber clinics 178 and embryology laboratories 179. The host of the network will lease or partner with existing core laboratories capable of providing embryology, cryogenic, and molecular genetic services (or some part of them) for embryos acquired in their service areas same day.

The network host's subscriber clinics 178 (FIG. 12) are points of patient contact and care services. The network host will lease or partner with a regional network of such local subscriber clinics, which, in some examples, are similar to reproductive medicine and genetics centers that operate today. Subscriber clinics 178 are the sites where patient interactions take place. Physicians and support staff working in these local clinics will be subscribers to the network host's systems. Among other things, to become a subscriber a clinic will have to include high security areas 179 in their clinics and computer linkages 181 that are managed by the network host 172 and devoted solely to network host operations at their site. Physicians and support staffs working in subscriber clinics 178 will all have been previously established as practitioners of reproductive endocrinology, infertility, and genetics.

Patients 183 seeking the network host's services are referred to a subscriber clinic located near their home or business. There need be only limited disruption of a patient's personal life while she is receiving services in the system. The ordering of the central host's embryological services, genetic testing, and obtaining of results will be as simple as ordering routine laboratory testing as practiced today.

We now review the process as would be seen and experienced by an individual patient 183.

The process begins with patient 183 entry at a local network subscriber clinic 178 and ends with embryo recovery at the clinic, followed by embryo diagnosis, decision, treatment if possible, and replacement of her embryos at the subscriber clinic 178 (FIG. 12). The steps of counseling, consenting, superovulation, artificial insemination, and lavage take place in subscriber clinics 178 under the direction of the clinic physician and staff. Network personnel perform lavage, transport, and processing of her embryos at the core laboratory 174, to return and transfer of her unaffected embryos back at the subscriber clinic 178, to followup and confirmation of her unaffected pregnancy in her local health care system.

Patient 183 entry begins at the subscriber clinic 178 where she and her partner have been referred by herself or by a physician in anticipation of her becoming pregnant. The family may be aware of that clinic by local reputation of that clinic as a provider of the network's technology. It will also be well known on the Internet. After review of the genetic reproductive history, a subscriber's reproductive endocrinologist geneticist will make the decision that the network's procedure is appropriate and will contact the network's core laboratory through their subscriber link. The patient's data will be entered locally at the subscriber clinic 178 along with appropriate demographics, financial, and insurance data.

The network regional coordinating center 172 will review the data entries and, as appropriate, approve of that patient's entry after review of history and laboratory data.

The network's nurse practitioner staff will see the patient in person at the subscriber clinic, customize and fit the lavage catheters to the specific anatomy of that patient using traditional or 3D ultrasound imaging, and approve her for launch (starting superovulatory drugs) of her cycle.

The network's regional coordinating center 172 will then authorize initiation of the drug induced superovulation induction. Subscriber clinic physicians will prescribe and administer superovulatory drugs under protocol, conduct the monitoring, and report the patient's progress in real time using online links to the network's regional coordinating center.

Superovulation (actual release of oocytes for fertilization) will be triggered by protocol and managed by subscriber clinic physicians. The woman will then appear in the subscriber clinic 178 with her partner, and after documenting security clearance using electronic chips and face-iris recognition (in other words, confirming that the woman is the person who she purports to be and is the patient to be processed), the subscriber clinic personnel, with approval by the network regional coordinating center 172, will perform intrauterine insemination of the woman at approximately 36 hours after triggered superovulation. Sperm samples will be prepared in the onsite network secure laboratory site 178 with identities reconfirmed electronically by the patient's and her partner's electronic identification cards that are programmed with confirmatory facial recognitions and iris scans.

Uterine lavage will be performed at the subscriber clinic by the network nurse practitioner at between 5 and 7 days after insemination. The recovery fluid is diluted with embryo protective transport media added immediately to the lavage fluid at recovery and is transported in sealed insulated containers 28b 31 (FIG. 13b) that are marked by electronic identification chips 189 (FIG. 13e) linked to the women 183,189 and her partner 183 (FIG. 12).

After lavage, the subscriber clinic 178 will electronically notify the core laboratory 174 by way of the secure computer network link of the status and location of all blastocysts in process in the network at that time. At each step in the process after lavage, information will be recorded electronically as identity chips attached to each clinical and laboratory step are scanned and stored in the network system data processing facilities to maintain a history of the steps and the current location of the embryos. Thus, the exact location of all embryos and cells retrieved from all patients will be known in real time as identification chips are passed through scanners from lavage, to recovery in the laboratory, to biopsy, to genetic diagnosis, genetic therapy, or sex determination (or any two or more of those), to freezing, thawing, and replacement back into the patient. The identity of all patients and their partners will be confirmed by iris/retina scans, electronic face recognition, and identification cards at each contact. Software will also be used to manage lab reports, clinical data from each patient and her partner, contact information, and billing and insurance arrangements.

Embryos are delivered to the core laboratory in the same lavage fluid, diluted in transport media that was used for the lavage recovery. The containers 28b in their insulated transport blocks 31 obtained from the day's procedures are carried in secure carrying cases 190 transported by the nurse practitioner. On arrival at the core laboratory and on delivery to the secure network laboratory space 192, the lavage containers 28b are matched electronically after scanning to the identification system and then placed in an individual space 192 (shown in the FIG. 13b) allocated only to those embryos. The identification database 194 (shown in the FIG. 12) maintained in the corporate regional coordinating center 172 contains all instructions on the type of biopsy procedure to be performed, and the diagnostic tests to be performed on the biopsied cells relevant to that patient.

After the embryologist manually isolates and confirms identify from scan of the electronic chip attached the transport container 28b, each embryo is graded for viability by embryologists, placed on a micromanipulator in it its electronically marked petri dish, and undergoes selective trophectoderm-inner cell mass biopsy. Approximately 10 to 20 trophectoderm 134 or inner cell mass cells are obtained and submitted to molecular genetic analysis as directed by orders in the patient's database and dependent upon indications for the specific procedure (for example, as shown in FIGS. 5,6).

A wide variety of analyses can be applied. For example, the molecular analysis can include one or more of the following: in situ hybridization to evaluate chromosomal structures, polymerase chain reaction directed to detect specific mutations or other defects gene organization, whole genome hybridization, microarray gene chips, exome sequencing, or analysis of the entire human genome as indicated (FIG. 6). Tests can be performed in duplicate for confirmation, because 10-20 cells should be adequate. The biopsied embryos are frozen or vitrified in liquid nitrogen for preservation. Within 24 to 48 hours, the results can be placed on the secure electronic network and reported to the subscribers and discussed with the patient and partner.

The status of each embryo and the results of the genetic analysis are reported by secure link in real time to each subscriber clinic through its secure computer terminal 179, 181 Internet 198 (FIG. 12). The subscriber clinic 178 will also contact the patient and her partner. The subscriber will select a strategy. Embryos identified as suitable for replacement will be delivered cryopreserved to the subscriber's clinic for replacement at a later time, weeks or months.

Figure 7A:
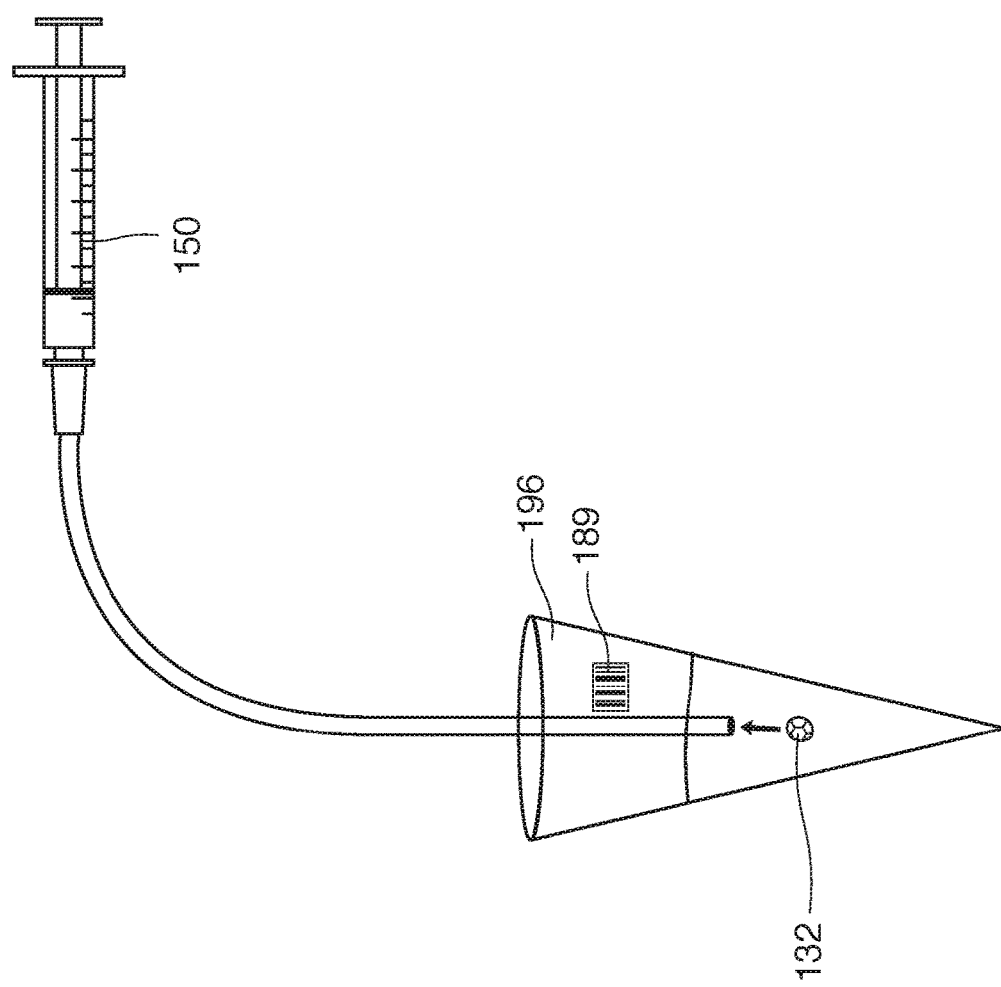
FIGS. 7a, 13c through 13f illustrates a step in a lavage procedure.
Figure 7B:
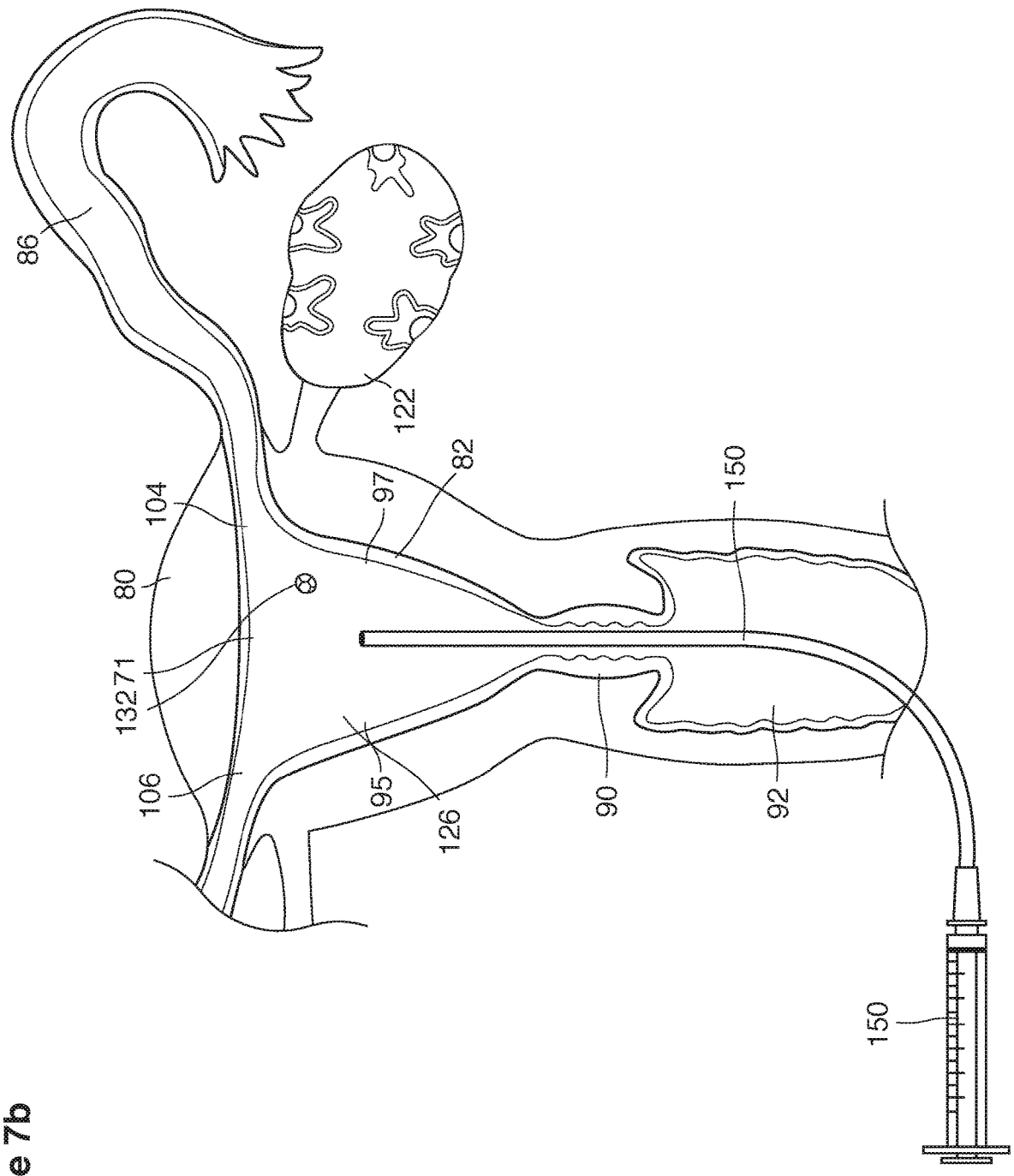

At an appointed time, the frozen blastocyst 132 selected for transfer (FIG. 7a) is delivered to the subscriber's clinic by the nurse practitioner in a security-coded container 196 that is matched to the identification of the patient and her partner using electronic identification chips 196. Identities of the patient and her partner are reconfirmed with facial recognition and iris/retina scans. The embryo is thawed in the subscriber's network protected facility 178, photographed, loaded into a transfer catheter under the supervision of the nurse practitioner, and then transferred into the patient by the network nurse practitioner (FIGS. 7a, 7b, 12)

Resulting pregnancies are followed by the subscriber clinic 168 and prenatal care will take place in the clinical infrastructure of the region.

Contractual arrangements with between the network system and core laboratories and subscriber clinics and laboratories will include secure space and equipment allocated exclusively to network operations. The glassware and all laboratory equipment involved with network will be color-coded and inventoried for no other uses except network patients and personnel specially employed or contracted by the network. Every step involved in the flow and management of embryos will be marked electronically and linked to the identity data of the patient and her partner. Births, perinatal outcomes, and genetic evaluations will also take place in the local infrastructure and will be documented and archived in the network database. Long-term follow-up of the births and progress of the children into adulthood will be readily achievable using information from the network database with confidentiality limits set within U.S. Government standards.

The network system will also negotiate and establish contracts with medical insurance companies for provision of its services on a basic pay for performance scale centering on, for example, a $30,000 fee for a viable unaffected pregnancy.

We now describe catheters and subassemblies that have a broad range of applications both within and in addition to uses in the network system and treatment of genetic disease. Details of the devices and components are described in text dealing with FIGS. 13-64e.

Uterine lavage devices have both reusable and disposable (one-time-use) elements. An operating frame 8 and hard stands 198 (FIG. 13b) used to stabilize them will be (significant) one time investments, for example, for clinics seeking to utilize the systems for other applications. In the case of uses for network system purposes, the network system will pay for and supply the frame and hard stands.

In some implementations, lavage fluid supply lines 20, suction cannulas 16, recovery traps 28, insulated shipping containers 31 and tubing may be (are likely to be) one time use disposables. Any two or more of them can be sold as kits for use on the network operating frames. The operating frames 8 are typically non-disposable and after each procedure are sterilized and are placed in a kit for usage.

In some implementations, the lavage device may be kitted with superovulatory drugs and/or GnRH antagonists. Such kits may include but are not limited to a kit for uterine lavage comprising a uterine lavage catheter configured for insertion into a woman's uterus to remove viable blastocysts; and one or more containers comprising a sufficient dosage amount of GnRH antagonist to cause desynchronization through corpus luteum apoptosis.

A kit for uterine lavage comprising a uterine lavage catheter configured for insertion into a woman's uterus to remove viable blastocysts from the uterus; one or more first containers comprising a sufficient dosage amount of FSH appropriate for induction of superovulation; one or more second containers comprising a sufficient dosage amount of a GnRH antagonist to silence the ovaries while causing superovulation; one or more third containers comprising a GnRH antagonist to be administered after superovulation.

Both permanent (reusable) and disposable (one time use) elements and related support services will have commercial application and market potential outside of preimplantation genetics.

Examples of applications of intrauterine lavage and the devices that we have described, outside of the network system could include the following. 1) Embryo donation: Uterine lavage can be used as a nonsurgical method for embryo donation that will compete with IVF. The availability of newer safeguards to protect donors from sexually transmitted viral diseases will allow uterine lavage to be used as a simpler and less expensive alternative. 2) Embryo banking: Uterine lavage will also be a useful technology allowing couples wishing to defer child bearing to cryopreserve and bank their own embryos for the benefit of career ascension, for example. An additional use could be deferred use in anticipation of technical advancements in genetic screening and gene therapy for a condition or disease for which there was no effective treatment at the time of the initial blastocyst recovery 3) Oncofertility: Uterine lavage may find application for patients with malignancies who wish to cryopreserve and bank their own embryos prior to cancer therapy. 4) Diagnosis of fertility and pregnancy wastage disorders: Uterine lavage may be useful in embryonic diagnosis of various fertility and pregnancy wastage disorders by facilitating recovery and diagnostic manipulation of preimplantation embryos conceived in vivo.

We overview general construction and clinical operation of examples of a device useful for intrauterine lavage. The principles of construction, operation, and use represented by the examples described and shown here can also be implemented in a wide variety of other examples.

In various configurations of the examples discussed here, the lavage devices have three elements in common (FIGS. 13-16;36-39): 1) an operating frame 8, 2) a suction-recovery cannula 16, and 3) one or two fluid supply catheters 36,64,66 passed though individual guide channels 34 extruded at manufacture into the inner walls of the suction-recovery cannula 16. In some implementations, each of these features, or two or more of them in combination may be incorporated in a device or parts of a device and a procedure or parts of a procedure without the other features. Each of the three features has significance of its own, as described below and can be used itself in a wide variety of devices and procedures.

In some examples of their use and operation, before the lavage, the three components are pre assembled with dimensions and settings that, in some cases, have been predetermined and customized for each woman. The steps can include the following.

1) The operating frame 8, with the disposable components secured to it, is mounted on a rigid stand. The hard stand 198 is a heavy-duty version of a common so-called Mayo table, which is readily available in the commercial marketplace. Such a table can be slightly modified to support the weight of the operating frame. One person manages the lavage, with both hands free to manipulate off and on functions of the external controller and to make adjustments in the collection apparatus. During the procedure, the patient is recumbent lying down and stabilized using soft restraints while the system is in operation. Two generic versions of the operating frame (version #1 and version #2a/2b) are shown in FIGS. 13-16 and 36-39.

The operating frame stabilizes the systems for cervical and intrauterine insertion of the suction-recovery cannula and its accessories and for steering the fluid supply catheters and their tip(s) before, during, and after lavage-recovery operations. The operating frames shown in FIGS. 13-16 and 36-39 include an operating slide 25, which stabilizes, guides, and slides the various catheters, fittings, guides, tubing, and accessories. The operating slide 25 is adjustable so as to limit insertion depths.

It is important, during the lavage procedure, that the frame of the instrument be held in a rigid position and orientation relative to the woman's reproductive anatomy. The setting of the position and orientation can be aided by ultrasound and other techniques. Careful positioning and orientation helps to assure that the cannula lies at an effective insertion distance within the woman and is properly seated by the stops and with a good fluid-tight seal provided by the balloon. During catheter insertion, because the instrument is held in an essentially fixed position and orientation relative to the woman's reproductive anatomy, the person performing the procedure can safely and effectively deploy and remove the catheter(s).

2) The suction recovery cannula 16, 22 (sometimes referred to as 22a or 22b) (FIGS. 13-17) includes a seamless conduit 22 that has a portion lying within a larger tube of the cannula 16 (discussed later) and a portion 22 that extends from the end of the larger tube for recovery of embryos in lavage fluid and transfer of those embryos to a glass recovery trap 28 mounted on the side of the operating frame 8. The suction recovery cannula 16, 22 embodies one suction recovery channel 23 and two or three accessory channels (FIGS. 17-22) imbedded within the larger tube of the cannula. One or two of these channels 34 are provided (depending on the implementation) to guide the deployment of one (version #1) or two (version #2a/3b) fluid supply catheters 36, 64, 66 into the uterus. The larger tube of the cannula also includes an insufflation channel 18 (occupying, for example, 2 to 8% of the cross-sectional area of the larger tube) delivers sterile fluid or air to an inflatable collar-funnel 12 at the tip of the suction cannula. (FIGS. 21, 22, 45, 46)

The suction cannula 16, 22 is tipped with an intracervical rubber inflatable collar 12 (FIG. 17, for example) which, when inflated 46 immediately after insertion with 1-3 ml of air or fluid, serves both as a watertight seal (of its outer wall) against the internal os 155 (to prevent fluid from leaking out of the uterus and into the cervix during the procedure, and also as a funnel-shaped intake port (defined by its inner wall) for collection and recovery of lavage fluid (FIGS. 16, 31-33, 35, 60, 61). After insertion of the cannula through the cervix and into the uterus, the rubber inflatable collar 46 is placed in a position immediately above the internal os 155 where it prevents completely the loss of lavage fluid around the suction-recovery cannula and outward through the cervix into the vagina. The proximal end of the suction line 22 is connected to a recovery trap 28a mounted on the left side of the operating frame 8 (FIGS. 13-16, 36-39). The trap 28 is connected to the pulse pump suction by a vacuum line 24. The trap is removed at the end of the procedure and the fluid it contains is scanned for embryos.

3) Fluid supply catheters, comprising one 20 (Version #1) or two 64, 66 (Version #2a/2b) lines, are pre-inserted into their guide channels 34 manufactured into the suction cannula 16, 22a, 22b prior to the arrival of the patient. The sizes and shapes of the catheters (which are disposable items) are selected to fit the patient and achieve effective lavage. They are connected to an external controller 205 (FIG. 13c) programmed to both deliver lavage liquid to the uterus and apply vacuum to the fluid supply catheters, which supplies uterine lavage fluid in a pulsed rhythm. The controller pump 232 is connected to the catheter supply line 20. A vacuum element alternates suction in pulses cadenced exactly the opposite as pulses used for fluid delivery (that is, when a pulse is applied, the suction is off, and vice versa correct). Suction pulses are managed via means of a pinch valve 231. Lavage fluid is supplied to the pump from an external reservoir through the intake port of the pump. For example, the pulsing can be done at a preset frequency in the range of one pulse per 0.5 to 4 seconds. The pulse rate is determined empirically in clinical trials to achieve the most effective and efficient flushing of the uterus to produce the maximum embryo yield. The pulse rate is programmed into the controller 205.

Uterine lavage (FIGS. 3, 4) is typically performed between 5 and 8 days after the LH dose or LH surrogate trigger that released in vivo the multiple oocytes resulting from the superovulation. At the optimal time (most likely day 5), blastocysts 88 are present suspended in uterine fluid in the potential space 126 between the anterior and posterior uterine walls at approximately the geometric center of the uterine cavity. This location is in close proximity to the ultimate site of implantation, which is believed would take place within one day or less after the procedure were there blastocysts remaining in the uterus afterward.

Preparatory to lavage, prior to superovulation and insemination, a practice lavage can be performed (approximately one or two months) before the live procedure is scheduled. In the practice lavage, the instruments are custom fitted, the guides, balloons, and other devices are attached into place on the operating frame 8 and measurements are taken (with the assistance of imaging technologies) that will enable the anatomy of each patient to be accommodated. Precise imaging of each woman's anatomy utilizes imaging devices, e.g., two-dimensional or three-dimensional ultrasound, magnetic resonance imaging, or other imaging technology. In one example, the length of fluid supply lines 64, 66 required to form a complete loop with the confines of the uterine cavity must be determined and recorded. In a second example the angle between the cervical stop 14 and the distal suction line 16 needs to be known in order to facilitate simple and comfortable insertion of the supply lines 64, 66. In a third example, the degree of cervical dilatation needs to be known and fitted into the instrument to be used on that patient.

On the day of the lavage procedure, prior to the arrival and positioning of the patient, a previously assembled catheter-operating frame 8 and supporting lavage instrumentation is assembled and set up in the treatment room adjacent to a gynecological examination table. Prior to the patient encounter, instruments are pre assembled from disposable and reusable elements, and adjusted as determined by the unique characteristics of each woman as previously determined and measured at the time of the trial lavage. Thus disposable fluid supply catheters 20, 64, 66 of the right size and configuration are preloaded into their respective channels initially fabricated in the suction-recovery cannula 16 at manufacture. The operating frame 8 and associated instruments are firmly secured on a fixed floor mounted hard stand 198 placed at the foot of the gynecological examination table. The pulsing and suction elements are connected so that the instrument is ready for the procedure.

In summary, in preparation for the live lavage, the disposable and reusable elements of the instrument are selected based on prior measurements and study of the woman's anatomy and assembled and attached to the pulsing and suction elements, ready for the procedure. In this way, the live lavage is expected to produce the most efficient and effective recovery of embryos possible.

In a live lavage (live in the sense that embryos are present), the procedure begins with the patient on her back in a dorsal lithotomy position. After insertion of a sterile vaginal speculum (not shown), the inner walls of the vagina 92 and the cervix 90 are cleansed with sterile tissue culture fluid. The bladder is left distended so that the procedure can be monitored in real-time by abdominal ultrasound. Two hours before the procedure, if needed for a woman with a strictured cervix 90, the endocervical canal 157, as described previously is dilated with a sterile laminaria ("dry seaweed") expander. To begin the procedure, the endocervical canal is then mechanically dilated, if necessary, to accommodate a #15 to #34 French device.

Lavage-embryo recovery operations are now performed in four steps: 1) Intracervical insertion of the suction-recovery cannula into the cervix; 2) Insufflation of the funnel balloon; 3) Intrauterine insertion, steerage and placement of fluid supply catheter(s) and lavage; and 4) Embryo recovery as follows.

1) Intracervical insertion: The procedure begins when the suction recovery cannula tipped by its endocervical guide is directed through the vagina into through the endocervical canal (FIG. 3). As the cannula is inserted, a cervical stop 14 flange on the distal end of the suction-recovery cannula comes to rest against the exocervix 90, 170 and limits the insertion depth of the guide. The system is now in place for deployment of lavage fluid supply catheters 20, 64, 66.

2) Insufflation: With the suction cannula endocervical guide 16, 22a, 22b inserted to its predetermined depth and its cervical stop 14 flange pushed firmly against the cervix at the internal os, the funnel balloon is insufflated with 1-3 cc of air or fluid (e.g., sterile water). Full insufflation of the funnel balloon 12, 46 seals off the endocervical canal and prevents any transcervical loss of lavage fluid and embryos.

3) Intrauterine insertion, steerage, and placement of fluid supply catheters, and lavage: With the funnel balloon 12, 44, 46 fully inflated and sealing the cervix, the fluid supply catheters 20, 64, 66 are then guided into the uterine cavity 126 using wheeled steering controls 26,26a, 26b and linkages mounted on the operating frame and customized to version #1 or version #2a or #2b. The instruments are connected to the controller delivery pump 232. The pump is energized and a total of, for example, from 10 to 100 ml of pulsating lavage fluid is infused through the system and uterine cavity and recovered over a period of, for example, 30 seconds to 5 minutes. The volume of fluid within the uterus is not to exceed 10 mL at any given time so as to not over pressurize the cavity or cause contractions, which would be painful to the patient and affect the recovery efficiency of the procedure.

Operations using version #1 and version #2a/2b are different and are described individually.

With Version #1, a (#10 to 16 French in various examples) (FIGS. 13-16) single lumen supply line catheter 20 constructed of medical grade biochemically inert medical grade composite (for example Teflon®) is used. It is tipped with a hollow steel ball 10 fabricated from very high-grade steel or composite machined in nanotechnology. In some implementations, the steel ball tip 10 contains two internally tapered ports 38 that direct lavage fluid downward in two distinctly formed and oppositely aimed streams that contact, break up, flush, and force mucous and cellular debris from the uterus into the wide, funnel-shaped suction port 43 which is located at the bottom of the uterine cavity in the base of the funnel balloon and is connected to the suction cannula and its suction recovery channel 23.

The two ports 38 in the steel ball tip are considerably larger than other ports 40 (FIG. 26) of the catheter and are internally tapered to deliver higher pressure, higher flow, and highly focused stream relative to the tapered ports. The configurations of the ports 40 are customized individually in accordance with the uterine anatomy of a particular patient, determined at trial lavage. The angle between the directions of the two streams will range from 90-degrees to 150-degrees from the axis of the catheter as required to direct the fluid stream away and inferiorly from both internal ostium 104, 106 structures (FIGS. 35e, 35f). After the angle is determined, catheters are supplied and customized for that one patient based on earlier measurements. The catheters are disposable. The fluid supply catheter 20 is keyed by an internal groove stop lock machine into its channel 34 and cannot be internally rotated inside the uterus. Therefore, the directions of flow of the two streams relative to the orientation of the walls of the uterus is fixed in the appropriate positions so that as the catheter is deployed the ports are properly oriented and the two streams will flush through the uterus effectively for embryo collection.

In some implementations, the catheter (and one or more of the other disposable elements) is custom fabricated by the manufacturer for each patient between the time of the test lavage and the time of the live lavage. In some implementations, the catheter or one or more of the other disposable elements of the instruments are supplied in a number of different sizes and configurations and can be assembled at the clinic without requiring custom manufacturing.

The customized fluid flows from the steel ball ports have directions, volumes, velocities and that functionally obstruct loss of lavage fluid into the oviducts 100,102 (FIG. 35e, 35f) by forming a hydraulic wall isolating the central uterine cavity from the internal ostia. In some implementations, the supply line contains from 8 to 10 secondary (4 or more on each side) low pressure ports that direct streams 102 of lavage fluid into the center of the uterine cavity 126 and downward into the funnel and its suction port 43. The flow of the lower pressure streams is restricted to the middle parts of the uterine cavity, are less forceful and less directed than the flows from the steel ball ports. The purpose of the lower pressure streams is to provide a diffuse pool of fluid that will solubilize the mucous matrix of the intrauterine fluid and facilitate a sweeping current containing all embryos in the uterus and facilitate their direction into the funnel and its suction port 43. Just as the orientations of the steel ball ports are fixed relative to the orientations of the walls of the uterus, so are the rows of ports in for the secondary streams that are positioned along the external walls of the catheters. This results in a controlled flow of fluid to achieve effective and efficient recovery of embryos.

In some examples of Version #2a/2b, two supply catheters are inserted and then guided along the lateral most walls of the uterine cavity to nearly meet at the upper end of the uterus (FIGS. 52, 53)(Version 1a) or snap together by their magnetic tips (FIGS. 64a-d) (Version 2b) at the top of the uterine cavity (FIG. 64a-d). The disposable supply catheters 64, 66 are pre inserted into the two supply channel suction recovery cannula 16, 22b into their own channels 34 with in the lateral internal walls of the suction cannula before its insertion into the uterus. They are keyed into their channels 34, 64, 66 and can be internally rotated inside the uterus yet restricted to rotation within a 90-degree arc as limited by interlocking grooves machined into the walls suction recovery 22a, 22b device in each of the respective supply line channels.

After the suction cannula is securely in place and the funnel balloon is fully inflated 46, 48, 50, the two supply catheters 64, 66 are advanced into the uterine cavity by manipulation from the respective control wheels and linkages 26, 26a, 26b. As they are advanced, they cling to both sidewalls of the uterus as directed by the shape memory of their shape memory materials 94, 98. The catheters are snaked (manipulated) into position by a combination of upward and torque forces as shown in FIGS. 63a-m.) directed by twisting the torque wheels 26a, 26b with linkages to the two channel slider block 119a, 119b and merger blocks 84a, 84b mounted on the operating frame. During insertion, they are directed away from and therefore pass by both internal ostia 104, 106 and then meet at the top of the uterine cavity 126. Ultrasound imaging can be used to aid the insertion process. In many cases, the operator will develop the ability to perform the insertion by "feel" without the need for imaging.

Both catheters contain ports 72, similar to the ones in the previously described version, that direct a flow of lavage fluid directly to the center of the uterus to break up the uterine fluid film, dislodge embryos, and direct them into the inflated funnel-balloon and its suction port 43 located at the internal os 155 of the uterine cavity 126 and held in place by funnel balloon 46 at the tip of the suction cannula.

Outside the woman's body, the suction cannula then directs the lavage fluid flow and embryos into the recovery trap 28a attached at the end of the vacuum line 24. The catheters are both keyed into their guides 34, 65, 66 so that the ports always face the middle uterine cavity and cannot force fluid into the internal ostia. During the lavage procedure, no embryos are lost via the internal ostia because all flow is directed toward the center of the endometrial cavity and then downward to the balloon funnel and suction port 43 at the internal os. Thus, there is no force or flow that would cause the embryos to flow toward or through the internal ostia into the Fallopian tubes where they would be lost. With Version 2a, the flow of fluid is stopped at the end of the procedure and the catheters and supportive elements are removed. With Versions 2b, the two lines, when they meet at the top of the uterine cavity, engage by their magnetized tips and form a closed perimeter around the embryos. The lavage fluid continues to flow as the device is withdrawn. The perimeter collapses around the embryos and continues to surround them and flush them from the uterus almost until the instrument is withdrawn (FIGS. 64a-64e). The collapsing perimeter is further assurance that no embryos are lost. In other words, the streams emanating from the catheters that form a looped perimeter continue to wash the embryos from the uterus towards the funnel in a sweeping action as the catheters are withdrawn and the perimeter closes in on the funnel.

We sometimes use other broad terms to refer to the flow of the fluid within the uterus from the delivery of the fluid to the collection of the fluid. For example, the multiple streams emanating from the catheter can form what is called a layer of fluid, or a curtain of fluid or a wash of fluid. We use all of these terms in a broad sense.

4) Embryo recovery: Lavage fluid containing embryos is delivered under intermittent suction into the suction cannula port 43 located at the base of the inflated funnel balloon 46 which occludes the cervix. Embryos in the fluid then flow through the seamless suction channel and tubing to the embryo recovery trap 28*a* snapped on to the side of the operating frame. At the end of the lavage procedure, the recovery trap 28*a* containing the lavage fluid is marked using electronic identification tags 184 (FIG. 13 13*b* and removed from the operating frame. The trap then is filled to a full mark with sterile transport media and sealed 28*b* with a glass stopper for transport to the core embryology genetics laboratory facility 174. The transport flask 28*b* is contained inside an insulated transfer block 31 and transported in an insulated carrying case The instruments are removed and the patient is discharged. The procedure from insertion of the suction cannula to embryo recovery in the trap is expected to take 15 minutes. The disposable portions of the instrument are discarded as medical waste, and the reusable portions are sterilized for reuse.

We now describe details of construction and mechanical operation of individual device components and illustrate them in FIGS. 13-64*e*.

FIG. 13 shows an example of the Version #1 operating frame and components in its undeployed configuration. It is a left side view of the completely assembled single catheter lavage instrument 8 in readiness mode (prior to uterine insertion). The operating frame 8 is a rigid platform for mounting and securing working elements of the system. The complete system, when mounted on the operating frame 8 platforms, is secured to an adjustable, movable, but rigid stand placed on the floor at the foot of the gynecological procedure table. The instrument is comprised of three elements on the operating frame: the operating frame 8, the suction recovery cannula 16, 22. As mentioned earlier, portion 22 of the suction recovery cannula is a tube that carries the embryos in fluid to the recovery container 28*a*; portion 22 extends into a larger diameter tube that is also part of the cannula and that we sometimes refer to as the large tube 16. Tube 16 also carries other elements of the instrument. Sometimes we refer to the cannula as cannula 16, 22.), and one fluid supply line 36 which is passed through an individual guide channel extruded at manufacture into the inner walls of the large tube of the suction recovery line 16, 22 at manufacture.

The fluid supply line 20 is attached to an external controller programmed to delivery lavage liquid to the uterus in pre-programmed periodic pulses. The operating frame platform 8, mounted on a hard stand 198 stabilizes the systems for cervical and intrauterine insertion of the suction recovery catheter 16, 22 and its steering control 26 for directing the fluid supply catheter 20 and its steel oval tip 10 before, during and after lavage recovery operations.

The operating frame 8 includes the operating slide 25 which stabilized, guides and slides the mechanically linked catheters, fittings, guides, tubing as they are directed into the uterus. The operating slide 25, calibrated in centimeters, is custom set before each procedure for each patient and limits uterine insertion depth of the suction line at its flanged tip 14 surrounded by a balloon collar 12.

Figure 13C:
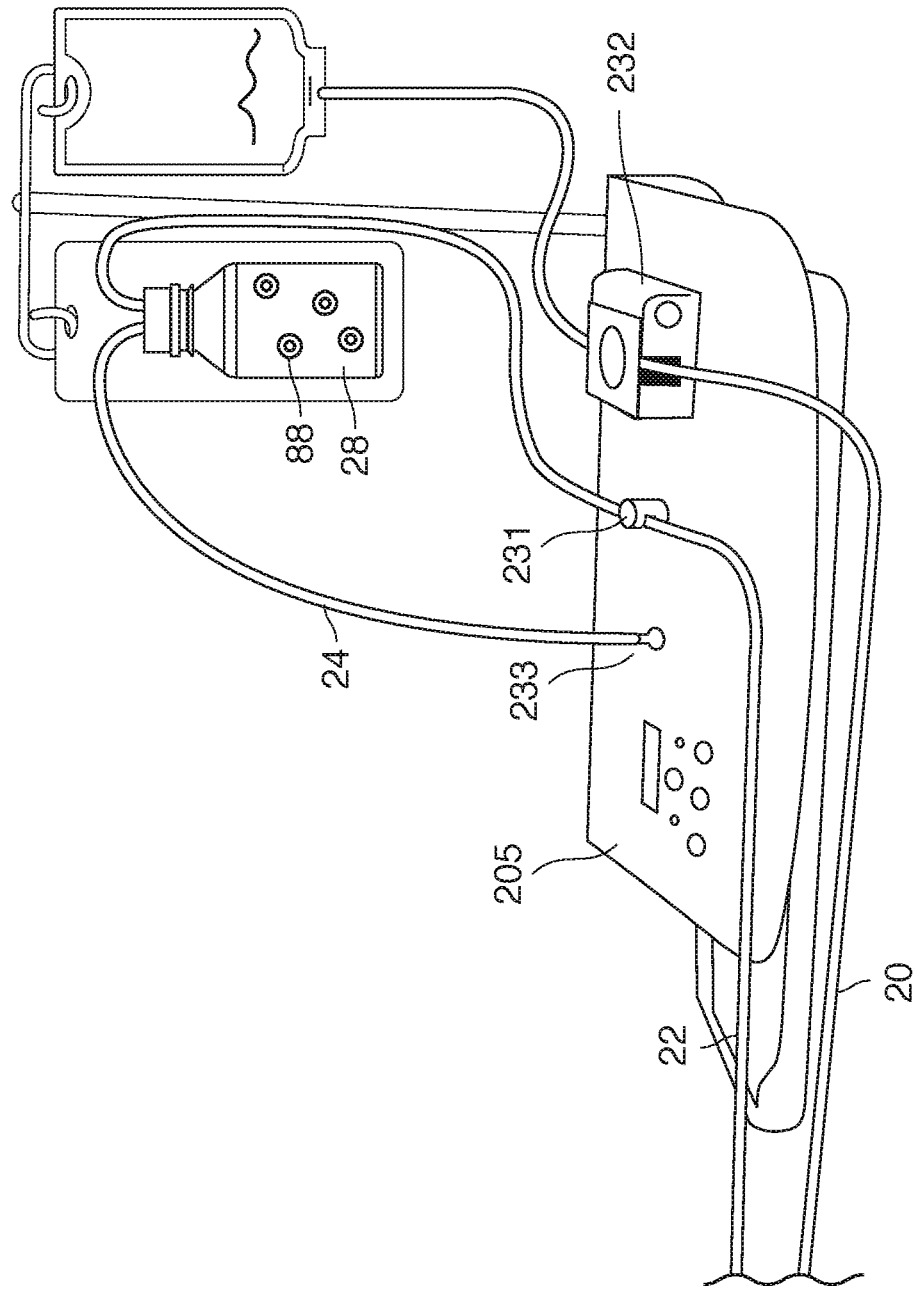
Figure 13D:
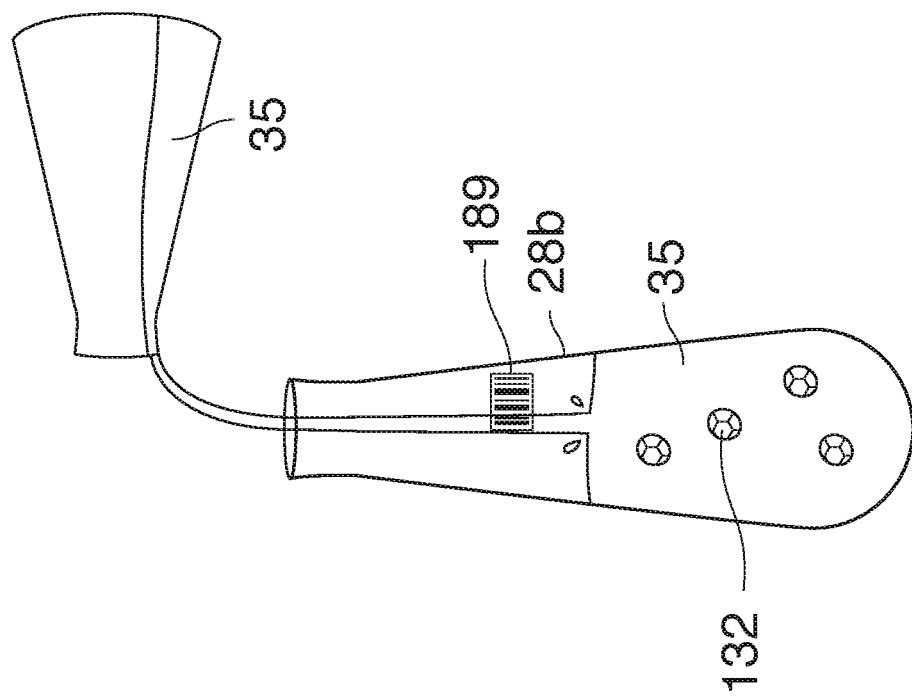
Figure 13E:
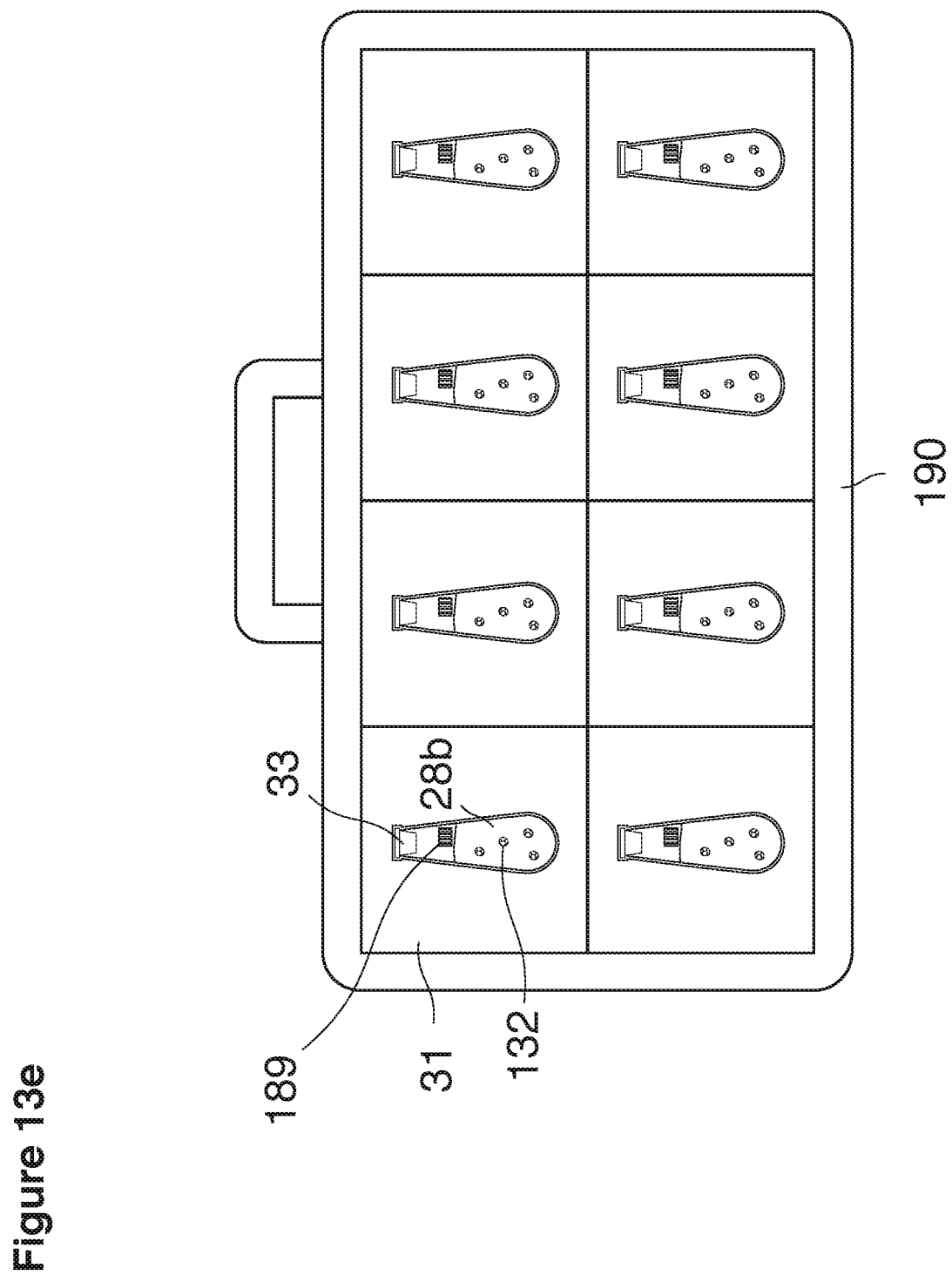
Figure 13F:
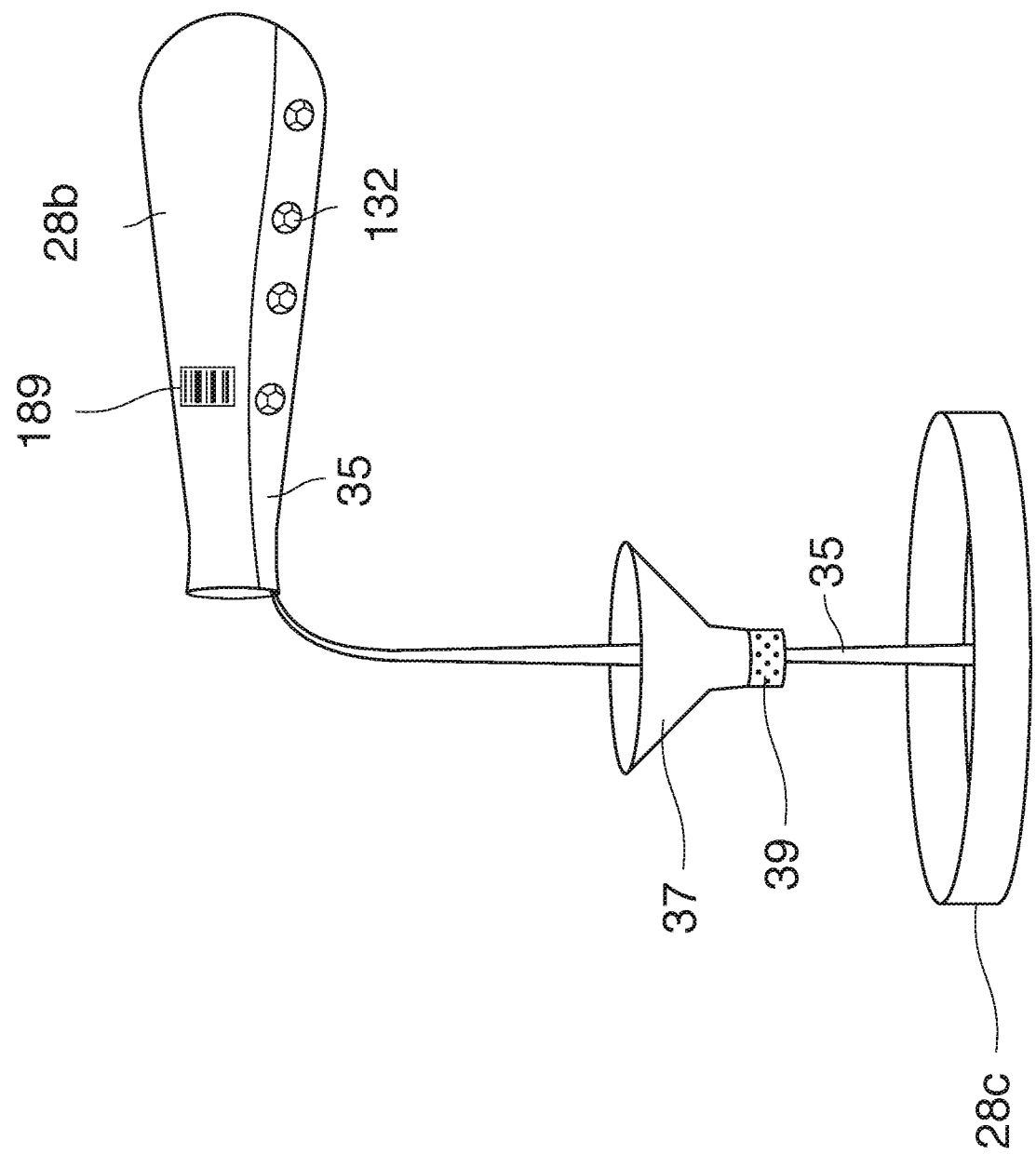

The vacuum line or port 24 is built into the base of the operating frame 8 and links directly to the vacuum pump 233 (FIG. 13*c*). The pump is controlled to apply an intermittent vacuum (syncopated to the pulsations of uterine lavage fluid that is being infused into the uterus) to the tubing and is connected to the embryo recovery trap 28*a* which collects all of the lavage fluid which contains all of the embryos. Vacuum pressure in the fluid delivery and collection device is managed via a pinch valve 231. The vacuum delivered in the embryo recovery trap is transmitted into the suction recovery cannula 22, which in turn is transmitted to the uterine cavity during lavage intrauterine infusion involved with embryo recovery. The trap 28*a* is removed at the end of the procedures and fluid recovered is transported in an insulated transport block 31 to the central embryo laboratory where it is scanned for embryos.

The suction recovery line 16, 22 is a seamless conduit for recovery of lavage fluid and embryos. The suction recovery line 16, 22 transports embryos seamlessly to the suction trap 28, which is mounted on the left side of the operating frame 8. The suction recovery line is manufactured by extrusion as a semi-rigid medical grade inert composite. The suction recovery line (FIGS. 18-25) 22 has a central suction recovery channel 23 (ranging from, 30-80% of its cross-sectional area in various versions) with two accessory channels, one channel for the fluid supply line 34 and the other for the balloon air supply 18, embedded into its walls at manufacture.

The embryo recovery trap 28 is connected to the vacuum pump through a perforated rubber stopper by a vacuum line. The outside diameter of the suction recovery cannula 22*a* ranges from 22-34 French according to design model and custom patient requirements.

At the beginning of the lavage procedure, the suction recovery cannula 22*a* is deployed through the cervix and into the uterus where it facilitates insertion and instrumentation of the uterus. A cervical stop 14 flange on the distal end of the suction recovery cannula 22*a*, rests against the external cervix and limits the depth of insertion of the suction recovery cannula 22*a* into the cervix. Custom adjustments ranging from 1.0 to 2.5 cm into the endocervix fix the depth and direction of the angled distal portion of the guide.

A cervical stop scale 74 is etched into the outside of the suction line arm 16 and marks the position of the cervical stop when it is custom-adjusted to each patient prior to insertion. The angle of the distal portion of the suction recovery line 22*a* is preset and varies from 0-45 degrees and is customized to individual women in order to accommodate the different anatomical variations of the uterine flexion.

The distal most portion of the suction recovery line 22*a* covers and shields the steel ball tip of the higher-pressure fluid supply line 20. The steel ball tip contains high precision double tapered ports for delivery of fluid under higher pressure relative to the tapered ports. The distal most portion of the suction recovery cannula endocervical guide 16 20, covers and shields the steel ball tip 10 of the fluid supply catheter (s) during insertion, maintains sterility, and avoids plugging of the higher pressured fluid supply catheter 20 with mucous.

The suction recovery catheter 16, 22*a* is tipped with an intracervical rubber inflatable collar 44, 46, 48, which when inflated immediately after insertion with 1-3 ml of air or fluid, serves as a watertight seal and funnel shaped intake port for recovery of lavage fluid. Its placement is immediately above the internal os of the lower uterus where it prevents completely the loss of lavage fluid around the suction recovery cannula 22 and 16 and outwards through the cervix into the vagina. It is connected to a controller programmed to both deliver lavage liquid to the uterus and apply vacuum in a pulse that alternates suction and pulses cadenced exactly the opposite fluid delivery at a preset frequency of, for example, 0.5 to 4.0 seconds.

The balloon collar is inflated using air or fluid delivered by an air supply syringe 116 connected to a channel extruded into the manufacture of the suction recovery line 22. The fluid or air is delivered through a balloon port 42.

The suction recovery line is connected seamlessly through a resin merger block 84 which links the recovery line 16, 22 seamlessly with the proximal line which delivers fluid into suction trap. The resin slide block 118, 120 is linked directly to a steering control wheel 26 which is manipulated by the hand of the operator and moves the supply line 20 back and forth into the supply line guide channel 34

The operating frame 8 is secured through an attachment hard point 199 to a rigid hard stand 198 fixed to the floor of the treatment room through a rigid handle 76 that contains and secures the suction line 24 port and channel.

A resin merger block 84 integrates the fluid supply line 20, suction line 16, 22, and balloon air supply line 18 into a seamless merger. The resin merger block is fixed to the main frame and does not slide. The slider block 118 moves with the operating slide 25 and can be locked into a fixed position by a slider block 120. The excursion of the operating slide is fixed proximally and distally, is adjusted individually for each individual patient, and is locked into position by its slider block 120.

Figure 14:
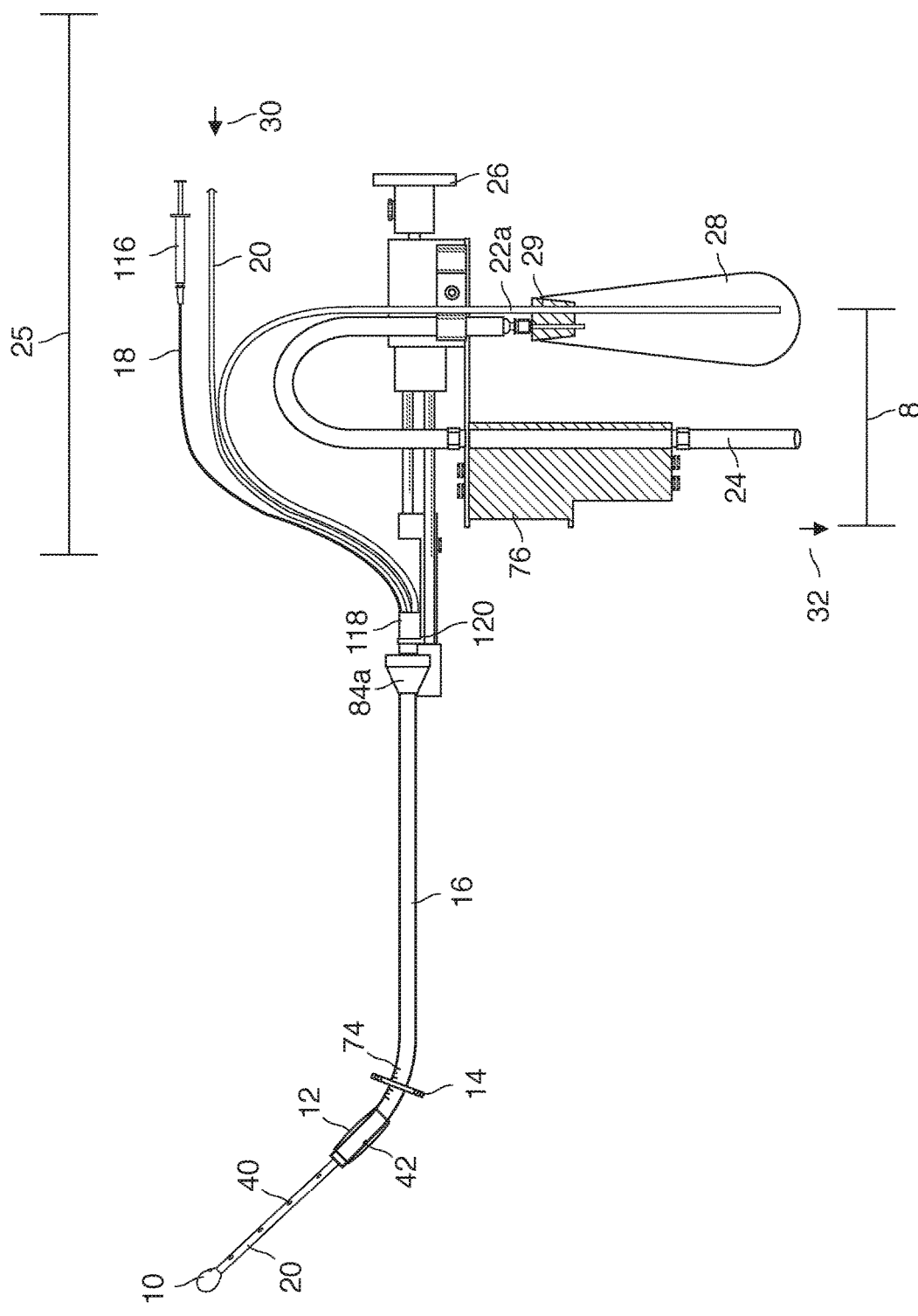

FIG. 14 shows an example of the Version #1 operating frame in its fully deployed configuration. It is a left side view of the completely assembled Version #1 uterine catheter instrument mounted on its operating frame 8 with its catheter mechanisms in fully deployed position (inserted fully into the uterus). The operating slide and control wheel are forward at maximum travel with the resin slider block 118 and the resin merger block 84 in full contact. The distal supply line 20 is fully extended with its steel ball tip 10 at maximum excursion where it would contact the top of the uterine cavity if actually inserted.

Uterine lavage fluid is delivered into the uterus at a low flow of fluid supply that does not exceed a maximum pressure of the device between about 2 PSI to 50 PSI through two tapered ports 38 machined into the steel ball tip 10 and twelve tapered ports machined into the middle and distal segments of lavage fluid supply line 20. Lavage fluid will be delivered in short low pressure pulses through the steel ball tip between 0.5 mL/s to 20 mL/s, e.g. 1 mL/s to 10 mL/s, e.g. 1 mL/s to 5 mL/s, e.g. about 1 mL/s with highly focused stream of fluid directed to the uterine cavity wall at a point below the internal ostia 126 so as to form a functional hydraulic wall through which the embryos cannot move retrograde from the middle uterine cavity into the respective right and left internal tubal ostia.

In this figure, the balloon collar 12 is uninflated. The cervical stop 14 will be pushed firmly against the cervix adjusted for the internal length of the endocervical canal. The balloon collar 12 is then fully inflated and is pulled taut over the endocervix determined by the setting of the cervical stop 14 to form a water tight funnel to the outside of the uterus to assure no losses of uterine lavage fluid.

Figure 15:
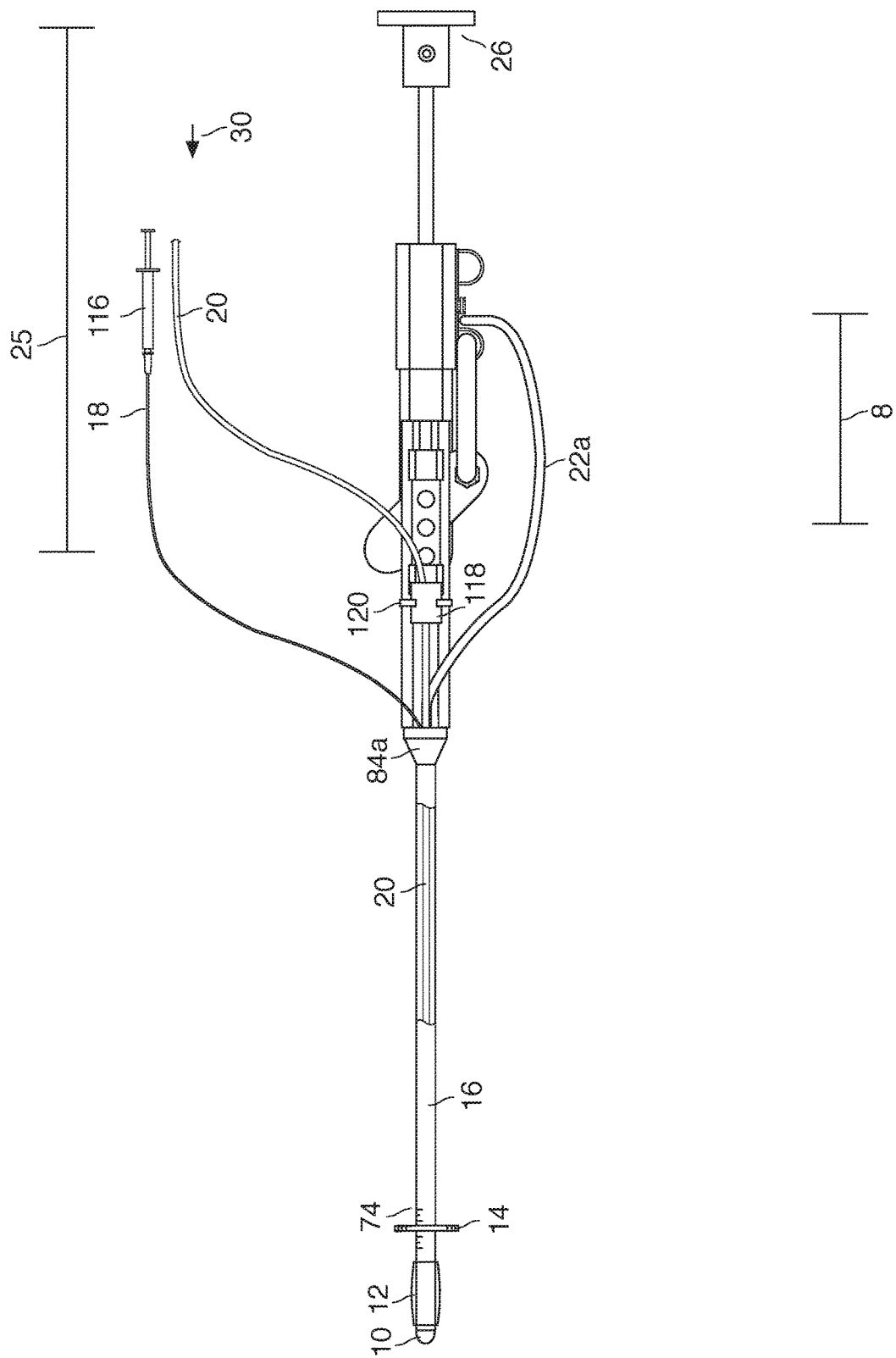

FIG. 15 is a top view of an example of the Version #1 operating frame and the uterine catheter instrument in its undeployed configuration. The distal suction line 16 port protects the distal steel ball tip 10. The uterine supply line 20 is linked to the controller fluid delivery pump 232. The steering control wheel 26, resin merger block and resin slider block are in their extended, undeployed position.

Figure 16:
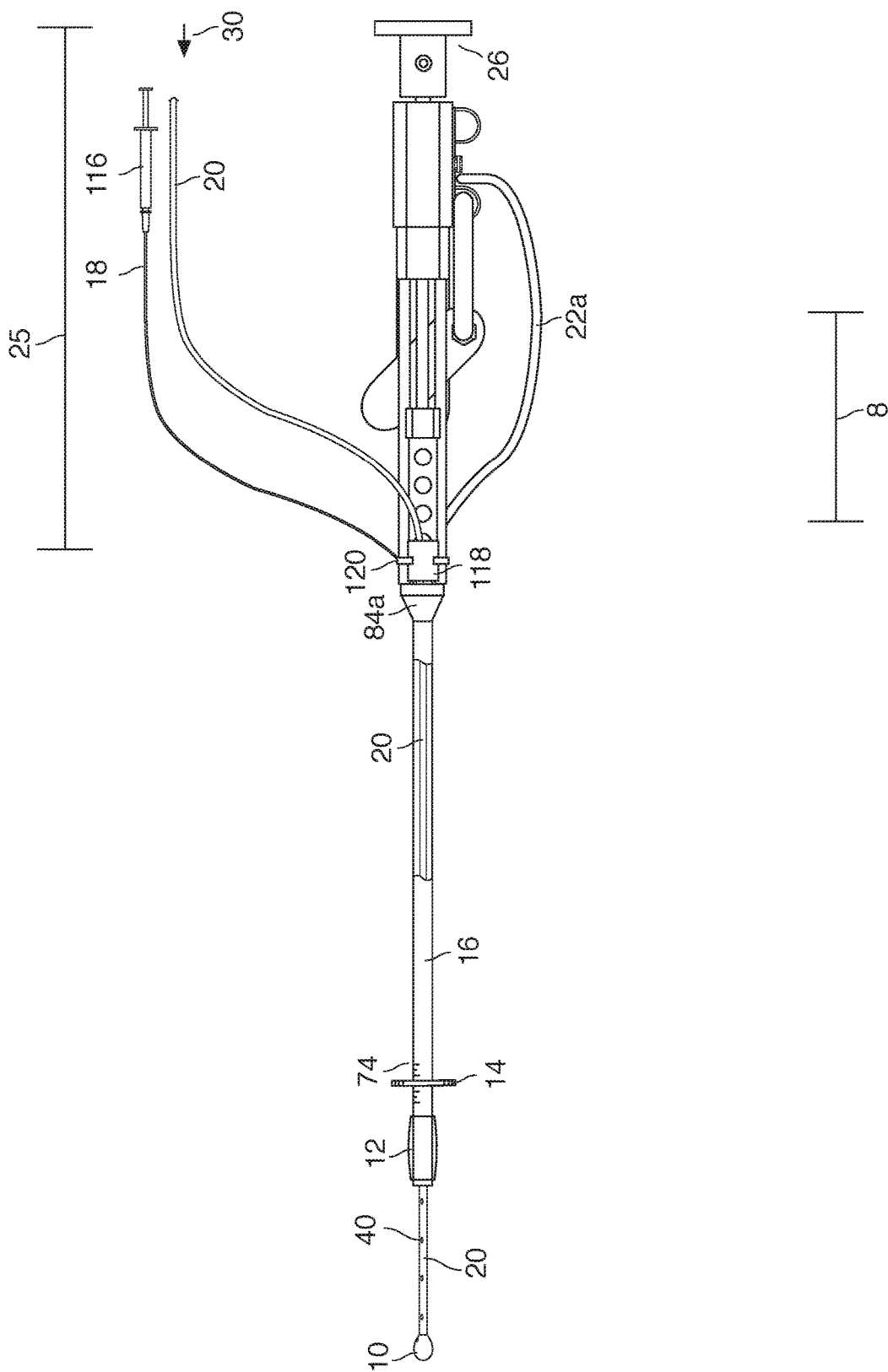

FIG. 16 is a top view of an example of the Version #1 operating frame 8 and the uterine catheter instrument in its fully deployed configuration. The resin slider block 118 is fully extended to the distal travel of the operating slide 25 and is pushed against the resin merger block 84*a*. The steel ball nozzle tip is fit to the uterine cavity exposing the tapered ports 40 to delivering lavage fluid into the central part of the uterus from the fluid supply line 20. The balloon collar 12 is not inflated. Cervical stop 14 is fixed by pre-measuring of the patient according the scale attached to suction line 16 and 22*a*.

FIG. 17 is a left side view of the Version #1 suction recovery line 22*a* and resin merger block 84*a* showing seamless integration of the suction recovery channel 23 and line 22, fluid supply line channel 34, and balloon air supply line 18 which are extruded into the catheter at manufacture. The fluid supply line 20 is not shown in this figure.

Figure 18:
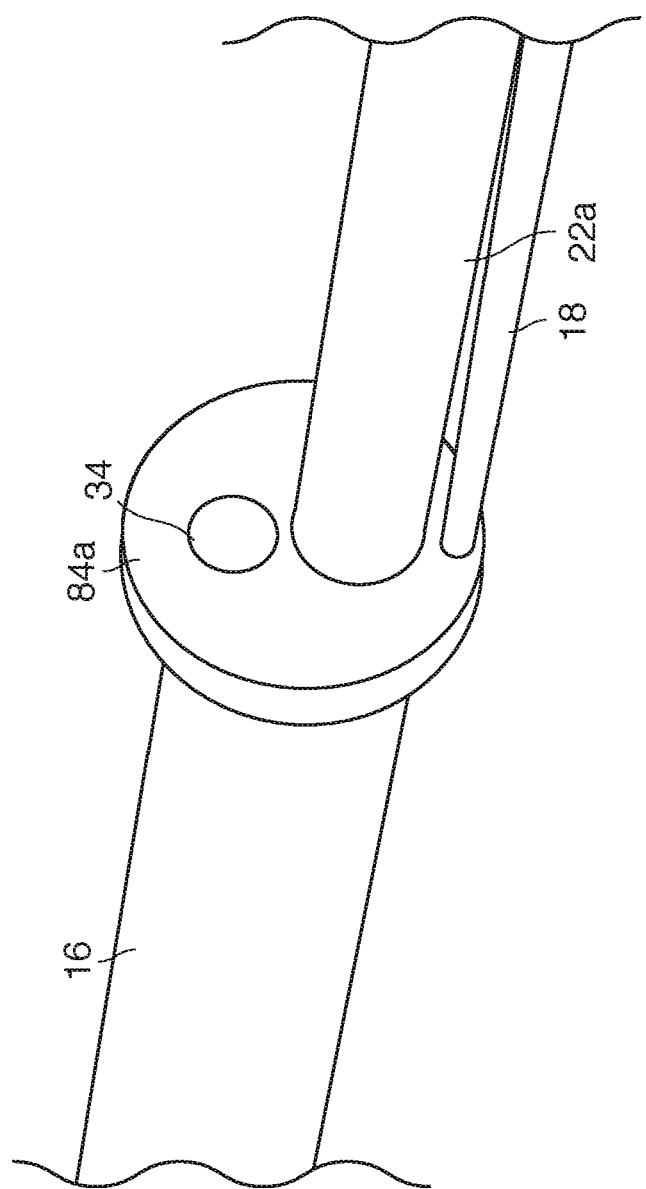

FIG. 18 is an enlarged ¾ view of the Version #1 resin merger block 118. The suction line 22*a* is connected seamlessly to the suction line extruded into 16 the suction arm 16 at manufacture. A single supply line channel 34 is supplied for insertion of the supply line 20, which is not in the figure. The balloon collar air line 18 runs in the wall extruded suction line arm 16 its full length to open in its port 42 inside the balloon collar at the tip of the catheter.

Figure 19:
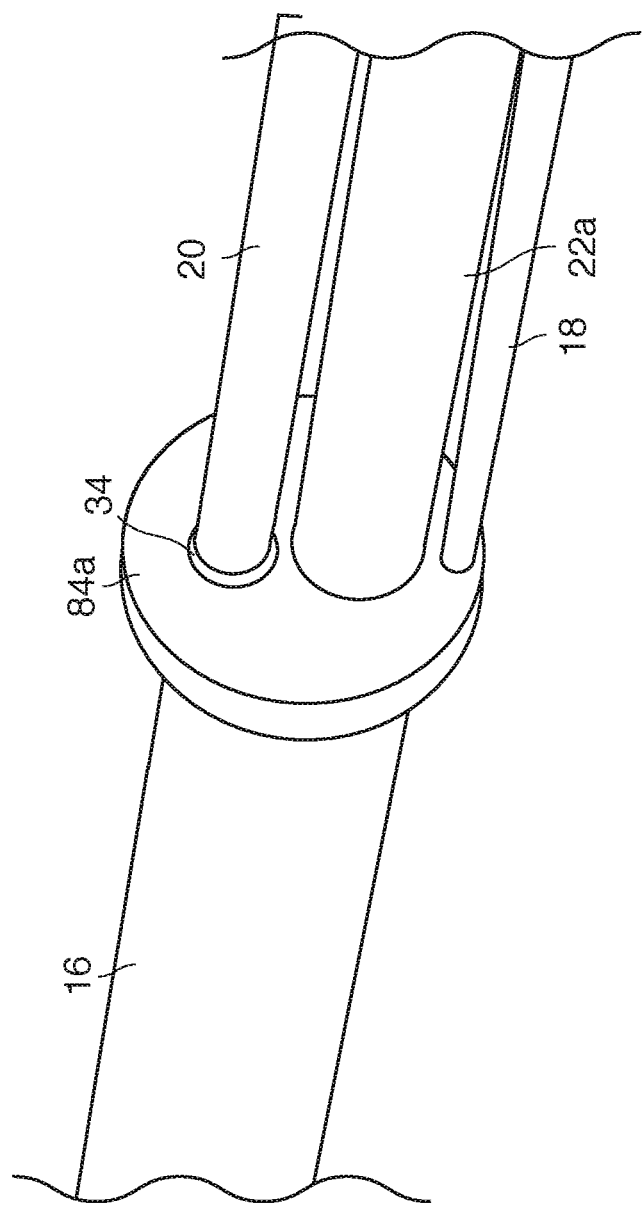

FIG. 19 shows the Version #1 merger block with the fluid supply line 20 now in place to its own port 34. The supply line 36 is attached rigidly to the resin slider block 118, which is linked to the steering control 26 and the operating slide 25 (FIG. 15,16).

FIG. 20 is a left longitudinal cutaway of the Version #1 distal suction line with the fluid supply line in undeployed mode. Tapered low flow ports 40 (six on each side) are spaced at fixed intervals to deliver lavage fluid directly into the middle part of the uterine cavity during lavage and break up the mucous content of the middle part of the uterus where embryos are located. The steel ball tip contains two highly machined tapered ports 38 delivering lavage fluid under higher pressure relative to the tapered ports directly just below the internal ostia against the uterine wall. This figure is an undeployed configuration.

Figure 21:
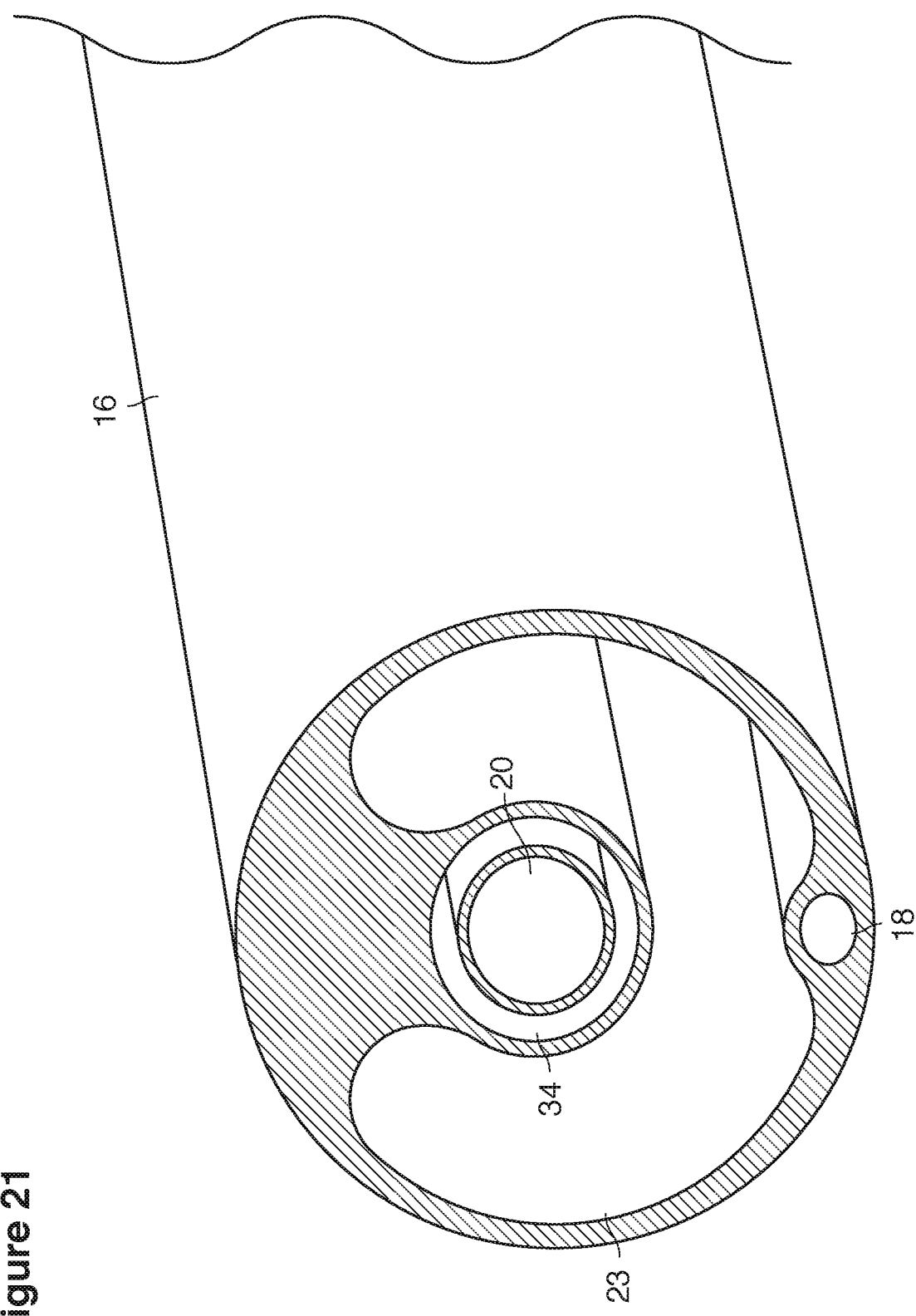

FIG. 21 is a left oblique cross section of the Version #1 distal suction line 16 showing the extruded configuration of the suction channel 23. Extruded seamlessly into the wall of the suction recovery line 16 is the channel for the lavage fluid supply line 34, the supply line 20, and the air line for the balloon collar 18

Figure 22:
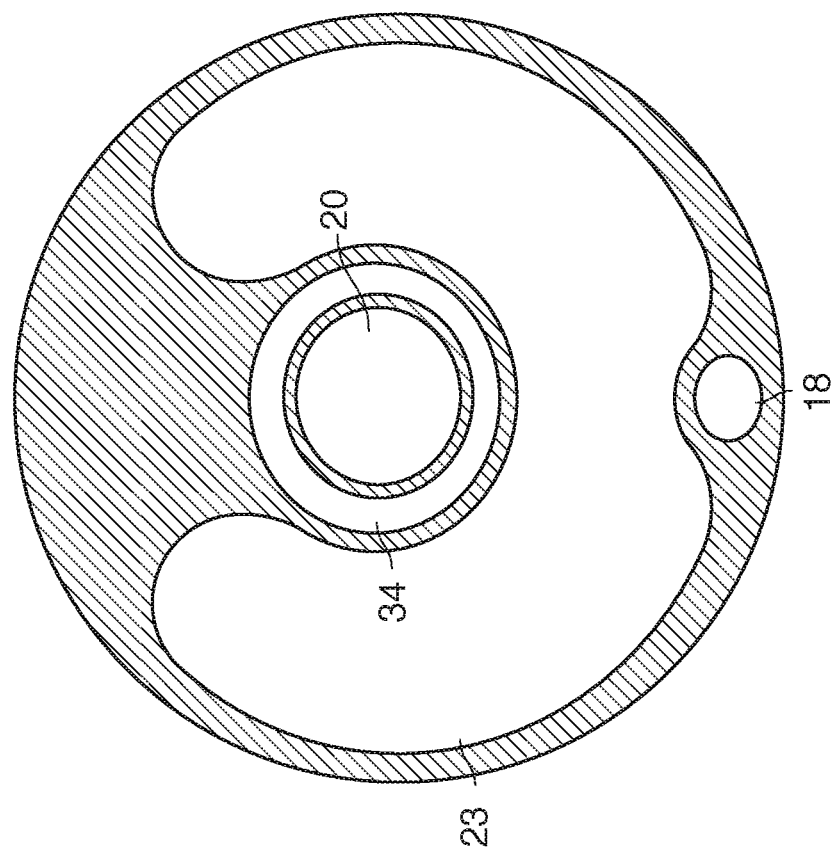

FIG. 22 is a cross section view of the Version #1 distal suction line 16 showing the configurations of the suction channel 23, the lavage fluid supply channel 34, the lavage fluid supply line 20, the balloon collar air line 18, and the arm of the suction catheter 22.

FIG. 23 is a left side view of the Version #1 distal suction line 16 showing the cervical stop 14, the etched centimeter scale to each patient 74, and the distal arm of the suction line 16.

Figure 24:
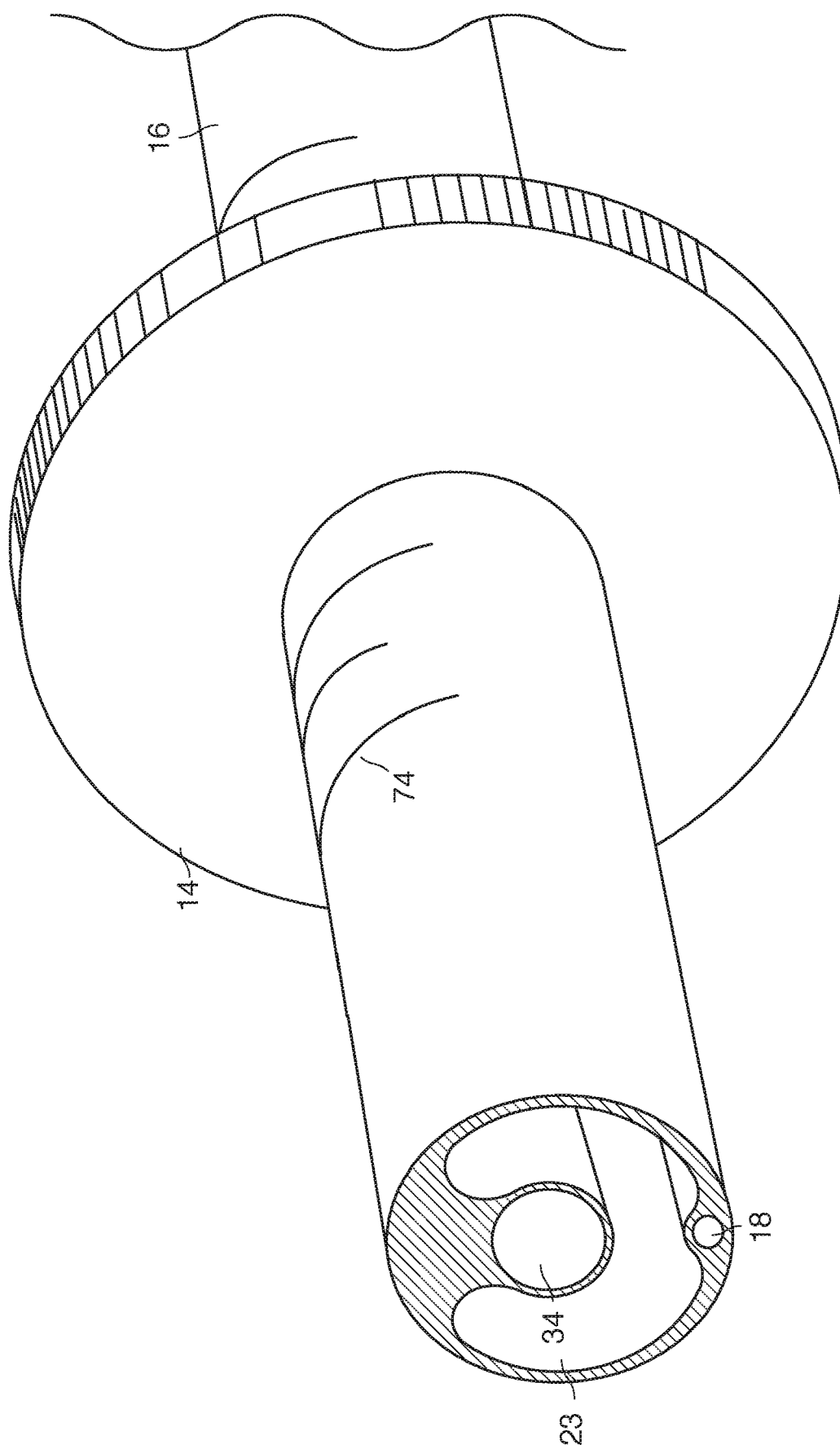

FIG. 24 is a left oblique cross section of the Version #1 distal suction line 16 showing the cervical stop 14, the cervical stop scale 74, the suction line 22, with suction channel 23, the balloon air supply line 18, and the fluid supply line guide channel 34.

Figure 25:
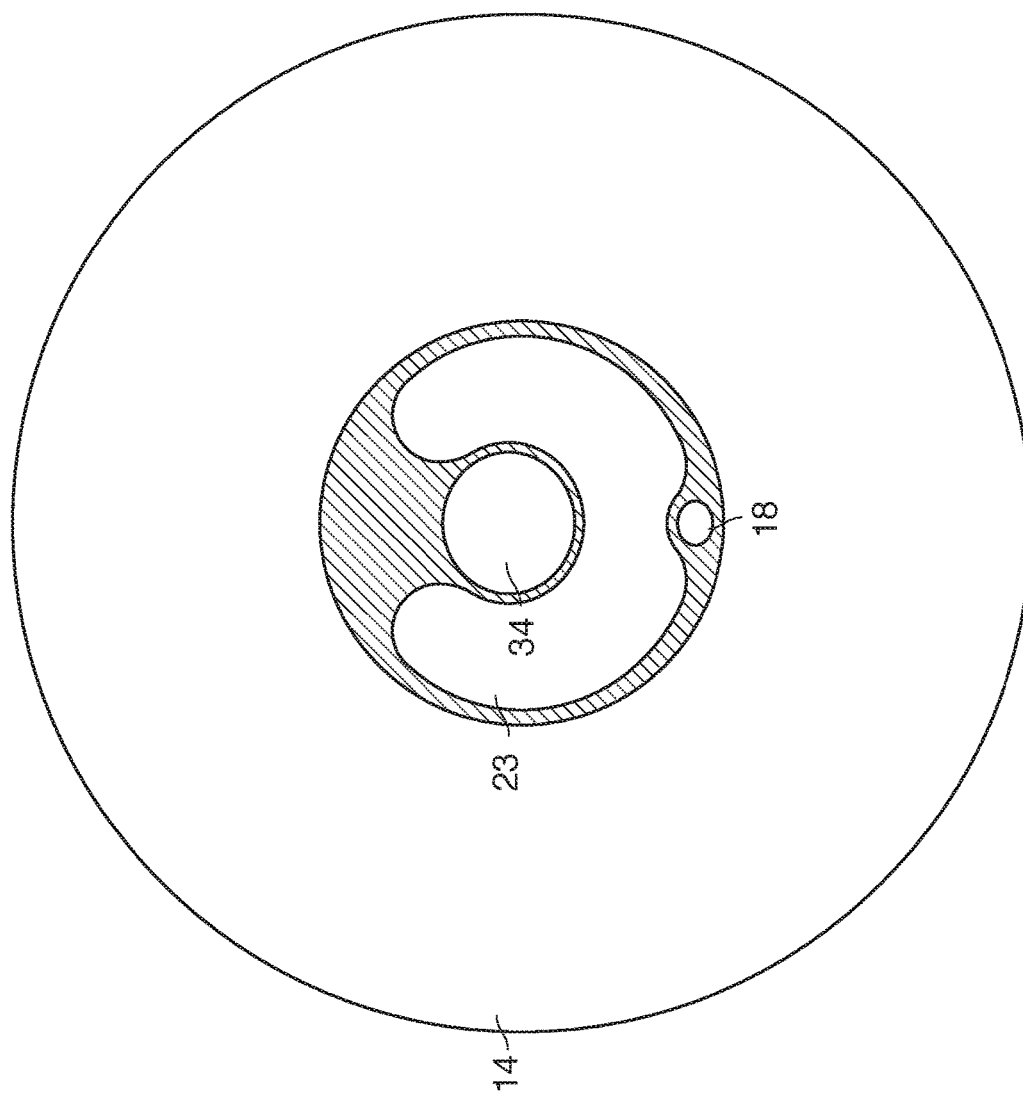

FIG. 25 is a cross section of the Version #1 distal suction line 16 showing the cervical stop 14, the suction channel 23, and the supply line channel 34. This distal cut is taken just distal to the cervical collar 14.

Figure 26:
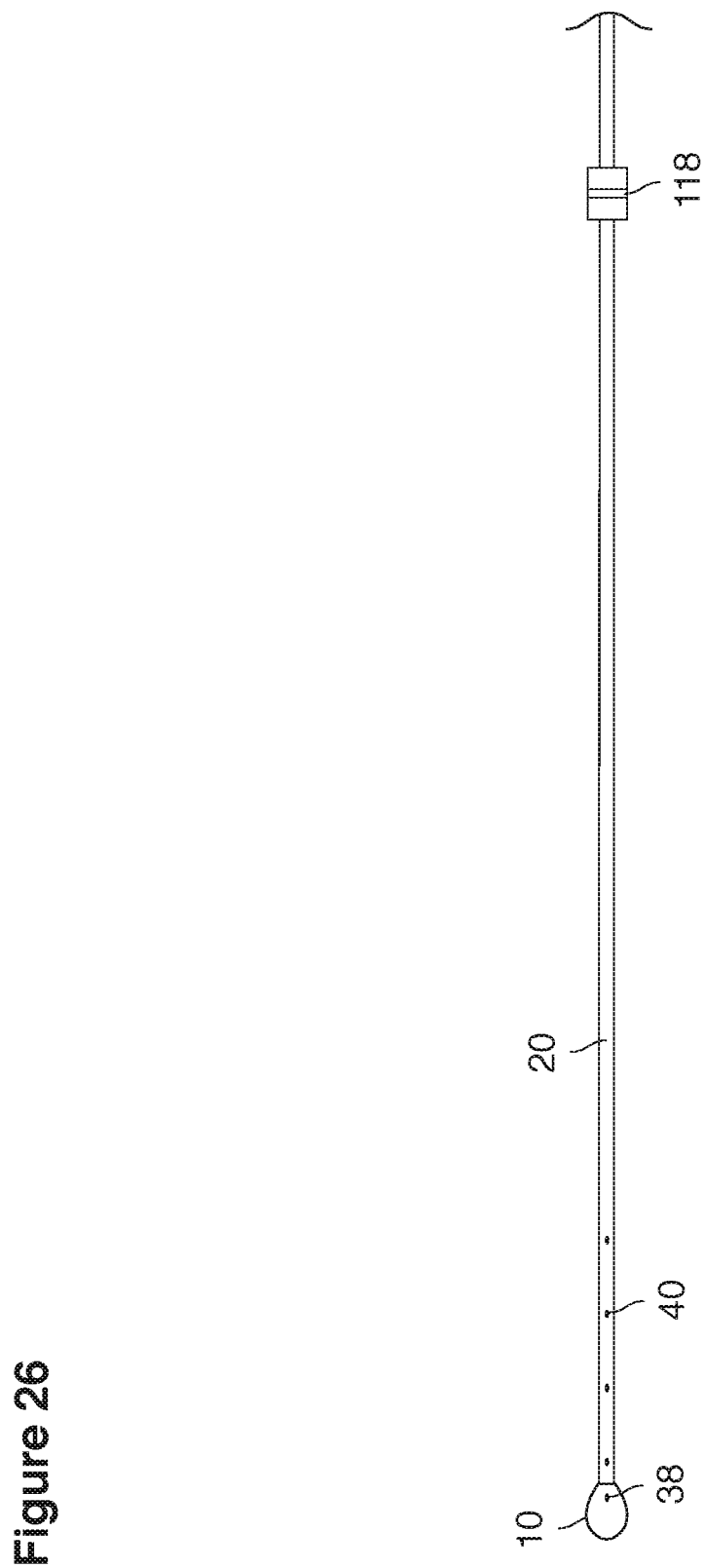

FIG. 26 is a left side view of the Version #1 fluid supply catheter showing the resin slider block 118 which is fixed to the operating slide 25, the tapered fluid delivery ports 40 delivering fluid to the middle of the uterine cavity, and the steel ball tip 10 with the tapering low pressure fluid delivery ports 38.

Figure 27:
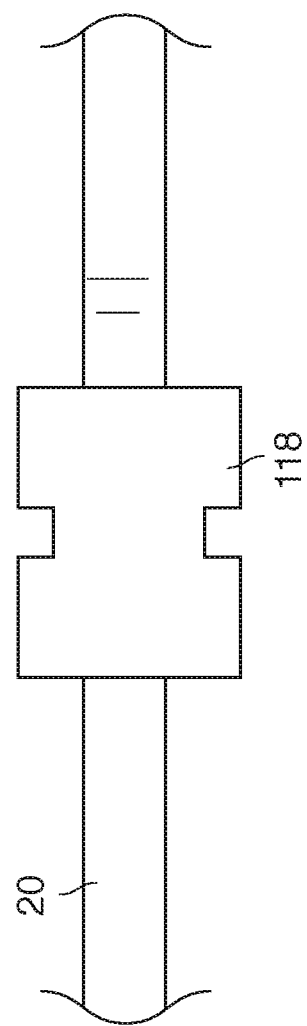

FIG. 27 is the Version #1 resin slider block 118 that fixes the fluid supply line 20 with notches that secure it to the operating slide 25.

Figure 28:
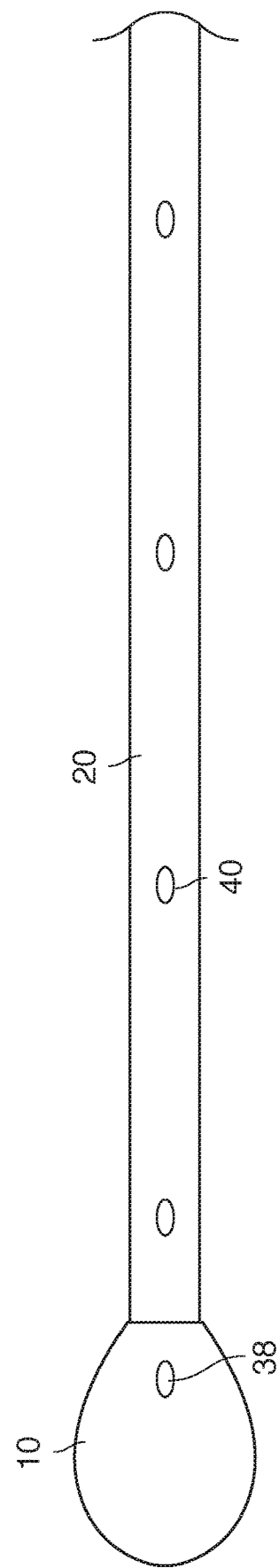

FIG. 28 is an enlarged left sided view of the Version #1 distal fluid supply line with the 8 tapered ports 40, steel ball tip 10, and tapered ports 38.

Figure 29:
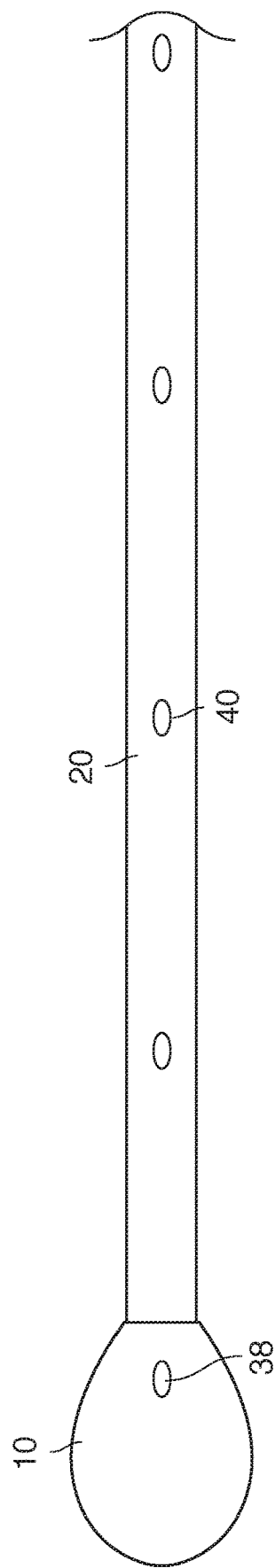

FIG. 29 is an enlarged right sided view of the Version #1 distal fluid supply line with the 8 tapered ports 40, steel ball tip 10, and tapered ports 38.

Figure 30:
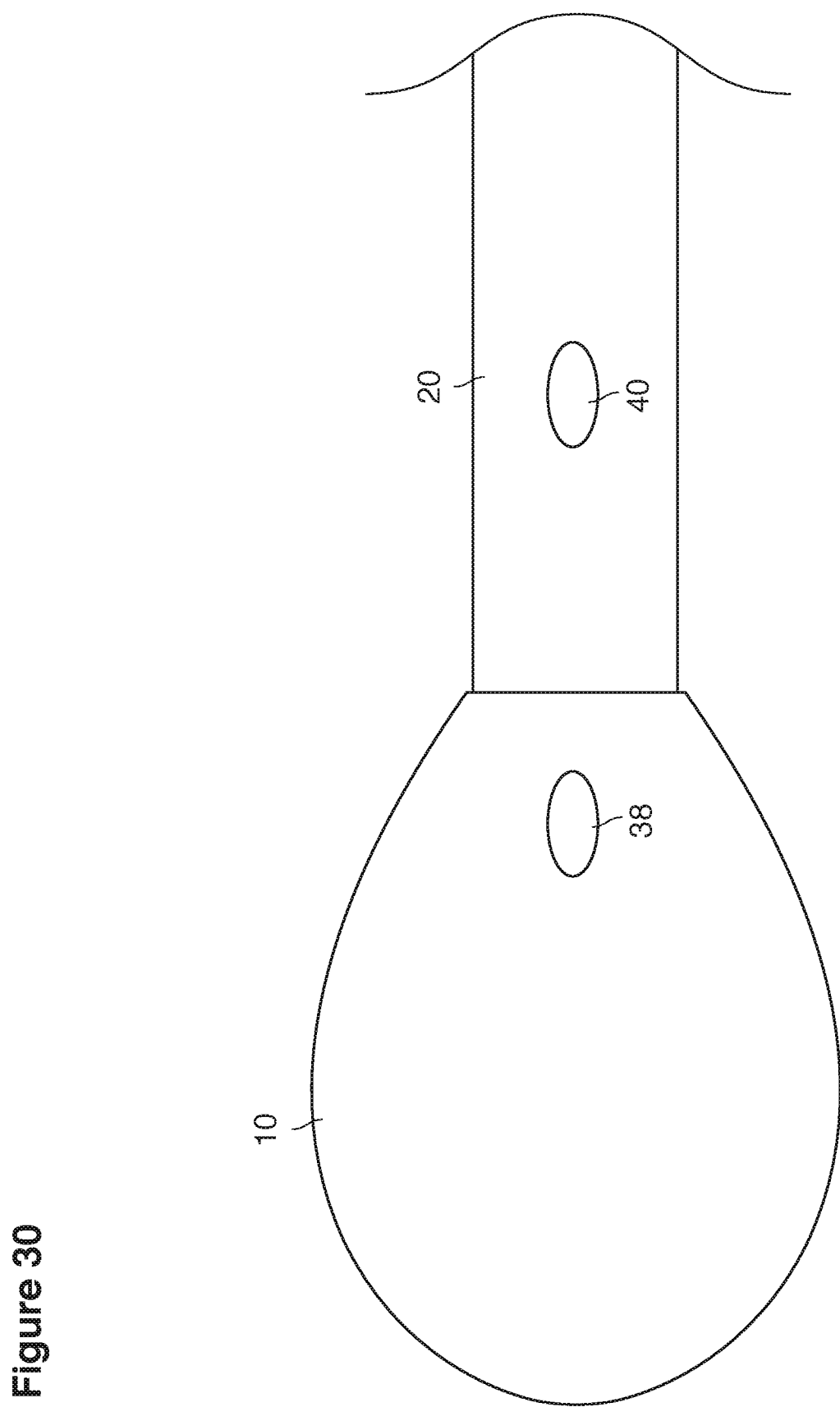

FIG. 30 is an enlarged view of the Version #1 steel ball tip 10 showing the tapered delivery ports 40 seamlessly attached to the distal fluid supply line 20 with one example of the 8 tapered ports designed for low pressure fluid delivery to the middle uterine cavity 126.

FIG. 31 is a half cutaway of the Version #1 steel ball tip showing the tapered ports machined into the steel ball 10 and the tapered ports 40 designed for low pressure delivery at the middle part of the supply line intended for delivery into the middle uterine cavity 126.

Figure 32:
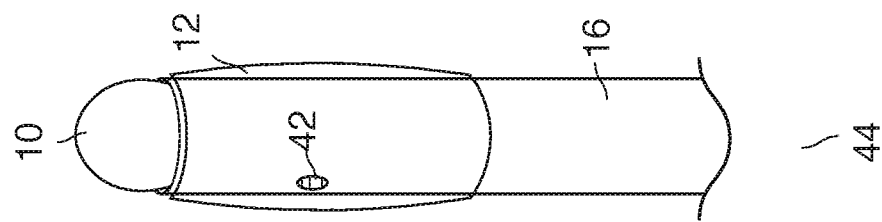

FIG. 32 left is the uninflated Version #1 balloon collar 12, the steel ball tip 10 which is undeployed and covered, and the port 42 for air delivery to the balloon 12.

Figure 33:
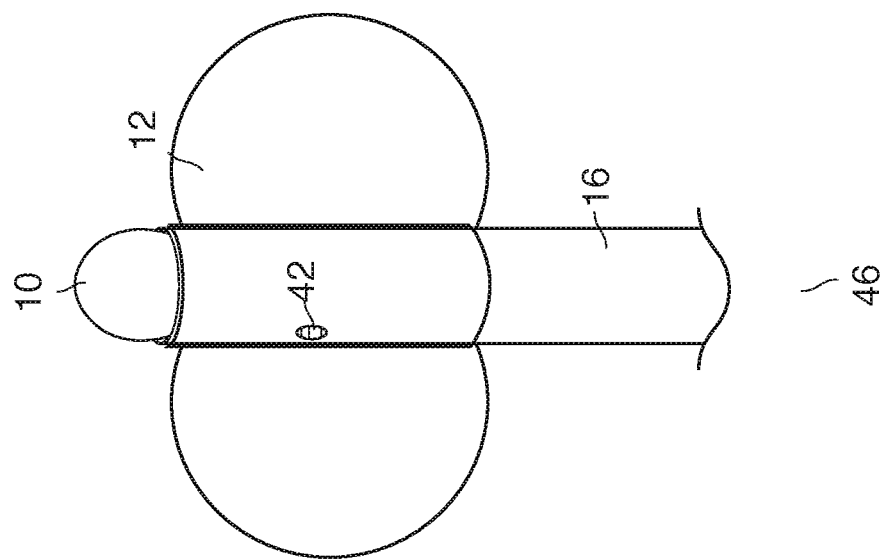

FIG. 33 right shows a balloon collar 12 deployed but free standing and not in the uterus so it is not deformed into a funnel.

Figure 34A:
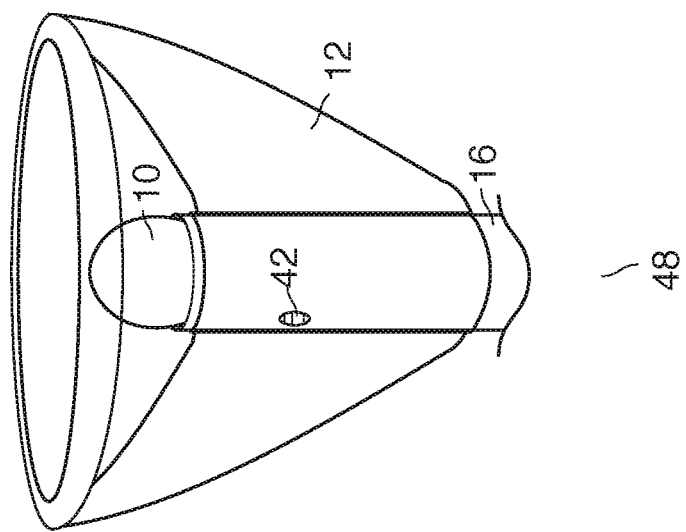
Figure 34B:
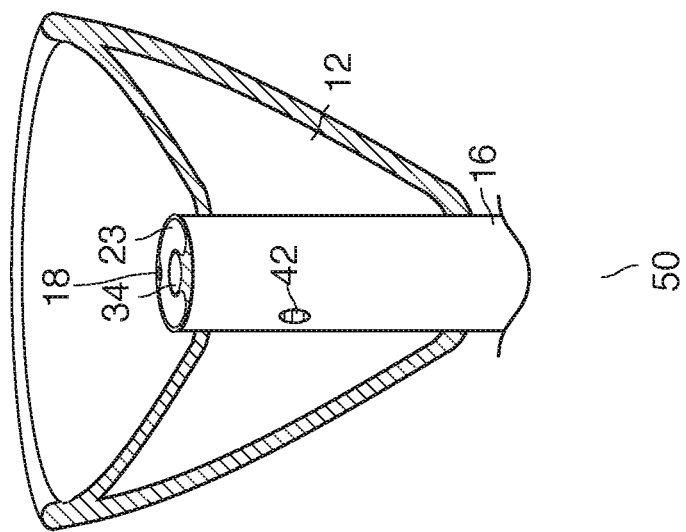

FIGS. 34a and 34b show the Version #1 balloon collar 12 deployed as it would be in the uterus at the internal os and lower uterine cavity 126. The steel ball tip 10 is undeployed. The tension of the cervical stop 14 causes the balloon 12 to deform into the shape of the lower uterine segment producing a water-tight seal so that lavage fluid cannot escape. When the balloon is deformed downward, it forms a water-tight funnel 48, 50.

FIGS. 35a-f illustrate Version 1 catheter placement and lavage fluid flow as it would be deployed in the uterine cavity.

In Version #1, a single supply line ending in a steel ball tip 10 with internally tapered ports 38, directs flow of lavage fluid from the steel ball tip 10 into the lateral uterine cavity 126 just below both internal tubal ostia 104 106 as well a fluid into the middle uterine cavity 126 from ports directly into uterine fluid surrounding the embryos 72 102.

As illustrated in FIGS. 35e and 35f, the fluid flow is then deflected from the lateral uterine wall into the fluid containing the embryos in middle uterus where it further dislodges them and directs them into the port of the suction line at the base of the funnel balloon. The steel ball tip produces a higher-pressure highly focused flow of lavage fluid relative to the tapered ports, which forms a hydraulic wall that functionally obstructs the internal ostia 104,106.

Figure 35A:
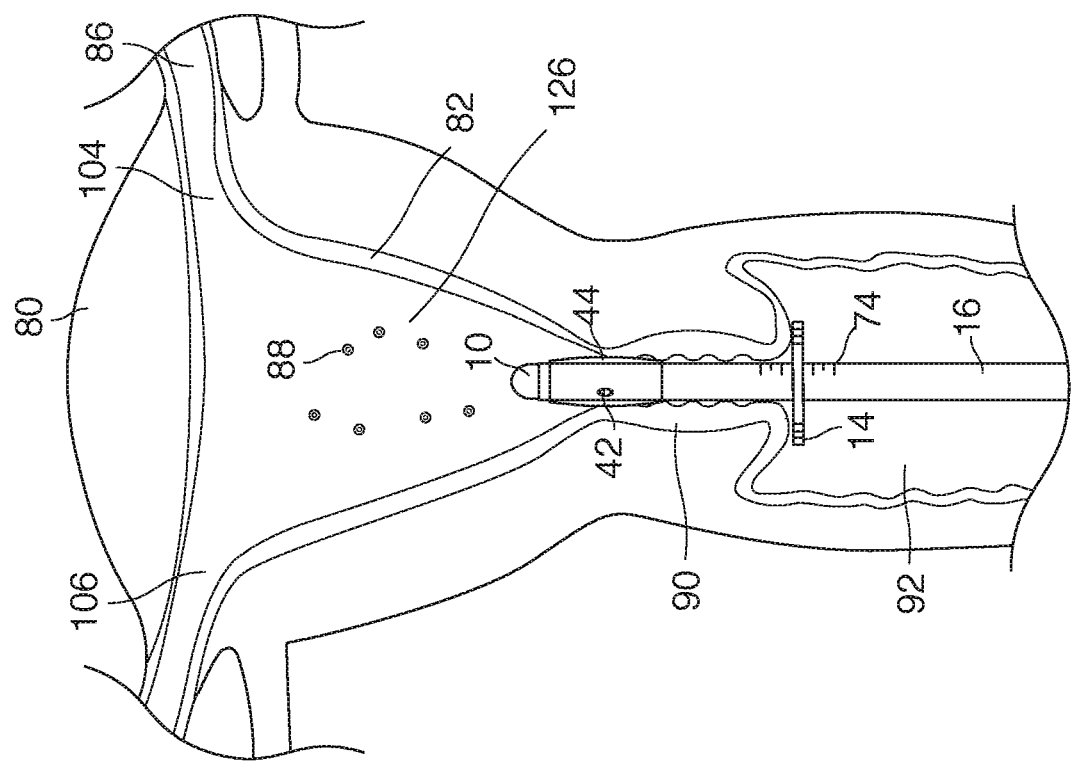
Figure 35B:
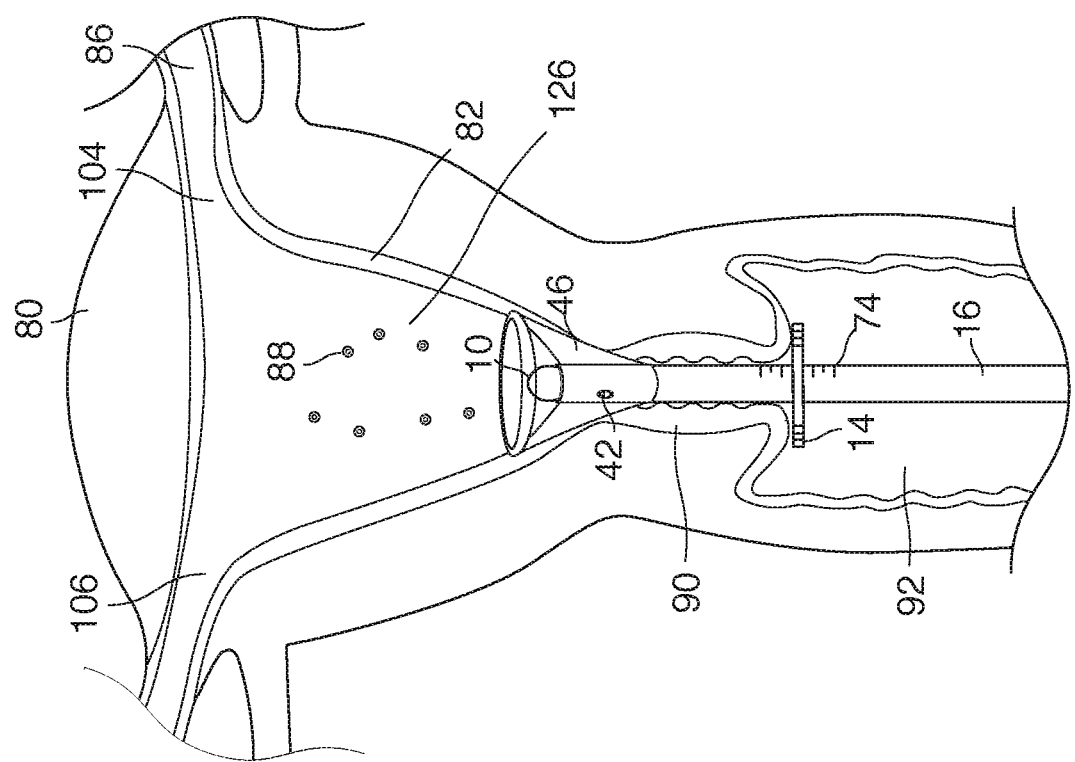
Figure 35C:
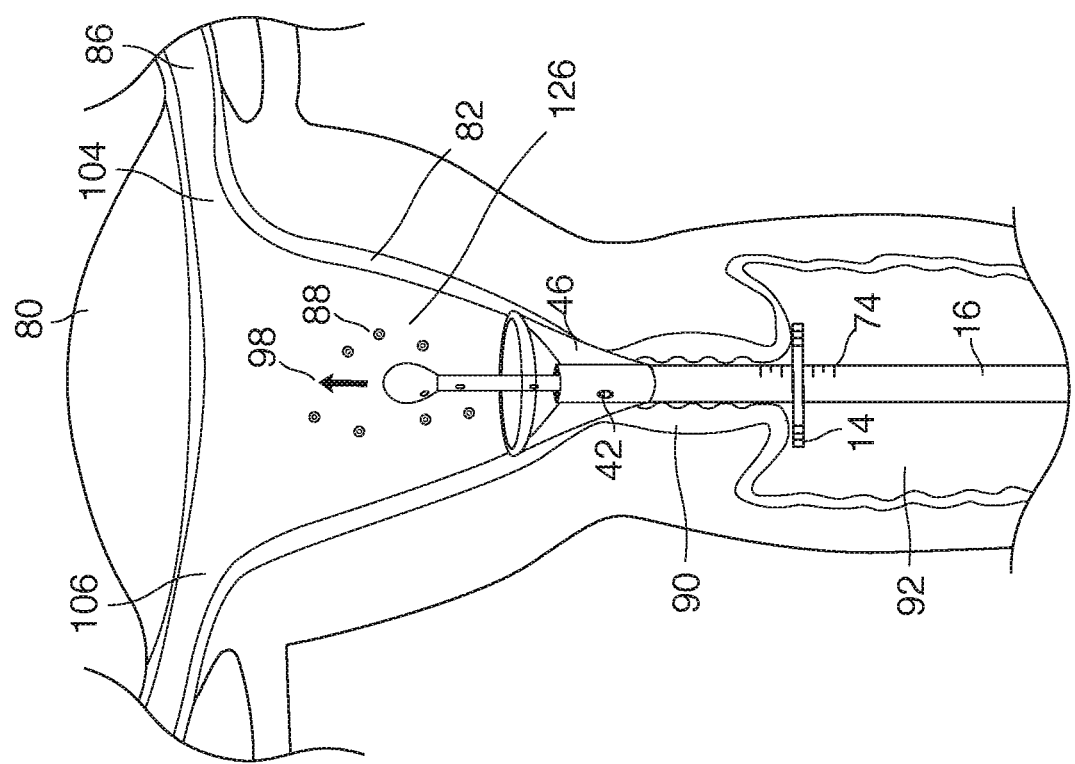

FIGS. 35a and 35b depicts the uterus at time of insertion of the Version #1 tip. In FIGS. 35a through 35d, the steel ball tip 10 and single supply line 22 are passed through the intrauterine fluid surrounding the embryos 102 in mid uterine cavity 126 just above the catheter tip. The balloon 44 is shown in FIG. 35a in a collapsed position; it will be filled with air or fluid which is insufflated through the balloon port 42. The cervical stop collar 14 is preset to allow introduction of the catheter tip to a precise pre-established depth. In FIG. 35a, the entire apparatus is passed through the vagina 92 to its position in the cervical canal protruding slightly into the cavity 106.

In FIG. 35b, the balloon collar 44 has been inflated 46 and is thereafter deformed into a funnel shape held tightly in the lower uterine cavity 126 by tension maintained by the cervical collar 14 at the external cervix. The tightly held funnel balloon collar 46 forms a watertight seal such that no lavage fluid loss can be lost through the cervical canal 90, 157, In FIG. 35c the steel ball tip 10 is introduced into the middle uterine cavity 98, 126 and passes through the embryos 88 on its way to the top of the uterine cavity 126 The deployment of the steel ball 10 is guided by to the steering control wheel 26 which can be used in a proximal and distal motion directed by the operating slide 25 where it is linked through the resin keyblock 120.

Figure 35D:
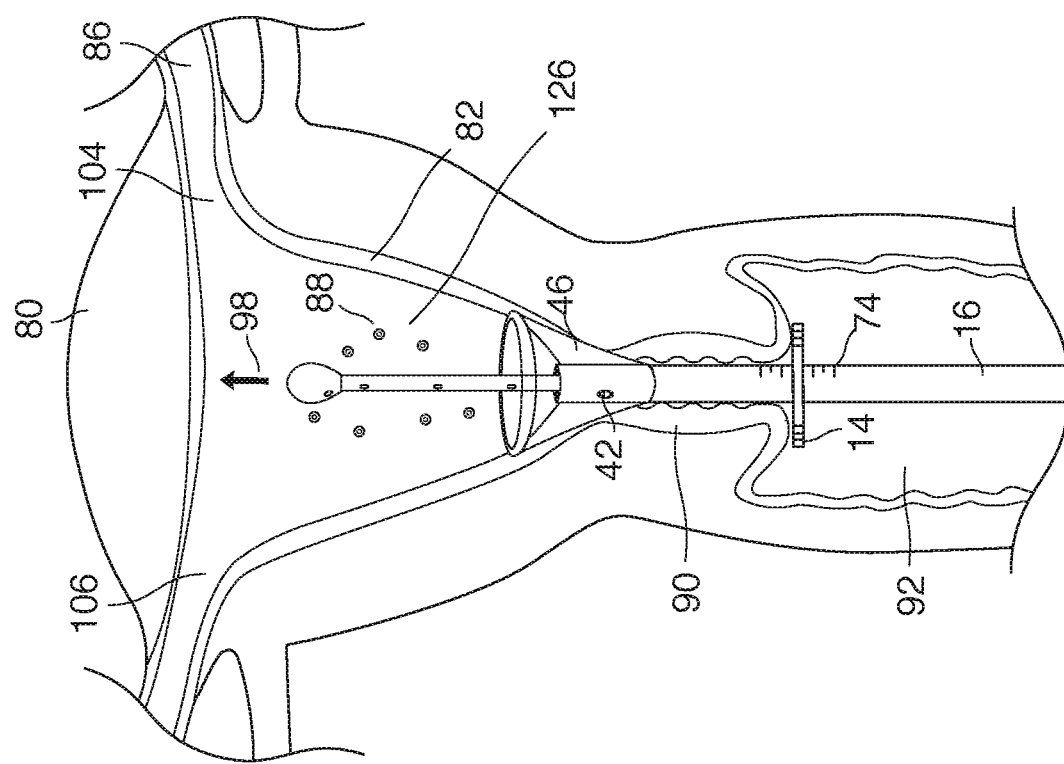
Figure 35E:
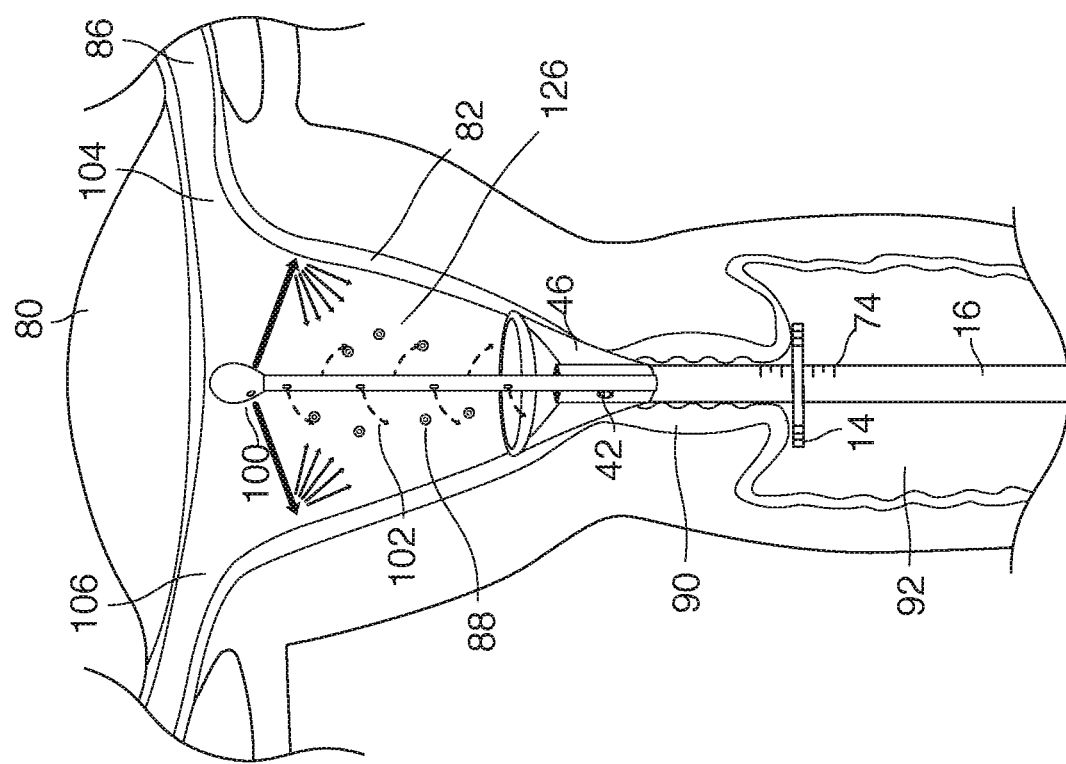
Figure 35F:
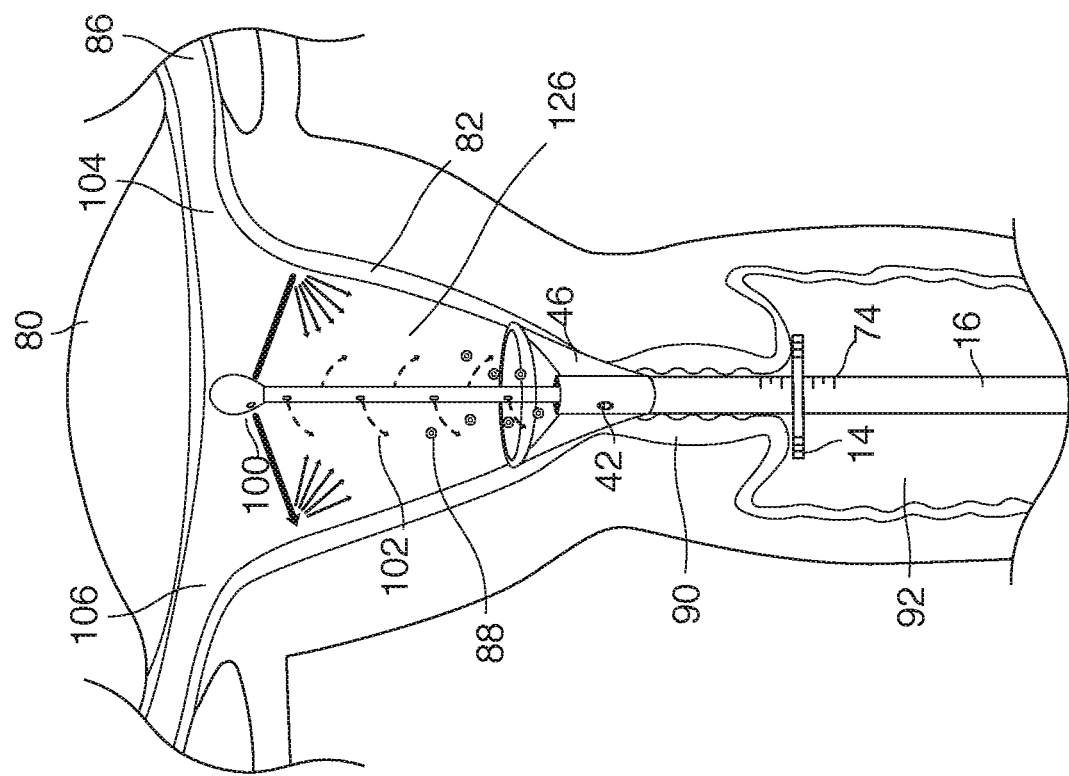

In FIG. 35d, the steel ball tip 10 is steered through the embryonic implantation sites 88 toward the top of the uterine cavity 80, 126. The embryos 88 are floating in uterine fluid 161 and would not be expected to be significantly dislodged by the passage of the supply line 20 and steel ball tip 10.

In FIG. 35e the steel ball tip 10 has been passed to the top of the uterine cavity and fundus 80. Fluid is delivered under low pulse pressure to the supply line 22 through tapered ports 38 in the oval steel tip 10. The steel ball tip 10 contains two internally tapered ports 38 delivering higher pressure and higher flow relative to the tapered ports, and highly focused fluid streams in directions that differ by, for example, 90-150 degrees and pointed immediately below both internal ostia 104 106. Their highly focused streams forms a hydraulic wall that functionally obstruct the internal ostia 104 106 so that no fluid escapes through the oviducts 86 104 106.

This angle of flow is customized to the unique anatomy of each individual patient as determined by pre-treatment ultrasound imaging. There should be no fluid escaping through the internal ostia to the oviduct 104 and 106. Under the same pulsatile pressure, lavage fluid is directed simultaneously through rows of proximal ports of the supply line 102 into the mid-segment in of the uterine cavity 126. Coincidentally suction is applied to the suction line 16 to the balloon funnel 46 to allow flow of the lavage fluid out the suction line 16 with no losses around the initiated by the funnel balloon 36. Intermittent pulsatile flow through the steel ball tip 10 and through the tapered catheter ports 38 allows for orderly breakup of uterine fluid containing embryos through the funnel in the suction line 16 to the embryo recovery trap 28. By the combination of direct low pressure stream-forcing embryos away from the internal ostia 104 and 106 combined with the funnel balloon 46 there should be no lavage fluid or embryonic losses. Thus this arrangement and other features of the instruments and procedure are designed to achieve the ideal goal of removing all of the embryos present in the uterus through the suction line, to leave none of them in the uterus, and to force none of them into the ostia.

In FIG. 35f, the blastocysts are delivered into the balloon funnel and the suction cannula port for transport through the suction catheter 16 and embryo trap 28. At the termination of the lavage procedure, the entire apparatus is removed from the patient and the procedure is terminated. The fluid collected in the embryo trap 28 is taken to the central laboratory for recovery and genetic processing of the embryos.

Figure 36:
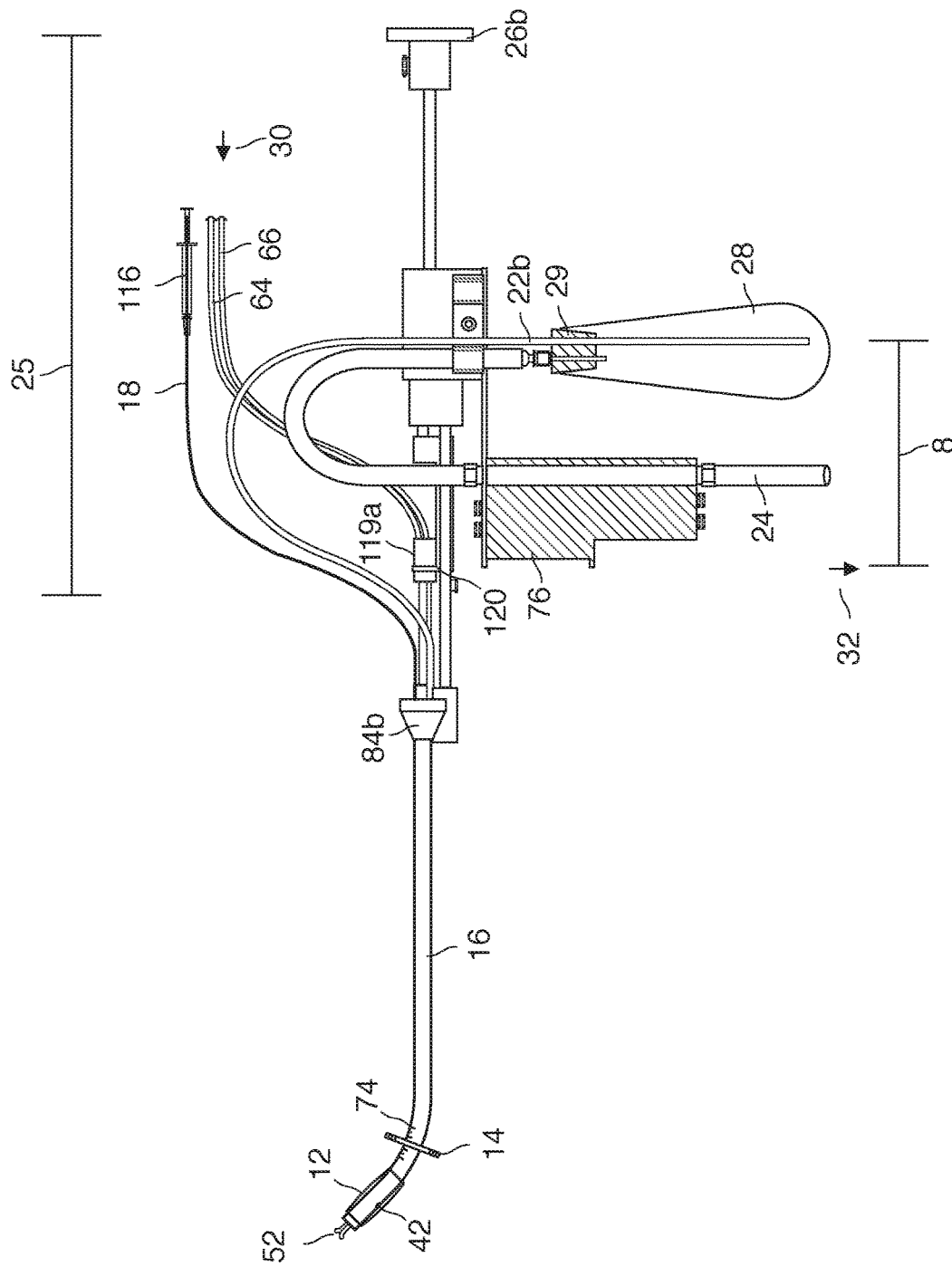

FIG. 36 is the Version 2a/2b operating frame in its undeployed configuration. It is a left side view of the completely assembled Version #2a/2b uterine catheter instrument mounted on its operating frame 8 in readiness mode (prior to uterine insertion). The operating frame 8 is a rigid platform for mounting and securing working elements of the system. The complete system, when mounted on the operating frame 8 platforms, is secured to an adjustable, movable, but rigid stand placed on the floor at the foot of the gynecological procedure table. The instrument is comprised of three elements on the operating frame: the operating frame 8, the suction recovery cannula 22b, and two fluid supply lines 64, 66 which are passed through individual guide channels extruded at manufacture into the inner walls of the suction recovery line 22b at manufacture. The fluid supply lines 64, 66 are attached to a controller programmed to both deliver lavage liquid to the uterus and apply vacuum to the fluid delivery and collection device in pre-programmed periodic pulses. The operating frame platform 8 stabilizes the systems for cervical and intrauterine insertion of the suction recovery catheter 22b and its steering controls 26a,26b for directing the fluid supply catheters 64 66 without or with magnetized tips 68 70 before, during, and after lavage recovery operations.

The operating frame 8 includes the two operating slides 25a 25b which stabilize, guide and slide individually the mechanically linked right and left fluid supply catheters 64,66, fittings, guides, tubing as they are directed into the uterus. The operating slide 25a 25b, calibrated in centimeters, are custom set before each procedure for each patient and limit uterine insertion depth of the supply lines 25a 25b. At insertion of the catheter, supply lines 25a 25b are stored at the flanged tip of the suction line 16 surrounded by a balloon collar 12.

The vacuum line external access port 24 is built into the base of the operating frame 8 hereafter it links directly to the vacuum element 233 of the programmable controller 205 and alternates vacuum to the pulsations of uterine lavage fluid that is being infused into the uterus. Suction tubing from the external access port 24 is connected to the embryo recovery trap 28 which collects lavage fluid containing recovered embryos. The vacuum delivered through the embryo recovery trap 28a is transmitted into the distal suction line 16, which in turn is transmitted to the uterine cavity during intrauterine lavage and embryo recovery. The embryo recovery trap 28a is removed at the end of the procedure where fluid recovered is transported to the core embryo laboratory 174 and scanned for embryos.

The suction line 16, 22b is a seamless conduit for recovery of lavage fluid and embryos. The suction recovery line 16, 22b transports embryos seamlessly to the suction trap 28, which is mounted on the left side of the operating frame 8. The suction recovery line 16, 22b is manufactured by extrusion as a semi-rigid medical grade inert composite. The suction recovery line 16, 22b has a central suction recovery channel 23 (ranging 30-80% of its area in different modifications) with three accessory channels, two channels for the two fluid supply lines 34 and the other for the balloon air supply 18, embedded into the walls of the suction catheter at manufacture. The embryo recovery trap 28 is connected to the controller vacuum element not shown through a perforated rubber stopper 29 by a vacuum line. The outside diameter of the suction recovery cannula 16 ranges from 22-34 French according to design model and custom patient requirements. At the beginning of the lavage procedure, the suction recovery cannula 16 is deployed through the cervix and into the uterus where it facilitates insertion and instrumentation of the uterus. A cervical stop 14 flange on the distal end of the suction recovery cannula 16, rests against the external cervix and limits the depth of insertion of the suction recovery cannula 16 into the cervix. Custom adjustments ranging from 1.0 to 2.5 cm into the endocervix fixate the depth and direction of the angulated distal portion of the guide. A cervical stop scale 74 is etched into the outside of the suction line arm 16 and marks the position of the cervical stop when it is custom-adjusted to each patient prior to insertion. The angle of the distal portion of the suction recovery line 16 is preset and varies from 0-45 degrees and is customized to individual women in order to accommodate the different anatomical variations of uterine flexion. The distal most portion of the suction recovery line 16 covers and shields the tips of the fluid supply lines 64, 66. The distal most portion of the suction recovery cannula endocervical guide 16, covers and shields the tips of 52 of the fluid supply catheters 64, 66 during insertion, maintains sterility, and avoids plugging of the fluid supply catheters 52, 64, 66 with uterine fluid 16 and debris.

The suction recovery catheter 16 is tipped with an intracervical rubber inflatable collar 44, 46 and 48, which when inflated immediately after insertion with 1-3 ml of air or fluid, serves as a watertight seal and funnel shaped intake port for recovery of lavage fluid. The balloon 46 placement is immediately above the internal os 155 of the lower uterine cavity 126 where it prevents completely the loss of lavage fluid around the suction recovery catheter 27 and outwards through the cervix into the vagina. It is connected with an external controller (not shown), which supplies uterine lavage fluid in a pulse rhythm to a vacuum element that alternates suction and pulses cadenced exactly the opposite of fluid delivery at a preset frequency of 0.5 to 4.0 seconds.

The balloon collar 12 is inflated with air or fluid delivered by an air supply syringe 116 connected to a channel extruded at manufacture into the walls of the suction recovery line 16. The fluid or air is delivered through a balloon port 42.

The suction recovery line 16 is connected seamlessly through a resin merger block 84b which links the proximal and distal suction recovery lines 16 22b seamlessly to deliver fluid into the embryo recovery suction trap 28. Two resin slider blocks 119a 119b are linked directly to right and left steering control wheels 26a 26b which are moved proximally or distally or rotated through 180 degree clockwise or counter clockwise arcs by the hand of the operator. The right and left steering controls manipulate supply lines 64,66 proximally and distally in their respective supply line guide channels 27b or rotate them through 180 arcs keyed to their respective resin slider blocks 119a 119b.

The operating frame 8 is secured through a hard point 199 to a rigid hard stand 198 fixed to the floor of the treatment room through a rigid handle 76 that contains and secures the suction line port 24 and channel.

A resin merger block 84b integrates the fluid supply lines, suction lines, 64 66 and the balloon air supply line 18 into a seamless merger. The resin merger block 84b is fixed to the main frame and does not slide. The slider blocks 119a 119b move with the operating slide 25a, 25b and can be locked into fixed position by a slider lock 120. The excursion of the operating slide is fixed proximally and distally, is adjusted individually for each individual patient, and is locked into position by its slider block 119a 119b.

Figure 37:
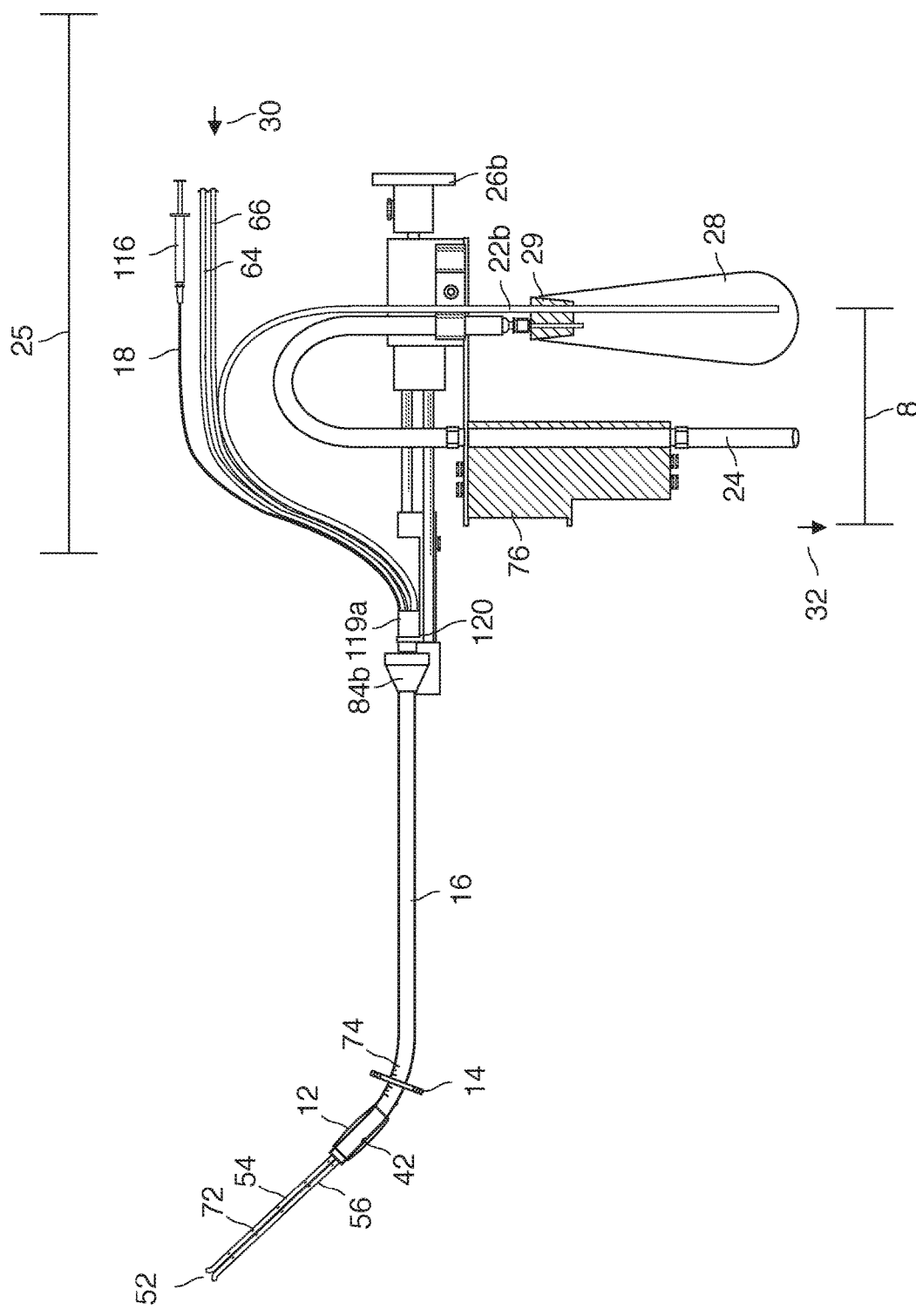

FIG. 37 is the Version 2a/2b operating frame in its fully deployed configuration. This is a left side view of the completely assembled Version #2a/2b uterine catheter instrument mounted on its operating frame 8 with its catheter mechanisms in fully deployed position (inserted fully into the uterus). The right and left operating slides 25a 25b and right and left steering controls 26a, 26b are forward at maximum travel with the resin slider block 118 the resin merger block 84a in full contact. The right and left distal supply lines 64,66 are fully extended with or without magnetized tips 68 70 at maximum excursion where they are steered along the top of the uterine cavity, if actually inserted, where they make contact to form a mechanical perimeter around the embryos located in the middle uterine cavity. Uterine lavage fluid is delivered in short low-pressure pulses through ports machined into both right and left supply lines and directed directly into the middle uterine cavity. In this figure, the balloon collar 12 is uninflated. The cervical stop 14 will be pushed firmly against the cervix adjusted for the internal length of the endocervical canal. The balloon collar 12 is then fully inflated and is pulled taught over the endocervix determined by the setting of the cervical stop 14 to form a water tight funnel to the outside of the uterus to assure no losses of uterine lavage fluid.

Figure 38:
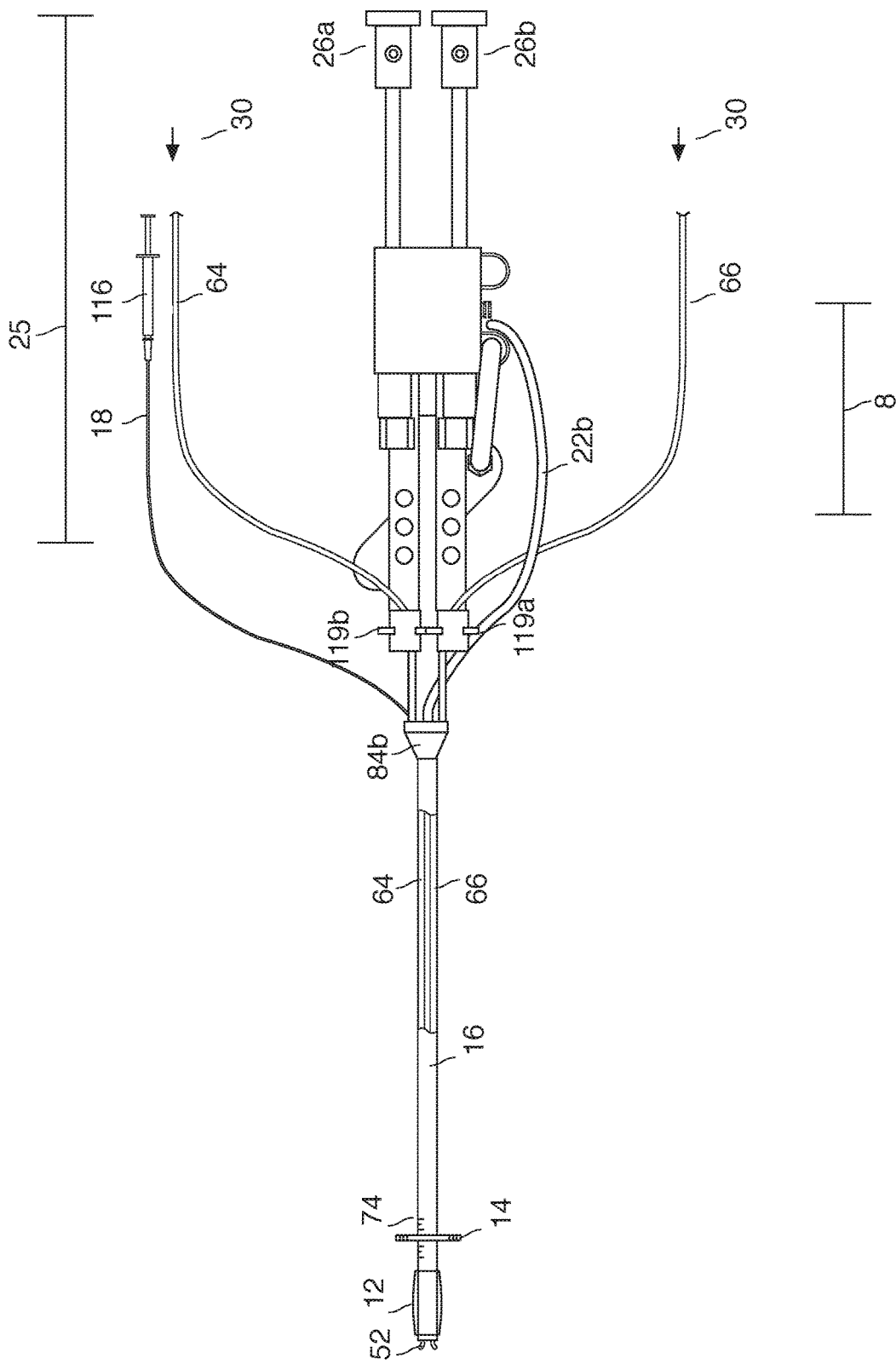

FIG. 38 is a top view of the Version #2 a/2b operating frame and the uterine catheter instrument in the undeployed configuration. The distal suction line 16 ports protect the double tips of the two supply lines 52. The two fluid supply lines 64, 66 are linked to the controller fluid delivery pump 232, and the suction line 24 is linked to the controller vacuum pump 233. The right and left steering controls 26a 26b, resin merger block 84a, and resin slider blocks 118a 118b are fully extended in their undeployed positions.

Figure 39:
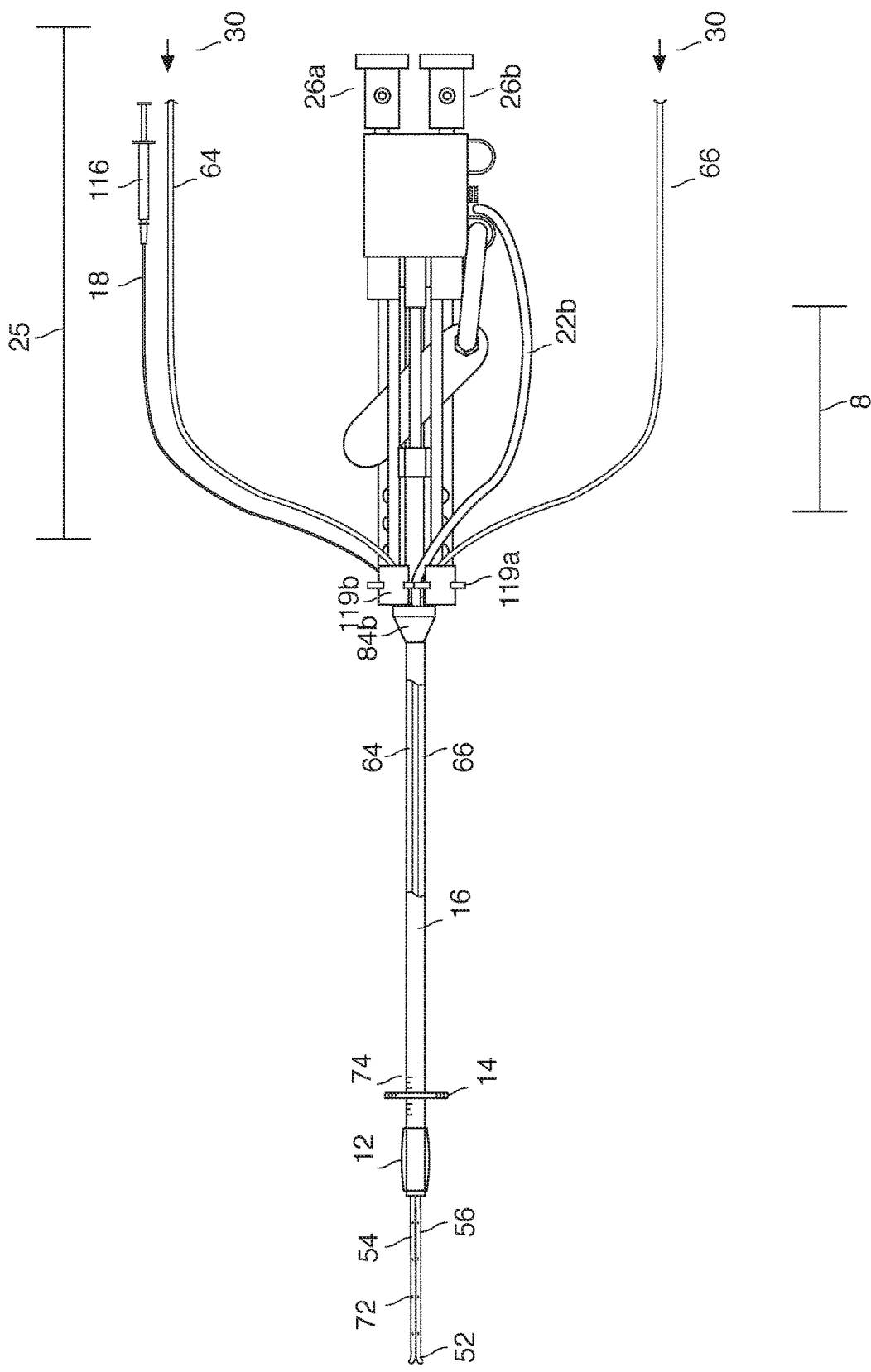

FIG. 39 are a top view of the Version #2 operating frame and uterine catheter instrument in fully deployed configuration. The resin slider blocks 118a 118b are fully extended to the distal travel of the operating slide 25a 25b and are pushed against the resin merger block 84b. The two fluid supply lines are in fully extended position without rotation so they point away from each other. If deployed in the uterus, they would have met and attached at their magnetized tips at the top of the uterus to form a mechanical and hydraulic perimeter around the embryos located in the middle of the uterine cavity. The balloon collar 12 is not inflated. Cervical stop 14 is fixed by pre-measuring of the patient according the scale attached to suction line 16

Figure 40:
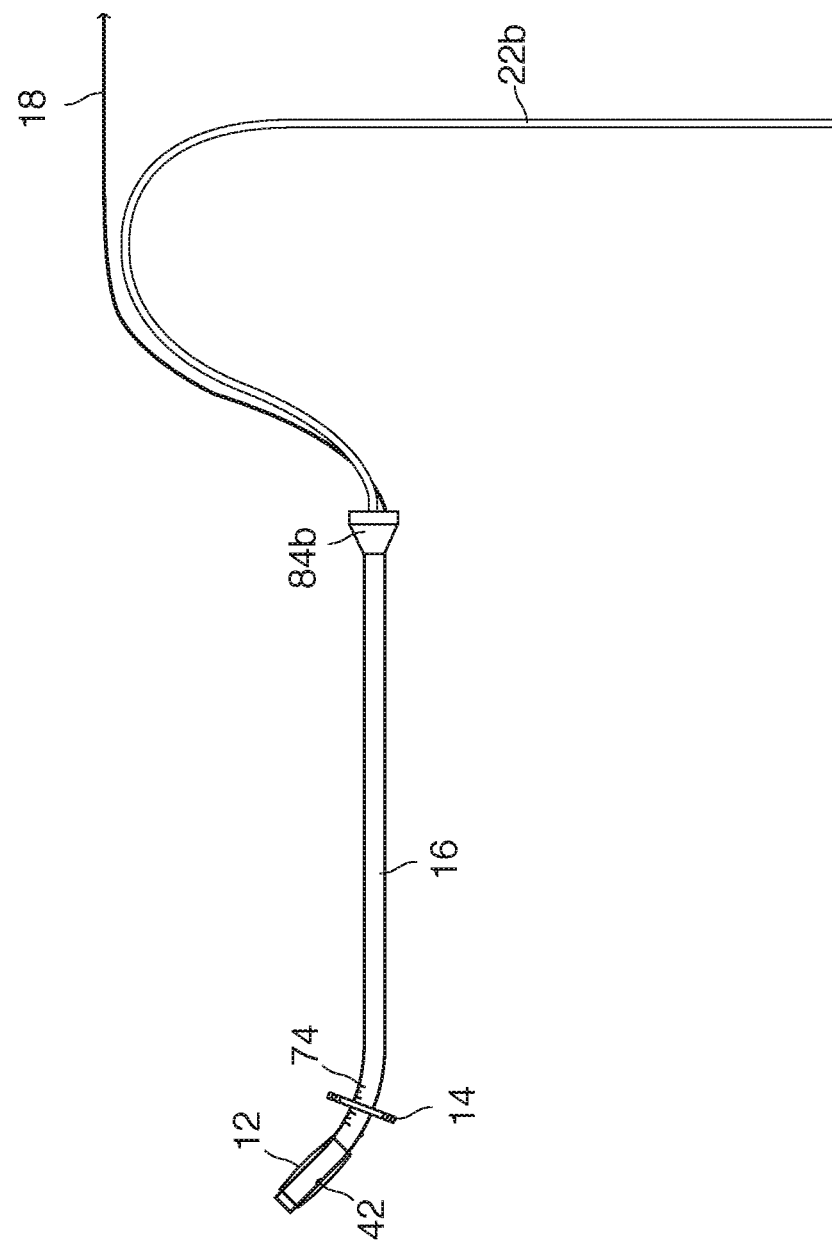

FIG. 40 is a left side view of the Version #2/2b suction line 16 which contains channels for two fluid supply lines 64, 66. The suction line 27 is a seamless conduit for recovering and transporting embryos contained in the lavage fluid for delivery to the embryo trap 28 by way of the resin merger block 84b. This version accommodates two fluid supply lines 64,66 that emerge together in the resin merger block 84a and can rotated 180 degrees by their mechanical linkage through right and left resin slider blocks 118a 118b. Which in turn are mechanically linked to the right and left steering controls 26a 26b.

Figure 41:
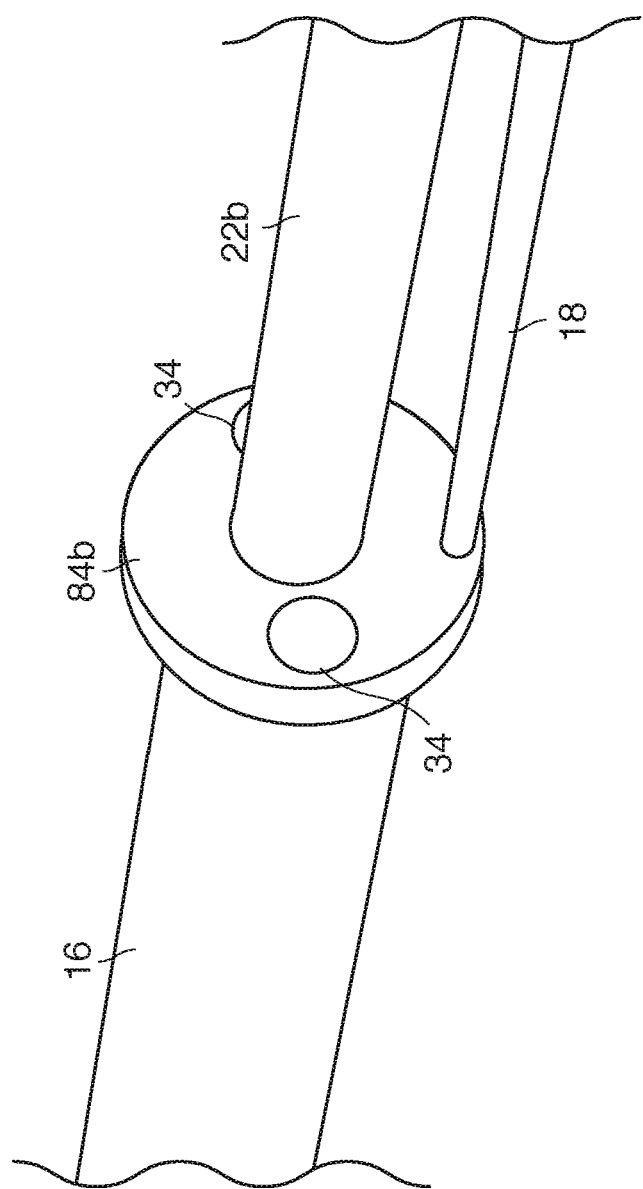

FIG. 41 is an enlarged ¾ view of the Version #2 resin merger block 84b. The suction line 16 is connected seamlessly to the suction line extruded into the suction arm 16 at manufacture. Two supply line channels 27a 27b are supplied for insertion of the supply lines 64 66, which are not in the figure. The balloon collar air line 18 runs in the wall of extruded suction line arm 16 its full length to open in its port 42 inside the balloon collar at the tip of the catheter.

Figure 42:
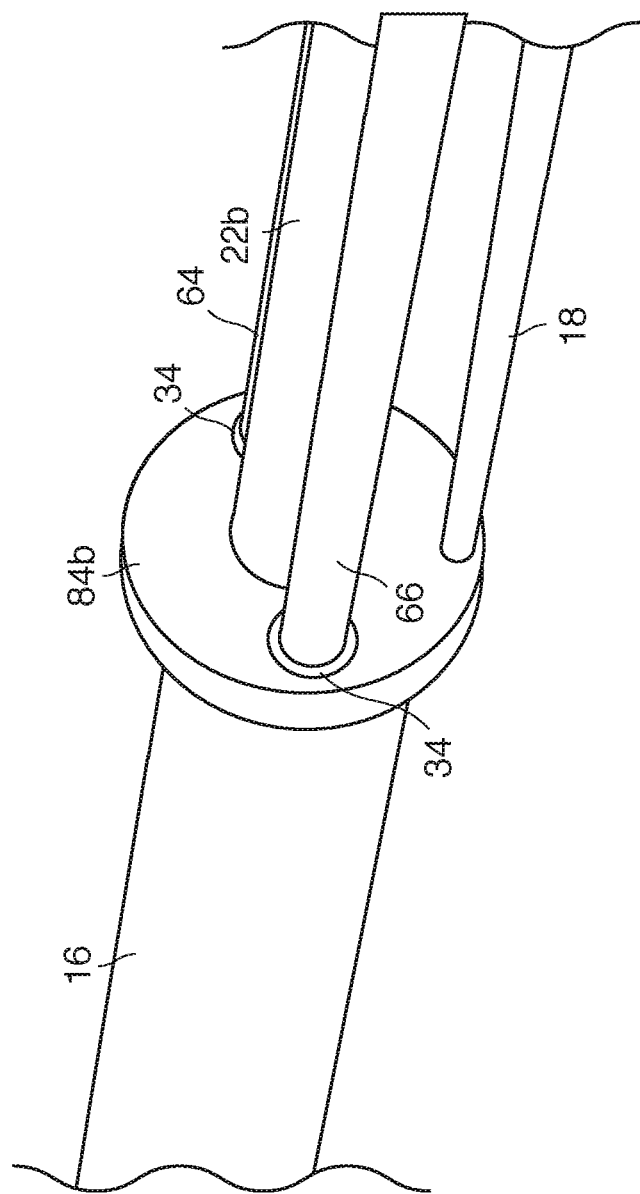

FIG. 42 shows the Version #2 resin merger block 84a with fluid supply lines 64,66 now in place to their own ports 27a 27b. The supply lines 64, 66 are attached rigidly to their respective resin slider blocks 118a 118b, which are linked to the steering controls 26a and 26b and the operating slide 25. This arrangement allows for 180 degrees within uterus rotation of both fluid supply lines from respective right and left resin slider blocks, which are mounted on their respective right and left operating slides.

FIG. 43 is a top side longitudinal cut of the Version #2 distal suction line 16 showing both fluid supply catheters 64, 66 in place. The catheter tips 52 protrude slightly from the tip. The lavage fluid supply ports 72 can be seen through the cut. The cervical stop flange 14 is shown in cross section.

FIG. 44 is a left longitudinal cut of the Version #2 distal suction line 16 shown from the left. On side view a right and left supply lines can be seen with their respective fluid supply line ports 72 and tips 52 protected by a distal suction line 16.

Figure 45:
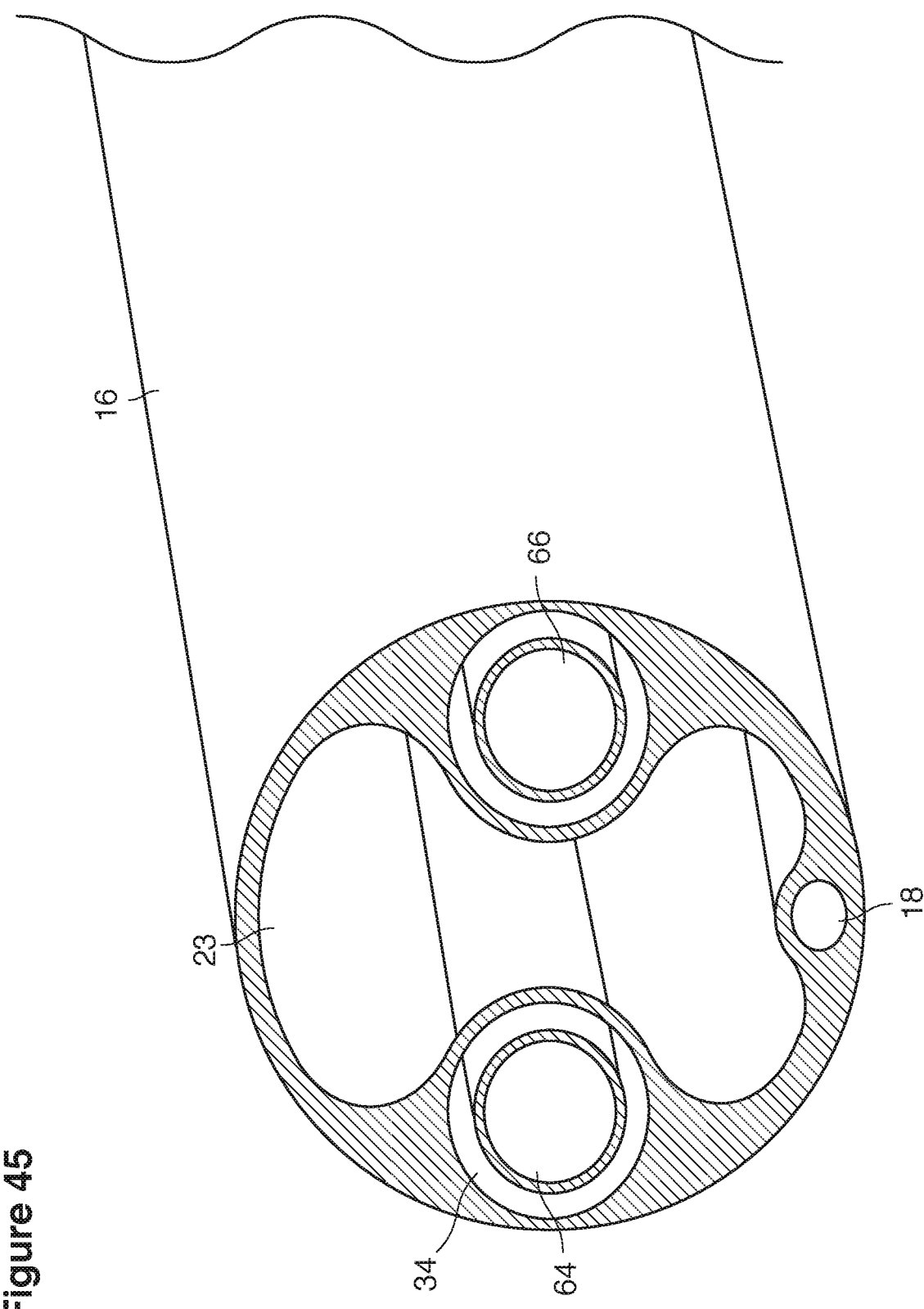

FIG. 45 is a left oblique view of the Version #2 cross section cut through the distal suction line 16 showing the suction channel 23 and balloon air channel 18, and two supply catheter channels 34 with fluid supply lines 64, 66 in place.

Figure 46:
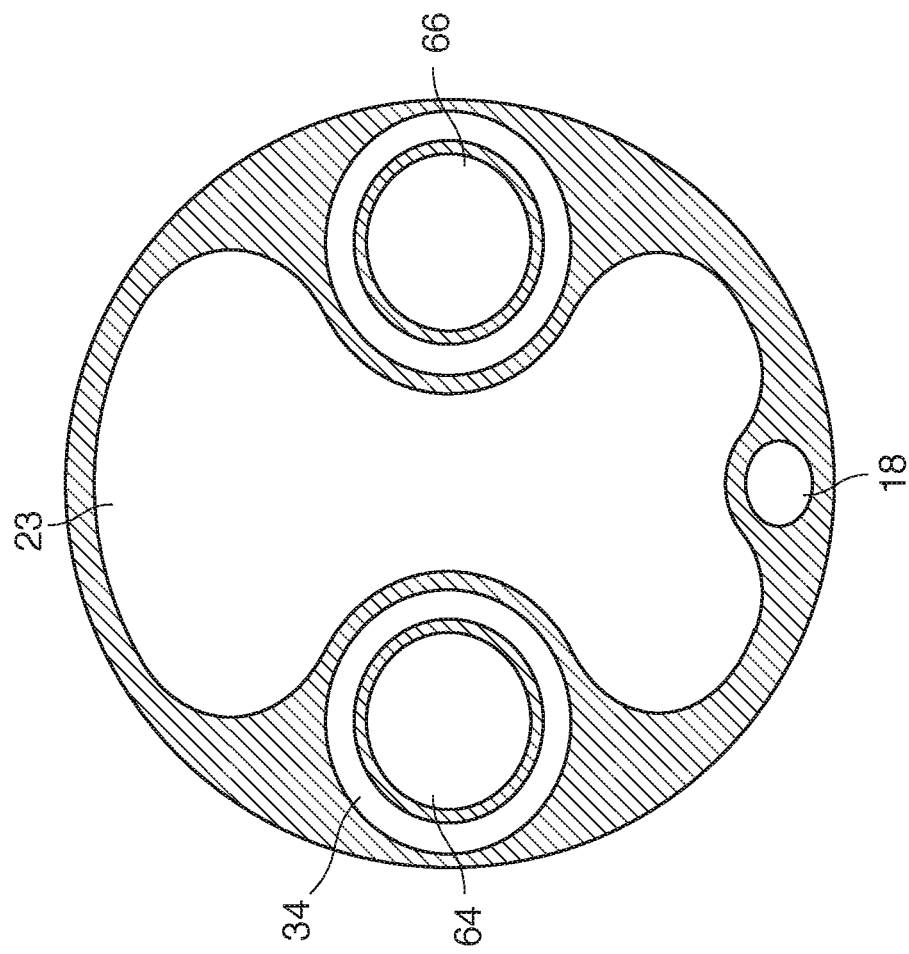

FIG. 46 is a cross section of the Version #2 distal suction line 16 showing the suction channel 27b, balloon air channel 18 and two supply catheter channels 27b with fluid supply catheters 64, 66 in place.

FIG. 47 is a left sided view of the distal Version 2 suction line 27 showing the cervical stop 14 in place with the centimeter graduated etched preset scale 74.

Figure 48:
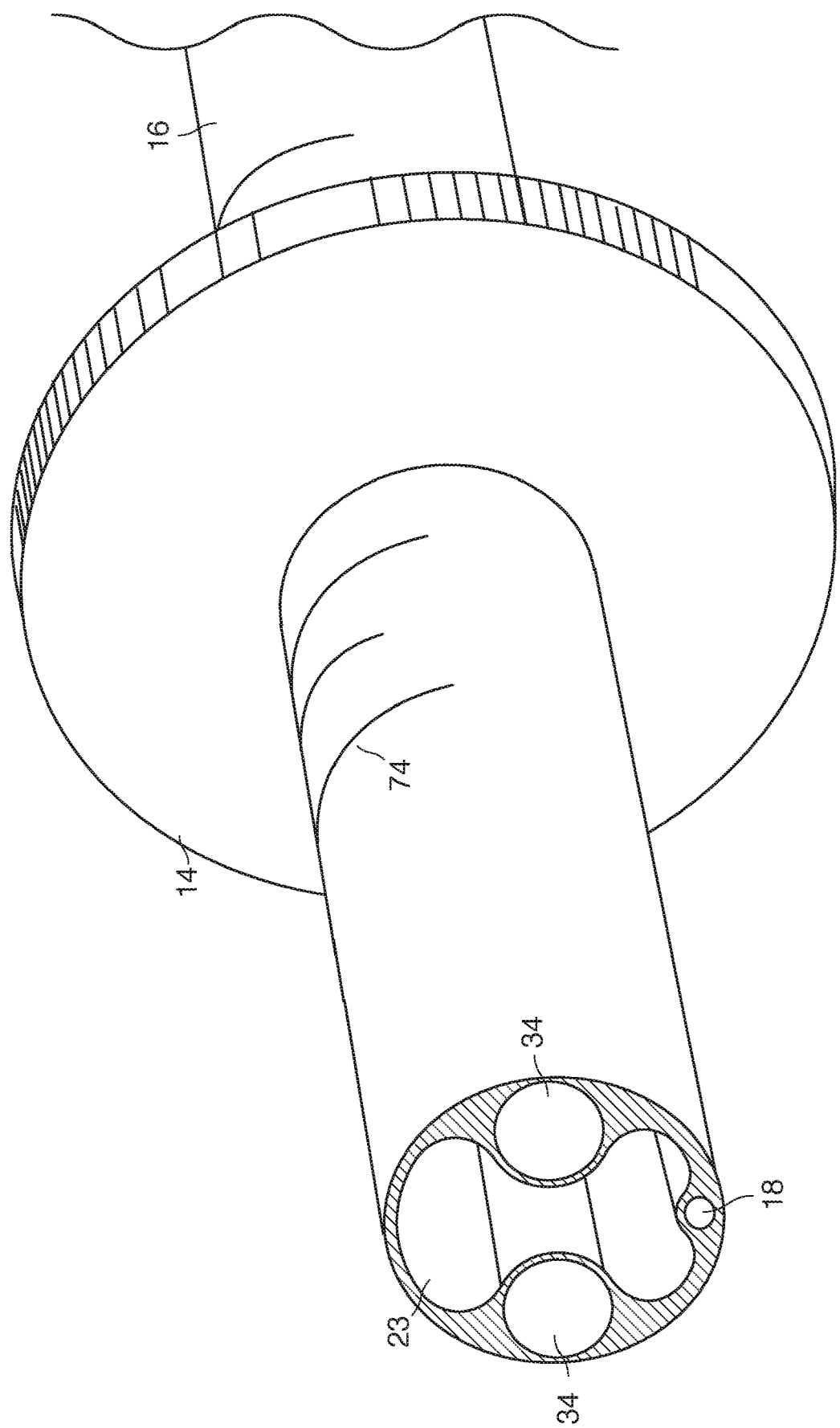

FIG. 48 is a left oblique cross section of the Version #2 distal suction line 27 showing the cervical stop 14, suction channel 27a, balloon air channel 18, and two fluid supply catheter channels 34

Figure 49:
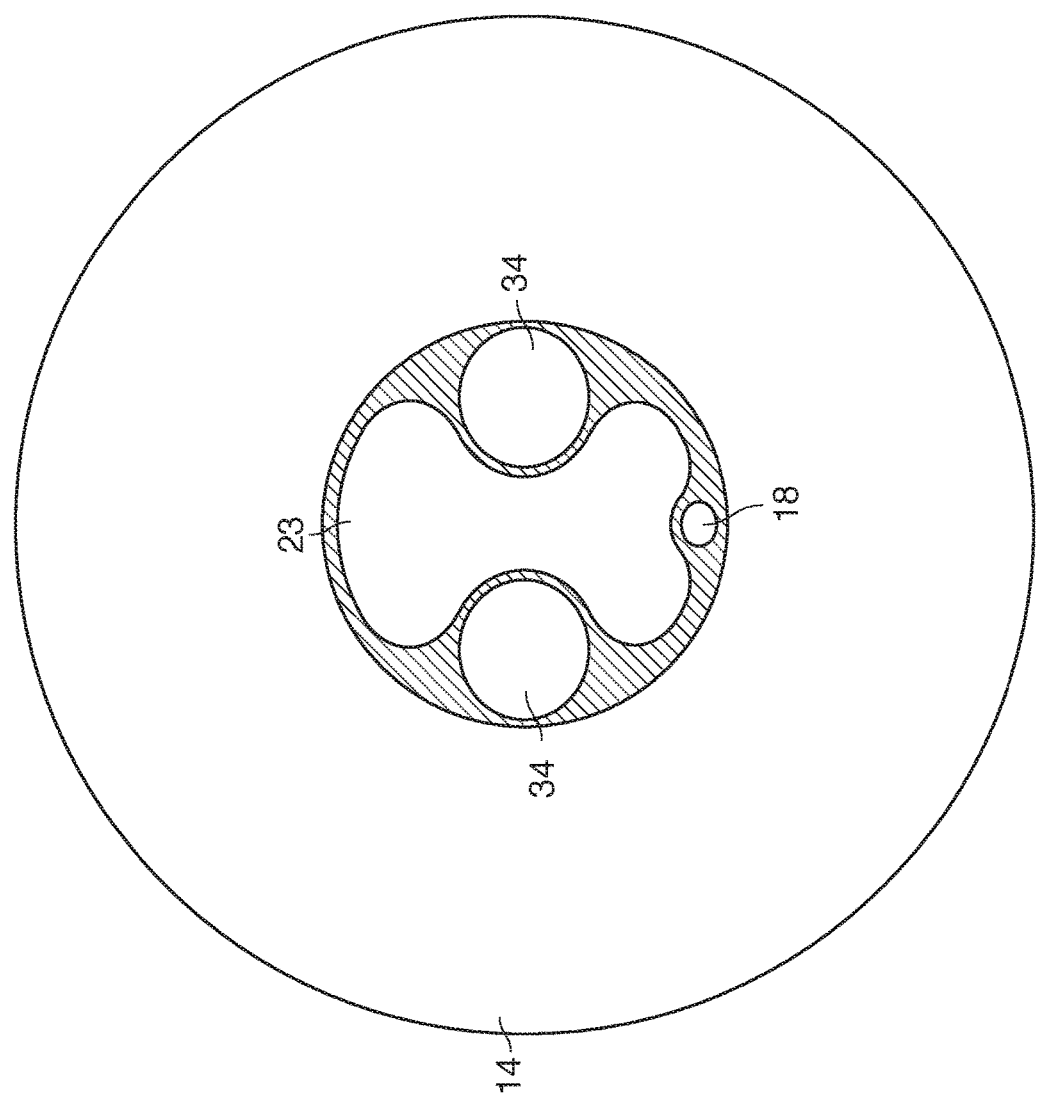

FIG. 49 is a cross section of the Version #2 distal suction line 16 showing the cervical stop 14, suction channel 23, balloon air channel 18, and two fluid supply catheter channels 34.

Figure 50:
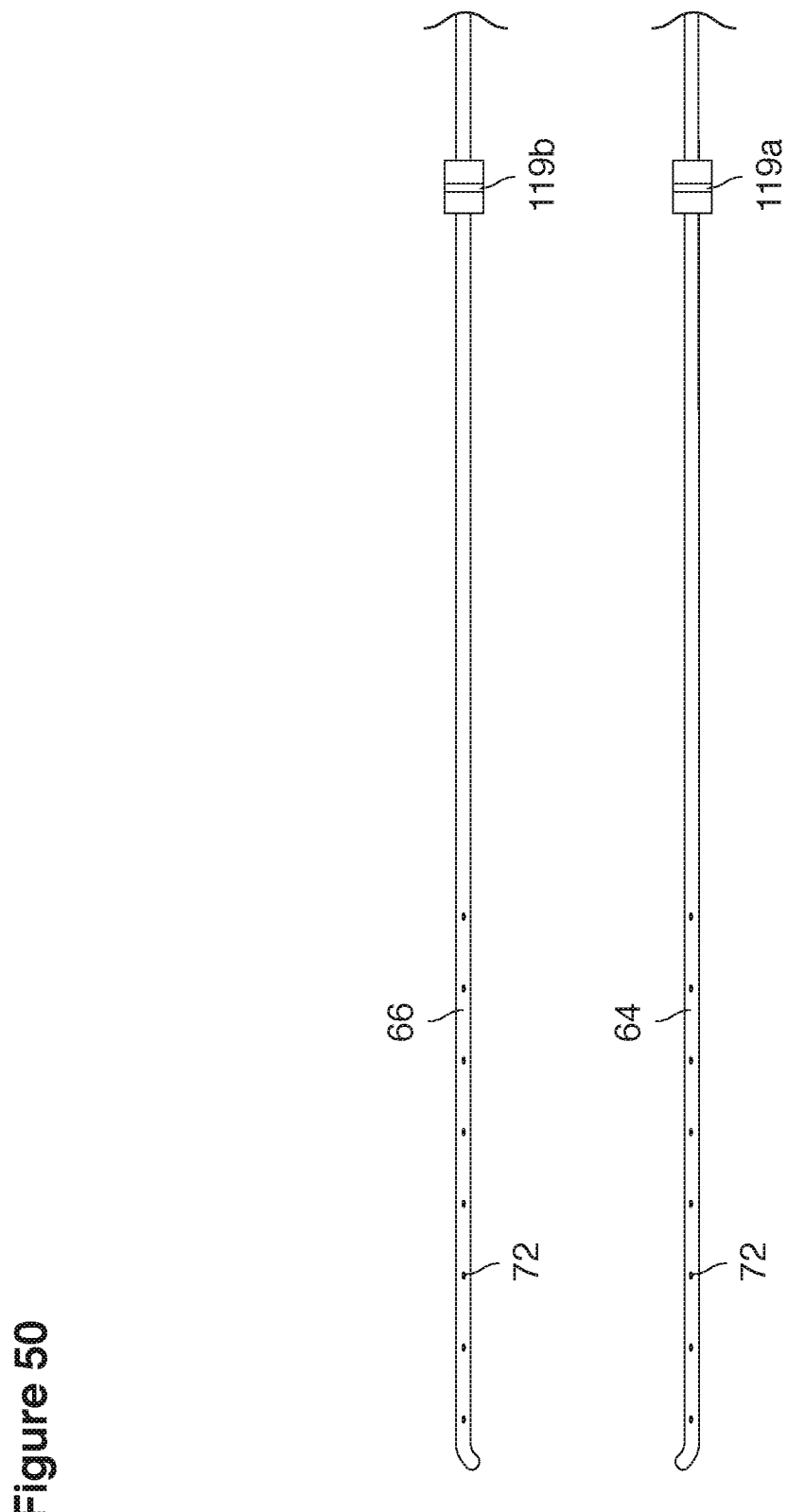

FIG. 50 is a right side view of the Version #2 left fluid supply catheter 64 at the top and a left side view of the patient's right fluid supply catheter 66 at the bottom. The catheters each contain nine internally tapered fluid delivery ports 72 which, when deployed in the uterus, are pointed to the middle of the uterine cavity. Individual resin slider blocks 119a 119b are linked mechanically to the right and left steering controls 26a, 26b, and lavage fluid delivery ports 64.

Figure 51:
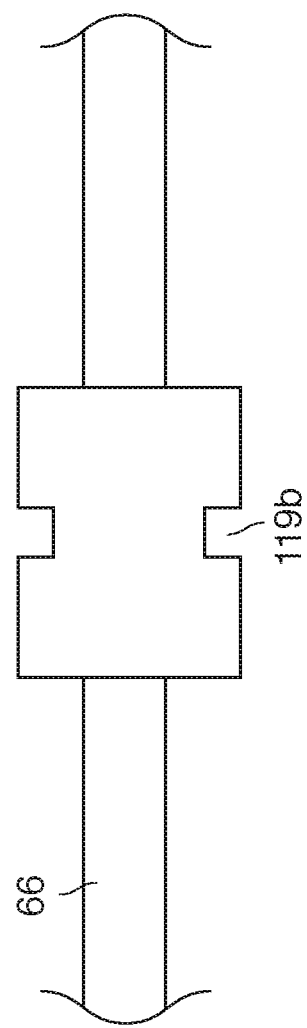

FIG. 51 is a left side view of the patient's right side Version #2 fluid supply catheter 66 at the level of the resin slider block 119b (119a not shown) with mechanical attachment points to the operating frame 8 and right and left steering controls 26a 26b.

Figure 52:
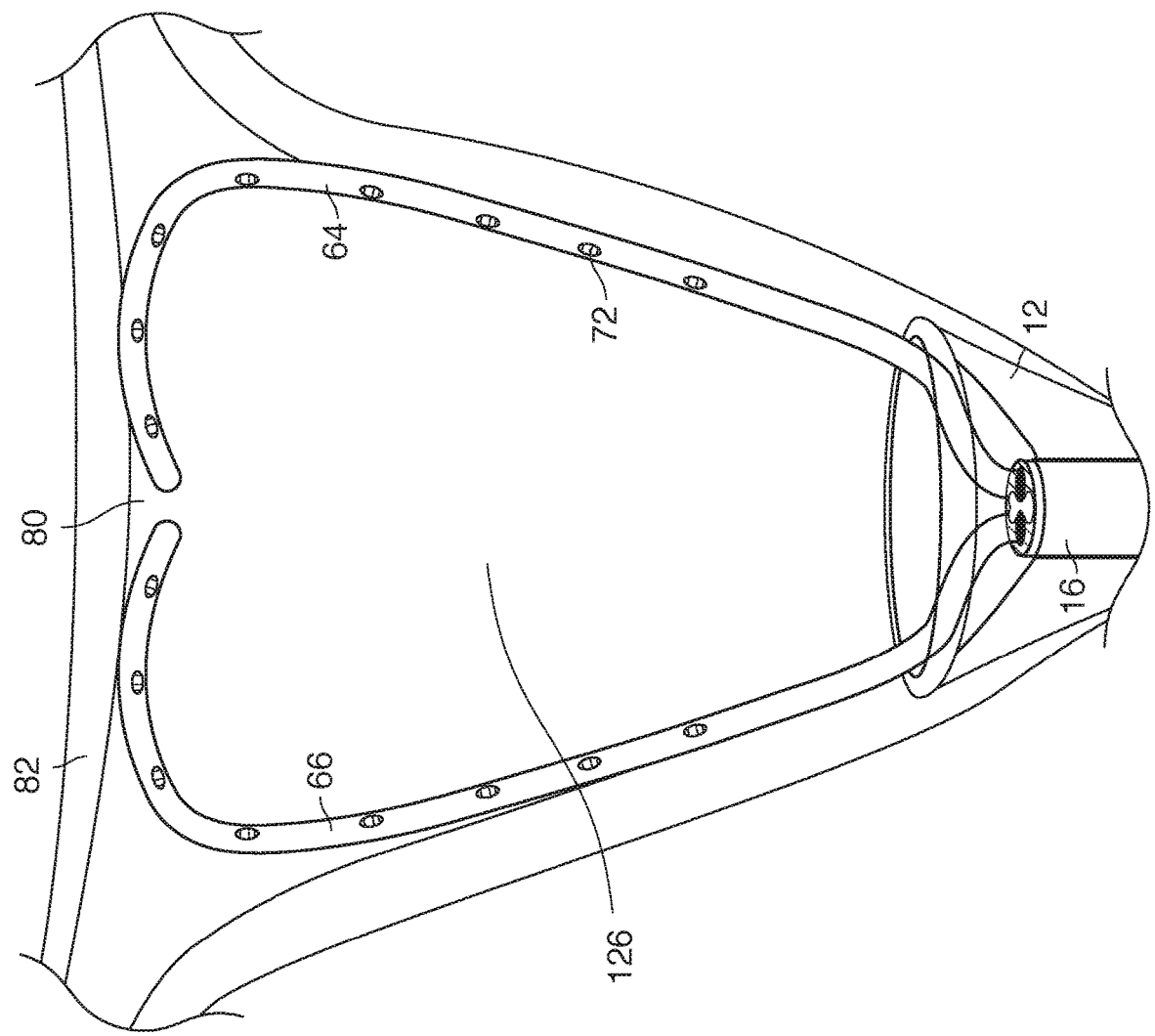

FIG. 52 is an anterior posterior view of the deployed Version 2 double supply line system with fully inflated funnel balloon 12 that completely occludes the internal os 155. The right sided 64 and left sided 66 fluid supply lines have been steered along respective right and left uterine walls within the cavity to nearly meet at the top of the uterine cavity 126. In this system all uterine lavage fluid is delivered away from the internal ostia directly into the lower uterine cavity and then to the funnel balloon 12 that occludes the endocervical canal. This system utilizes intermittent pulsatile delivery of fluid and suction to break up the uterine cavity fluid 161 and mucous and move the embryos to the funnel balloon 12 in the lower uterine cavity 126.

Figure 53:
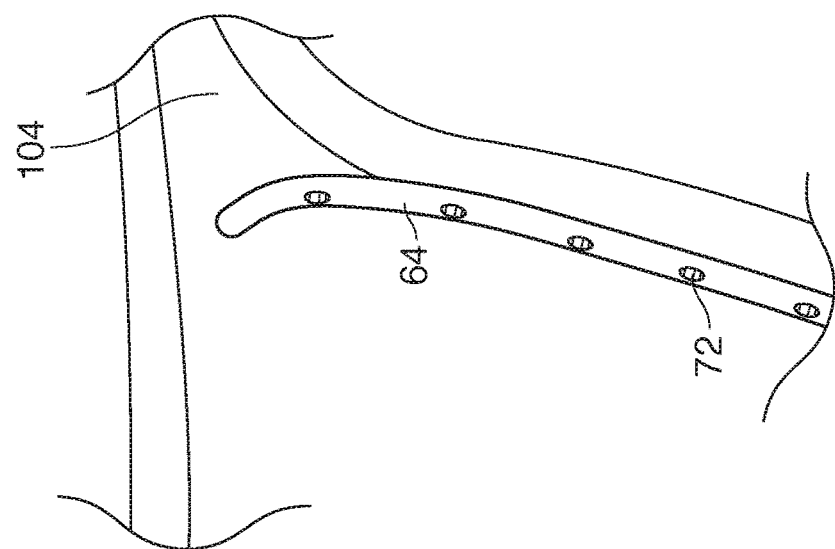
Figure 53:
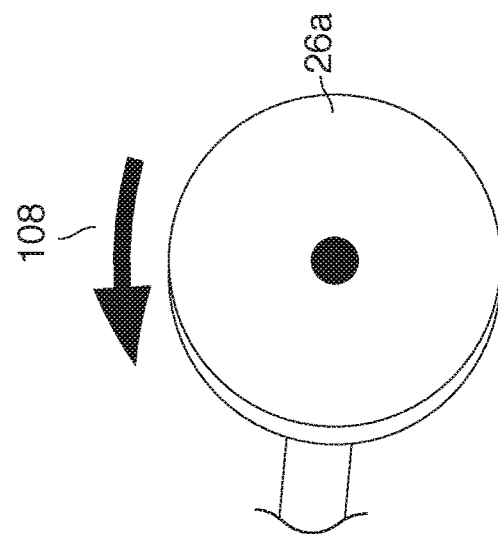
Figure 53:
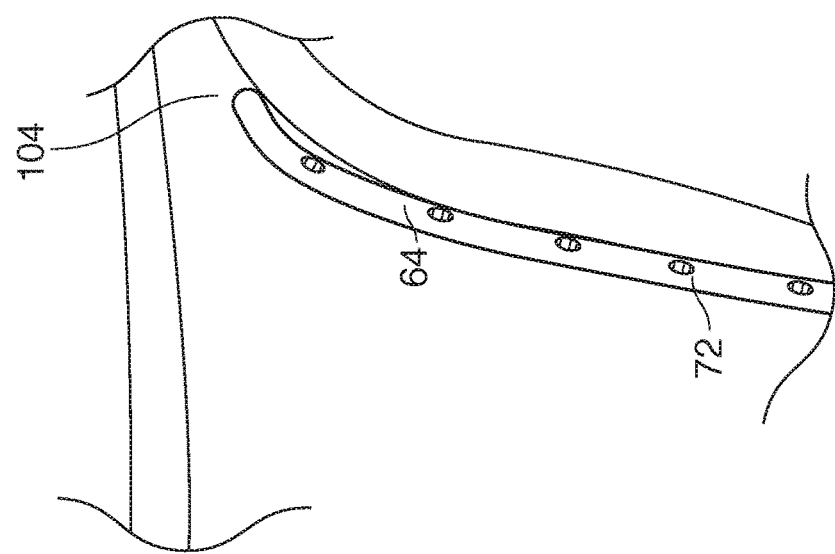

FIG. 53 is an anterior posterior view showing the Version 2 method of insertion and rotation of the patient's left fluid supply line 64 into and then away from the left internal ostium 104. This is achieved by rotation of the left steering control 26b steering the tip away from the left internal ostium 104 to the top of the uterine cavity 126. The opposite maneuver takes for the right catheter 66 that allows the device to be deployed fully to the top of the uterus to direct lavage fluid away from the internal ostia 104,106. Rotation of the wheel in counter clockwise fashion on the left side 26b allows for this deployment. Placement and rotation 108,110 of these catheters are performed under ultrasound guidance.

Figure 54:
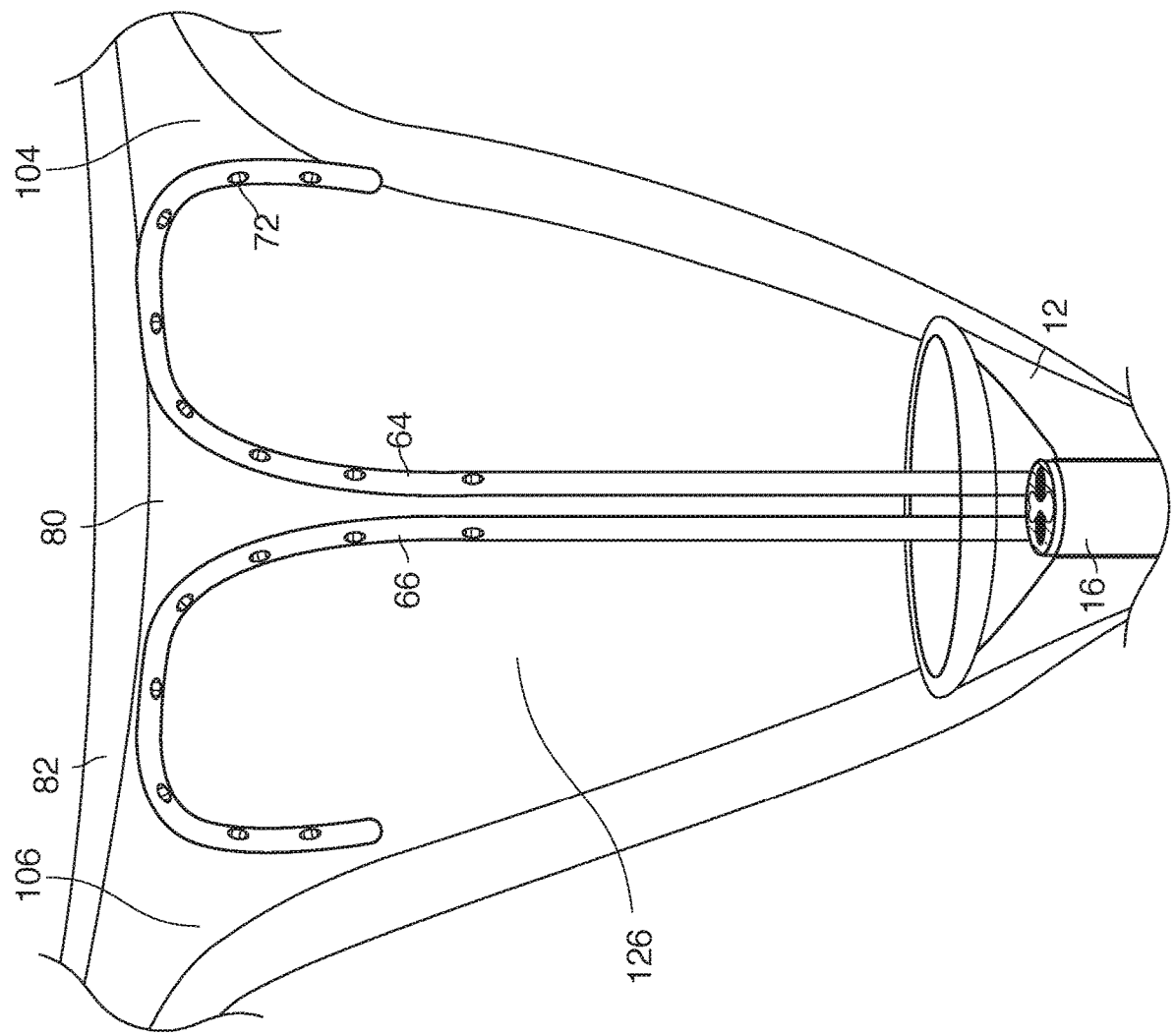

FIG. 54 is an anterior posterior view of the uterus showing an alternative Version 2a, strategy for insertion and rotation of both the supply lines 64 66 up the middle of the uterus to the top of the uterine cavity 126 with rotation of the control wheels 26a, 26b away from and downward from the internal tubal ostia 104, 106. This allows for lavage fluid to be delivered away from the internal ostia 104,106 and directly to the inner cervical funnel balloon 48 allowing for the embryos to be recovered with 100% efficiency and low risk of retrograde flow into the oviducts through the internal ostia 104,106 into the tubes 86.

Figure 55:
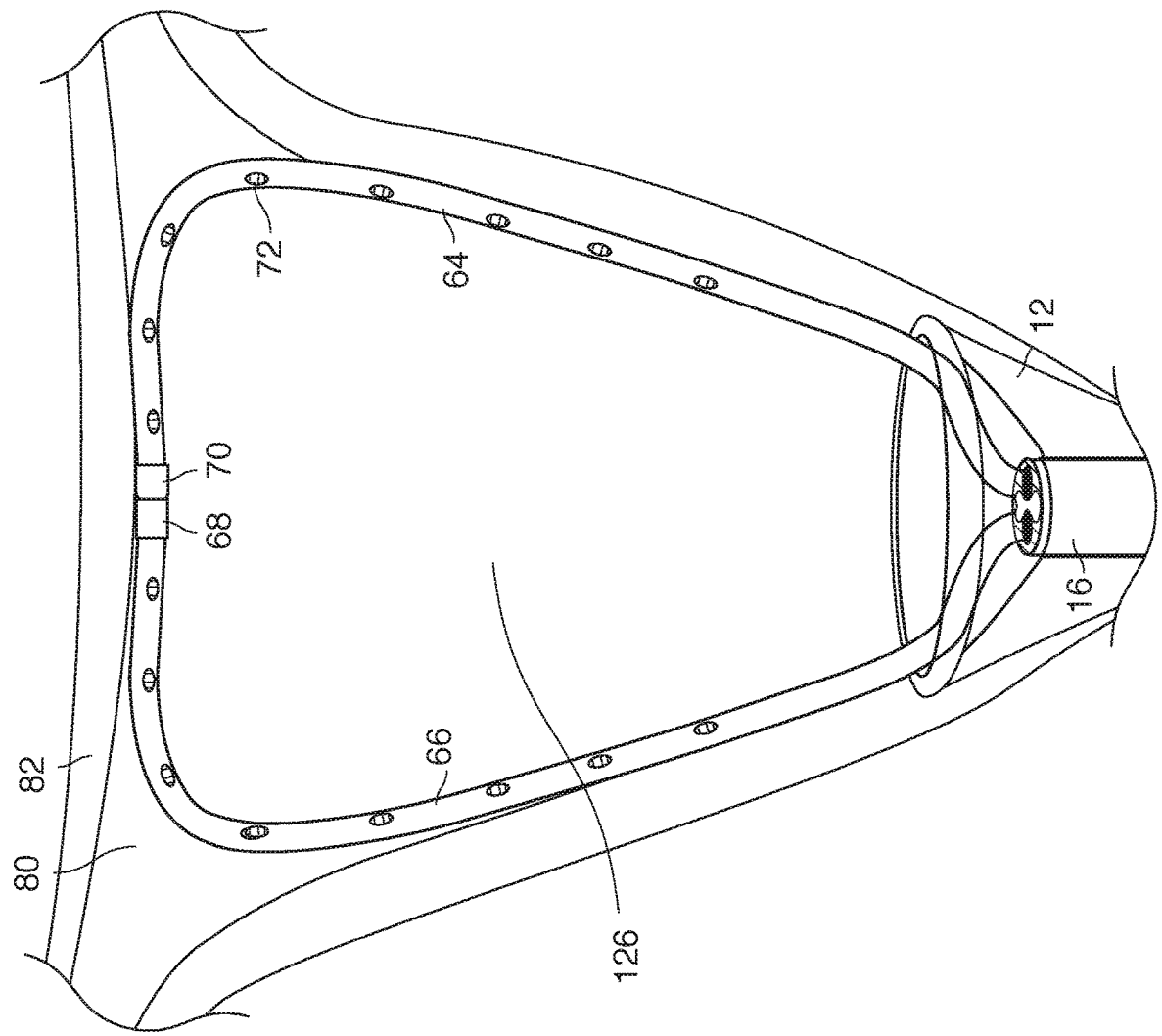

FIG. 55 is an anterior posterior view of the uterus showing Version 2b right and left fluid supply lines with magnetized tips 68, 70 that allow linkage of the catheters together at the top of the uterine cavity 126. This maneuver surrounds embryos within a closed mechanical perimeter. The magnetic tipped catheters are guided with the steering controls 26a 26b. With ultrasound control, the magnetic tips are directed together and linked firmly at the top and middle of the uterine cavity 126 thus surrounding the embryos. Lavage fluid is then infused under high pulse pressure that breaks up the uterine fluid and mucous in the lower part of the uterine cavity 126 and delivers embryos to the internal funnel balloon 48 and suction line port at the bottom of the uterus.

Figure 56:
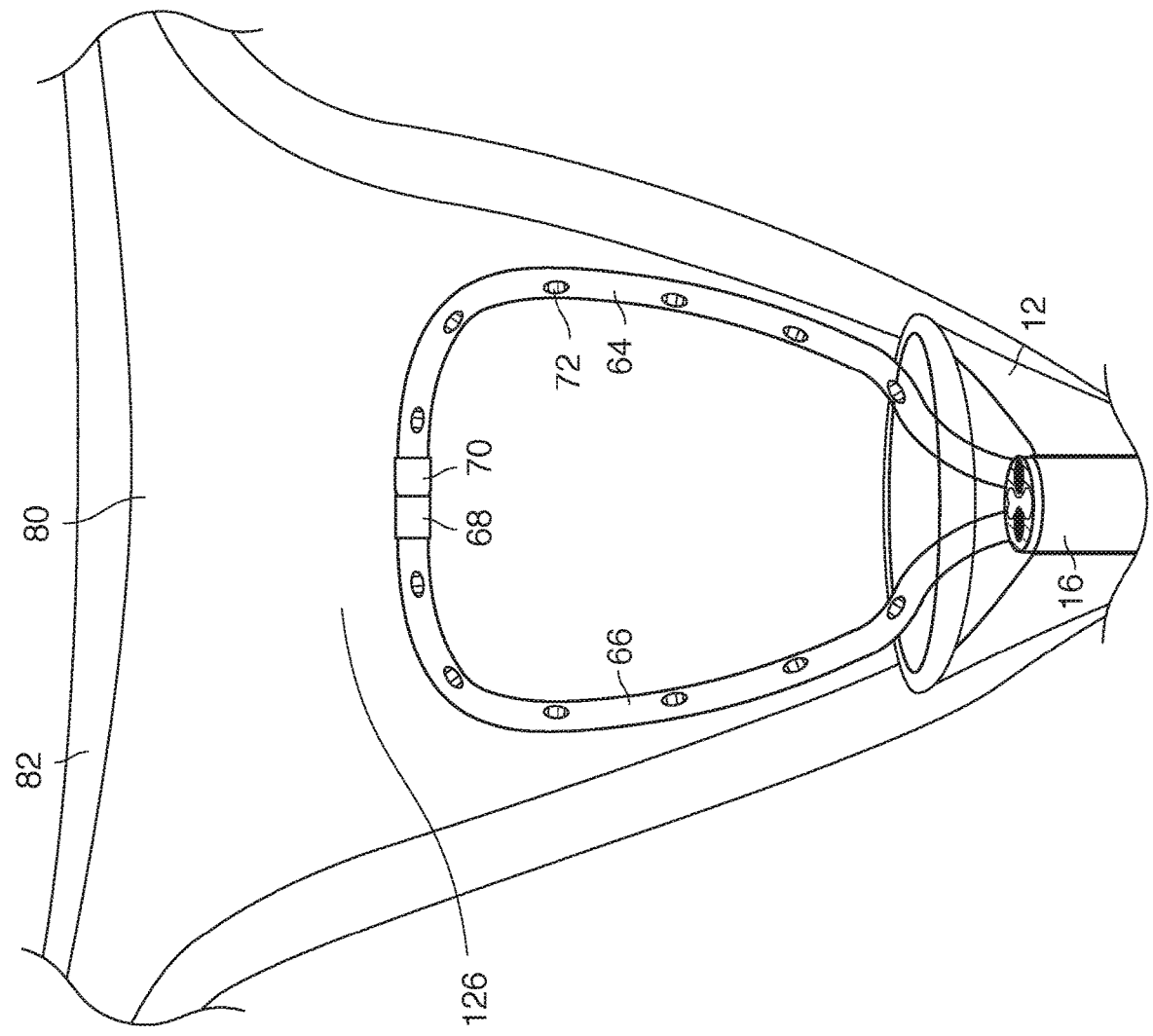

FIG. 56 shows the effect of withdrawing the Version 2b catheter during the lavage by linking and pulling the steering controls outward simultaneously. The perimeter around the embryos shrinks with this maneuver. Continued delivery of pulsatile fluid inside the shrinking perimeters allows the embryos to be delivered with virtually 100% recovery to the internal suction port at the base of the balloon funnel.

Figure 57:
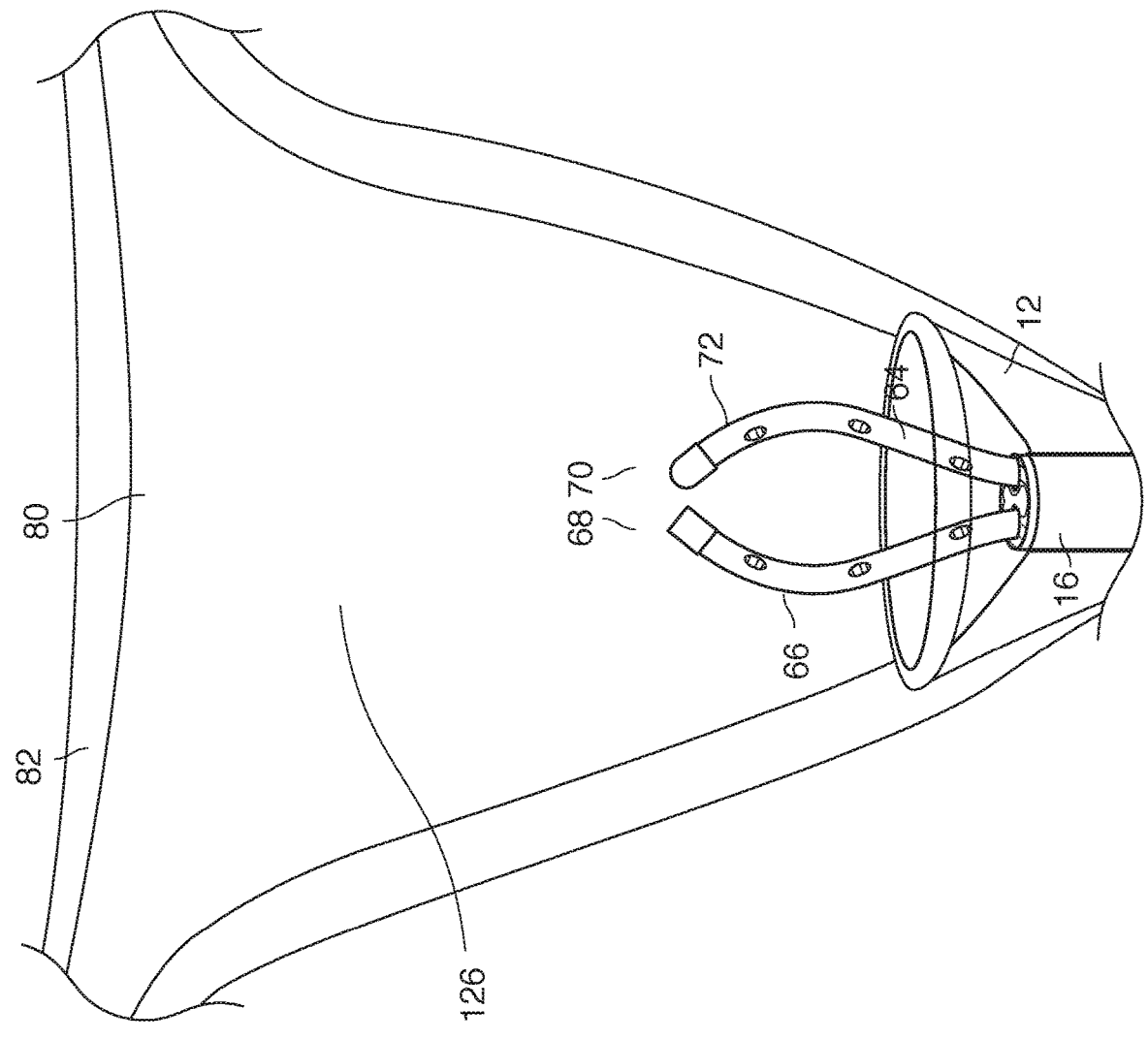

FIG. 57 is an anterior posterior view of the Version 2b right and left fluid supply lines 64, 66 with magnetic tips 68, 70 breaking contact at this point as the fluid supply lines 68, 70 are withdrawn simultaneously from the uterine cavity. The magnetized tips break the perimeter after embryos have already been delivered through the suction port to the suction line.

Figure 58:
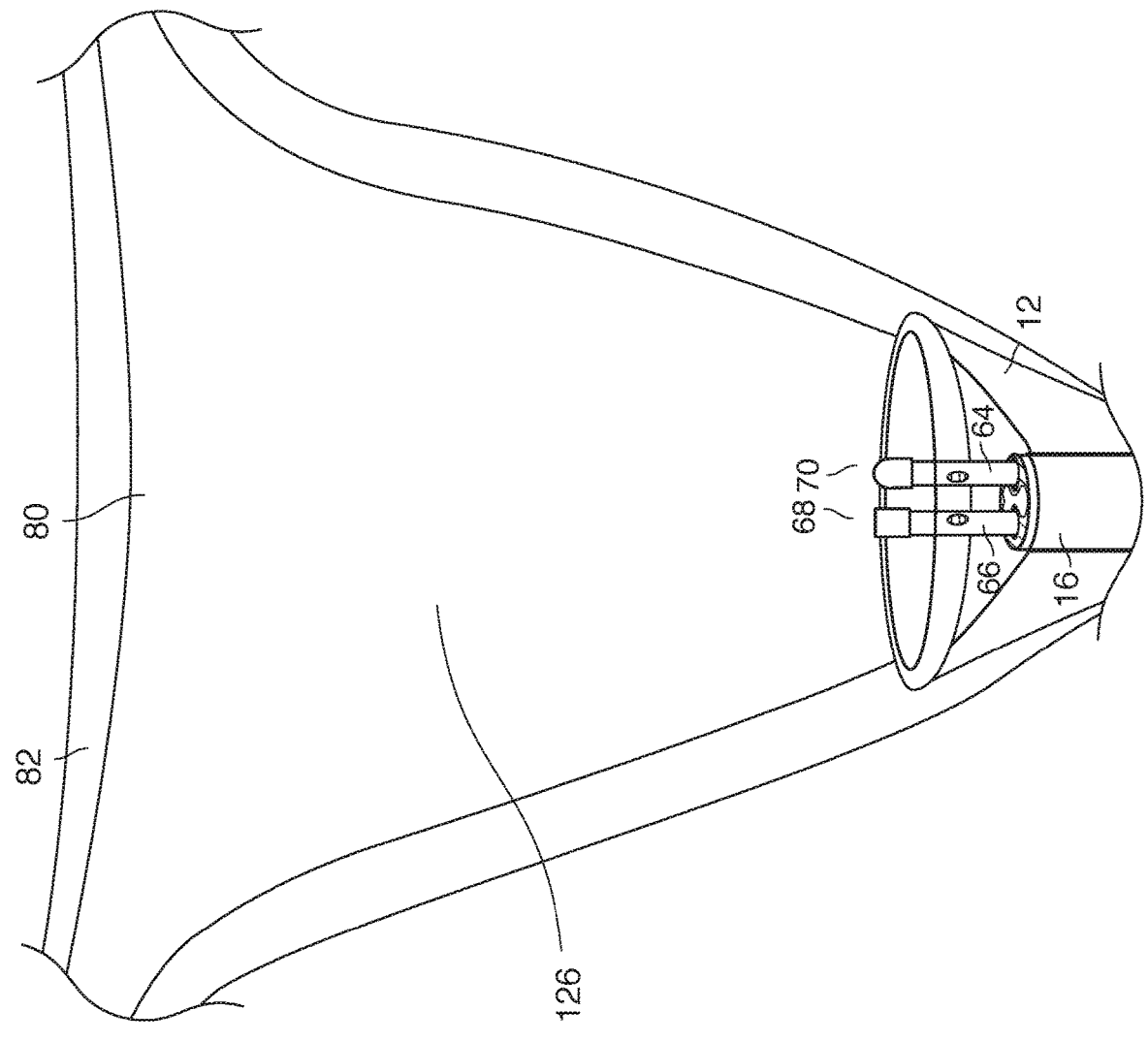

FIG. 58 is an anterior portion of the Version 2b right and left fluid supply line with magnetized tips 68 70 not making contact and being withdrawn separately from the uterine cavity 68 and 70.

FIG. 59a shows the separated ball and socket magnetized tips 68 70 at the top of the fundus.

FIG. 59b shows the ball and socket 68, 70 magnetized tips in engaged position.

FIG. 60a shows details of the ball and socket magnetic tips 68 70 with oblique views 68 and 70.

FIG. 60b is a cutaway 66 and 70.

Figure 61A:
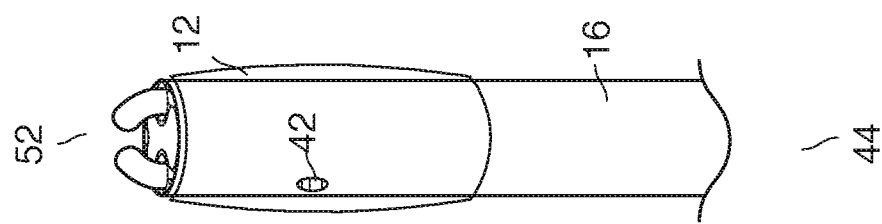

FIG. 61a shows the anterior and posterior views of the deflated funnel balloon.

Figure 61B:
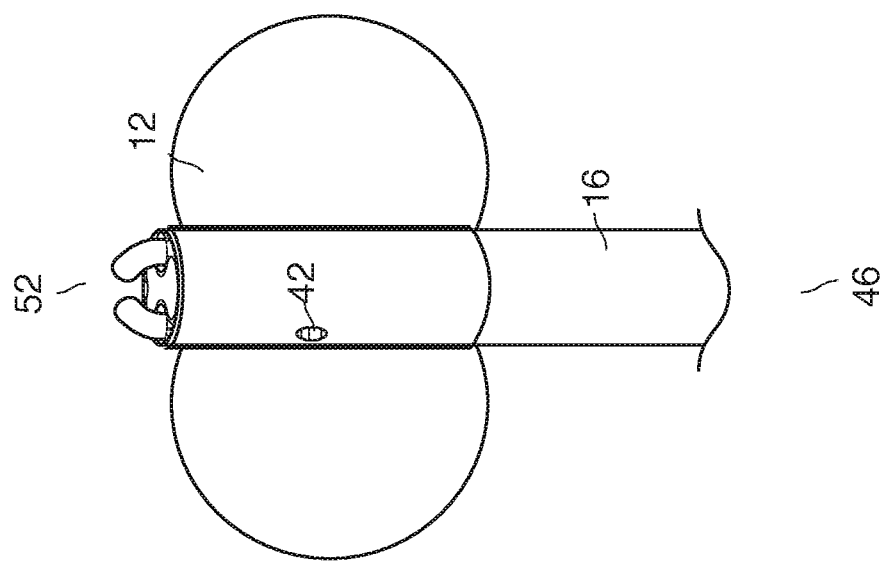

FIG. 61b shows a fully inflated balloon and showing the dual tips of the right and left fluid delivery catheters 64, 66.

Figure 62A:
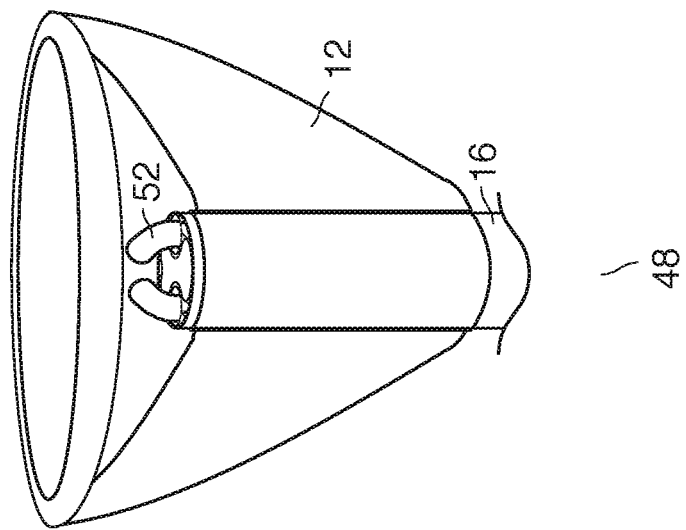

FIG. 62a shows the Version 2 fully inflated funnel balloon from the outside left.

Figure 62B:
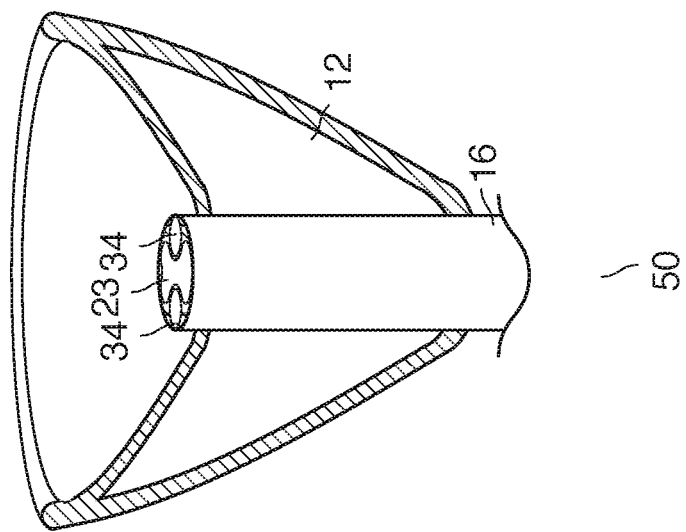

FIG. 62b shows the fully inflated funnel balloon in cutaway.

FIGS. 63 a-q show the Version 2a catheter placement and direction of lavage fluid flow. Lavage fluid emanating from the ports of the right and left catheters 64, 66 direct embryos into the inflated balloon funnel for egress into the intake ports of the uterine suction line 16 and into the recovery trap 28. Version 2a, using double fluid supply lines, produced a flow of intrauterine fluid during lavage, as shown in FIGS. 63 a-q.

Figure 63A:
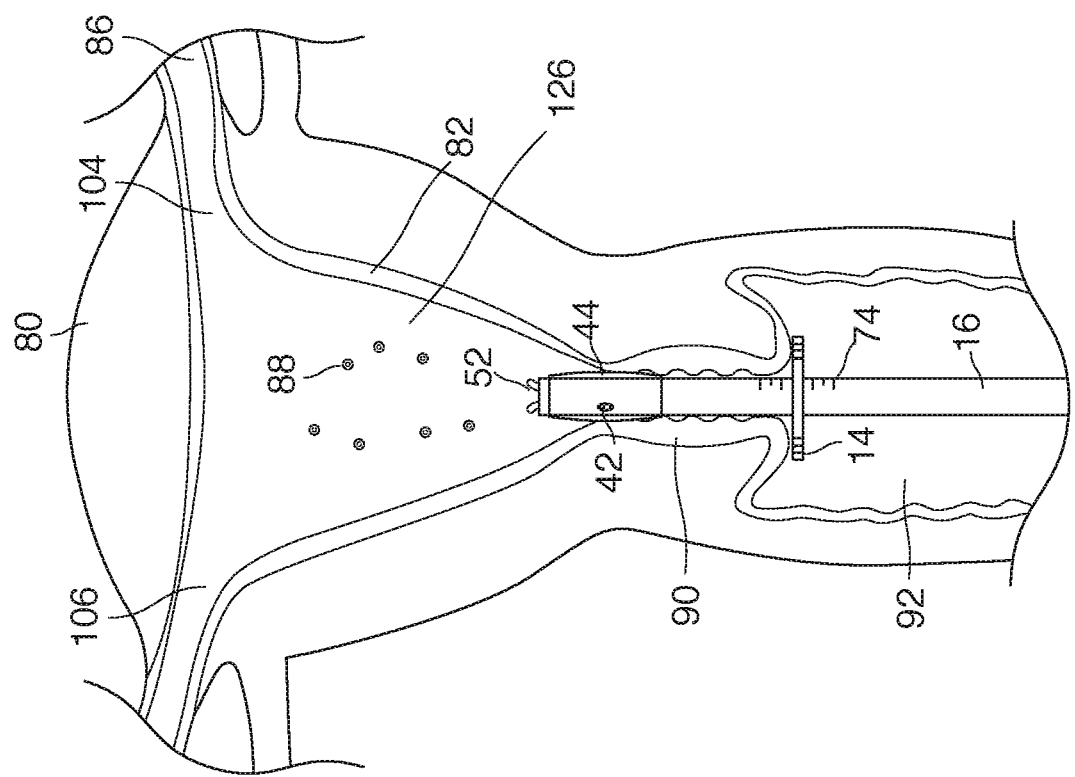

In FIG. 63a the device with double supply lines 64, 66 is inserted into the endocervical canal to a limit preset by the cervical stop 14. The balloon collar 12 is shown uninflated 44. The embryos are shown in the middle of the uterine cavity 88.

Figure 63B:
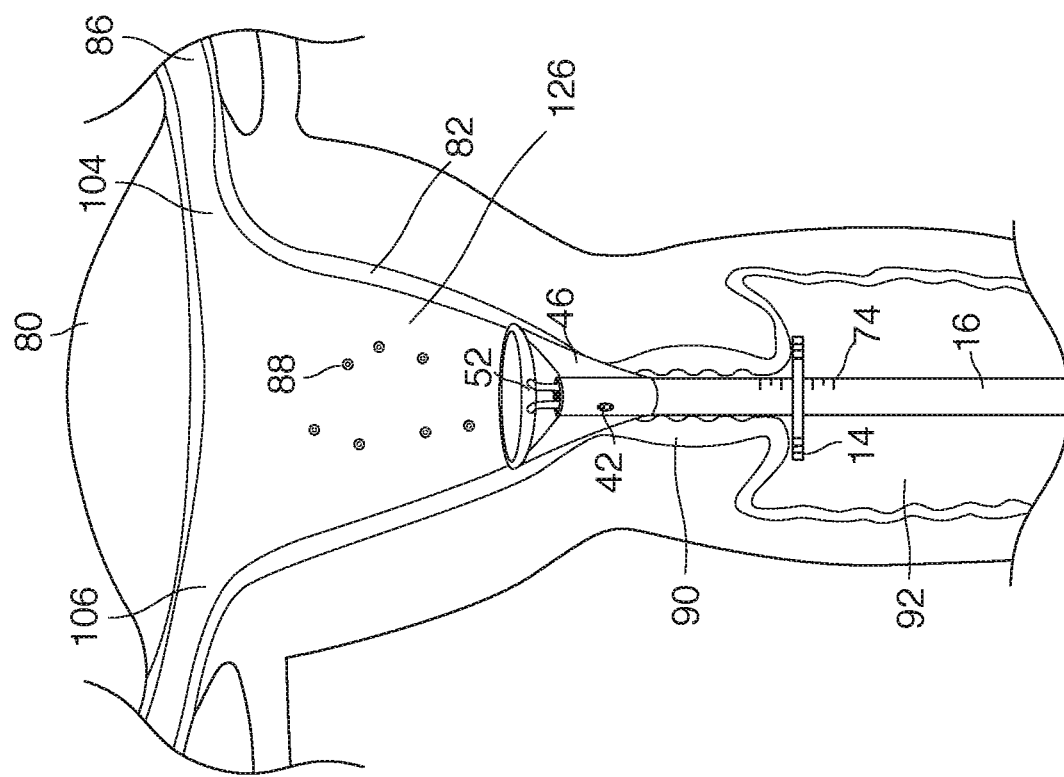

In FIG. 63b the balloon collar is deployed 46 under tension from the supply line 16 and cervical collar stop 14. Upon inflation the balloon forms a watertight funnel at the endocervical canal. The two supply line catheter tips, left 64 and right 66, are protected inside the balloon collar at the very distal tip of the supply line 16.

Figure 63C:
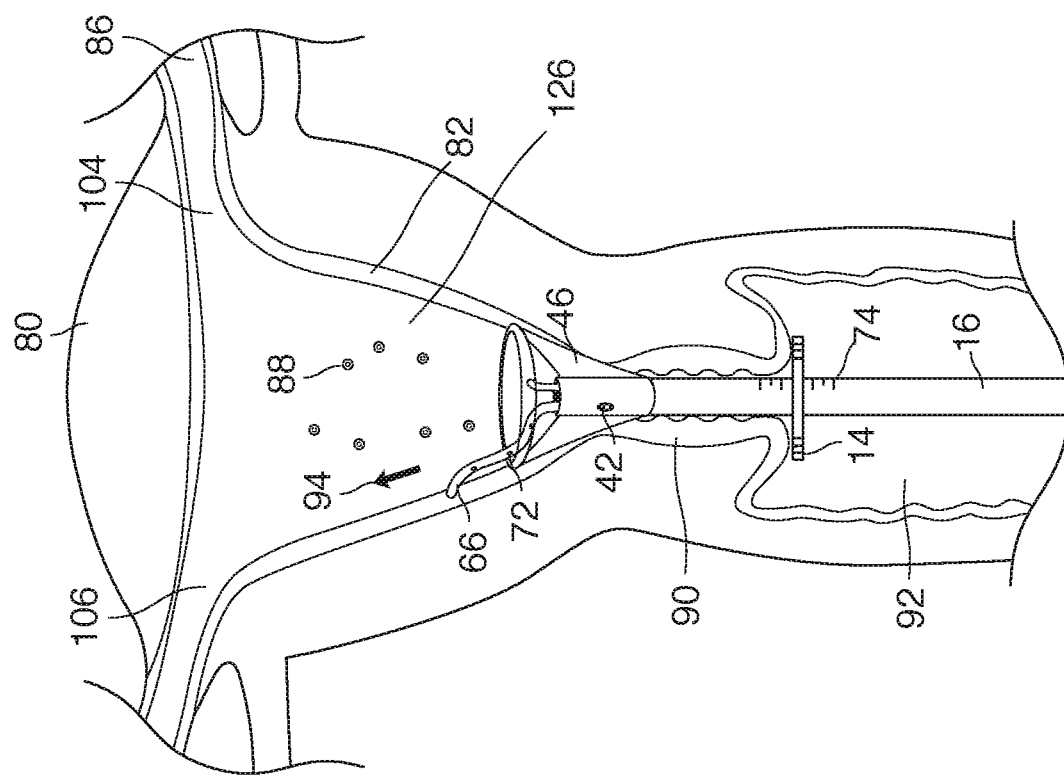

In FIG. 63c the right supply line 66 is being deployed to the right uterine wall snug tightly by the internal memory of the catheter tip. Proximal and distal steering of the supply line 66 is controlled by proximal and distal motion of the steering control right side 26a that motion is directed through the resin slider block 118, which in turn is linked to the right operating slide.

Figure 63D:
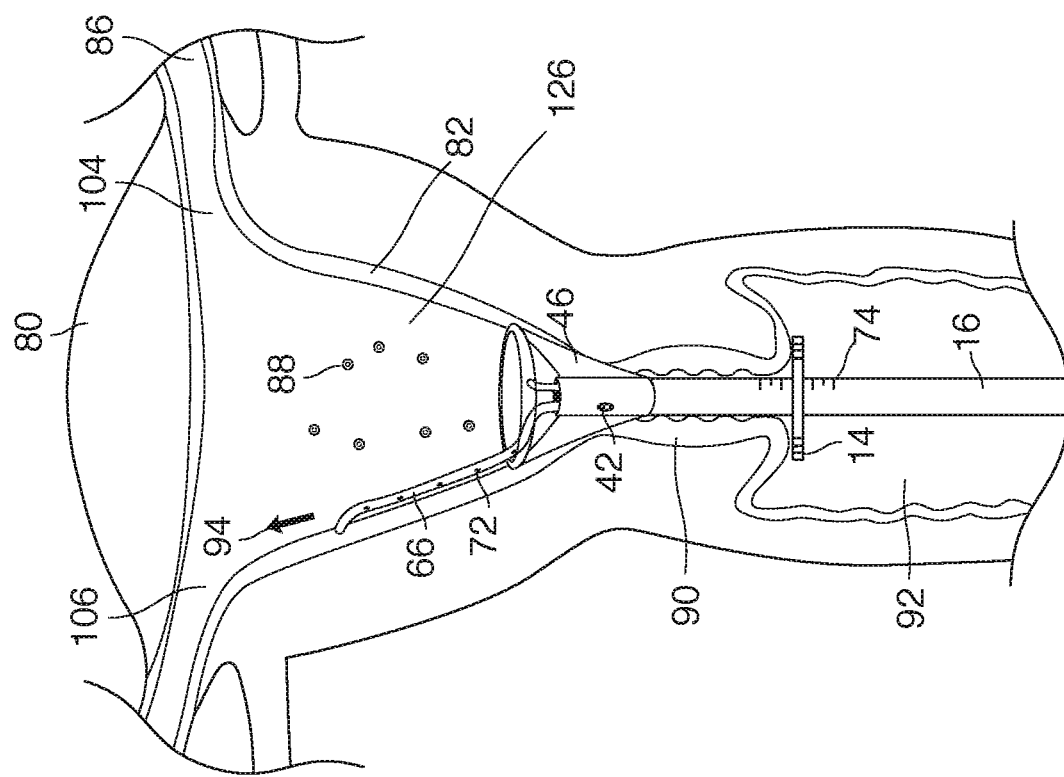

In FIG. 63d the right supply line and its tip is directed up the uterine wall toward the internal ostia. It is steered away from the embryos 88 to the ostium on the right 106. The embryos 88 are not disturbed in the middle part of the uterine cavity.

Figure 63E:
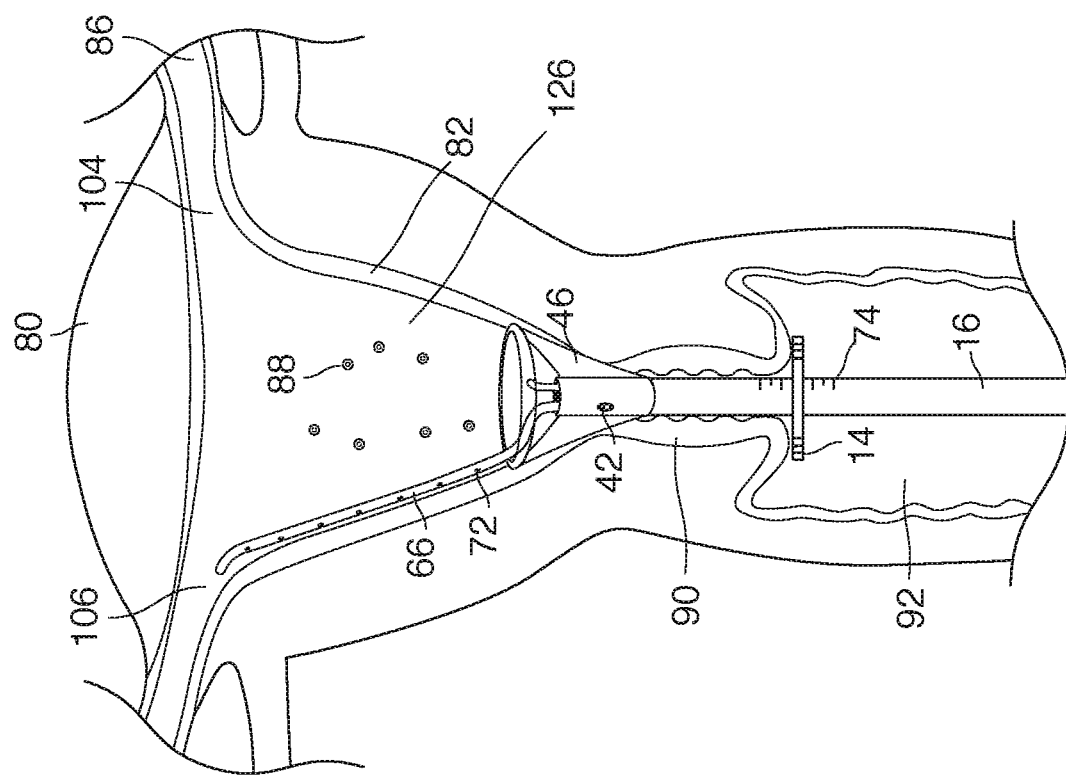

In FIG. 63e the supply line catheter tip has been introduced to the internal ostium 106 and 66. Its memory directs it along the uterine wall.

Figure 63F:
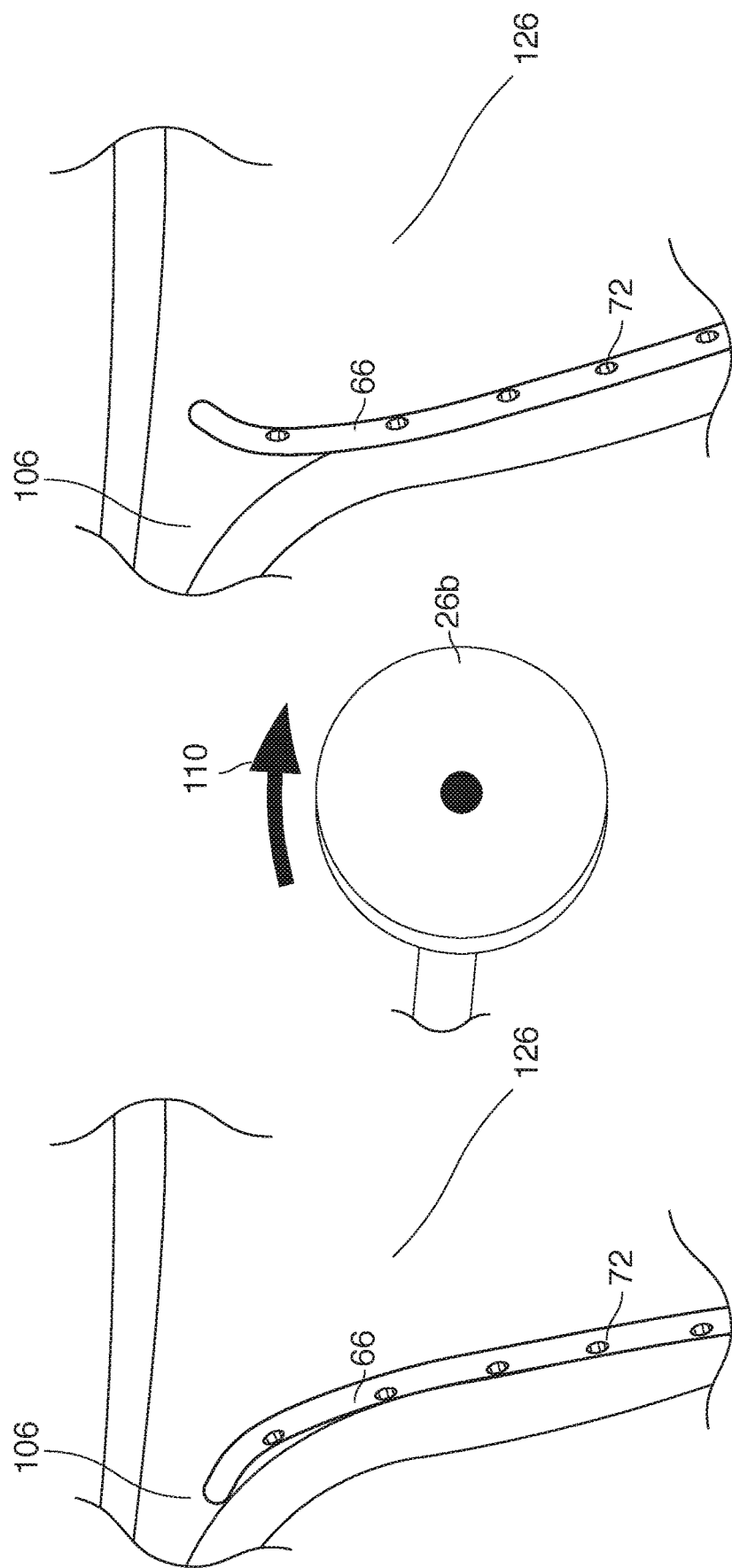

In FIG. 63f once the supply line has been imbedded into the ostium 106, the catheter is rotated 180 degrees by a clockwise torsion of the steering control right 26a.

Figure 63G:
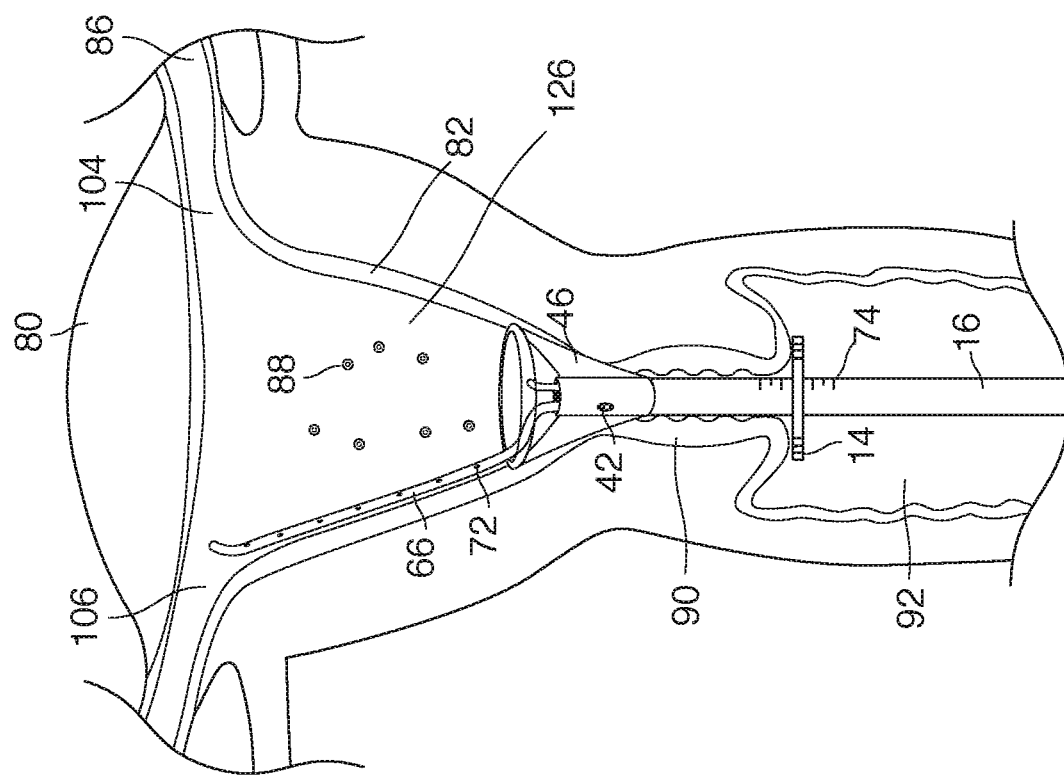

FIG. 63g right shows 180 degrees torsion of the supply line and the ports 72 and the flow direction of the supply line 66, its memory reversed by the rotation.

Figure 63H:
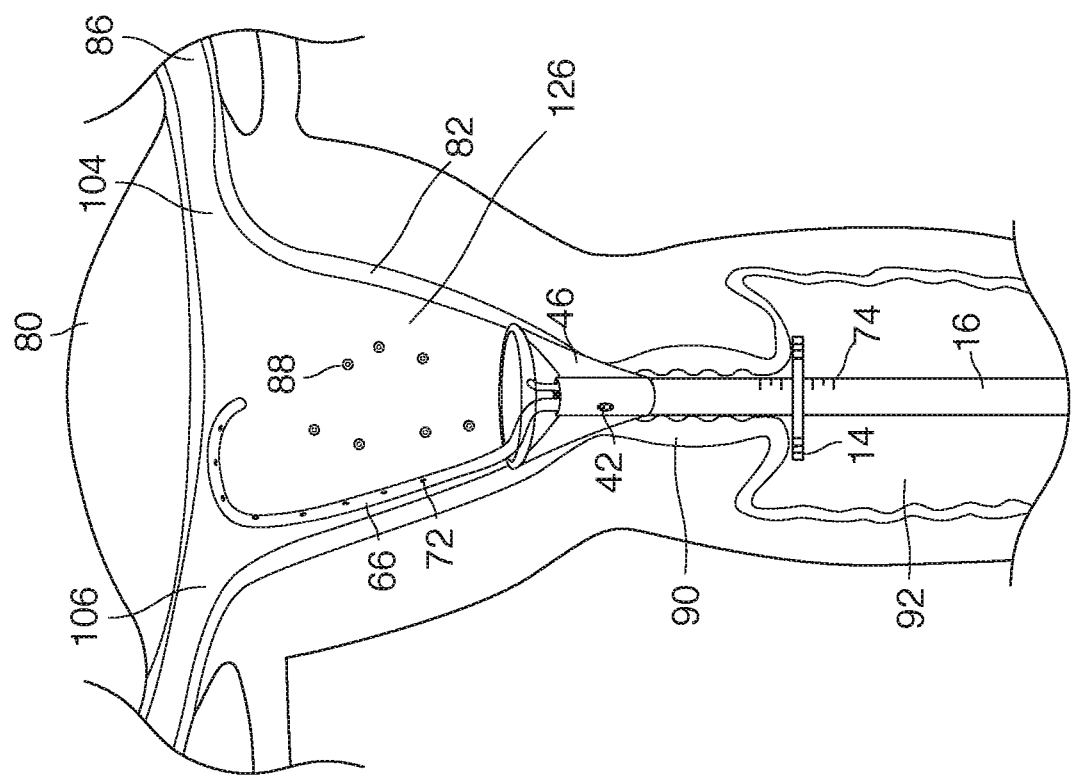

FIG. 63h shows continued advancement of right fluid supply line 64 where it contacts the uterine cavity 126 sidewalls and with continued advancement reaches the middle part of the upper uterine cavity 126 then contacting at the very top of the cavity 126

Figure 63I:
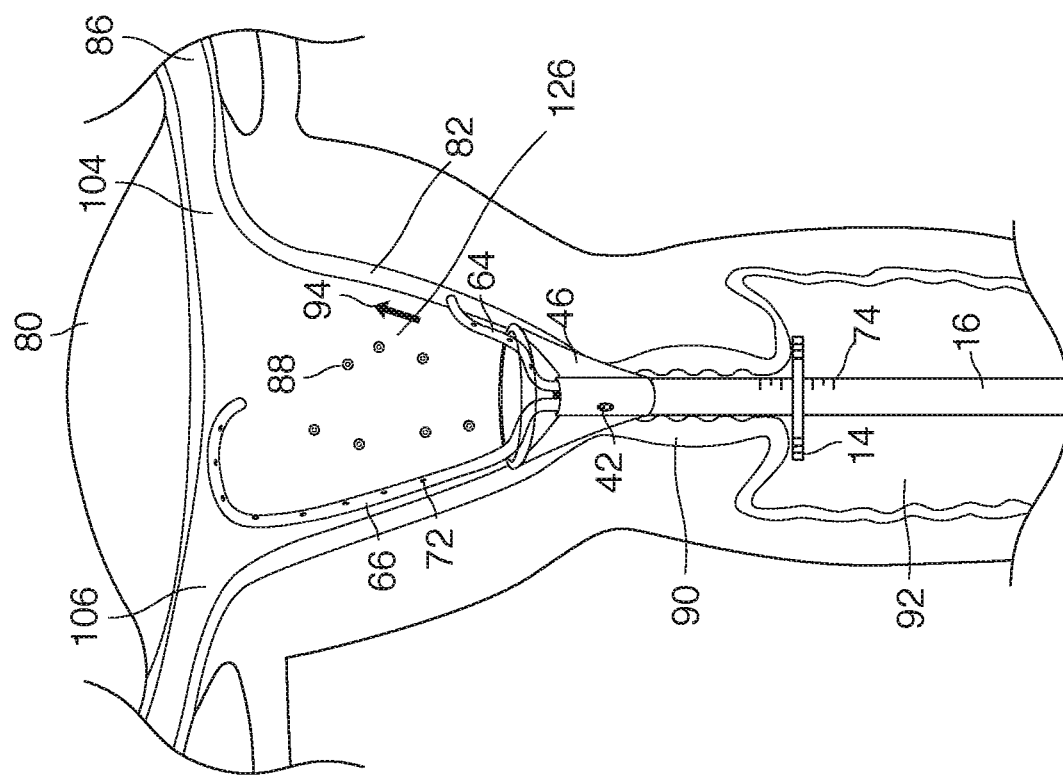

In FIG. 63i the left supply line 64 is now advanced along the left uterine wall.

Figure 63J:
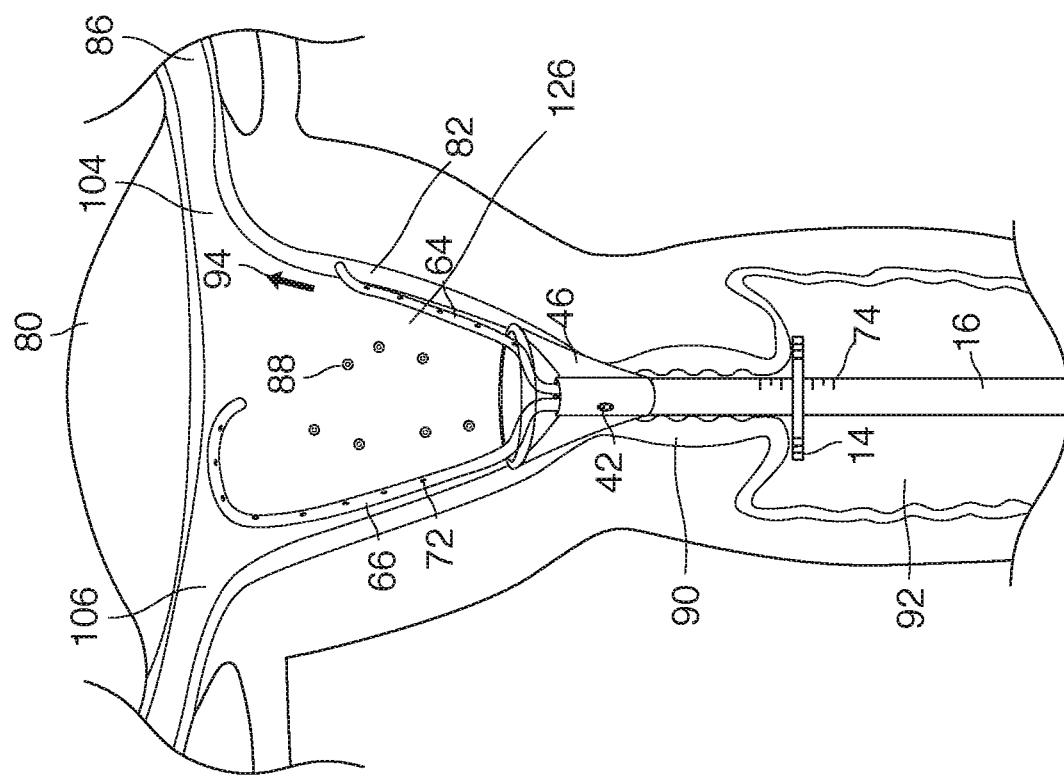

In FIG. 63j the advancement continues unrestricted by the memory of the left supply line 64 and continues it advancement to the left internal ostium 104.

Figure 63K:
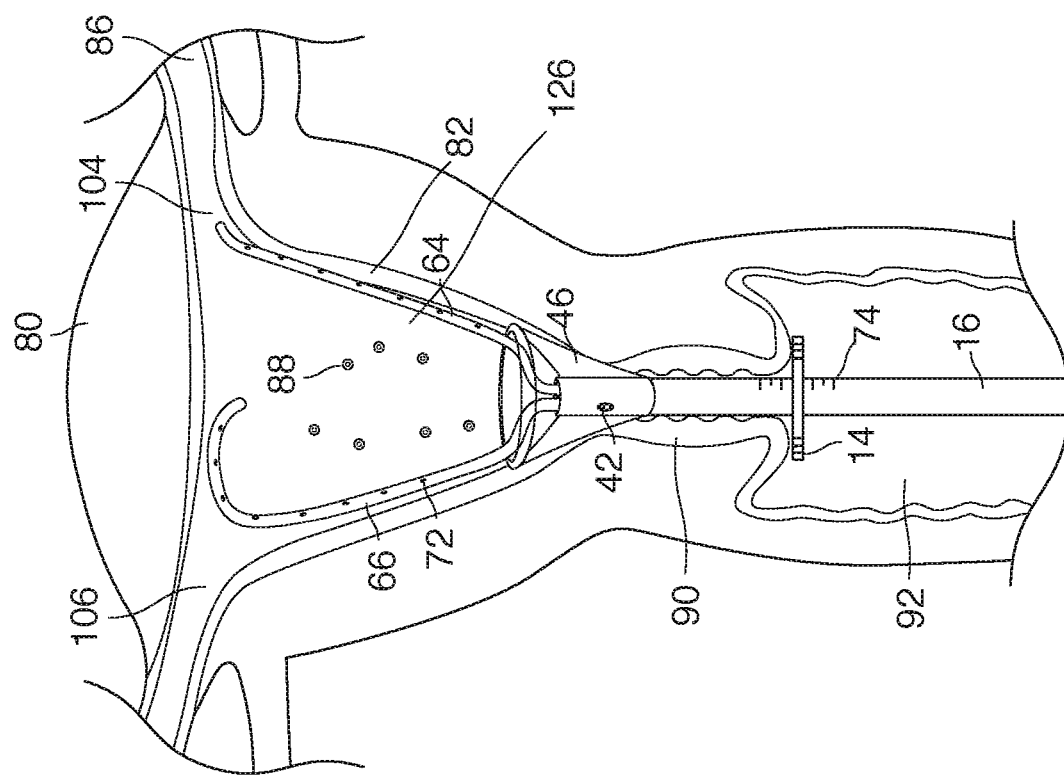
Figure 63I:
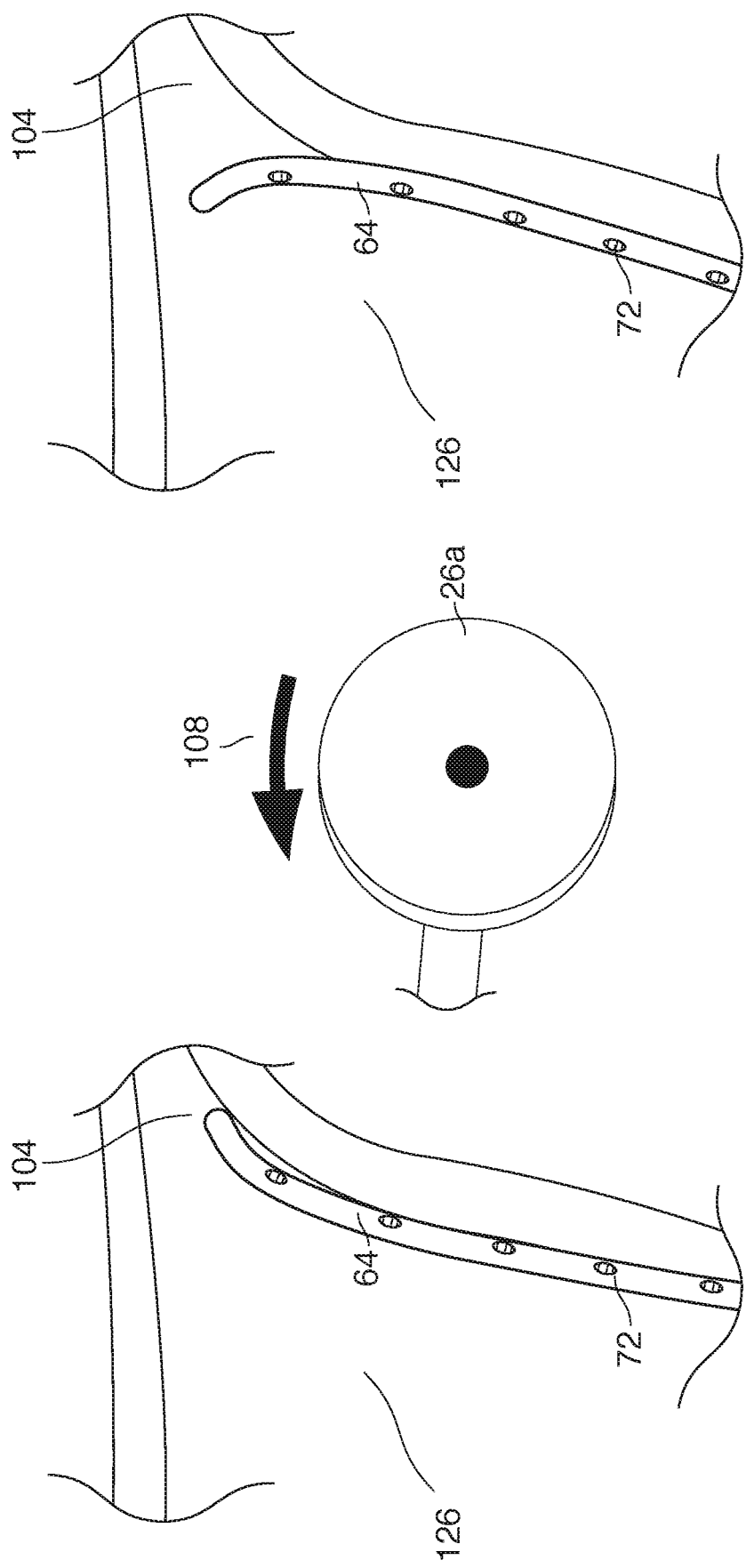

In FIG. 63k the left uterine supply line 64 has reached the internal ostium 104 on the left and is partly inserted into the internal ostium 104 but not advanced any further. The steering control left 36b is rotated counterclockwise 180 degrees and the catheter 64 is then redirected by internal memory to the middle part of the uterine fundus.

In FIG. 63l the advanced supply line meets its companion at the top of the uterine cavity 126 where they may touch.

Figure 63M:
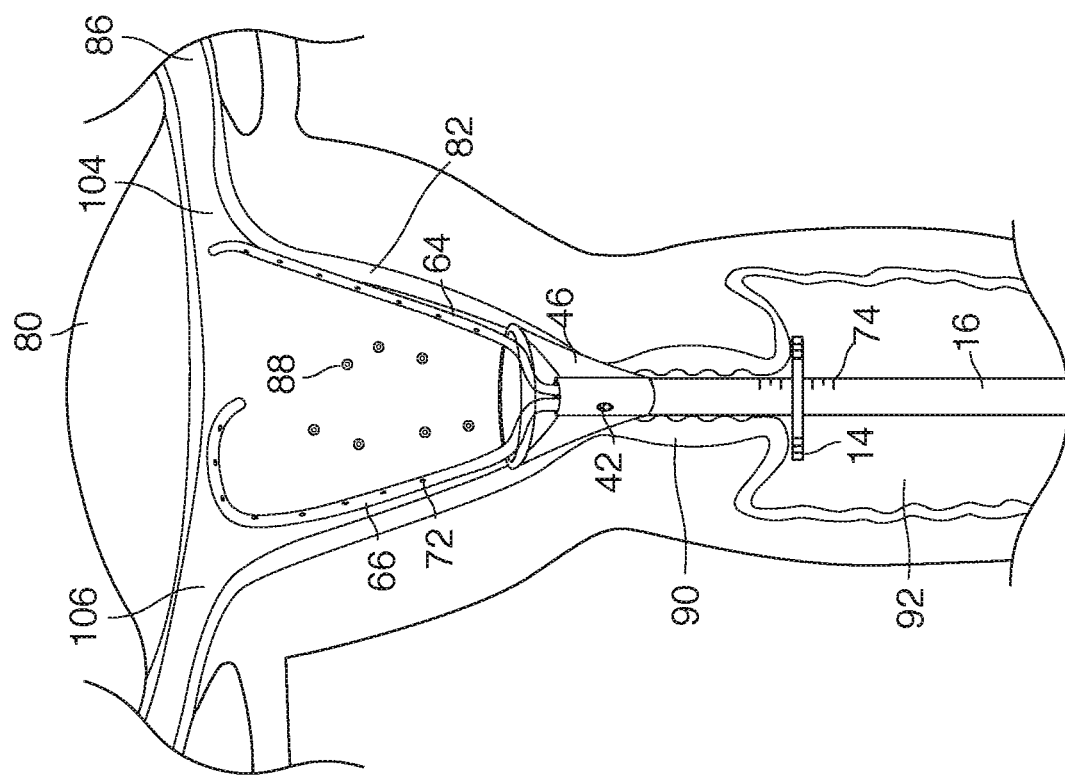

In FIG. 63m pulsing flow has begun by prompting the programmable controller (not shown) linked by the uterine supply lines 64, 66. Fluid flow from the both the left and right supply lines 64 and 66 is directed to the center of the uterine cavity 126 where the embryos are located 88 and the mechanical perimeter is formed around the embryos 88 and all fluid directed away from the internal ostia 106 and 104 into the balloon collar 46 and in alternating sequence of pulse and suction.

Figure 63N:
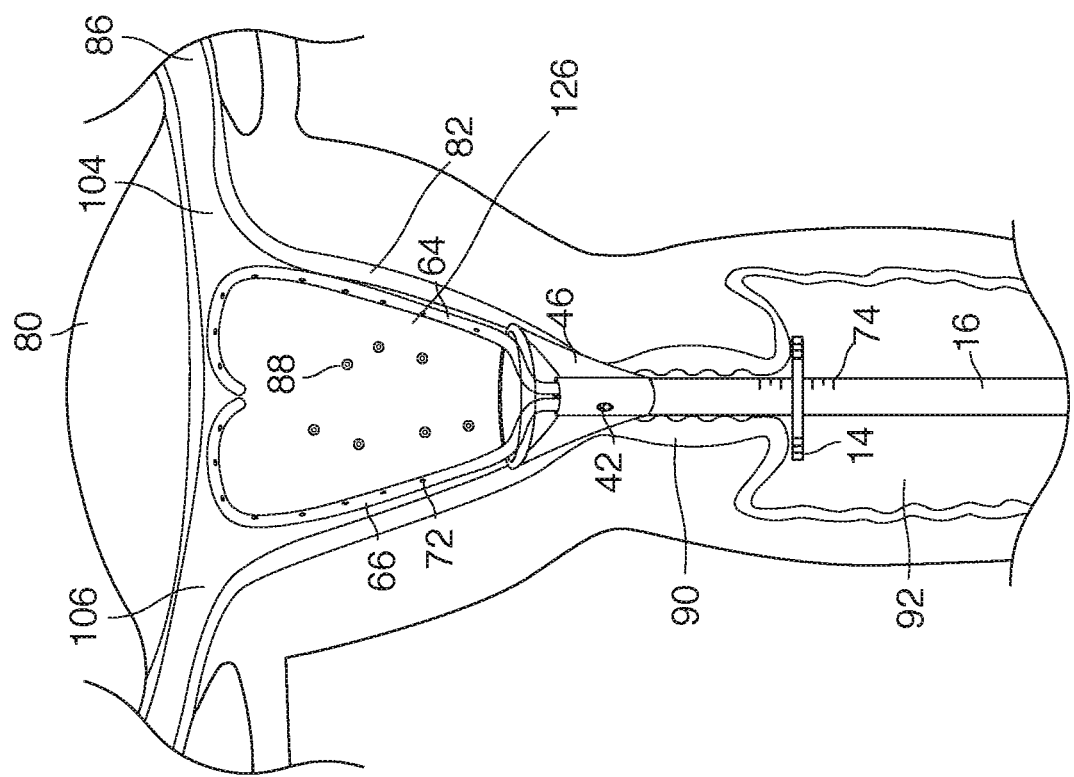

In FIG. 63n embryos are directed into the suction line 16 through the funnel collar 46 at the base of the funnel 46.

Figure 63O:
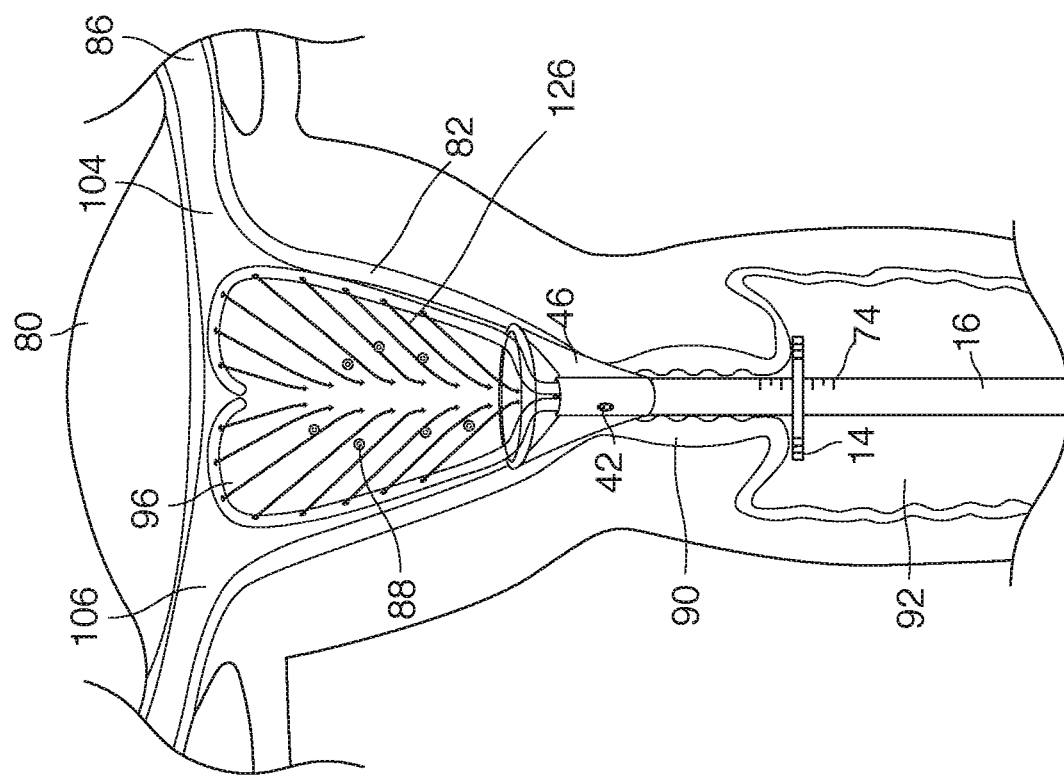
Figure 63P:
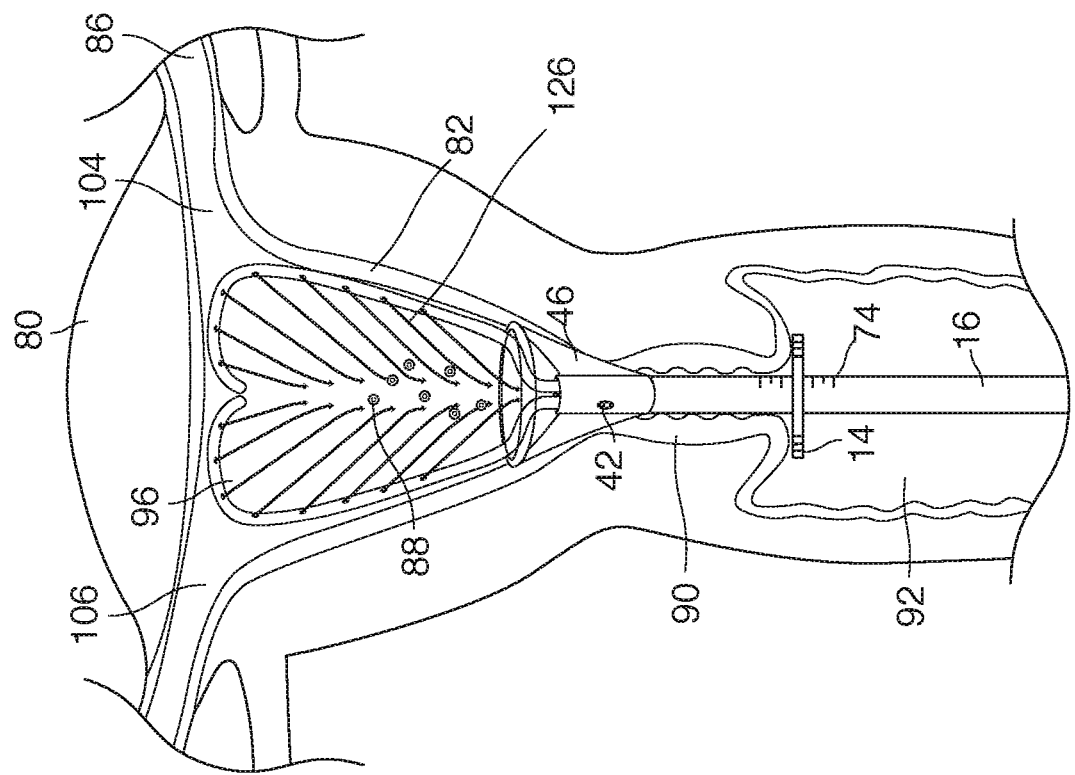
Figure 63Q:
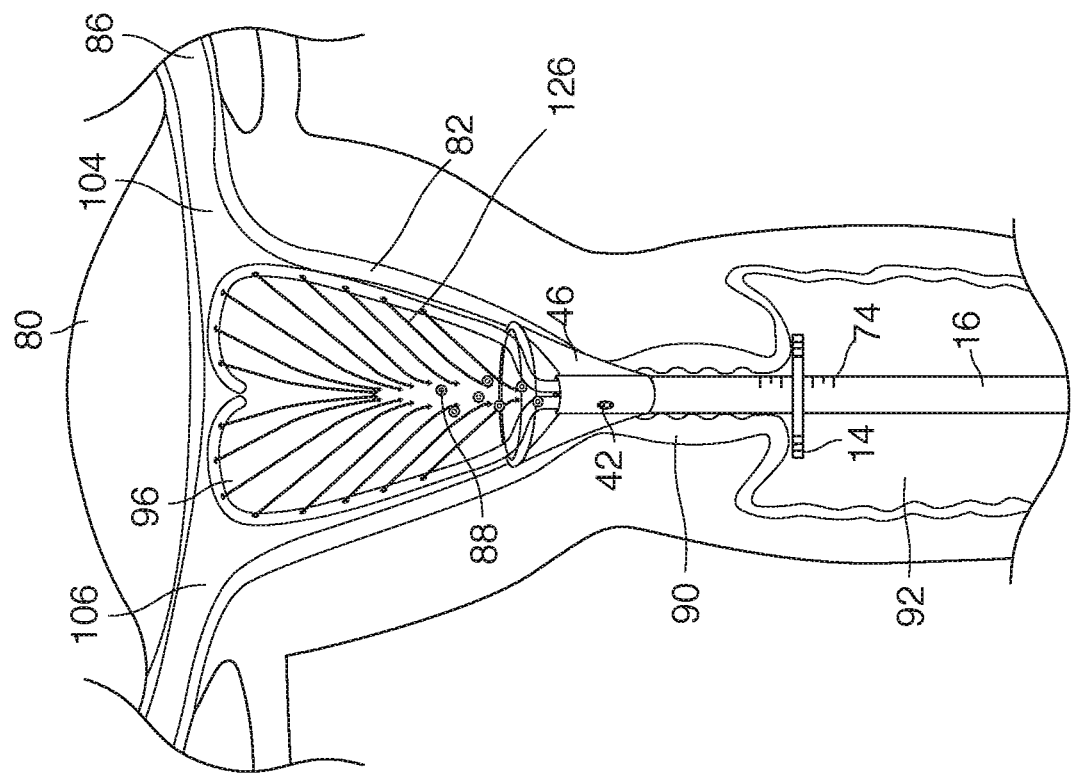

In FIG. 63o-q embryos are passing progressively into the port of the suction line 16 at the base of the balloon collar funnel 46, cleared completely from the uterine cavity, and are delivered into the embryo trap 28a. The fluid is taken the laboratory for evaluation of recovered embryos.

FIG. 64a shows the Version 2b with magnetic tips 68, 70 placement, method of embryo entrapment and direction of fluid flow. Fluid emanating from the ports of the right and left catheters direct embryos into the inflated balloon funnel for egress into the intake port of the uterine suction line and into the recovery trap. The magnetic tip catheter is in mechanical perimeter to entrap embryos completely with withdrawal of both sides simultaneously allowing for virtually no escape of embryos into the internal ostia. The pull of the catheters as they approach the funnel allows the magnetic tips to break contact and then lead to withdrawal of both catheters.

FIGS. 64 b-e depict intrauterine flow from dual supply lines directed to the endocervical balloon guide collar 46. This system differs from Version #2b in that both tips have powerful magnets that allow them to join at the top of the fundus at full deployment.

In FIGS. 64b, this Version 2b system uses, for example, the same catheter lengths as does the Version 2a system. In some implementations, there is no difference between systems other than the magnetic tips.

In FIG. 64c, the left supply line 66 and right supply line link at the top of the fundus firmly attached by magnetic tips 68 and 70. The embryos are surrounded by a mechanical and fluid barrier and cannot escape through the internal ostia 106 and 104 Pulsating fluid is delivered to the central part of the uterine cavity where the embryo is located 84 and alternating suction is delivered to the balloon collar 46 and suction line 16 and the embryos are delivered into the suction. Because of mechanical perimeter and the flow of fluid, there should be no loss of fluid either to the internal ostium 104 and 106 or through the cervix.

In FIG. 64d the complimentary magnetic tips maintain a perimeter around the embryos, which gently collapses contracting because the catheter is being withdrawn. The catheters at this stage cannot separate 64 and 66 because they are held firmly together by a magnetic tip 68 and 70. The embryos are entrapped into diminishing perimeter while they are being delivered into the suction line 16 at the base of the balloon collar 46. The perimeter is in its smallest dimension and the catheters 64 and 66 are withdrawn and the magnetic tips 68 and 70 are being separated. The flow of fluid is stopped at this point.

In FIG. 64e the right and left distal supply lines are now withdrawn into their ports at the base of the balloon collar at the distal the suction line. The procedure is now ended and the instruments are removed.

We have described a variety of implementations of the devices and techniques that we have introduced above. A wide variety of other implementations, examples, and applications fall within the scope of our concepts.

For example, other approaches to recovering the embryos from the woman's uterus may be possible using other fluid-based and possibly non-fluid-based techniques and combinations of two or more of them. Important goals in whatever techniques are used are to recover essentially all of the embryos that are present in the uterus (which improves the efficiency of the process), to avoid delivering any fluid or other foreign material into the Fallopian tubes, to perform the procedure safely and with the least discomfort to the woman, and to perform the procedure in the shortest time and with the least expertise necessary.

Once the embryos are recovered, a wide variety of procedures, diagnoses, and treatments can be applied to them, not limited to genetic diagnosis or sex determination and associated treatment. The embryos could be used for and treated in accordance with any ethical purpose.

When lavage is used to recover the embryos, a wide variety of approaches and parameters can be applied. For example, any fluids or combinations of two or more of them can be used, provided that they are safe and effective and can successfully cause the embryos to be flushed from the uterus. Although we have referred to the fluid as entraining the embryos for removal, other fluidic mechanisms to remove them may be safe and effective, including flushing, spraying, pooling, or any combination of those and others.

We have referred to pulsating the lavage fluid during the procedure, and pulsating and aspiration to remove the fluid from the uterus, possibly in synchronization with the delivery pulses. A wide variety of other regimes may be effective, including no pulsing of the delivery fluid, and profiles of changing delivery pressure and suction that might not be characterized as pulsing. We use the term pulsating broadly to include all of such regimes, for example. Similarly there may or may not be synchronization of the delivery pressure and suction pressure.

We have suggested above that one aspect of achieving a high recovery rate for the embryos is to seal the uterus during the procedure so that essentially none of the lavage fluid leaks out of the woman (possibly with embryos in the fluid). Other techniques that might not be characterized as sealing may be possible to use to achieve a similar high recovery percentage of the fluid and embryos. When sealing is used, the sealing may be done at other locations than at the entry of the cervix into the uterus. In any case, it is considered useful to do the sealing in a manner that is relatively simple, easy to achieve, safe, effective, and can be effected from outside the woman's body by the same person who is performing the other steps of the procedure. Sealing can be achieved in a variety of ways other than or in combination with an inflatable balloon, including other inflatable or non-inflatable devices or mechanisms. In some examples, it is useful to arrange the sealing device so that it can be inserted in a non-inflated or non-deployed state and then be inflated or deployed.

In many of the examples that we mentioned earlier, the lavage is achieved by multiple streams of fluid aimed toward the center of the uterus. A wide variety of approaches and combinations of them may be possible. In general, a goal is to assure that all parts of the uterus, and especially the central region where the preimplantation embryos tend to be located, are washed by fresh lavage fluid so that every embryo is impacted by the fluid. Then the fluid with the embryos present is collected by any technique that can avoid the loss of embryos.

It is useful as part of the procedure to seat the lavage instrument at a predetermined insertion position relative to the woman's specific anatomy in order for the fluid to be effectively delivered and recovered. We have described examples in which the distance between two elements of the instrument is adjusted according to the distance between the end of the cervix that opens into the vagina and the end of the cervix that opens into the uterus. This technique could be combined or replaced by other techniques for seating the instrument in a position and orientation that permit safe and effective lavage of essentially all of the embryos in the uterus. The seating of the device is useful to assure a good seal against the leakage of fluid, and also to assure that the fluid carrying elements of the device can be deployed easily and effectively and in the best location for lavage.

We have described implementations in which the lavage delivery and recovery elements of the instrument are manipulated and deployed by rotation and extension of those elements relative to a static support. A variety of techniques can be used for deployment in combination with or in substitution for that described approach with the goals of relatively quick and easy deployment, effective lavage, and comfort of the woman, among others.

The examples of lavage instruments that we have described include lavage elements and sealing elements that can be moved, inserted, deployed, manipulated, and later withdrawn relative to a fixed or static portion of the device. In some examples, the lavage and sealing elements ride within a tube that is part of the static device. In some implementations, devices for carrying fluid both for delivery and recovery, and elements that enable manipulation from the proximal end of the tool are located outside the woman during the procedure.

A wide variety of other or supplemental configurations of the tool are possible alone or in combination. The configurations, materials, constructions, sizes, and interrelationships of the static and movable elements of the instrument can vary widely depending on the particular approach chosen to achieve lavage. More than two catheters could be used. Each catheter could have more or fewer nozzles than in the examples discussed earlier. The arrangement, sizes, shapes, and directions of the nozzles can be varied. The manner in which the catheters move and are manipulated relative to the fixed part of the instrument can be varied. Any configuration that enables easy, quick, effective, safe, and comfortable lavage procedure could be considered.

The balloon, if used, could have a non-funnel shape. More than one balloon could be used. The suction drain need not be located in the funnel.

Other implementations are within the scope of the following claims.

For ease of reference, the following key identifies numerals on the figures and related items associated with those numerals.

Operating Frame 8
Steel Ball Tip—10
Balloon Collar—12
Cervical Stop—14
Suction Line Distal—16
Balloon Air Supply—18
Fluid Supply Line—20
Suction Recovery Line with One Supply Line Channel—22a
Suction Recovery Line with Two-Supply Line Channels—22b
Suction Recovery Channel—23
Vacuum Line External Access Port—24
Operating Slide—25
Operating Slide Right—25a
Operating Slide Left—25b
Steering Control—26
Right Steering Control—26a
Left Steering Control—26b
Embryo Recovery Trap—28a
Sealed Transport Vial 28b
Flat Petri Dish Large—28c
Flat petri dish Small—28d
Embryo Recovery Trap Perforated Stopper—29
From Pulse Supply Pump—30
To Pulse Suction Vacuum—32
Insulated Transport Block—31
Glass Stopper—33
Fluid Supply Guide Channel—34
Transport Media (e.g. Heapes Buffer)—35
Fluid Supply Line—36
Funnel—37
Beveled High Flow Port—38
Filter—39
Beveled Low Flow Port—40
Balloon Suction Port—42
Collapsed Balloon—44
Inflated Balloon—46
Funnel Balloon under stretch from Cervical Stop—48
Funnel Balloon under stretch from Cervical Stop Sectional View—50
Supply Catheter Tips—52
Fluid Supply Line Patient Left—64
Fluid Supply Line Patient Right—66
Magnetized Steel Cup—68
Magnetized Steel Ball—70
Top Endometrial Cavity—71
Fluid Supply Port—72
Cervical Stop Scale—74
Catheter Platform Hand piece—76
Magnetized Tips Disengaged—78
Uterus—80
Endometrial Lining—82
Merger Block one Supply Line Channel—84a
Merger Block two Supply Line Channels—84b
Proximal Fallopian Tube—86
Distal Fallopian Tube—87
Embryos (Blastocysts)—88
Peritubal Ovarian Interface—89
Cervix—90
Embryos Pronucleate (one cell) Stage—91
Vagina—92
Move Catheter up the uterine wall—94
Right Middle Endometrial Cavity—95
Fluid flow—96
Left Middle Endometrial Cavity—97
Move Catheter up the center of the uterus—98
Hi flow fluid—100
Low flow fluid—102
Tubal Ostium Patient Left—104
Tubal Ostium Patient Right—106
Turn counterclockwise—108
Turn clockwise—110
Magnetized Tips Engaged—112
Pull Catheters Downward—114
Air Supply Syringe—116
Slider Block Version #1—118
Slider Block Version #2 Left—119a
Slider Block Version #2 Right—119b
Slider Block Lock—120
Ovary—122
Oocytes—124
Uterine Cavity—126
Expanded Uterine Cavity 127
Sperm—128
Insemination Catheter—130
Blastocyst that have been selected or treated—132
Zona Pellucida—133
Trophectoderm Cells—134
Inner Cell Mass—135
Holding Pipette—136
Suction Biopsy Pipette—138
x Chromosome Signal—140
18 Chromosome Signal—142
13 Chromosome Signal—144
21 Chromosome Signal—146
Molecular Diagnosis of Trisomy 21 In Situ Hybridization—148
Embryo Transfer Catheter—150
Superovulation—152
Fundus—153

Artificial Insemination—154
Internal os—155
In Vivo Fertilization—156
Endocervical Canal—157
Uterine Lavage—158
Embryo Blastocyst Recovery—159
Embryo Biopsy—160
Uterine Fluid—161
Preimplantation (Molecular) Diagnosis—162
Preimplantation Genetic Therapy Intervention—164
Blastocyst Replacement—166
Cryopreservation—165
Birth—168
External os—170
Corporate Regional Coordinating Center—172
Core Laboratory—174
Service Area with 150-Mile Radius—176
Subscriber Clinic—178
Secure Area Subscriber Clinic—179
Secure Computer Terminal—181
Woman Patient and Male Partner—183
Electronic Identification Chip—189
Transport Vial Carrying Case—190
Secure Space Core Embryology Lab—192
Secure Computer Terminal—194
Frozen Blastocyst Container—196
Hard Stand—198
Hard Stand Attachment Point—199
External Controller—205
218—GnRH agonists
220—GnRH antagonist
222—LH
223—hCG
224—FSH
226—Progesterone antagonist
228—Progesterone
230—Estradiol
231—Pinch Valve
232—Controller Pump
233—Vacuum Pump

What is claimed is:

1. A system for recovering one or more blastocysts from the uterus of a human, comprising:
   a uterine lavage catheter,
   a controller programmed to cyclically deliver lavage fluid through the catheter to the uterus in at least two cycles, wherein the controller is programmed to deliver, in the first cycle of the at least two cycles, a first amount of lavage fluid to form a first puddle encompassing one or more entrained blastocysts, and, in the second cycle of the at least two cycles, to deliver a second amount of lavage fluid into the uterus to form a second puddle encompassing one or more entrained blastocysts, and to apply a vacuum to the catheter to aspirate the lavage fluid containing the entrained blastocysts from the uterus; and
   a pharmaceutically acceptable container comprising a GnRH antagonist in an amount sufficient to cause desynchronization of the endometrium to reduce the a chance that any embryos remaining in the uterus will form a viable pregnancy.

2. The system of claim 1, wherein the controller is programmed to automatically cyclically deliver the lavage fluid to the uterus via the catheter and automatically apply vacuum to the catheter from a vacuum source remote from the catheter.

3. The system of claim 1, wherein the controller comprises a pump for delivering the lavage fluid and a pump for applying the vacuum to aspirate the lavage fluid containing the entrained blastocysts from the uterus.

4. The system of claim 3, wherein the controller comprises electro-mechanical means for controlling the delivery of lavage fluid and the application of the vacuum.

5. The system of claim 1, wherein the controller is programmed to cyclically deliver varying amounts of lavage fluid to the uterus via the catheter in three or more cycles with the amount of lavage fluid delivered increasing in each subsequent cycle.

6. The system of claim 1, further comprising a container for storing the entrained blastocysts in the lavage fluid.

7. The system of claim 6, wherein the container is configured to uniquely identify the entrained blastocysts and associate the entrained blastocysts with the human with information, the information including data that tracks transportation and processing of the entrained blastocysts.

8. The system of claim 1, wherein the container comprising the GnRH antagonist comprises doses ranging from 0.25 to 3.0 mg.

9. The system of claim 1, further comprising a lavage fluid bag for supplying the lavage fluid.

10. The system of claim 1, further comprising an embryo recovery trap for receiving the aspirated lavage fluid and entrained blastocysts.

11. The system of claim 1, wherein the system does not include a composition that stimulates human ovulation.

12. A system for recovering one or more blastocysts from the uterus of a human, comprising:
    a uterine lavage catheter;
    a controller programmed to cyclically deliver lavage fluid through the catheter to the uterus in at least two cycles, wherein the controller is programmed to deliver, in the first cycle of the at least first two cycles, a first amount of lavage fluid to form a first puddle encompassing one or more blastocysts, and, in the second cycle of the at least two cycles, to deliver a second amount of lavage fluid into the uterus to form a second puddle encompassing one or more blastocysts, and to apply a vacuum to the catheter to aspirate the lavage fluid containing the entrained blastocysts from the uterus; and
    a pharmaceutically acceptable container comprising a composition in an amount sufficient to cause desynchronization of the endometrium to reduce a chance that any embryos remaining in the uterus will form a viable pregnancy.

13. The system of claim 12, wherein the system does not include a composition that stimulates human ovulation.

14. A process for recovering one or more blastocysts from the uterus of a human, comprising:
    placing a catheter trans-vaginally into the cervical canal; and
    cyclically delivering lavage fluid through the device to the uterus in at least two cycles,
    wherein the first cycle of the at least first two cycles comprises:
       delivering a first amount of lavage fluid to form a first puddle encompassing the one or more blastocysts; and
    the second cycle of the at least two cycles comprises:
       delivering a second amount of lavage fluid into the uterus to form a second puddle and applying a vacuum to the uterus to aspirate the lavage fluid containing entrained blastocysts from the uterus, and administering a composition to the human in an amount sufficient to cause desynchronization of the endometrium to reduce the a chance that any embryos remaining in the uterus will form a viable pregnancy.

15. The process of claim 14, wherein the catheter comprises a fluid delivery port for delivering the lavage fluid into the uterus and a suction port for aspirating the lavage fluid containing the entrained blastocysts from the uterus such that in use the lavage fluid is deliverable from the fluid delivery port to travel through the suction port from the uterus.

16. The process of claim 15, wherein the fluid delivery port is non-circular in shape to provide directional control of fluid spray.

17. The process of claim 14, further comprising a controller programmed to automatically cyclically deliver the lavage fluid to the uterus and apply vacuum to the catheter from a vacuum source remote from the catheter.

18. The process of claim 17, wherein the controller comprises a pump for delivering the lavage fluid and a pump for applying the vacuum.

19. The process of claim 17, wherein the controller comprises electro-mechanical means for controlling the delivery of the lavage fluid and the application of the vacuum.

20. The process of claim 17, wherein the controller is programmed to cyclically deliver varying amounts of the lavage fluid to the uterus in three or more cycles with the amount of lavage fluid delivered increasing in each subsequent cycle.

21. The process of claim 14, wherein the administering comprises administering a GnRH antagonist in a dosage ranging from 0.25 to 3.0 mg.

* * * * *